US007078169B2

(12) United States Patent
Ashby et al.

(10) Patent No.: US 7,078,169 B2
(45) Date of Patent: Jul. 18, 2006

(54) METHODS FOR THE IDENTIFICATION OF INHIBITORS OF AN ISOPRENOID METABOLIC PATHWAY

(75) Inventors: Matthew Ashby, Mill Valley, CA (US); Stewart Scherer, Moraga, CA (US); John W. Phillips, Kirkland, WA (US); Michael Ziman, Seattle, WA (US); Nicholas Marini, San Francisco, CA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 357 days.

(21) Appl. No.: 10/205,841

(22) Filed: Jul. 26, 2002

(65) Prior Publication Data

US 2003/0093226 A1 May 15, 2003

Related U.S. Application Data

(63) Continuation of application No. 09/540,806, filed on Mar. 31, 2000, now abandoned.

(60) Provisional application No. 60/127,223, filed on Mar. 31, 1999.

(51) Int. Cl.

| | |
|---|---|
| ***C12Q 1/68*** | (2006.01) |
| ***C12Q 1/02*** | (2006.01) |
| ***G01N 33/53*** | (2006.01) |
| ***C12N 15/63*** | (2006.01) |
| ***C07H 21/02*** | (2006.01) |

(52) U.S. Cl. ............................ 435/6; 435/7.1; 435/29; 435/455; 536/23.1

(58) Field of Classification Search .................... 435/6, 435/29, 91.2; 536/23.1, 23.4, 24.1; 702/19
See application file for complete search history.

(56) References Cited

U.S. PATENT DOCUMENTS

| | | | |
|---|---|---|---|
| 5,223,408 | A | 6/1993 | Goeddel et al. |
| 5,225,538 | A | 7/1993 | Capon et al. |
| 5,510,270 | A | 4/1996 | Fodor et al. |
| 5,556,752 | A | 9/1996 | Lockhart et al. |
| 5,569,588 | A | 10/1996 | Ashby et al. |
| 5,569,888 | A | 10/1996 | Kamani et al. |
| 5,578,832 | A | 11/1996 | Trulson et al. |
| 5,668,255 | A | 9/1997 | Murphy |
| 5,777,888 | A | 7/1998 | Rine et al. |
| 5,783,398 | A | 7/1998 | Marcy et al. |
| 5,821,047 | A | 10/1998 | Garrard et al. |
| 5,965,352 | A | 10/1999 | Stoughton et al. |
| 5,981,207 | A | 11/1999 | Burbaum et al. |
| 6,203,987 | B1 | 3/2001 | Friend et al. |
| 6,218,122 | B1 | 4/2001 | Friend et al. |
| 6,324,479 | B1 | 11/2001 | Friend et al. |

FOREIGN PATENT DOCUMENTS

| | | |
|---|---|---|
| DE | 19502584 A | 1/1995 |
| DE | 19713572 A | 4/1997 |
| WO | WO 98/38329 | 9/1993 |
| WO | WO97/47763 | 12/1997 |
| WO | WO 98/06874 | 2/1998 |
| WO | WO 98/38331 | 9/1998 |
| WO | WO-00/58521 A2 * | 10/2000 |

OTHER PUBLICATIONS

U.S. Appl. No. 09/220,142, filed Dec. 23, 1998, Stoughton et al.
U.S. Appl. No. 09/220,275, filed Dec. 23, 1998, Stoughton et al.
U.S. Appl. No. 09/282,243, filed Mar. 31, 1999, Roberts.
U.S. Appl. No. 09/946,290, filed Sep. 4, 2001, Roberts.
U.S. Appl. No. 60/090,046, filed Jun. 19, 1998, Friend et al.
U.S. Appl. No. 60/090,004, filed Jun. 19, 1998, Friend et al.
U.S. Appl. No. 60/084,742, filed May 8, 1998, Friend et al.
U.S. Appl. No. 60/056,109, filed Aug. 20, 1997, Friend et al.
Agrawal et al., 1997, "Perspectives in antisense therapeutics", Pharmacol Ther. 76(1-3):151-60. peutics, 76: 151-60.
Altschul et al., 1997,"Gapped BLAST and PSI-BLAST: a new generation of protein database search programs", Nucleic Acids Res. 1997 25(17):3389-402.
Arnone and Davidson, 1997, "Green Fluorescent Protein in the sea urchin: new experimental approaches to transcriptional regulatory analysis in embryos and larvae", Development 124:1851-1864.
Blanchard et al., 1996, "Sequence to array: Probing the genome's secrets", Nature Biotechnology 14:1649.
Brachmann et al., 1998, "Designer deletion strains derived from *Saccharomyces cerevisiae* S288C: a usefu set of strains and plasmids for PCR-mediated gene disruption and other applications", Yeast, 14:115-32.
Blanco P, Sieiro C, Reboredo NM, Villa TG. Jul. 15, 1998 FEMS Microbiol Lett. 164(2):249-55. "Cloning, molecular characterization, and expression of an endo-polygalacturonase-encoding gene from *Saccharomyces cerevisiae* IM1-8b.".

(Continued)

*Primary Examiner*—John Brusca
*Assistant Examiner*—Shubo (Joe) Zhou
(74) *Attorney, Agent, or Firm*—Jones Day

(57) ABSTRACT

The present invention relates to methods of identifying genes whose expression is indicative of activation of a particular biochemical or metabolic pathway or a common set of biological reactions or functions in a cell ("regulon indicator genes") The present invention provides an example of such an indicator gene. The present invention also relates to methods of partially characterizing a gene of unknown function by determining which biological pathways, reactions or functions its expression is associated with, thereby placing the gene within a functional genetic group or "regulon". These partially characterized genes may be used to identify desirable therapeutic targets of biological pathways of interest ("regulon target genes") The present invention provides examples of such target genes. Methods for identifying effectors (activators and inhibitors) of regulon target genes are provided. The present invention also provides examples of regulon target gene inhibitors.

22 Claims, 87 Drawing Sheets

OTHER PUBLICATIONS

Castanotto et al., 1998, "Structural similarities between hammerhead ribozymes and the spliceosomal RNAs could be responsible for lack of ribozyme cleavage in yeast", .Antisense and Nucleic Acid Drug Development, 8:1-13.
Chien et al., 1991, "The two-hybrid system: a method to identify and clone genes for proteins that interact with a protein of interest", Proc. Natl. Acad. Sci. USA, 88(21):9578-82.
Clackson et al., 1998, "Redesigning small molecule-protein interfaces", .Curr. Opin. Struct. Biol., 8:451-8.
Cleves AE, Cooper DN, Barondes SH, Kelly RB. 1996. J Cell Biol. Jun.;133(5):1017-26."A new pathway for protein export in *Saccharomyces cerevisiae*.".
Courchesne WE, Kunisawa R, Thorner J. 1989, Cell. Sep. 22;58(6):1107-19. "A putative protein kinase overcomes pheromone-induced arrest of cell cycling in *S. cerevisiae*.".
Crooke et al., 1998, "Antisense therapeutics", Biotechnology and Genetic Engineering Reviews, 15:121-57.
Cunningham et al., 1997, "Minimized proteins", Curr. Opin. Struct. Biol. 7:457-62.
Derisi et al., 1997, "Exploring the Metabolic and Genetic Control of Gene Expression on a Genomic Scale", Science,278:680-686.
Dimster-Denk et al., 1999, "Comprehensive evaluation of isoprenoid biosynthesis regulation in *Saccharomyces cerevisiae* utilizing the Genome Reporter Matrix", J Lipid Res. 40(5):850-60.
Drenser et al., 1995, "Control of Gene Expression in Yeast Using Hairpin Ribozymes" Protein Engineering, Oxford Univ. Press Surrey, 8(supp):88.
Eckstein et al., 1997, "Exogenous application of ribozymes for inhibiting gene expression", .Ciba Foundation Symposium, 207-217.
Eisen et al., 1998, "Cluster Analysis and Display of Genome-Wide Expression Patterns", Proc.Natl. Acad. Sci. USA: 95:14863-14868.
Ferbeyre et al., 1996, "Cell cycle arrest promotes trans-hammerhead ribozyme action in yeast", J Biol Chem. 271(32):19318-23.
Fodor et al., 1991, "Light-directed, spatially addressable parallel chemical synthesis", Science 251:767-773.
Formosa, et al., 1991, "Using protein affinity chromatography to probe structure of protein machines", Methods Enzymol 208:24-45.
Formosa, et al., 1983, "Affinity purification of bacteriophage T4 proteins essential for DNA replication and genetic recombination", Proc. Natl. Acad. Sci. USA 80(9):2442-6.
Gachotte et al., 1999, "Characterization of the *Saccharomyces cerevisiae* ERG27 gene Encoding the 3-keto reductase Involved in C-4 Sterol Demethylation", Proc.Natl. Acad.Sci. USA 96(22): 12655-60.
Gachotte et al.,1998, "Characterization of the *Saccharomyces cerevisiae* ERG26 gene encoding the C-3 sterol dehydrogenase (C-4 decarboxylase) involved in sterol biosynthesis" Proc. Natl. Acad. Sci. USA 95:13794-99.
Garfinkel et al., 1998, "Ty Mutagenesis", Methods in Microbiology, 26:101-118.
Gautier et al., 1987, "Alpha-DNA. IV: Alpha-anomeric and beta-anomeric tetrathymidylates covalently linked intercalating oxazolopyridocarbazole. Synthesis, physicochemical properties and poly (rA) binding", Nucl. Acids Res. 15: 6625-6641.
Gawantka et al., 1998, "Gene Expression Screening in Xenopus Identifies Molecular Pathways, Predicts Gene Function andn Provides a Global View of Embryonic Patterning", Mechanisms of Development, 77(2):95-141.
Gietz and Sugino, 1988, "New Yeast-*Eschericia Coli* Shuttle Vectors Constructed With In Vitro Mutagenized Yeast Genes Lacking Six-Base Pair Restriction Sites", Gene 74:527-34.
Goffeau et al., 1996, "Life with 6000 genes", Science 274:546-567.
Gorczyca et al., 1993, "Insulin-like receptor and insulin-like peptide are localized at neuromuscular junctions in Drosophila", J. Neurosci. 13:3692-3704.
Huang et al., 1997, "Disruption of Six Novel Yeast Genes Reveals Three Genes Essential for Vegetative Growth and One Required For Growth at Low Temperature", Yeast 13(12):1181-94.
Hubbard et al., 1997, "Can drugs be designed?", Curr. Opin. Biotechnol., 8:696-700.
Huse et al., 1989, "Generation of a large combinatorial library of the immunoglobulin repertoire in phage lambda", Science 246: 1275-1281.
Inoue et al., 1987, "Synthesis and hybridization studies on two complementary nona(2'-O-methyl)ribonucleotides", Nucl. Acids Res. 15: 6131-6148.
Inoue et al., 1987,"Sequence-dependent hydrolysis of RNA using modified oligonucleotide splints and RNase H", FEBS Lett. 215: 327-330.
Ito et al., 1983, "Transformation of intact yeast cells treated with alkali cations", J. Bacteril., 153:163-168.
Johnston M, Andrews S, Brinkman R, Cooper J, Ding H, Dover J, Du Z, Favello, A, Fulton L, Gattung S, et al. Sep. 30, 1994 Science, 265(5181):2077-82. "Complete nucleotide sequence of *Saccharomyces cerevisiae* chromosome VIII.".
Kleinberg et al., 1995, "New approaches and technologies in drug design and discovery", Am. J. Health Syst. Pharm. 52: 1323-36.
Kolchanov et al., 1999, "Transcription Regulatory Regions Database (TRRD):its status in 1999", Nucleic Acids Res. 27(1):303-6.
Kubinyi et al., 1995, "Strategies and recent technologies in drug discovery", pharmazie, 50:647-62.
Kubo K, Ohno S, Matsumoto S, Yahara I, Suzuki K. Mar. 15, 1989. Gene. 76(1):177-80. "A novel yeast gene coding for a putative protein kinase.".
Lavrovsky et al., 1997, "Therapeutic potential and mechanism of action of oligonucleotides and ribozymes", biochem. And Molec. Medicine, 62:11-22.
Lockhart et al., 1996, "Expression monitoring by hybridization to high-density oligonucleotide arrays", Nature Biotechnology 14:1675-1680.
Madhani and Fink, 1998, "Sequence-dependent hydrolysis of RNA using modified oligonucleotide splints and RNase H", Trends in Genetics 14:151-155.
Maskos and Southern, 1992, "Oligonucleotide hybridizations on glass supports: a novel linker oligonucleotide synthesis and hybridization properties of oligonucleotides synthesized in situ", Nuc. Acids. Res. 20:1679-1684.
Mattos et al., 1996, "Locating and characterizing binding sites on proteins", Nature Biotechnol., 14:595-9.
McGall et al., 1996, "Light-directed synthesis of high-density oligonucleotide arrays using semiconductor photoresists", Proc. Natl. Acad. Sci. USA 93: 13555.
Mitchell and Martin et al., 1995, "A novel cytochrome b5-like domain is linked to the carboxyl terminus of the *Saccaromyces cerevisiae* delta-9 fatty acid desaturase", J. Biol. Chem., 270(50):29766-72.

Nakamura T, Namba H, Ohmoto T, Liu Y, Hirata D, Miyakawa T. Nov. 7, 1995. Gene. 165(1):25-9. Cloning and characterization of the *Saccharomyces cerevisiae* SVS1 gene which encodes a serine- and threonine-rich protein required for vanadate resistance.

Pearson et al, 1990, "Rapid and sensitive sequence comparison with FASTP and FASTA", Methods in Enzymology, 183:63-98.

Pease et al., 1994, "Light-generated oligonucleotide arrays for rapid DNA sequence analysis", Proc. Natl. Acad. Sci. U.S.A. 91:5022-5026.

Robinson, G., et al., 1993, "Conservation between Human and Fungal Squalene Synthetases: Similarities in Structure, Function and Regulation", Mol. Cell. Biol. 13:2706-2717.

Roth et al., 1998, "Finding DNA RegulatoryMotifs Within Unaligned Noncoding Sequences Clustered by Whole Genome mRNA Quantitation", Nature Biotechnol., 16:939-45.

Rothstein B.,1991, "Targeting, disruption, replacement, and allele rescue: integrative DNA transformation in yeast", Meth. Enzymol. 194:281-301.

Ryley, J. and Barret-Bee, K., 1990, Chapter 21: "Screening for Antifungal Activity" *Handbook of Experimental Pharmacology*, 1990, Springer-Verlag, Heidelberg, JF Ryley, eds.

Schena et al., 1996, "Parallel human genome analysis: microarray-based expression monitoring of 1000 genes", Proc. Natl. Acad. Sci. U.S.A. 93:10614.

Schena et al., 1995, "Quantitative monitoring of gene expression patterns with complementary DNA micro-array", Science 270:467-470.

Schiestl et al., 1989, "High efficiency transformation of intact yeast cells using single stranded nucleic acids as a carrier", Curr. Genet. 16:339-46.

Sherman et al., 1991, "Getting Started with Yeast", Methods Enzymol. 194:3-21.

Sherman et al, 1991, "Mapping Yeast Genes", Methods Enzymol., 194:38-57.

Stark et al., 1998, "Studying Essential Genes: Generating and Using Promoter Fusions and Conditional Alleles", Methods In Microbiology, 26:83-100.

Stein et al., 1988, "Physicochemical properties of phosphorothioate oligodeoxynucleotides", Nucl. Acids Res. 16: 3209.

Sternberg, S., 1994, "The Emerging Fungal Threat", Science 266:1632-34.

Tamayo et al., 1999, "Interpreting Patterns of Gene Expression with Self-Organizing Maps: Methods and Application to Hematopoietic Differentiation", Proc. Natl. Acad. Sci. USA 96:2907-2912.

Vanderbol et al. Dec. 1994 Yeast 10:S35-S40. "DNA sequencing of a 36.2kb fragment located between the FASI and LAP4 LOCI of Chrosomosome XI of *Saccharomyces cerevisiae.*".

Veitia et al., 1999, "A Novel Human Gene, Encoding a Potential Membrane Protein Conserved From Yeast to Man, is_Strongly Expressed In Testis and Cancer Cell Lines", Cytogenetics and Cell Genetics, 85:217-220.

Wach et al., 1994, "New heterologous modules for classical or PCR-based gene disruptions in *Saccharomyces cerevisiae*", Yeast 10:1793-1808.

White et al., 1997, "Inhibition of the multiple antibiotic resistance (mar) operon in *Escherichia coli* by antisense DNA analogs", Antimicrob Agents Chemother. Dec. 1997;41(12):2699-704.

Yu et al., 1998, "Human CUL-1 associates with the SKP1/SKP2 complex and regulates p21 CIP1/WAF1 and cyclin D proteins", Proc.Natl.Acad.Sci. USA 95-11324-11329.

Zhao et al., 1998, "Rules for ribozymes", Mol.Cell. Neurosci., 11:92-97.

http://mips.gsf.de/genre/proj/yeast/ (formally http://www.mips.biochem.mpg.de/mips/yeast/) Comprehensive Yeast Genome Database (CYGD) maintained by Munich Information Center for Protein Sequences (MIPS), May 19, 2005.

http://www.yeastgenome.org/ (formally http://genome-www.stanford.edu/Saccharomyces/) *Saccharomyces* Genome Database maintained by Department of Genetics of School of Medicine, Stanford University. May 19, 2005.

http://www.ncbi.nlm/nih.gov/entrez/ Genbank accession No. Z75145. *S. Cerevisiae* chromosome XV reading fram ORF YOR237w. Direct submission on Jul. 4, 1996 by Boyer et al. (Data collected by MIPS on behalf of the European yeast chromosome XV sequence project).

* cited by examiner

YJL105w

| | |
|---|---|
| GenBank No. | 1008286 |
| Chromosome | X |
| Protein | 559 amino acids |
| | 63,867 Daltons |
| Comments: | contains a PHD finger |

Figure 1.

Regulated Expression of YJL105w

| Expt | Level | Natural Log Ratio | Treatment [baseline] |
|---|---|---|---|
| 1455 | 9.1 | +3.2 | 4.0ug/ml Fluvastatin - 18 hr [0.09] |
| 1454 | 8.1 | +3.1 | 8.0ug/ml Fluvastatin - 18 hr [0.13] |
| 1537 | 7.9 | +3.1 | 20ug/ml Lovastatin in 1 Ethanol - 18 hr [0.10] |
| 1420 | 7.8 | +3.1 | 20ug/ml Atorvastatin in 1 DMSO - 18 hr [0.14] |
| 3455 | 7.8 | +3.1 | 20ug/ml Lovastatin - 18 hr [0.20] |
| 3456 | 7.8 | +3.1 | 25ug/ml Lovastatin - 18 hr [0.20] |
| 1944 | 6.5 | +2.9 | 30ug/ml Mevastatin in 1.5 Ethanol - 18 hr [0.20] |
| 1943 | 6.4 | +2.9 | 15ug/ml Simvastatin in 1.5 Ethanol - 18 hr [0.13] |
| 1554 | 5.8 | +2.8 | 5ug/ml Simvastatin in 1 Ethanol - 18 hr [0.12] |
| 1419 | 5.2 | +2.7 | 30ug/ml Atorvastatin in 1 DMSO - 18 hr [0.12] |
| 1553 | 5.1 | +2.6 | 10ug/ml Simvastatin in 1 Ethanol - 18 hr [0.11] |
| 3454 | 5.1 | +2.6 | 10ug/ml Lovastatin - 18 hr [0.15] |
| 1538 | 4.8 | +2.6 | 10ug/ml Lovastatin in 1 Ethanol - 18 hr [0.09] |
| 1421 | 4.4 | +2.5 | 10ug/ml Atorvastatin in 1 DMSO - 18 hr [0.12] |
| 1541 | 4.2 | +2.4 | 10ug/ml Mevastatin in 1 Ethanol - 18 hr [0.08] |
| 1456 | 4.1 | +2.4 | 2.0ug/ml Fluvastatin - 18 hr [0.06] |
| 1539 | 4.0 | +2.4 | 5ug/ml Lovastatin in 1 Ethanol - 18 hr [0.08] |
| 1540 | 4.0 | +2.4 | 20ug/ml Mevastatin in 1 Ethanol - 18 hr [0.10] |
| 2756 | 3.9 | +2.4 | [hmgs - ABY244.1 regulated (60)] - 18 hr [0.21] |
| 2757 | 3.8 | +2.3 | [hmgs - ABY244.1 regulated (80)] - 18 hr [0.20] |
| 2061 | 3.3 | +2.2 | 35ug/ml Atorvastatin in 1 Ethanol - 18 hr [0.08] |
| 1982 | 3.0 | +2.1 | 0.125ug/ml Clotrimazole in 1 Methanol - 18 hr [0.19] |
| 2060 | 2.9 | +2.1 | 25ug/ml Atorvastatin in 1 Ethanol - 18 hr [0.07] |
| 1542 | 2.8 | +2.0 | 5ug/ml Mevastatin in 1 Ethanol - 18 hr [0.08] |
| 1999 | 2.7 | +2.0 | 20ug/ml Atorvastatin in 1 Ethanol - 18 hr [0.08] |
| 3279 | 2.7 | +2.0 | 0.15ug/ml Clotrimazole in 1 DMSO - 18 hr [0.13] |
| 1935 | 2.6 | +2.0 | 0.04ug/ml Econazole in 1 Methanol - 18 hr [0.18] |
| 1478 | 2.5 | +1.9 | 2.0ug/ml Fluconazole in 0.9 Saline - 18 hr [0.27] |
| 1477 | 2.5 | +1.9 | 3.0ug/ml Fluconazole in 0.9 Saline - 18 hr [0.31] |
| 1983 | 2.5 | +1.9 | 0.15ug/ml Clotrimazole in 1 Methanol - 18 hr [0.15] |
| 3468 | 2.5 | +1.9 | 20ug/ml Lovastatin [ABY139] - 18 hr [0.58] |
| 2754 | 2.5 | +1.9 | [hmgs - ABY244.1 regulated (20)] - 18 hr [0.19] |

Figure 3.

YMR134w

| | |
|---|---|
| GenBank No. | 606432 |
| Chromosome | XIII |
| Protein | 236 amino acids |
| | 27,911 Daltons |
| Comments: | involved in iron metabolism; potential transmembrane domain |

Figure 5.

Treatments Causing Highest Expression of YMR134w

| Experiment | Level | log ratio | Treatment [baseline] |
|---|---|---|---|
| 1943 | 1.3 | +1.8 | 15ug/ml Simvastatin in 1.5 Ethanol - 18 hr [0.13] |
| 1944 | 1.2 | +1.7 | 30ug/ml Mevastatin in 1.5 Ethanol - 18 hr [0.20] |
| 1419 | 1.2 | +1.7 | 30ug/ml Atorvastatin in 1 DMSO - 18 hr [0.12] |
| 1537 | 1.2 | +1.7 | 20ug/ml Lovastatin in 1 Ethanol - 18 hr [0.10] |
| 1454 | 1.2 | +1.7 | 8.0ug/ml Fluvastatin - 18 hr [0.13] |
| 1477 | 1.0 | +1.5 | 3.0ug/ml Fluconazole in 0.9 Saline - 18 hr [0.31] |
| 1553 | 0.9 | +1.5 | 10ug/ml Simvastatin in 1 Ethanol - 18 hr [0.11] |
| 1455 | 0.9 | +1.5 | 4.0ug/ml Fluvastatin - 18 hr [0.09] |
| 3455 | 0.9 | +1.5 | 20ug/ml Lovastatin - 18 hr [0.20] |
| 3456 | 0.9 | +1.5 | 25ug/ml Lovastatin - 18 hr [0.20] |
| 1538 | 0.9 | +1.4 | 10ug/ml Lovastatin in 1 Ethanol - 18 hr [0.09] |
| 3454 | 0.9 | +1.4 | 10ug/ml Lovastatin - 18 hr [0.15] |
| 1478 | 0.8 | +1.4 | 2.0ug/ml Fluconazole in 0.9 Saline - 18 hr [0.27] |
| 1540 | 0.8 | +1.3 | 20ug/ml Mevastatin in 1 Ethanol - 18 hr [0.10] |
| 1420 | 0.8 | +1.3 | 20ug/ml Atorvastatin in 1 DMSO - 18 hr [0.14] |
| 1611 | 0.8 | +1.3 | 10ug/ml Fluconazole - 21 hr [0.04] |
| 1554 | 0.7 | +1.2 | 5ug/ml Simvastatin in 1 Ethanol - 18 hr [0.12] |
| 3279 | 0.7 | +1.2 | 0.15ug/ml Clotrimazole in 1 DMSO - 18 hr [0.13] |
| 3469 | 0.7 | +1.2 | 25ug/ml Lovastatin [ABY139] - 18 hr [0.57] |
| 1605 | 0.7 | +1.2 | 5ug/ml Fluconazole - 21 hr [0.04] |
| 1936 | 0.7 | +1.1 | 0.05ug/ml Econazole in 1 Methanol - 18 hr [0.14] |
| 3468 | 0.7 | +1.1 | 20ug/ml Lovastatin [ABY139] - 18 hr [0.58] |

Figure 7.

Blastp search of GenBank

```
                                                                      Score    E
Sequences producing significant alignments:                          (bits)  Value

sp|P40207|YM17_YEAST  HYPOTHETICAL 27.9 KD PROTEIN IN REC114-PSO...   483    e-136
sp|P17948|VGR1_HUMAN  VASCULAR ENDOTHELIAL GROWTH FACTOR RECEPTO...    34    1.3
gi|3132831  (AF063657) vascular endothelial growth factor recept...    34    1.3
gi|2088746  (AF003142) contains similarity to C2H2-type zinc fin...    33    2.2
gi|886766  (U27832) Smt4p [Saccharomyces cerevisiae]                   32    2.9
sp|P40537|SMT4_YEAST  SMT4 PROTEIN >gi|1077779|pir||S49947 SMT4 ...    32    2.9
sp|P48034|ADO_BOVIN  ALDEHYDE OXIDASE >gi|1149575|emb|CAA60701| ...    32    2.9
sp|Q06278|ADO_HUMAN  ALDEHYDE OXIDASE >gi|2117502|pir||A49634 al...    32    5.0
```

tblastn search of dbest

No hits found

Figure 8.

YER044c

| | |
|---|---|
| GenBank No. | 603277 |
| Chromosome | V |
| Protein | 148 amino acids<br>17,140 Daltons |
| Comments: | unknown function; potential transmembrane domain |

Figure 9.

Treatments Causing Highest Expression of YER044c

| Experiment | Level | log ratio | Treatment [baseline] |
|---|---|---|---|
| 1419 | 4.2 | +1.7 | 30ug/ml Atorvastatin in 1 DMSO - 18 hr [0.12] |
| 1420 | 3.6 | +1.5 | 20ug/ml Atorvastatin in 1 DMSO - 18 hr [0.14] |
| 1617 | 3.3 | +1.4 | 20ug/ml Fluconazole - 21 hr [0.04] |
| 1454 | 3.2 | +1.4 | 8.0ug/ml Fluvastatin - 18 hr [0.13] |
| 1537 | 3.1 | +1.4 | 20ug/ml Lovastatin in 1 Ethanol - 18 hr [0.10] |
| 1943 | 3.0 | +1.3 | 15ug/ml Simvastatin in 1.5 Ethanol - 18 hr [0.13] |
| 1623 | 3.0 | +1.3 | 100ug/ml Fluconazole - 21 hr [0.04] |
| 3456 | 3.0 | +1.3 | 25ug/ml Lovastatin - 18 hr [0.20] |
| 3455 | 3.0 | +1.3 | 20ug/ml Lovastatin - 18 hr [0.20] |
| 1611 | 2.9 | +1.3 | 10ug/ml Fluconazole - 21 hr [0.04] |
| 1553 | 2.7 | +1.2 | 10ug/ml Simvastatin in 1 Ethanol - 18 hr [0.11] |
| 3454 | 2.5 | +1.1 | 10ug/ml Lovastatin - 18 hr [0.15] |
| 1605 | 2.5 | +1.1 | 5ug/ml Fluconazole - 21 hr [0.04] |
| 3279 | 2.5 | +1.1 | 0.15ug/ml Clotrimazole in 1 DMSO - 18 hr [0.13] |
| 1455 | 2.4 | +1.1 | 4.0ug/ml Fluvastatin - 18 hr [0.09] |
| 1669 | 2.4 | +1.1 | 100ug/ml Fluconazole - 8 hr [0.05] |

Figure 11.

Blastp search of GenBank

| Sequences producing significant alignments: | (bits) | Value |
|---|---|---|
| sp\|P40030\|YEN4_YEAST HYPOTHETICAL 17.1 KD PROTEIN IN SAH1-MEI4 ... | 308 | 1e-83 |
| gnl\|PID\|e1331603 (AL031854) conserved hypothetical protein [Sch... | 110 | 5e-24 |
| gi\|3540193 (AC004122) Unknown protein [Arabidopsis thaliana] | 46 | 1e-04 |
| sp\|P54142\|SRB7_CAEEL SRB-7 PROTEIN >gi\|1584522\|prf\|\|2123261V ch... | 31 | 3.4 |

tblastn search of dbest

| Sequences producing significant alignments: | (bits) | Value |
|---|---|---|
| gb\|AA271118\|AA271118 va86e12.r1 Soares mouse NML Mus musculus c... | 81 | 9e-15 |
| gb\|AA048103\|AA048103 mj23f09.r1 Soares mouse embryo NbME13.5 14... | 81 | 9e-15 |
| gb\|AI172515\|AI172515 UI-R-C2p-nu-d-02-0-UI.s1 UI-R-C2p Rattus n... | 81 | 9e-15 |
| gb\|AA711847\|AA711847 vu59b09.r1 Soares mouse mammary gland NbMM... | 81 | 9e-15 |
| gb\|AA153659\|AA153659 mq60h05.r1 Soares 2NbMT Mus musculus cDNA ... | 80 | 2e-14 |
| gb\|W44146\|W44146 mc74h02.r1 Soares mouse embryo NbME13.5 14.5 M... | 80 | 2e-14 |
| gb\|AA269958\|AA269958 va55c03.r1 Soares mouse 3NME12 5 Mus muscu... | 80 | 2e-14 |
| gb\|W08023\|W08023 mb37b04.r1 Soares mouse p3NMF19.5 Mus musculus... | 78 | 6e-14 |
| gb\|AA014348\|AA014348 mi67g10.r1 Soares mouse embryo NbME13.5 14... | 73 | 1e-12 |
| gb\|AA272544\|AA272544 va75e02.r1 Soares mouse NML Mus musculus c... | 73 | 1e-12 |
| gb\|W13627\|W13627 ma93h01.r1 Soares mouse p3NMF19.5 Mus musculus... | 70 | 1e-11 |
| gb\|W28235\|W28235 43h8 Human retina cDNA randomly primed sublibr... | 70 | 2e-11 |
| gb\|W27040\|W27040 19e6 Human retina cDNA randomly primed sublibr... | 68 | 8e-11 |

Figure 12.

Mouse EST with similarity to YER044c

```
gb|AI386195|AI386195 mq60h05.y1 Soares 2NbMT Mus musculus cDNA clone IMAGE:583161 5'
           similar to SW:YEN4_YEAST P40030 HYPOTHETICAL 17.1 KD
           PROTEIN YER044c. ;, mRNA sequence
           [Mus musculus]
           Length = 455

 Score = 81.5 bits (198), Expect = 6e-15
 Identities = 40/114 (35%), Positives = 68/114 (59%)
 Frame = +3

Query: 23  LPKWLLFISIVSVFNSIQTYVSGLELTRKVYERKPTETTHLSARTFGTWTFISCVIRFYG 82
            L  WL+ +SI+++ N++Q++      L  K+Y  KP      L ARTFG WT +S VIR
Sbjct: 93  LRSWLVMVSIIAMGNTLQSFRDHTFLYEKLYTGKPNLVNGLQARTFGIWTLLSSVIRCLC 272

Query: 83  AMYLNEPHIFELVFMSYMVALFHFGSELLIFRTCKLGKGFMGPLVVSTTSLVWM 136
            A+ ++    ++ +   ++++AL HF SEL +F T      G + PL+V++ S++ M
Sbjct: 273 AIDIHNKTLYHITLWTFLLALXHFLSELFVFGTAAPTVGVLAPLMVASFSILGM 434
```

Human EST with similarity to YER044c

```
gb|W28235|W28235 43h8 Human retina cDNA randomly primed sublibrary Homo sapiens
           cDNA.
           Length = 839

 Score = 69.9 bits (168), Expect = 2e-11
 Identities = 33/94 (35%), Positives = 55/94 (58%)
 Frame = +1

Query: 23  LPKWLLFISIVSVFNSIQTYVSGLELTRKVYERKPTETTHLSARTFGTWTFISCVIRFYG 82
            L  WL+ +SI+++ N++Q++      L  K+Y  KP      L ARTFG WT +S VIR
Sbjct: 112 LRSWLVMVSIIAMGNTLQSFRDHTFLYEKLYTGKPNLVNGLQARTFGIWTLLSSVIRCLC 291

Query: 83  AMYLNEPHIFELVFMSYMVALFHFGSELLIFRTC 116
            A+ ++    ++ +   ++++AL HF SEL +   C
Sbjct: 292 AIDIHNKTLYHITLWTFLLALGHFLSELFVLWNC 393
```

Figure 13.

Rat EST with similarity to YER044c

```
gb|AI172515|AI172515 UI-R-C2p-nu-d-02-0-UI.s1 UI-R-C2p Rattus norvegicus cDNA clone
          UI-R-C2p-nu-d-02-0-UI 3', mRNA sequence [Rattus
          norvegicus]
          Length = 475

 Score = 80.8 bits (196), Expect = 1e-14
 Identities = 40/114 (35%), Positives = 68/114 (59%)
 Frame = -3

Query: 23  LPKWLLFISIVSVFNSIQTYVSGLELTRKVYERKPTETTHLSARTFGTWTFISCVIRFYG 82
            L  WL+ +SI+++ N++Q++     L  K+Y  KP     L ARTFG WT +S VIR
Sbjct: 404 LRSWLVMVSIIAMGNTLQSFRDHTFLYEKLYTGKPNLVNGLQARTFGIWTLLSSVIRCLC 225

Query: 83  AMYLNEPHIFELVFMSYMVALFHFGSELLIFRTCKLGKGFMGPLVVSTTSLVWM 136
            A+ ++   ++ +   ++++AL HF SEL +F T     G + PL+V++ S++ M
Sbjct: 224 AIDIHNKTLYHITLWTFLLALGHFLSELFVFGTAAPTVGVLAPLMVASFSILGM 63
```

Figure 14.

YLR100w

| | |
|---|---|
| GenBank No. | 1360483 |
| Chromosome | XII |
| Protein | 347 amino acids |
| | 39,725 Daltons |
| Comments: | unknown function; see S. Huang et al., Biochemistry, 26, pp. 8242-46 (1987) |

Figure 15.

Treatments Causing Highest Expression of YLR100w

| Experiment | Level | Treatment [baseline] |
|---|---|---|
| 6092 | 8.3 | 20ug/ml Lovastatin in 1 Ethanol [ABY12.1] - 24 hr [0.15] |
| 8717 | 6.7 | 10ug/ml Simvastatin in 1 DMSO [ABY12.1] - 24 hr [0.14] |
| 6093 | 6.3 | 10ug/ml Lovastatin in 1 Ethanol [ABY12.1] - 24 hr [0.16] |
| 8716 | 6.1 | 7.5ug/ml Simvastatin in 1 DMSO [ABY12.1] - 24 hr [0.13] |
| 8715 | 4.9 | 5ug/ml Simvastatin in 1 DMSO [ABY12.1] - 24 hr [0.12] |
| 6094 | 4.4 | 5ug/ml Lovastatin in 1 Ethanol [ABY12.1] - 24 hr [0.13] |
| 8705 | 2.7 | [erg11 - ABY210 regulated (100)] - 24 hr [0.17] |
| 6088 | 2.6 | 0.1ug/ml Sulconazole in 1 DMSO [ABY12.1] - 24 hr [0.12] |
| 8341 | 2.5 | 0.025ug/ml Miconazole in 1 DMSO [ABY12.1] - 24 hr [0.15] |
| 8460 | 2.4 | 0.1ug/ml Clotrimazole in 1 DMSO [ABY12.1] - 24 hr [0.12] |
| 8462 | 2.3 | 0.135ug/ml Clotrimazole in 1 DMSO [ABY12.1] - 24 hr [0.17] |
| 8461 | 2.3 | 0.12ug/ml Clotrimazole in 1 DMSO [ABY12.1] - 24 hr [0.14] |
| 8342 | 2.3 | 0.03ug/ml Miconazole in 1 DMSO [ABY12.1] - 24 hr [0.19] |
| 8703 | 2.1 | [erg11 - ABY210 regulated (80)] - 24 hr [0.14] |
| 8340 | 2.0 | 0.02ug/ml Miconazole in 1 DMSO [ABY12.1] - 24 hr [0.12] |
| 8463 | 2.0 | 0.15ug/ml Clotrimazole in 1 DMSO [ABY12.1] - 24 hr [0.25] |
| 8701 | 1.9 | [erg11 - ABY210 regulated (60)] - 24 hr [0.14] |

Figure 17.

Blastp search of GenBank

| Sequences producing significant alignments: | Score (bits) | E Value |
|---|---|---|
| pir\|\|S64936 probable membrane protein YLR100w - yeast (Saccharo... | 668 | 0.0 |
| emb\|CAA21246\| (AL031852) short-chain dehydrogenase [Schizosacch... | 183 | 1e-45 |
| dbj\|BAA13878\| (D89217) similar to Saccharomyces cerevisiae L800... | 182 | 3e-45 |
| emb\|CAA75742\| (Y15733) 17-beta-hydroxysteroid dehydrogenase typ... | 85 | 9e-16 |
| gi\|1397235 (U44803) ovarian-specific protein [Rattus norvegicus] | 84 | 1e-15 |
| emb\|CAB07971\| (Z93941) YuxA [Bacillus subtilis] >gi\|2635794\|emb... | 46 | 5e-04 |
| emb\|CAA19277\| (AL023705) hypothetical protein [Schizosaccharomy... | 43 | 0.004 |
| dbj\|BAA19567\| (AB002410) 17-beta-hydroxysteroid dehydrogenase [... | 39 | 0.046 |
| gi\|1086892 (U41277) similar to the insect-type alcohol dehydrog... | 38 | 0.079 |
| pir\|\|S56475 hypothetical protein f261a - Escherichia coli >gi\|5... | 38 | 0.10 |
| emb\|CAA63039\| (X91985) glycoprotein 100 [gallid herpesvirus 1] | 38 | 0.10 |
| gb\|AAD20218\| (AF100931) carbonyl reductase/20beta-hydroxysteroi... | 38 | 0.10 |

tblastn search of dbest

| Sequences producing significant alignments: | Score (bits) | E Value |
|---|---|---|
| gb\|AI226514\|AI226514 uj07d08.y1 Sugano mouse liver mlia Mus mus... | 63 | 5e-09 |
| gb\|AI528381\|AI528381 ui96g06.y1 Sugano mouse liver mlia Mus mus... | 52 | 1e-05 |
| gb\|R92053\|R92053 yp96c01.r1 Homo sapiens cDNA clone 195264 5'. | 44 | 0.003 |
| gb\|AI472243\|AI472243 tj86g08.x1 Soares_NSF_F8_9W_OT_PA_P_S1 Hom... | 37 | 0.36 |
| gb\|AI321571\|AI321571 d9f02nm.f1 Neurospora crassa morning cDNA ... | 34 | 3.1 |
| gb\|AI211149\|AI211149 o0a06a1.r1 Aspergillus nidulans 24hr asexu... | 32 | 9.1 |
| gb\|AA219246\|AA219246 zq16h06.r1 Stratagene fetal retina 937202 ... | 32 | 9.1 |

Figure 18.

Alignment of YLR100w to Mammalian ESTs

```
 gb|AI226514|AI226514 uj07d08.y1 Sugano mouse liver mlia Mus musculus cDNA clone
           IMAGE:1891215 5' similar to TR:Q62904 Q62904
           OVARIAN-SPECIFIC PROTEIN. ;, mRNA sequence [Mus
           musculus]           Length = 1039

 Score = 63.2 bits (151), Expect = 5e-09
 Identities = 53/223 (23%), Positives = 108/223 (47%), Gaps = 11/223 (4%)

Query: 3   RKVAIVTGTNSNLGLNIVFRLIETEDTNVRLTIVVTSRTLPRVQEVINQIKDFYNKSGRV 62
            RKV ++TG +S +GL +  RL+  +D    L + +  R L + + V + +   +  +
Sbjct: 52  RKVVLITGASSGIGLALCGRLLAEDDD---LHLCLACRNLSKARAVRDTLLASHPSA--- 213

Query: 63  EDLEIDFDYLLVDFTNMVSVLNAYYDINKKYRAINYLFVNAA---------QGIFDGIDW 113
                +   + +D +++ SV+    ++ +K++ ++YL++NA          +  F GI +
Sbjct: 214 -----EVSIVQMDVSSLQSVVRGAEEVKQKFQRLDYLYLNAGILPNPQFNLKAFFCGI-F 375

Query: 114 IGAVKEVFTNPLEAVTNPTYKIQLVGVKSKDDMGLIFQANVFGPYYFISKILPQLTRGK- 172
               V  +FT   E +       +    G++        +F+ N+FG +  I ++ P L
Sbjct: 376 SRNVIHMFTTA-EGILTQNDSVTADGLQE------VFETNLFGHFILIRELEPLLCHADN 534

Query: 173 -AYIVWISSIMSDPKYLSLNDIELLKTNASYEGSKRLVDLLHLATYKDLKKLGI 225
             + ++W SS  +      SL DI+  K    Y    +   DLL++A  ++ K  G+
Sbjct: 535 PSQLIWTSSRNAKKANFSLEDIQHFKGPEPYSSFQYATDLLNVAXNREFKPEGL 696


 gb|AI528381|AI528381 ui96g06.y1 Sugano mouse liver mlia Mus musculus cDNA clone
           IMAGE:1890298 5' similar to TR:Q62904 Q62904
           OVARIAN-SPECIFIC PROTEIN. ;, mRNA sequence [Mus
           musculus]           Length = 837

 Score = 52.3 bits (123), Expect = 1e-05
 Identities = 59/260 (22%), Positives = 119/260 (45%), Gaps = 11/260 (4%)

Query: 3   RKVAIVTGTNSNLGLNIVFRLIETEDTNVRLTIVVTSRTLPRVQEVINQIKDFYNKSGRV 62
            RKV ++TG +S +GL +  RL+  +D    L + +  R L + + V + +   +  +
Sbjct: 52  RKVVLITGASSGIGLALCGRLLAEDDD---LHLCLACRNLSKARAVRDTLLASHPSA--- 213

Query: 63  EDLEIDFDYLLVDFTNMVSVLNAYYDINKKYRAINYLFVNAA---------QGIFDGIDW 113
                +   + +D +++ SV+    ++ +K++ ++YL++NA          +  F GI +
Sbjct: 214 -----EVSIVQMDVSSLQSVVRGAEEVKQKFQRLDYLYLNAGILPNPQFNLKAFFCGI-F 375

Query: 114 IGAVKEVFTNPLEAVTNPTYKIQLVGVKSKDDMGLIFQANVFGPYYFISKILPQLTRGK- 172
               V  +FT   E +       +      + D + +F+ N+   + I ++ P L
Sbjct: 376 SRNVIHMFTTA-EGILTQNDSV------TADRLQEVFETNLSCHFILIRELEPLLLHADN 534

Query: 173 -AYIVWISSIMSDPKYLSLNDIELLKTNASYEGSKRLVDLLHLATYKDLKKLGINQYVVQ 231
             + ++W SS  +      SL D +          Y  +   DLL++A  + + G+    +
Sbjct: 535 PSQLIWTSSRNAXKANFSLEDXQHSIGPGPYSSFQYATDLLNVALNXNXNQKGLYSSRMC 714

Query: 232 PGIFTSHSFSEYLNFFTYFGMLCLFYLARLL 262
            PG+  ++         TY G+L  FYL  LL
Sbjct: 715 PGVVMTN--------MTY-GILPPFYLDVLL 780


 gb|R92053|R92053 yp96c01.r1 Homo sapiens cDNA clone 195264 5'.Length = 454

 Score = 44.1 bits (102), Expect = 0.003
 Identities = 26/84 (30%), Positives = 40/84 (46%), Gaps = 2/84 (2%)
 Frame = +1

Query: 150 FQANVFGPYYFISKILPQLTRGK--AYIVWISSIMSDPKYLSLNDIELLKTNASYEGSKR 207
            F+ NVFG +  I ++ P L       + ++W SS  +     SL D +  K    Y  SK
Sbjct: 1   FETNVFGHFILIRELEPLLCHSDNPSQLIWTSSRSARKSNFSLEDFQHSKGKEPYSSSKY 180

Query: 208 LVDLLHLATYKDLKKLGINQYVVQPG 233
             DLL +A  ++   + G+   V  PG
Sbjct: 181 ATDLLSVALNRNFNQQGLYSNVACPG 258
```

Figure 19.

YER034w

| | |
|---|---|
| GenBank No. | 603267 |
| Chromosome | V |
| Protein | 185 amino acids<br>21,186 Daltons |
| Comments: | unknown function; see S. Huang et al., Biochemistry, 26, pp. 8242-46 (1987) |

Figure 20.

Mutation of the *YER034w* Gene Leads to Increased Pseudohyphal Growth

YKL077w

| | |
|---|---|
| GenBank No. | 486110 |
| Chromosome | XI |
| Protein | 392 amino acids |
| | 46,042 Daltons |
| Comments: | unknown function; potential transmembrane domain |

Figure 23.

Expression Correlation of YKL077w

| Rank | Gene | Correlation | Exp | Function |
|---|---|---|---|---|
| 1 | YKL077w | +1.00 | 0.5 - 9.1 | |
| 2 | SGV1 | +0.92 | 0.7 - 14.4 | CDC28/cdc2 related protein kinase |
| 3 | RHO1 | +0.88 | 1.3 - 20.9 | GTP-binding protein |
| 4 | YKL075c | +0.86 | 0.2 - 2.5 | |
| 5 | SRA3 | +0.84 | 0.3 - 4.6 | catalytic subunit of PKA |
| 6 | RPB4 | +0.84 | 0.3 - 7.8 | subunit of RNA polymerase II |
| 7 | PKC1 | +0.84 | 0.6 - 11.7 | putative protein kinase |

Figure 25.

Blastp search of GenBank

```
                                                                        Score      E
Sequences producing significant alignments:                             (bits)   Value

sp|P36081|YKH7_YEAST   HYPOTHETICAL 46.0 KD PROTEIN IN SMY1-MUD2 ...     785    0.0
gi|1172087   (U19568) squamous cell carcinoma antigen [Homo sapie...      35    0.75
sp|P54634|POLN_LORDV   NON-STRUCTURAL POLYPROTEIN [CONTAINS: RNA-...      35    0.75
sp|P29508|SCC1_HUMAN   SQUAMOUS CELL CARCINOMA ANTIGEN 1 (SCCA-1)...      35    0.75
pir||I38201  squamous cell carcinoma antigen 1 - human                   35    0.75
gi|3063469   (AC003981) F22O13.31 [Arabidopsis thaliana]                 35    0.98
pir||S23760  polyphenolic adhesive protein - blue mussel (fragme...      34    2.2
sp|P37222|MAOC_LYCES   MALATE OXIDOREDUCTASE, .CHLOROPLAST (MALIC ...     32    5.0
```

tblastn search of dbest

```
                                                                        Score      E
Sequences producing significant alignments:                             (bits)   Value

gb|T38483|T38483   EST103979 Saccharomyces cerevisiae cDNA 3' end.        99    6e-20
gb|T36426|T36426   EST101359 Saccharomyces cerevisiae cDNA 3' end.        69    1e-10
gb|AA724136|AA724136  ai07b06.s1 Soares parathyroid tumor NbHPA ...       32    9.2
```

Figure 26.

YGR046w

| | |
|---|---|
| GenBank No. | 1323049 |
| Chromosome | VII |
| Protein | 385 amino acids |
| | 44,219 Daltons |
| Comments: | essential gene in yeast |

Figure 27.

Expression Correlation to YGR046w

| Gene | Correlation | Levels | Function |
|---|---|---|---|
| YGR046w | +1.00 | 0.9 - 10.1 | similar to phage 1C ANTP-139 protein PIR:S46430 |
| IRA2 | +0.90 | 0.3 - 5.4 | GTPase activating protein, neurofibromin homolog |
| RLR1 | +0.89 | 0.8 - 6.1 | Regulatory protein, post-transcription initiation |
| NUT1 | +0.85 | 0.4 - 3.2 | Negative regulator of HO endonuclease promoter |
| SRO7 | +0.84 | 0.3 - 4.9 | Drosphila tumor suppressor homolog, rho3 suppressor |
| DST1 | +0.84 | 0.5 - 4.5 | RNA polymerase II elongation factor |
| MTR3 | +0.84 | 1.4 - 11.8 | mRNA transport |
| TPD3 | +0.82 | 2.6 - 22.0 | protein phosphatase (PP2A regulatory subunit) |
| SYF3 | +0.80 | 0.1 - 2.0 | similar to Drosophila probable cell cycle control |
| MEX67 | +0.78 | 1.2 - 14.1 | INvolved in nuclear mRNA export, binds both poly(A) |
| YNK1 | +0.78 | 1.1 - 24.2 | Nucleoside diphosphate kinase |
| MPD2 | +0.78 | 0.3 - 6.0 | protein disulfide isomerase related protein |
| BEM2 | +0.77 | 0.7 - 10.7 | Rho-type GTPase activating protein (GAP |

Figure 29.

Treatments Causing the Most Significant Changes in Expression of YGR046w

| Expenment | Levels | log ratio | Treatment [baselines] |
|---|---|---|---|
| 11757 | 10 1/5 0 | 0 9 | 20ug/ml 2,4-Dinitrophenol in 1% DMSO [ABY 12 6144C yx-101] - 24 hr [0 19/0 05] |
| 7571 | 7 3/3 9 | 0 8 | 2000ug/ml p-Aminosalicylic Acid in 2% DMSO [ABY12 1] - 24 hr [0.21/0 08] |
| 10815 | 7 7/4 3 | 0 8 | 1500ug/ml Acetylsalicylic Acid in 1% DMSO [ABY12] - 24 hr [0 20/0 05] |
| 10482 | 8 2/4 6 | 0 7 | 600ug/ml Sodium Nitnte in 1% DMSO [ABY12.1] - 24 hr [0 23/0 07] |
| 10819 | 7 2/4 2 | 0 7 | 900ug/ml Acetylsalicylic Acid 10 ug/ml Methotrexate in 1% DMSO [ABY12] - 24 hr [0 14/0 05] |
| 7877 | 8 2/4 8 | 0 7 | 1200ug/ml p-Aminosalicylic Acid in 1% DMSO [ABY12 1] - 24 hr [0.22/0.09] |
| 10814 | 7 3/4 3 | 0 7 | 1200ug/ml Acetylsalicylic Acid in 1% DMSO [ABY12] - 24 hr [0 15/0 05] |
| 10822 | 7 0/4 2 | 0 7 | 300ug/ml Acetylsalicylic Acid 20 ug/ml Methotrexate in 1% DMSO [ABY12] - 24 hr [0 09/0 05] |
| 9107 | 6 3/3 8 | 0 7 | 550ug/ml Thiourea in 1% DMSO [ABY12.1] - 24 hr [0 12/0 05] |
| 7573 | 6 5/3 9 | 0 7 | 2130ug/ml p-Aminosalicylic Acid in 2% DMSO [ABY12.1] - 24 hr [0 21/0 08] |
| 10481 | 7 6/4 6 | 0 7 | 500ug/ml Sodium Nitnte in 1% DMSO [ABY12 1] - 24 hr [0 18/0 07] |
| 8362 | 5 6/3 4 | 0 7 | 6ug/ml 8-Hydroxyquinoline in 1% DMSO [ABY12.1] - 24 hr [0 07/0 06] |
| 9613 | 6 2/3 8 | 0 7 | 0 1ug/ml Azoxystrobin in 1% DMSO [ABY12.1] - 24 hr [0 15/0 06] |
| 10983 | 2.2/5 2 | -0 7 | 50ug/ml Maleimide in 1% DMSO [ABY12] - 24 hr [0.14/0 07] |
| 8737 | 2 0/5 0 | -0 7 | 2ug/ml 5-Fluorocytosine in 1% DMSO [ABY12.1] - 24 hr [0 12/0 06] |
| 8263 | 1 8/4 4 | -0 7 | 4 5ug/ml Dimethyl Sulfoxide in 1% DMSO [ABY12.1] - 24 hr [0 18/0.06] |
| 11679 | 1 6/4 0 | -0.7 | 600ug/ml Tricyclazole in 2% DMSO [ABY 12 6144C yx-101] - 24 hr [0 33/0 05] |
| 8435 | 1 8/4 6 | -0 8 | 20ug/ml Benomyl in 1% DMSO [ABY12.1] - 24 hr [0 27/0 06] |
| 10802 | 1 6/4 2 | -0 8 | 20ug/ml Cumene Hydroperoxide in 1% DMSO [ABY12] - 24 hr [0 11/0 06] |
| 9633 | 1 4/3 7 | -0 8 | 80ug/ml Pyrimethanil in 1% DMSO [ABY12.1] - 24 hr [0 27/0 06] |
| 9340 | 1 3/4 0 | -0 9 | 0 03ug/ml Cycloheximide in 1% DMSO [ABY12 1] - 24 hr [0 25/0 06] |
| 8354 | 1 3/4 1 | -1 | 100ug/ml Quinacrine in 1% DMSO [ABY12 1] - 24 hr [0.10/0 06] |
| 11774 | 1 5/4 7 | -1 | 5ug/ml Sodium azide in 1% DMSO [ABY 12 6144C yx-101] - 24 hr [0 13/0 06] |
| 9588 | 1 1/3 5 | -1 | 600ug/ml Hydrogen Peroxide in 1% DMSO [ABY12 1] - 24 hr [0 14/0.08] |
| 10574 | 1 7/5 3 | -1 | 300ug/ml Pyroquilon in 1% DMSO [ABY12] - 24 hr [0.34/0 10] |
| 12366 | 1 4/4 7 | -1 | 0 2ug/ml Thimerosal in 1% DMSO [ABY 12 6144C yx-101] - 24 hr [0 10/0 07] |
| 8429 | 1 1/3 8 | -1 1 | 250ug/ml Benfluorex Hydrochlonde in 1% DMSO [ABY12 1] - 24 hr [0 15/0 06] |
| 11775 | 1 3/4 7 | -1 1 | 6ug/ml Sodium azide in 1% DMSO [ABY 12 6144C yx-101] - 24 hr [0 21/0 06] |
| 12327 | 1 4/5 1 | -1 1 | 1000ug/ml Benzimidazole in 1% DMSO [ABY 12 6144C yx-101] - 24 hr [0 16/0 07] |
| 11595 | 0 9/4 7 | -1 5 | 10ug/ml Sodium azide in 1% DMSO [ABY 12 6144C yx-101] - 24 hr [0.27/0 05] |

09 25 44 PST - 26 Mar 1999

Figure 30.

YJR041c

| | |
|---|---|
| GenBank No. | 1015693 |
| Chromosome | X |
| Protein | 1173 amino acids<br>135,096 Daltons |
| Comments: | essential gene in yeast; contains a leucine zipper; potential transmembrane domain |

Figure 31.

Correlation to YJR041c

| Gene | Correlation | Exp | Function |
|---|---|---|---|
| YJR041c | +1.00 | 0.2 - 1.7 | similar to Podospora anserina NADH dehydrogenase |
| MED7 | +0.83 | 0.3 - 0.9 | Stoichiometric member of mediator complex |
| SNP2 | +0.82 | 0.5 - 2.0 | snRNP G protein (the homologue of the human Sm-G) |
| RPA43 | +0.82 | 0.5 - 2.4 | DNA-dependent RNA polymerase I subunit A43 |
| SLS1 | +0.81 | 0.3 - 1.5 | 73 kDa mitochondrial integral membrane protein |
| SEC53 | +0.80 | 0.7 - 4.1 | phosphomannomutase |
| EMP47 | +0.76 | 0.3 - 1.5 | 47 kDa type I transmembrane protein |
| POP4 | +0.76 | 0.2 - 1.0 | RNase P and RNase MRP subunit |
| RPL1A | +0.75 | 1.4 - 5.8 | homolog of bacterial ribosomal proteins of L1 family |
| RPC53 | +0.74 | 0.2 - 0.9 | RNA polymerase III (C) subunit |
| SKI6 | +0.72 | 0.5 - 2.4 | ExtraCellular Mutant; ribosomal RNA processing |
| UPF3 | +0.72 | 0.1 - 0.4 | Stimulates decay of mRNAs with premature stop codons |
| TAF19 | +0.71 | 0.1 - 0.4 | TFIID subunit |
| RPL37B | +0.71 | 1.5 - 7.8 | 60S ribosomal protein YL35 |
| GCD10 | +0.71 | 0.5 - 2.3 | RNA-binding subunit, translation initiation factor 3 |

Figure 33.

Blastp search of GenBank

| Sequences producing significant alignments: | Score (bits) | E Value |
|---|---|---|
| sp\|P47108\|YJ11_YEAST HYPOTHETICAL 135.1 KD PROTEIN IN GEF1-NUP8... | 2238 | 0.0 |
| emb\|CAA89570\| (Z49542) ORF YJR041c [Saccharomyces cerevisiae] | 2127 | 0.0 |
| sp\|Q09804\|YAB2_SCHPO HYPOTHETICAL 150.5 KD PROTEIN C2G11.02 IN ... | 53 | 8e-06 |
| emb\|CAA91167\| (Z54354) hypothetical protein [Schizosaccharomyce... | 53 | 8e-06 |
| gi\|3929312 (AF100426) fimbriae-associated protein Fap1 [Strepto... | 43 | 0.012 |
| gi\|2688777 (AE001181) exonuclease SbcC (sbcC) [Borrelia burgdor... | 38 | 0.51 |
| gi\|2462828 (AF000657) hypothetical protein [Arabidopsis thaliana] | 35 | 2.6 |
| pir\|\|S43557 coiled coil protein B0284.1 - Caenorhabditis elegan... | 35 | 2.6 |
| gi\|2315501 (AF016451) No definition line found [Caenorhabditis ... | 35 | 2.6 |
| sp\|P13496\|DYNA_DROME 150 KD DYNEIN-ASSOCIATED POLYPEPTIDE (DP-1... | 34 | 5.8 |
| sp\|Q58042\|Y625_METJA HYPOTHETICAL ATP-BINDING PROTEIN MJ0625 >g... | 34 | 5.8 |
| gb\|AAD18581\| (AE001626) ClpC Protease [Chlamydia pneumoniae] | 34 | 5.8 |
| gi\|3098583 (AF049495) gag polyprotein [Human immunodeficiency v... | 34 | 7.5 |
| sp\|P44581\|NHAA_HAEIN NA(+)/H(+) ANTIPORTER 1 >gi\|1075053\|pir\|\|C... | 33 | 9.9 |
| gi\|2062752 U92845) kinesin motor protein [Ustilago maydis] | 33 | 9.9 |

tblastn search of dbest

| Sequences producing significant alignments: | Score (bits) | E Value |
|---|---|---|
| gb\|AI201151\|AI201151 qf64h07.x1 Soares_testis_NHT Homo sapiens ... | 36 | 3.7 |
| gb\|AA747649\|AA747649 nx77g11.s1 NCI_CGAP_Ew1 Homo sapiens cDNA ... | 34 | 8.4 |
| gb\|AI248270\|AI248270 qh75g09.x1 Soares_fetal_liver_spleen_1NFLS... | 34 | 8.4 |

Figure 34.

*HES1*

| | |
|---|---|
| GenBank No. | 1420543 |
| Chromosome | XV |
| Protein | 433 amino acids<br>49,502 Daltons |
| Comments: | implicated in ergosterol pathways; related to human oxysterol binding protein |

Figure 35.

Expression Correlation to HES1

| Gene | Correlation | Exp | Function |
|---|---|---|---|
| HES1 | +1.00 | 0.1 - 7.2 | homology to human oxysterol binding protein |
| ERG2 | +0.90 | 0.1 - 5.3 | C-8 sterol isomerase |
| PAU5 | +0.89 | 0.1 - 4.7 | member of seripauperin protein/gene family |
| ERG7 | +0.83 | 0.2 - 3.0 | lanosterol synthase |
| CYB5 | +0.83 | 0.4 - 17.8 | cytochrome b5 |
| YJL105w | +0.81 | 0.1 - 4.7 | similar to Ykr029p |
| YER044c | +0.79 | 0.3 - 3.7 | |
| ERG11 | +0.79 | 0.3 - 13.0 | cytochrome P450 lanosterol 14a-demethylase |
| HEM14 | +0.76 | 0.1 - 1.3 | protoporphyrinogen oxidase |
| ERG9 | +0.76 | 0.8 - 8.8 | squalene synthetase |
| TIR1 | +0.74 | 0.2 - 6.8 | cold-shock induced - serine-alanine-rich |
| ERG8 | +0.70 | 0.3 - 6.0 | phosphomevalonate kinase |
| ERG6 | +0.69 | 0.5 - 9.6 | SAM: delta 24-methyltransferase |

Figure 36.

Treatments that Induce the *HES1* Reporter

| Experiment | Levels | log ratio | Treatment [baselines] |
|---|---|---|---|
| 9923 | 7.2/0.1 | 4.1 | 20ug/ml Simvastatin in 1% DMSO [ABY12.1] - 24 hr [0.19/0.07] |
| 9930 | 4.6/0.1 | 3.6 | 40ug/ml Lovastatin in 1% DMSO [ABY12.1] - 24 hr [0.18/0.07] |
| 9708 | 4.5/0.1 | 3.6 | 15ug/ml Atorvastatin in 1% DMSO [ABY12.1] - 24 hr [0.17/0.05] |
| 9709 | 4.4/0.1 | 3.6 | 20ug/ml Atorvastatin in 1% DMSO [ABY12.1] - 24 hr [0.16/0.05] |
| 9924 | 4.2/0.1 | 3.6 | 40ug/ml Simvastatin in 1% DMSO [ABY12.1] - 24 hr [0.27/0.07] |
| 6092 | 4.4/0.1 | 3.5 | 20ug/ml Lovastatin in 1% Ethanol [ABY12.1] - 24 hr [0.16/0.08] |
| 9909 | 3.8/0.1 | 3.5 | 10ug/ml Fluvastatin in 1% DMSO [ABY12.1] - 24 hr [0.18/0.07] |
| 9707 | 3.7/0.1 | 3.5 | 10ug/ml Atorvastatin in 1% DMSO [ABY12.1] - 24 hr [0.15/0.05] |
| 8465 | 3.0/0.1 | 3.2 | 0.03ug/ml Econazole in 1% DMSO [ABY12.1] - 24 hr [0.26/0.06] |
| 9922 | 2.8/0.1 | 3.2 | 10ug/ml Simvastatin in 1% DMSO [ABY12.1] - 24 hr [0.14/0.07] |
| 8463 | 2.7/0.1 | 3.1 | 0.15ug/ml Clotrimazole in 1% DMSO [ABY12.1] - 24 hr [0.25/0.06] |
| 9797 | 2.6/0.1 | 3.1 | 6ug/ml Fluvastatin in 1% DMSO [ABY12.1] - 24 hr [0.12/0.05] |
| 6093 | 2.7/0.1 | 3 | 10ug/ml Lovastatin in 1% Ethanol [ABY12.1] - 24 hr [0.18/0.08] |
| 8717 | 2.4/0.1 | 3 | 10ug/ml Simvastatin in 1% DMSO [ABY12.1] - 24 hr [0.14/0.06] |
| 9706 | 2.2/0.1 | 2.9 | 5ug/ml Atorvastatin in 1% DMSO [ABY12.1] - 24 hr [0.11/0.05] |
| 9908 | 2.1/0.1 | 2.9 | 6ug/ml Fluvastatin in 1% DMSO [ABY12.1] - 24 hr [0.14/0.07] |
| 9929 | 2.1/0.1 | 2.8 | 20ug/ml Lovastatin in 1% DMSO [ABY12.1] - 24 hr [0.16/0.07] |
| 8716 | 2.1/0.1 | 2.8 | 7.5ug/ml Simvastatin in 1% DMSO [ABY12.1] - 24 hr [0.13/0.06] |
| 8461 | 1.8/0.1 | 2.7 | 0.12ug/ml Clotrimazole in 1% DMSO [ABY12.1] - 24 hr [0.14/0.06] |
| 8342 | 1.8/0.1 | 2.7 | 0.03ug/ml Miconazole in 1% DMSO [ABY12.1] - 24 hr [0.19/0.06] |
| 9796 | 1.7/0.1 | 2.7 | 4ug/ml Fluvastatin in 1% DMSO [ABY12.1] - 24 hr [0.10/0.05] |
| 8462 | 1.7/0.1 | 2.7 | 0.135ug/ml Clotrimazole in 1% DMSO [ABY12.1] - 24 hr [0.17/0.06] |
| 6088 | 1.4/0.1 | 2.6 | 0.1ug/ml Sulconazole in 1% DMSO [ABY12.1] - 24 hr [0.12/0.07] |
| 8341 | 1.5/0.1 | 2.5 | 0.025ug/ml Miconazole in 1% DMSO [ABY12.1] - 24 hr [0.15/0.06] |
| 8460 | 1.3/0.1 | 2.4 | 0.1ug/ml Clotrimazole in 1% DMSO [ABY12.1] - 24 hr [0.12/0.06] |
| 8715 | 1.3/0.1 | 2.3 | 5ug/ml Simvastatin in 1% DMSO [ABY12.1] - 24 hr [0.12/0.06] |
| 9921 | 1.1/0.1 | 2.3 | 5ug/ml Simvastatin in 1% DMSO [ABY12.1] - 24 hr [0.18/0.07] |

Figure 37.

FIGURE 39. *YJL105w* DNA Sequence

Sequence contains 1200bp of 5' promoter sequence.
Symbols: 1 to: 2883 from: chr10.gcg ck: 4711, 223552 to: 226434
Chromosome X Sequence
EMBO J. 15:2031-2049 [8641269] (1996) Complete nucleotide sequence of Saccharomyces cerevisiae chromosome X.
Galibert, F., Alexandraki, D., Baur, A., Boles, E., Chalwatzis, N., Chuat, J. C., Coster, F., Cziepluch, C., De Haan, M., Domdey, H., . . .

gcgseq.tmp.4454 Length: 2883 March 26, 1999 16:51 Type: N Check: 6274 ..

```
   1 TGGAAAAGCT CACTGTGAGG TTCCTTGGAG CCAATAGTAA TACAGCACAA
  51 TCCAAGGAAA AATCTGGCCT ATATGCAAGG AAGGAGAGAT AGTCAAAAGC
 101 ATTCTTTCCC CTAGAAGTTG GTGCATATAT GGCATCGTTA AAACATATTA
 151 CCCCCAAAAT TTCTTCTCTA AACGATGTGC TTGGCCTTTG TTTTGGTTTT
 201 TGATGTCGGT CGTTTGAGGC CCCTTGCGGA AAATCGAGAT CGCCGAATGG
 251 CACGCGAGGG AAGGGAAATA AGGTTTAAAG GCACTGAAAC AATAGGCAAG
 301 AAGTAGGCGA GAGCCGACAT ACGAGACTAA TGTGTCCGCG TTTCTAAGGC
 351 CACTTTTCAA TGAAACGGAT ATTGATATGC TAGTAAAAGG ACGAGCTCAA
 401 GAGCGAAAAT ATAAGTAAAG AATTCGAGTG CACTTGTCTC CATGCAGCAA
 451 GATTTCATAT GAGTCTTTTT TATCTTTTTA CTTTTTACAT TACACGATAT
 501 GCACTTTATG AAAATTTAAC GAGGTTGGAA GCCGGATAAT CAACCAAAAT
 551 CAGGCACGAA GGCACACTCG TATATGCATG TTGTTGAAAC TCTGTTACGC
 601 TGAACTAACA ATCACACATG TAGAGGTCAC CGGGAAAAGT TGCGACCCCA
 651 TGGAAGGTCG ATCTCTTCGT TTGGCTTTGC TTGGCTGGCG GCATTGCGCT
 701 TCTTCGCTTA TACCCGTCTC TTGACGCTCG AGCTCGTTCA TTGAGATACC
 751 TTTATTCTTG CACATTTTCT GGCTTTTTTC GCTACTCGGG TACATGTAAT
 801 CATGCACACA GAAGGTGCTG TAGGGTGAAA GTTCCTTTGT GCTGTCGTTT
 851 GTTTTTAATG CCAAACTTTC TGGTGATCAA TAACCACCTC TTTTTCCTTC
 901 AGGAAACCTT ATTATTGTTC TTGGATAGTA CTAGGAAGTA TATAAGGAAC
 951 CTCGATTTTG GTATTGCACG GCTATACACA TCTAAGAAAC TTTGTATAAA
1001 AGGTGGCTAC CCTATTCATA GCTTGATATC AATAGGCCAT CTCATCACTT
1051 TTTATTGAAA AGGAAAGGAG GGAAATATAT CTGATTCAAA TTACTTGTTT
1101 GCTTCTCTTT AAGACAAAAG CATAGATAAT TTCAGCGTGG AACGCCGGAA
1151 TAAGATTGGT ACCCTCGTCA GAAAGTTACA AATACCGCTT CATCTTCAAA
1201 ATGACTTCAC CGGAATCACT ATCTTCTCGT CATATCAGGC AAGGAAGGAC
1251 ATACACAACC ACAGACAAGG TCATATCGCG GTCGTCGTCG TACTCATCTA
1301 ATAGTTCAAT GTCTAAAGAT TACGGCGATC ACACACCCTT GTCCGTCAGC
1351 AGTGCAGCTT CAGAGACATT ACCCTCACCT CAGTATATGC CGATAAGGAC
1401 ATTCAATACA ATGCCTACAG CTGGCCCAAC GCCTTTACAT TTATTTCAAA
1451 ATGACAGGGG CATTTTCAAC CATCATTCTT CATCAGGCTC ATCAAAAACG
1501 GCATCAACAA ATAAAAGAGG AATAGCAGCA GCAGTAGCAT TGGCAACTGC
1551 TGCCACCATA CCATTTCCAC TGAAAAAACA GAATCAAGAT GATAATTCCA
1601 AGGTCTCGGT AACACACAAT GAATCATCGA AAGAAAATAA AATTACACCC
1651 TCCATGAGAG CAGAAGATAA CAAACCTAAA AATGGTTGCA TCTGCGGTTC
1701 AAGTGACTCC AAGGATGAGT TGTTTATACA GTGTAACAAA TGTAAAACGT
1751 GGCAGCACAA GTTATGTTAT GCTTTCAAAA AATCAGATCC AATAAAAAGA
1801 GATTTTGTTT GCAAAAGATG TGACAGTGAT ACGAAAGTGC AGGTTAATCA
1851 AGTAAAACCA ATGATATTCC CTAGAAAAAT GGGAGATGAG CGATTATTTC
1901 AATTTTCATC CATAGTGACA ACTTCAGCAT CGAACACAAA TCAGCATCAA
1951 CAGTCTGTGA ATAACATAGA GGAACAGCCC AAGAAACGTC AACTTCATTA
2001 TACCGCCCCA ACAACTGAAA ATAGCAATAG TATACGGAAA AAATTGAGGC
2051 AAGAAAAACT GGTAGTATCA AGCCACTTTC TGAAGCCACT ACTGAATGAG
2101 GTAAGTTCTT CCAATGACAC GGAATTCAAA GCAATAACAA TATCAGAGTA
```

```
2151  TAAGGACAAA TATGTTAAGA TGTTTATTGA TAACCATTAT GATGACGATT
2201  GGGTTGTTTG TTCTAACTGG GAAAGCTCAA GGTCAGCTGA CATCGAGGTA
2251  AGAAAATCAT CAAATGAAAG AGATTTTGGA GTCTTCGCTG CAGATTCTTG
2301  TGTTAAAGGT GAGCTAATTC AAGAATATTT GGGCAAAATT GATTTTCAAA
2351  AAAATTATCA GACAGATCCA AATAATGACT ATCGTTTGAT GGGAACGACA
2401  AAACCTAAAG TACTTTTTCA TCCACATTGG CCTTTATATA TAGACTCTCG
2451  AGAAACAGGC GGATTAACAA GATACATAAG ACGGAGTTGT GAGCCCAATG
2501  TGGAACTAGT AACGGTAAGA CCGCTTGACG AAAAACCAAG AGGAGATAAT
2551  GATTGTAGAG TTAAATTTGT TTTAAGGGCT ATAAGAGATA TTCGTAAGGG
2601  AGAAGAGATA AGCGTAGAAT GGCAATGGGA TTTGAGAAAT CCTATTTGGG
2651  AGATAATAAA TGCATCTAAA GATTTGGATT CCCTACCGGA TCCCGACAAG
2701  TTCTGGTTGA TGGGGTCAAT AAAGACTATT TTAACAAATT GTGATTGTGC
2751  ATGTGGGTAC TTGGGCCATA ATTGTCCAAT AACTAAAATC AAAAACTTTT
2801  CTGAAGAATT CATGAGGAAT ACGAAGGAAT CCCTATCTAA TAAATCTTAC
2851  TTTAATACAA TAATGCACAA CTGTAAGCCA TAA
```

FIGURE 39, cont.

FIGURE 40. *YJL105W* Protein Sequence

EMBO J. 15:2031-2049 [8641269] (1996) Complete nucleotide sequence of Saccharomyces cerevisiae chromosome X.

Galibert, F., Alexandraki, D., Baur, A., Boles, E., Chalwatzis, N., Chuat, J. C., Coster, F., Cziepluch, C., De Haan, M., Domdey, H., Durand, P., Entian, K. D., Gatius, M., Goffeau, A., Grivell, L. A., et al.

YJL105W Length: 560 March 26, 1999 16:52 Type: P Check: 103 ..

```
  1 MTSPESLSSR HIRQGRTYTT TDKVISRSSS YSSNSSMSKD YGDHTPLSVS

 51 SAASETLPSP QYMPIRTFNT MPTAGPTPLH LFQNDRGIFN HHSSSGSSKT

101 ASTNKRGIAA AVALATAATI PFPLKKQNQD DNSKVSVTHN ESSKENKITP

151 SMRAEDNKPK NGCICGSSDS KDELFIQCNK CKTWQHKLCY AFKKSDPIKR

201 DFVCKRCDSD TKVQVNQVKP MIFPRKMGDE RLFQFSSIVT TSASNTNQHQ

251 QSVNNIEEQP KKRQLHYTAP TTENSNSIRK KLRQEKLVVS SHFLKPLLNE

301 VSSSNDTEFK AITISEYKDK YVKMFIDNHY DDDWVVCSNW ESSRSADIEV

351 RKSSNERDFG VFAADSCVKG ELIQEYLGKI DFQKNYQTDP NNDYRLMGTT

401 KPKVLFHPHW PLYIDSRETG GLTRYIRRSC EPNVELVTVR PLDEKPRGDN

451 DCRVKFVLRA IRDIRKGEEI SVEWQWDLRN PIWEIINASK DLDSLPDPDK

501 FWLMGSIKTI LTNCDCACGY LGHNCPITKI KNFSEEFMRN TKESLSNKSY

551 FNTIMHNCKP
```

FIGURE 41. *YMR134w* DNA Sequence

Sequence contains 1200bp of 5' promoter sequence.
Symbols: 1 to: 1914 from: chr13.gcg ck: 8335, 536637 to: 538550
Chromosome XIII Sequence
Nature 387:90-93 [97313268] (1997) The nucleotide sequence of
Saccharomyces cerevisiae chromosome XIII.
Bowman, S., Churcher, C., Badcock, K., Brown, D., Chillingworth, T.,
Connor, R., Dedman, K., Devlin, K., Gentles, S., Hamlin, N., Hunt, S., . . .

gcgseq.tmp.31828 Length: 1914 March 26, 1999 16:58 Type: N Check: 3324 ..

```
   1  TACAATAACA AGCCAGGTGC AAGGCAATAA TAACGGTACA AAGGTCTGTT
  51  TCACAGAAGG TCCAAAAGTT AGTAGCTACA CAAATCCGAA CACGCAATTT
 101  CAAACTCAAA ACATGATTAT GGATTTCAGT CAACGTTATC AGGAAGAATC
 151  TGAAAGAGAG TCAAATAATC GTTCAAATAT AACTTTACCA CACGACAGCA
 201  TTCAAATAGC TCAACAAATA TGGCCAAACA CGGATTTAAA TGTAGTACAA
 251  TCTTCACAAG ACCTCAACAC TCCAATGGCT ACGCAAACTG TTTTGGGTCG
 301  TCCTGAGTCG CTAATTGTAC AGCCATTGGA GGTTTCTCAA TCTCCACCAA
 351  ACACTACCAA CTGCCTTCCT AATGCAGAAA ACAAAAAGAA AAAAGTCGAC
 401  ACCACTTCTG ATTTTACTTC AAGAAAGGAG ATTGCTCTGT GTAAAACTGG
 451  TTTATTAGAA ACTATTCATA TACCAAAGGA AAGGGAAAGT CAGATGCAAA
 501  GCGTCACTGG TTTAGATGCA ACACCAACGA TTATATGGAG CCCCGGGAAA
 551  GACAACACGG CGAAGAAAAA TACCAGTAAT AAGAAAAATA TTGATGATAA
 601  ACTAACAAAC CCCCAAAAAT CTGGAAATAC ACATACCCCT GATAGAAATA
 651  AAGAAGTGCT ACCTAACGGC ACACTTAATG AAACGAGGAA AGAAGCATCG
 701  CCAAGCGAAG GATTAACGAT AAGAGTTAAA AACGTTAATC GGAATGCGTC
 751  AAGAAAAATA TCTAAGCGGC TAATCAAGGA AAAGTTGAAA GACGAAGAAT
 801  TCATGAAATG GGTATGTATG CATTTGCAAG AAACTGAGCT GTTTCCCCCT
 851  CTTATCCACT CATTTTCTCT GACTTGACAA AGAAATACTA ACTAACAACT
 901  TTTGCCACTA CAAATATGAA TGAAAAGGTT AATAAGGTTG AAACGGTTCT
 951  CAATAAAATG TTCGAAAAGT GAACCCTTTT TTTGCAATTC CTTTTTACAC
1001  TAGCCACGAA GTAAAATGGA AAAGTAAACC CGAGTTTCGG CAATATCGCT
1051  AAGCAAGAAG AGCAAGCTCG TTTAAGTAAG CCTTTATGAA AAAAAAACAA
1101  AATATAAAGC ATTATAAAAA TTGAATCACA TCGCAAATCT GCAATATACT
1151  TGGAAGTGTT TATAGCAAAG TGTGGTATAG AAAAAGAACC AAAGGCCGGT
1201  ATGTCGTTAA AGGATAGGTA TCTAAATCTC GAATTAAAAT TAATAAATAA
1251  ACTACAGGAG TTGCCATATG TTCATCAATT TATCCATGAT CGAATAAGTG
1301  GTAGGATAAC TCTCTTTTTG ATAGTGGTTG GTACGCTTGC ATTTTTTAAC
1351  GAACTGTATA TAACGATCGA AATGAGTCTT CTACAAAAGA ACACATCAGA
1401  AGAACTAGAG CGTGGAAGAA TCGATGAAAG TCTGAAGCTT CATCGGATGT
1451  TGGTGAGTGA TGAATATCAC GGTAAAGAAT ACAAAGACGA GAAAAGCGGT
1501  ATTGTTATTG AAGAGTTCGA AGATCGCGAT AAGTTTTTTG CAAAACCTGT
1551  GTTTGTATCA GAATTGGATG TCGAATGTAA TGTTATTGTA GATGGGAAAG
1601  AACTTCTGTC CACCCCATTA AAATTTCATG TTGAATTTTC TCCAGAGGAT
1651  TATGAAAATG AAAAAAGACC TGAGTTTGGT ACTACCTTGC GTGTATTGAG
1701  GCTGAGACTT TACCACTACT TTAAAGATTG CGAAATATAT CGCGATATAA
1751  TTAAGAATGA GGGCGGTGAA GGGGCAAGAA AGTTTACGAT TTCCAACGGT
1801  GTCAAAATTT ACAATCATAA AGATGAACTA CTGCCATTGA ATATCGATGA
1851  TGTTCAATTA TGTTTCCTGA AGATTGATAC GGGAAACACG ATAAAATGCG
1901  AATTCATACT ATGA
```

FIGURE 42. *YMR134w* Protein Sequence

Nature 387:90-93 [97313268] (1997) The nucleotide sequence of Saccharomyces cerevisiae chromosome XIII.

Bowman, S., Churcher, C., Badcock, K., Brown, D., Chillingworth, T., Connor, R., Dedman, K., Devlin, K., Gentles, S., Hamlin, N., Hunt, S., Jagels, K., Lye, G., Moule, S., Odell, C., Pearson, D., Rajandream, et al.

YMR134W Length: 237 March 26, 1999 16:59 Type: P Check: 2966 ..

```
  1  MSLKDRYLNL ELKLINKLQE LPYVHQFIHD RISGRITLFL IVVGTLAFFN

 51  ELYITIEMSL LQKNTSEELE RGRIDESLKL HRMLVSDEYH GKEYKDEKSG

101  IVIEEFEDRD KFFAKPVFVS ELDVECNVIV DGKELLSTPL KFHVEFSPED

151  YENEKRPEFG TTLRVLRLRL YHYFKDCEIY RDIIKNEGGE GARKFTISNG

201  VKIYNHKDEL LPLNIDDVQL CFLKIDTGNT IKCEFIL
```

FIGURE 43. *YER044c* DNA Sequence

Sequence contains 1200bp of 5' promoter sequence.

Symbols: 1 to: 1647 from: chr5.gcg /rev ck: 9036, 237569 to: 239215

Chromosome V Sequence
Nature 387:78-81 [97313264] (1997) The nucleotide sequence of
Saccharomyces cerevisiae chromosome V.
Dietrich, F. S., Mulligan, J., Hennessy, K., Yelton, M. A., Allen, E.,
Araujo, R., Aviles, E., Berno, A., Brennan, T., Carpenter, J., Chen, . . .

gcgseq.tmp.2512 Length: 1647 March 26, 1999 16:38 Type: N Check: 8794 ..

```
   1 AACACTCCAA ATCTTGTTAG TTTCTCATTA TTCGCATCGC ATAGATTCTG
  51 ATTCTTCTTT TAAGAGGACA CTGATAGACG TTCATGTTTT CAATTTCATC
 101 GCCAAGTTTC TGTTTAATAG AATTTTATTG AAGAAGAACC AAAACGATCC
 151 AAAATGGCTT CAAAACTTTT ACGACCAGGG AGATGGCAAA CATTTATGTG
 201 ATAAAGTTGA CTACAAGCGC TTGTGTTCGT TGCATTTTAC CCTTATTTAC
 251 TCTATTATTA ACATTCAACT CATCAAAATC AAGACAAACC AAACATTTGA
 301 ACCGCAGATA TTAAAATACG TATCTGTTCT GAAATTAATT GAACACATAC
 351 TTATCATCAT CGAAAGTCTG ATACATGTAC TTATTAGATT TGTATCGAAG
 401 CATAAACTAA TATGCATCAA CCGGAAAAAG GCGTACTGTC GAGTATACCT
 451 CGAAAGAGAA TTGAGTTTGA AGAAAACCTA CTTAAAGAAC TTTTACAGTG
 501 TAATAAGCGG TGTCCCAGAA AAAGAGTTAG GGGGTCTATT GAAAATACTC
 551 AAGATAGTTA TTCTATCATT GCTCGAGACA TTTGAAAGCA TTGAATGGCA
 601 GCACTTAAAA CCTTTCCTGG AAAAATTTCC GGCTCATGAA ATATCGCTTC
 651 AGAAGAAAAG GAAATATATA CAGGCGGCCT TATTAATTAC TGCCGAAAGA
 701 AATTTGATAG CGCGCTTTCG ATTGTCAAGA TGGTTCAATG AGACAGAAAA
 751 CATTTAATTT TTCTTTTGCA GTAGGAGGCG CATTATAAAA CACAAAAATA
 801 TCGAAAGCTC TTTCATTTCG GGGACAACAA CTTCAGTTGA AAATTACAGT
 851 GAACACAACA TCTTCCCCAA CAGACCTACA TTAAAACGCT TCTTCCGGAC
 901 TTGCCCATGA TTAACCTAAT CTTATACGAA CTGAATTAAA CTTTACGGTA
 951 TTACCGATAG GAAACTTCTA TTTTATGATT TTTTCGTTCG GGGACGGAAC
1001 GAACAGGAAA CAAAAAAAAA GGTACGATCC ATTGTATTCT CTACCCCCGT
1051 ATATAAAACT AAGCTGAACA AGCCTGTTGT TTTGCTTTAC TATTGCTACT
1101 ATTTTTGACG TAAACGCATT GACTAATTTC AGGTTTTTAT ATTCTTGACA
1151 CTAGCTAGAC CATAGTATCG AAGGATTCAA ATACACTAAA GTATCAGATA
1201 ATGTTCAGCC TACAAGACGT AATAACTACA ACCAAGACCA CCTTGGCAGC
1251 AATGCCAAAA GGTTACTTAC CAAAATGGTT ACTTTTCATT TCCATTGTAT
1301 CAGTCTTCAA TTCTATCCAG ACTTACGTTT CTGGTTTAGA ATTGACACGT
1351 AAAGTCTACG AAAGAAAACC CACTGAAACA ACCCATTTGA GTGCAAGAAC
1401 TTTCGGTACT TGGACCTTTA TTTCCTGTGT TATCAGATTC TATGGGGCTA
1451 TGTACTTGAA TGAACCACAC ATTTTCGAAT TGGTCTTCAT GTCTTATATG
1501 GTTGCCCTAT TCCACTTCGG CTCTGAATTA TTGATCTTTA GAACTTGTAA
1551 GTTGGGAAAG GGATTCATGG GTCCATTGGT TGTCTCAACC ACCTCTTTGG
1601 TTTGGATGTA CAAACAAAGA GAATACTACA CTGGTGTTGC TTGGTAA
```

FIGURE 44. *YER044c* Protein Sequence

Nature 387:78-81 [97313264] (1997) The nucleotide sequence of Saccharomyces cerevisiae chromosome V.

Dietrich, F. S., Mulligan, J., Hennessy, K., Yelton, M. A., Allen, E., Araujo, R., Aviles, E., Berno, A., Brennan, T., Carpenter, J., Chen, E., Cherry, J. M., Chung, E., Duncan, M., Guzman, E., Hartzell, G., et al.

YER044C Length: 148 March 26, 1999 16:40 Type: P Check: 3540 ..

```
  1  MFSLQDVITT TKTTLAAMPK GYLPKWLLFI SIVSVFNSIQ TYVSGLELTR

 51  KVYERKPTET THLSARTFGT WTFISCVIRF YGAMYLNEPH IFELVFMSYM

101  VALFHFGSEL LIFRTCKLGK GFMGPLVVST TSLVWMYKQR EYYTGVAW
```

**FIGURE 45. Mouse EST with Similarity to *YER044c***

```
LOCUS       AI386195      455 bp    mRNA            EST       27-JAN-1999
DEFINITION  mq60h05.y1 Soares 2NbMT Mus musculus cDNA clone IMAGE:583161 5'
            similar to SW:YEN4 YEAST P40030 HYPOTHETICAL 17.1 KD PROTEIN IN
            SAH1-MEI4 INTERGENIC REGION. ;, mRNA sequence.
ACCESSION   AI386195
NID         g4199658
KEYWORDS    EST.
SOURCE      house mouse.
  ORGANISM  Mus musculus
            Eukaryota; Metazoa; Chordata; Craniata; Vertebrata; Mammalia;
            Eutheria; Rodentia; Sciurognathi; Muridae; Murinae; Mus.
REFERENCE   1  (bases 1 to 455)
  AUTHORS   Marra,M., Hillier,L., Kucaba,T., Martin,J., Beck,C., Wylie,T.,
            Underwood,K., Steptoe,M., Theising,B., Allen,M., Bowers,Y.,
            Person,B., Swaller,T., Gibbons,M., Pape,D., Harvey,N., Schurk,R.,
            Ritter,E., Kohn,S., Shin,T., Jackson,Y., Cardenas,M., McCann,R.,
            Waterston,R. and Wilson,R.
  TITLE     The WashU-NCI Mouse EST Project 1999
  JOURNAL   Unpublished (1999)
COMMENT
            Contact: Marra M/WashU-NCI Mouse EST Project 1999
            Washington University School of Medicine
            4444 Forest Park Parkway, Box 8501, St. Louis, MO 63108, USA
            Tel: 314 286 1800
            Fax: 314 286 1810
            Email: mouseest@watson.wustl.edu
            This clone is available royalty-free through LLNL ; contact the
            IMAGE Consortium (info@image.llnl.gov) for further information.
            MGI:357809
            This read is a RESEQUENCE of a previously sequenced mouse clone
            This read has been verified (found to hit its original self in the
            correct orientation)
            Seq primer: -40RP from Gibco
            High quality sequence stop: 455.
FEATURES             Location/Qualifiers
     source          1..455
                     /organism="Mus musculus"
                     /strain="C57BL/6J"
                     /note="Vector: pT7T3D-Pac (Pharmacia) with a modified
                     polylinker; Site_1: Not I; Site_2: Eco RI; 1st strand cDNA
                     was primed with a Not I - oligo(dT) primer [5'
                     TGTTACCAATCTGAAGTGGGAGCGGCCGCGTTTTTTTTTTTTTTTTTTTTTTTT
                     3']; double-stranded cDNA was ligated to Eco RI adaptors
                     (Pharmacia), digested with Not I and cloned into the Not I
                     and Eco RI sites of the modified pT7T3 vector. RNA
                     provided by Dr. Bertrand Jordan. Library went through two
                     rounds of normalization, and was constructed by Bento
                     Soares and M.Fatima Bonaldo."
                     /db_xref="taxon:10090"
                     /clone="IMAGE:583161"
                     /clone_lib="Soares 2NbMT"
                     /sex="male"
                     /tissue_type="Thymus"
```

```
                     /dev_stage="4 weeks"
                     /lab_host="DH10B"
BASE COUNT       94 a    131 c    112 g    117 t      1 others
ORIGIN
        1 tgcggatgct gctgatactg ctgcagtagt actggatcgt caggcagagc gccctctctt
       61 ggagggggagt catgagccgc ttcctgaatg tgttacgaag ctggctggtt atggtgtcca
      121 ttatagccat ggggaacaca ctccagagct tccgagacca cacttttctc tacgagaagc
      181 tctacactgg caagccaaac cttgtgaatg gcctccaagc ccggaccttt gggatctgga
      241 cgctgctctc atcagtgatt cgctgcctct gtgccattga catccacaac aaaacactct
      301 atcacatcac actgtggaca ttcctcctcg ccctgngaca cttcctctca gagttgtttg
      361 tatttggaac agcagctccc acagttggtg tgctggcacc cctgatggta gcaagtttct
      421 caatcctggg catgctggtc gggctcccgt accta
//
```

FIGURE 45, cont.

**FIGURE 46. Human EST with Similarity to *YER044c***

```
LOCUS       W28235        839 bp    mRNA            EST       08-MAY-1996
DEFINITION  43h8 Human retina cDNA randomly primed sublibrary Homo sapiens
            cDNA, mRNA sequence.
ACCESSION   W28235
NID         g1308183
KEYWORDS    EST.
SOURCE      human.
  ORGANISM  Homo sapiens
            Eukaryota; Metazoa; Chordata; Craniata; Vertebrata; Mammalia;
            Eutheria; Primates; Catarrhini; Hominidae; Homo.
REFERENCE   1  (bases 1 to 839)
  AUTHORS   Macke, J., Smallwood, P. and Nathans, J.
  TITLE     Adult Human Retina cDNA
  JOURNAL   Unpublished (1996)
COMMENT
            Contact: Dr. Jeremy Nathans
            Dr. Jeremy Nathans, Dept. of Molecular Biology and Genetics
            Johns Hopkins School of Medicine
            725 North Wolfe Street, Baltimore, MD 21205
            Tel: 410 955 4678
            Fax: 410 614 0827
            Email: jeremy_nathans@qmail.bs.jhu.edu
            Clones from this library are NOT available.
            PCR PRimers
            FORWARD: CTTTTGAGCAAGTTCAGCCTGGTTAAGT
            BACKWARD:-GAGGTGGCTTATGAGTATTTCTTCCAGGGTAA
            Seq primer: GGGTAAAAAGCAAAAGAATT.
FEATURES             Location/Qualifiers
     source          1..839
                     /organism="Homo sapiens"
                     /note="Organ: eye; Vector: lambda gt10; Site_1: EcoRI;
                     Site_2: EcoRI; The library used for sequencing was a
                     sublibrary derived from a human retina cDNA library.
                     Inserts from retina cDNA library DNA were isolated,
                     randomly primed, PCR amplified, size-selected, and cloned
                     into lambda gt10.  Individual plaques were arrayed and
                     used as templates for PCR amplification, and these PCR
                     products were used for sequencing."
                     /db_xref="taxon:9606"
                     /clone_lib="Human retina cDNA randomly primed sublibrary"
                     /sex="mixed (males and females)"
                     /tissue_type="retina"
                     /dev_stage="adult"
                     /lab_host="E. coli strain K802"
BASE COUNT      127 a    141 c    136 g    140 t    295 others
ORIGIN
        1 gnnnnnngnn nnnnnnnnnt tnttgagnac cgcagtngca gcagcagcag ccgctgncgc
       61 aaacaagccc tcccacgttt gaggggagtc atgagccgtt tcctgaatgt gttaagaagt
      121 tggctggtta tggtgtccat catagccatg gggaacacgc tgcagagctt ccgagaccac
      181 acttttctct atgaaaagct ctacactggc aagccaaacc ttgtgaatgg cctccaagct
      241 cggacctttg ggatctggac gctgctctca tcagtgattc gctgcctctg tgccattgac
      301 attcacaaca agacgctcta tcacatcaca ctctggacct tcctccttgc cctggggcat
      361 ttcctctctg agttgtttgt cttatggaac tgcagctccc acgattggng tcctggcanc
```

```
421 cctgatggtg gnaagtttct ccatcctggg tattgtggtc ggctccngta ttttagaagt
481 agaaccagtt ccagacagaa gaagagaact gaggcagaat atcaacccca gggtggatca
541 antgggttac aagtggttna aaannnnnnn nnnnnnnnnc nnnntnntnt naannnnnnn
601 nnnnnnnnnn nnnnnnnnna nnnnnnnnnn nnnnnnnnnn nnnnnnnnnn nnnnnnnnnn
661 nnnnnnnnnn nnnnnnnnnn nnnnnnnnnn nnnnnnnnnn nnnnnnnnnn nnnnnnnnnn
721 nnnnnnnnnn nnnnnnnnnn nnnnnnnnnn nnnnnnnnnn nnnnnnnnnn nnnnnnnnnn
781 nnnnnnnnnn nnnnnnnnnn nnnnnnnnnn nnnnnnnnnn nnnnnnnnnn nnnnnnnnc
//
```

FIGURE 46, cont.

**FIGURE 47. Rat EST with Similarity to *YER044c***

```
LOCUS       AI172515      475 bp    mRNA            EST       11-FEB-1999
DEFINITION  UI-R-C2p-nu-d-02-0-UI.s1 UI-R-C2p Rattus norvegicus cDNA clone
            UI-R-C2p-nu-d-02-0-UI 3', mRNA sequence.
ACCESSION   AI172515
NID         g3712555
KEYWORDS    EST.
SOURCE      Norway rat.
  ORGANISM  Rattus norvegicus
            Eukaryota; Metazoa; Chordata; Craniata; Vertebrata; Mammalia;
            Eutheria; Rodentia; Sciurognathi; Muridae; Murinae; Rattus.
REFERENCE   1  (bases 1 to 475)
  AUTHORS   Bonaldo,M.F., Lennon,G. and Soares,M.B.
  TITLE     Normalization and subtraction: two approaches to facilitate gene
            discovery
  JOURNAL   Genome Res. 6 (9), 791-806 (1996)
  MEDLINE   97044477
COMMENT
            Contact: Soares, MB
            Program for Rat Gene Discovery and Mapping
            University of Iowa
            451 Eckstein Medical Research Building Iowa City, IA 52242, USA
            Tel: 319 335 8250
            Fax: 319 335 9565
            Email: msoares@blue.weeg.uiowa.edu
            The sequence tag present in the cDNA between the NotI site and the
            oligo dT track served to identify it as a clone from the normalized
            adult Placenta library. cDNA Library Preparation: M. Fatima
            Bonaldo, Ph.D. Clone distribution: clones will be available through
            Research Genetics
            Seq primer: M13 Forward.
FEATURES             Location/Qualifiers
     source          1..475
                     /organism="Rattus norvegicus"
                     /strain="Sprague-Dawley"
                     /note="Vector: pT7T3D-Pac (Pharmacia) with a modified
                     polylinker; Site_1: Not I; Site_2: Eco RI; The UI-R-C2p
                     library is a subtracted library derived from the UI-R-C1
                     library, which is a subtracted library derived from the
                     UI-R-C0 library.  The UI-R-C0 library consisted of a
                     mixture of individually tagged normalized  libraries
                     constructed from rat placenta, adult lung, brain, liver,
                     kidney,  heart, spleen, ovary, muscle, 8, 12 and 18-day
                     embryo. The tag is a string of  3-5 nucleotides present
                     between the Not I site and the oligo-dT track which allows
                     identification of the library of origin of a clone within
                     the mixture. The subtracted library (UI-R-C2p) was
                     constructed as follows: PCR amplified cDNA inserts from
                     UI-R-C1 clones from which 3' ESTs had been derived was
                     used as a driver in a hybridization with the UI-R-C1
                     library in the form of single-stranded circles. The
                     remaining single-stranded circles (subtracted library) was
                     purified by hydroxyapatite column chromatography,
                     converted to double-stranded circles and electroporated
```

```
                     into DH10B bacteria (Life Technologies) to generate the
                     UI-R-C2p library. This procedure has been previously
                     described (Bonaldo, Lennon and Soares, Genome Research 6:
                     791-806, 1996)"
                     /db_xref="taxon:10116"
                     /clone="UI-R-C2p-nu-d-02-0-UI"
                     /clone_lib="UI-R-C2p"
                     /dev_stage="adult"
                     /lab_host="DH10B (Life Technologies)"
BASE COUNT      115 a    112 c    126 g    119 t      3 others
ORIGIN
        1 tttttttttt tttttttctg tctggatact ggttctgctt ctaggtaccg gagcccaact
       61 agcataccca ggattgagaa acttgctacc atcaagggtg ccagcacacc aactgtggga
      121 gccgctgttc caaatacaaa caactccgag aggaagtgtc ccagggcaag gaggaatgtc
      181 cacagtgtga tgtgatagag tgttttgttg tggatgtcaa tggcacagag gcagcgaatc
      241 actgaagaga gcagcgtcca gatcccaaag gtccgggctt ggaggccatt cacaaggttt
      301 ggtttgccag tgtanagctt ttcatanaga aaagtgtggt ctcggaagct ctggagcgtg
      361 ttncccatgg ctatgatgga caccataacc agccagcttc gtagcacatt caggaagcgg
      421 ctcatgactc ccctcaaaga gagggcgctc tgcctgaccc tcgtgccgaa ttctt
//
```

FIGURE 47, cont.

FIGURE 48. YLR100w DNA Sequence

Sequence contains 800bp of 5' promoter sequence.
Symbols: 1 to: 1844 from: chr12.gcg ck: 2436, 341011 to: 342854
Chromosome XII Sequence
Nature 387:87-90 [97313267] (1997) The nucleotide sequence of
Saccharomyces cerevisiae chromosome XII.
Johnston, M., Hillier, L., Riles, L., Albermann, K., Andre, B.,
Ansorge, W., Benes, V., Bruckner, M., Delius, H., Dubois, E., . . .

gcgseq.tmp.10136 Length: 1844 March 26, 1999 15:19 Type: N Check: 2071 ..

1 ACGTACAAAA AAGAGCACGC TGCTTTATTT ATACTTTTGT GCCACAAGAA
51 TGATCAACAT CAACATAAAT ATCAACTAGT ATCTGCAACA CATCTGCTCC
101 ACGGAACTAA ACCCGTTGAG CAGTGCCCCG TGGAAACGTA AACTATCGCA
151 AATTGGGATT AACAAGCCAA AAACAGCCAA GCAAGATTCA CGAAACCGCG
201 CCTCGTTTGG ACCCCGAAGG CCCATTTAAC GGCCGGCCGT TACAAGCAAG
251 ATCGGCAGAG CAAACCACTC CCCAGCACCA CAGCACATCA CTGCACGAGC
301 AACAATAACT AGAACATGGC AGATAGCGAG GATACCTCTG TGATCCTGCA
351 GGGCATCGAC ACAATCAACA GCGTGGAGGG CCTGGAAGAA GATGGTTACC
401 TCAGCGACGA GGACACGTCA CTCAGCAACG AGCTCGCAGA TGCACAGCGT
451 CAATGGGAAG AGTCGCTGCA ACAGTTGAAC AAGCTGCTCA ACTGGGTCCT
501 GCTGCCCCTG CTGGGCAAGT ATATAGGTAG GAGAATGGCC AAGACTCTAT
551 GGAGTAGGTT CATTGAACAC TTTGTATAAG TGTTTGTTGT TTATGTATCC
601 GCATATAGCA GTTATAACAG ATAAATGGCA CTTTTCGCAC ACCCGTTGTT
651 TTATCTCCGA TAGTACGTGG GCCTTTATTT ATGGTCGTTT AACGAAAGAA
701 CGGCATCTTG AATTGAGCAG GTATTTAAAA GATAGGACGA GAAACAAGCA
751 CATGATCTGT GTCGAAAAAA AGTAGCAAAG AGAAAAAGTA GGAGGATAGG

801 ATGAACAGGA AAGTAGCTAT CGTAACGGGT ACTAATAGTA
ATCTTGGTCT
851 GAACATTGTG TTCCGTCTGA TTGAAACTGA GGACACCAAT
GTCAGATTGA
901 CCATTGTGGT GACTTCTAGA ACGCTTCCTC GAGTGCAGGA
GGTGATTAAC
951 CAGATTAAAG ATTTTTACAA CAAATCAGGC CGTGTAGAGG
ATTTGGAAAT
1001 AGACTTTGAT TATCTGTTGG TGGACTTCAC CAACATGGTG
AGTGTCTTGA
1051 ACGCATATTA CGACATCAAC AAAAAGTACA GGGCGATAAA
CTACCTTTTC
1101 GTGAATGCTG CGCAAGGTAT CTTTGACGGT ATAGATTGGA
TCGGAGCGGT
1151 CAAGGAGGTT TTCACCAATC CATTGGAGGC AGTGACAAAT
CCGACATACA
1201 AGATACAACT GGTGGGCGTC AAGTCTAAAG ATGACATGGG
GCTTATTTTC
1251 CAGGCCAATG TGTTTGGTCC GTACTACTTT ATCAGTAAAA
TTCTGCCTCA
1301 ATTGACCAGG GGAAAGGCTT ATATTGTTTG GATTTCGAGT
ATTATGTCCG
1351 ATCCTAAGTA TCTTTCGTTG AACGATATTG AACTACTAAA
GACAAATGCC
1401 TCTTATGAGG GCTCCAAGCG TTTAGTTGAT TTACTGCATT
TGGCCACCTA
1451 CAAAGACTTG AAAAAGCTGG GCATAAATCA GTATGTAGTT
CAACCGGGCA
1501 TATTTACAAG CCATTCCTTC TCCGAATATT TGAATTTTTT
CACCTATTTC
1551 GGCATGCTAT GCTTGTTCTA TTTGGCCAGG CTGTTGGGGT
CTCCATGGCA
1601 CAATATTGAT GGTTATAAAG CTGCCAATGC CCCAGTATAC
GTAACTAGAT
1651 TGGCCAATCC AAACTTTGAG AAACAAGACG TAAAATACGG
TTCTGCTACC
1701 TCTAGGGATG GTATGCCATA TATCAAGACG CAGGAAATAG
ACCCTACTGG
1751 AATGTCTGAT GTCTTCGCTT ATATACAGAA GAAGAAACTG
GAATGGGACG
1801 AGAAACTGAA AGATCAAATT GTTGAAACTA GAACCCCCAT TTAA

FIGURE 48, cont.

FIGURE 49. *YLR100w* Protein Sequence

Nature 387:87-90 [97313267] (1997) The nucleotide sequence of Saccharomyces cerevisiae chromosome XII.

Johnston, M., Hillier, L., Riles, L., Albermann, K., Andre, B., Ansorge, W., Benes, V., Bruckner, M., Delius, H., Dubois, E., Dusterhoft, A., Entian, K. D., Floeth, M., Goffeau, A., Hebling, U., et al.

YLR100W Length: 347 March 26, 1999 15:20 Type: P Check: 2853 ..

```
  1 MNRKVAIVTG TNSNLGLNIV FRLIETEDTN VRLTIVVTSR TLPRVQEVIN

 51 QIKDFYNKSG RVEDLEIDFD YLLVDFTNMV SVLNAYYDIN KKYRAINYLF

101 VNAAQGIFDG IDWIGAVKEV FTNPLEAVTN PTYKIQLVGV KSKDDMGLIF

151 QANVFGPYYF ISKILPQLTR GKAYIVWISS IMSDPKYLSL NDIELLKTNA

201 SYEGSKRLVD LLHLATYKDL KKLGINQYVV QPGIFTSHSF SEYLNFFTYF

251 GMLCLFYLAR LLGSPWHNID GYKAANAPVY VTRLANPNFE KQDVKYGSAT

301 SRDGMPYIKT QEIDPTGMSD VFAYIQKKKL EWDEKLKDQI VETRTPI
```

**FIGURE 50. Human EST with Similarity to *YLR100w***

```
LOCUS       R92053         454 bp    mRNA            EST       25-AUG-1995
DEFINITION  yp96c01.r1 Soares fetal liver spleen 1NFLS Homo sapiens cDNA clone
            IMAGE:195264 5', mRNA sequence.
ACCESSION   R92053
NID         g959593
KEYWORDS    EST.
SOURCE      human.
  ORGANISM  Homo sapiens
            Eukaryota; Metazoa; Chordata; Craniata; Vertebrata; Mammalia;
            Eutheria; Primates; Catarrhini; Hominidae; Homo.
REFERENCE   1  (bases 1 to 454)
  AUTHORS   Hillier,L., Clark,N., Dubuque,T., Elliston,K., Hawkins,M.,
            Holman,M., Hultman,M., Kucaba,T., Le,M., Lennon,G., Marra,M.,
            Parsons,J., Rifkin,L., Rohlfing,T., Soares,M., Tan,F.,
            Trevaskis,E., Waterston,R., Williamson,A., Wohldmann,P. and
            Wilson,R.
  TITLE     The WashU-Merck EST Project
  JOURNAL   Unpublished (1995)
COMMENT
            Contact: Wilson RK
            Washington University School of Medicine
            4444 Forest Park Parkway, Box 8501, St. Louis, MO 63108
            Tel: 314 286 1800
            Fax: 314 286 1810
            Email: est@watson.wustl.edu
            Insert Size: 1067
            High quality sequence stops: 337
            Source: IMAGE Consortium, LLNL
            This clone is available royalty-free through LLNL ; contact the
            IMAGE Consortium (info@image.llnl.gov) for further information.
            Insert Length: 1067   Std Error: 0.00
            Seq primer: M13RP1
            High quality sequence stop: 337.
FEATURES             Location/Qualifiers
     source          1..454
                     /organism="Homo sapiens"
                     /note="Organ: Liver and Spleen; Vector: pT7T3D (Pharmacia)
                     with a modified polylinker; Site_1: Pac I; Site_2: Eco RI;
                     1st strand cDNA was primed with a Pac I - oligo(dT) primer
                     [5' AACTGGAAGAATTAATTAAAGATCTTTTTTTTTTTTTTTTTTT 3'],
                     double-stranded cDNA was ligated to Eco RI adaptors
                     (Pharmacia), digested with Pac I and cloned into the Pac I
                     and Eco RI sites of the modified pT7T3 vector.  Library
                     went through one round of normalization. Library
                     constructed by Bento Soares and M.Fatima Bonaldo."
                     /db_xref="GDB:3764314"
                     /db_xref="taxon:9606"
                     /clone="IMAGE:195264"
                     /clone_lib="Soares fetal liver spleen 1NFLS"
                     /sex="male"
                     /dev_stage="20 week-post conception fetus"
                     /lab_host="DH10B (ampicillin resistant)"
BASE COUNT      115 a    111 c     96 g    129 t      3 others
```

ORIGIN
          1 tttgagacca atgtctttgg ccattttatc ctgattcggg aactggagcc tctcctctgt
         61 cacagtgaca atccatctca gctcatctgg acatcatctc gcagtgcaag gaaatctaat
        121 ttcagcctcg aggacttcca gcacagcaaa ggcaaggaac cctacagctc ttccaaatat
        181 gccactgacc ttttgagtgt ggctttgaac aggaacttca accagcaggg tctctattcc
        241 aatgtggcct gtccaggtac agcattgacc aatttgacat atggaattct gcctccgttt
        301 atatggacgc tgttggatgc cggcaatatt gctacttcgc ttttttggca aatggcattc
        361 actttggaca ccatataatg ggaacaggaa gntatgggta tgggnttttc ccaccaaaag
        421 gctggaatcn tttcaatcct ctggatccaa atat
//

FIGURE 50, cont.

**FIGURE 51. Mouse EST with Similarity to *YLR100w***

```
LOCUS       AI226514     1039 bp    mRNA            EST       29-OCT-1998
DEFINITION  uj07d08.y1 Sugano mouse liver mlia Mus musculus cDNA clone
            IMAGE:1891215 5' similar to TR:Q62904 Q62904 OVARIAN-SPECIFIC
            PROTEIN. ;, mRNA sequence.
ACCESSION   AI226514
NID         g3809567
KEYWORDS    EST.
SOURCE      house mouse.
  ORGANISM  Mus musculus
            Eukaryota; Metazoa; Chordata; Craniata; Vertebrata; Mammalia;
            Eutheria; Rodentia; Sciurognathi; Muridae; Murinae; Mus.
REFERENCE   1  (bases 1 to 1039)
  AUTHORS   Marra,M., Hillier,L., Allen,M., Bowles,M., Dietrich,N., Dubuque,T.,
            Geisel,S., Kucaba,T., Lacy,M., Le,M., Martin,J., Morris,M.,
            Schellenberg,K., Steptoe,M., Tan,F., Underwood,K., Moore,B.,
            Theising,B., Wylie,T., Lennon,G., Soares,B., Wilson,R. and
            Waterston,R.
  TITLE     The WashU-HHMI Mouse EST Project
  JOURNAL   Unpublished (1996)
COMMENT
            Contact: Marra M/Mouse EST Project
            WashU-HHMI Mouse EST Project
            Washington University School of MedicineP
            4444 Forest Park Parkway, Box 8501, St. Louis, MO 63108
            Tel: 314 286 1800
            Fax: 314 286 1810
            Email: mouseest@watson.wustl.edu
            This clone is available royalty-free through LLNL ; contact the
            IMAGE Consortium (info@image.llnl.gov) for further information.
            MGI:975539
            Seq primer: custom primer used
            High quality sequence stop: 509.
FEATURES             Location/Qualifiers
     source          1..1039
                     /organism="Mus musculus"
                     /strain="C57BL"
                     /note="Organ: liver; Vector: pME18S-FL3; Site_1: DraIII
                     (CACTGTGTG); Site_2: DraIII (CACCATGTG); 1st strand cDNA
                     was primed with an oligo(dT) primer
                     [ATGTGGCCTTTTTTTTTTTTTTTTT]; double-stranded cDNA was
                     ligated to a  DraIII adaptor [TGTTGGCCTACTGG], digested
                     and cloned into distinct DraIII sites of the pME18S-FL3
                     vector (5' site CACTGTGTG, 3' site CACCATGTG). XhoI should
                     be used to isolate the cDNA insert.  Size selection was
                     performed to exclude fragments <1.5kb.  Library
                     constructed by Dr. Sumio Sugano (University of Tokyo
                     Institute of Medical Science).  Custom primers  for
                     sequencing: 5' end primer CTTCTGCTCTAAAAGCTGCG and 3' end
                     primer CGACCTGCAGCTCGAGCACA."
                     /db_xref="taxon:10090"
                     /clone="IMAGE:1891215"
                     /clone_lib="Sugano mouse liver mlia"
                     /sex="female"
```

```
                     /dev_stage="adult"
                     /lab_host="DH10B"
BASE COUNT      245 a    267 c    251 g    272 t      4 others
ORIGIN
        1 ggctaagaga accccggtgc agttctactt cggtgcaggg cgtggaagat gcggaaggtg
       61 gttttgatca ccggggcgag cagtggcatt gggctagccc tttgcggtcg actgctggca
      121 gaagacgatg acctccacct gtgtttggcg tgtaggaacc tgagcaaagc aagagctgtt
      181 cgagataccc tgctggcctc tcacccctcc gccgaagtca gcatcgtgca gatggatgtc
      241 agcagcctgc agtcggtggt ccggggtgca gaggaagtca agcaaaagtt tcaaagatta
      301 gactacttat atctgaatgc tggaatcctg cctaatccac aattcaacct caaggcattt
      361 ttctgcggca tcttttcaag aaatgtgatt catatgttca ccacagcgga aggaattttg
      421 acccagaatg actcggtcac tgccgacggg ttgcaggagg tgtttgaaac caatctcttt
      481 ggccacttta ttctgattcg ggaactggaa ccacttctct gccatgccga caacccctct
      541 cagctcatct ggacgtcctc tcgcaatgca aagaaggcta acttcagcct ggaggacata
      601 cagcacttca aaggcccgga accctacagc tctttccaat atgctaccga cctcctgaat
      661 gtggctntga acagggaatt caaaccagaa ggtctggtat tcagtggtga ttgccgaggg
      721 cgtctgatga ccaatatgac gtatggaaat ttgccttcct ttatcctgac cgtggttcta
      781 cccttaagtg ggctccttcg ctttttttgaa aatgccctca cctgggaccc cgtaccactg
      841 atcaaaagct ctgggtgtgt ttctttcaca tataaccgga ggcttttatt ctttgaccaa
      901 atacgcgagc tccaccttgg tagtgggact atataccgac cggtcccacg aatgcactca
      961 tttaacacct tgtcaaaact ttttatagtt ttacctgttg tgataacgtg gtgntacccc
     1021 cttcgtantt gnaataccc
//
```

FIGURE 51, cont.

**FIGURE 52. Mouse EST with Similarity to *YLR100w***

```
LOCUS       AI528381      837 bp    mRNA            EST       18-MAR-1999
DEFINITION  ui96g06.y1 Sugano mouse liver mlia Mus musculus cDNA clone
            IMAGE:1890298 5' similar to TR:Q62904 Q62904 OVARIAN-SPECIFIC
            PROTEIN. ;, mRNA sequence.
ACCESSION   AI528381
NID         g4442516
KEYWORDS    EST.
SOURCE      house mouse.
  ORGANISM  Mus musculus
            Eukaryota; Metazoa; Chordata; Craniata; Vertebrata; Mammalia;
            Eutheria; Rodentia; Sciurognathi; Muridae; Murinae; Mus.
REFERENCE   1  (bases 1 to 837)
  AUTHORS   Marra,M., Hillier,L., Kucaba,T., Martin,J., Beck,C., Wylie,T.,
            Underwood,K., Steptoe,M., Theising,B., Allen,M., Bowers,Y.,
            Person,B., Swaller,T., Gibbons,M., Pape,D., Harvey,N., Schurk,R.,
            Ritter,E., Kohn,S., Shin,T., Jackson,Y., Cardenas,M., McCann,R.,
            Waterston,R. and Wilson,R.
  TITLE     The WashU-NCI Mouse EST Project 1999
  JOURNAL   Unpublished (1999)
COMMENT
            Contact: Marra M/WashU-NCI Mouse EST Project 1999
            Washington University School of Medicine
            4444 Forest Park Parkway, Box 8501, St. Louis, MO 63108, USA
            Tel: 314 286 1800
            Fax: 314 286 1810
            Email: mouseest@watson.wustl.edu
            This clone is available royalty-free through LLNL ; contact the
            IMAGE Consortium (info@image.llnl.gov) for further information.
            MGI:974622
            Possible reversed clone: similarity on wrong strand
            Seq primer: custom primer used
            High quality sequence stop: 429.
FEATURES             Location/Qualifiers
     source          1..837
                     /organism="Mus musculus"
                     /strain="C57BL"
                     /note="Organ: liver; Vector: pME18S-FL3; Site_1: DraIII
                     (CACTGTGTG); Site_2: DraIII (CACCATGTG); 1st strand cDNA
                     was primed with an oligo(dT) primer
                     [ATGTGGCCTTTTTTTTTTTTTTTTTT]; double-stranded cDNA was
                     ligated to a  DraIII adaptor [TGTTGGCCTACTGG], digested
                     and cloned into distinct DraIII sites of the pME18S-FL3
                     vector (5' site CACTGTGTG, 3' site CACCATGTG). XhoI should
                     be used to isolate the cDNA insert.  Size selection was
                     performed to exclude fragments <1.5kb.  Library
                     constructed by Dr. Sumio Sugano (University of Tokyo
                     Institute of Medical Science).  Custom primers  for
                     sequencing: 5' end primer CTTCTGCTCTAAAAGCTGCG and 3' end
                     primer CGACCTGCAGCTCGAGCACA."
                     /db_xref="taxon:10090"
                     /clone="IMAGE:1890298"
                     /clone_lib="Sugano mouse liver mlia"
```

```
                     /sex="female"
                     /dev_stage="adult"
                     /lab_host="DH10B"
BASE COUNT      191 a    222 c    212 g    208 t      4 others
ORIGIN
        1 ggctaagaga accccggtgc agttctactt cggtgcaggg cgtggaagat gcggaaggtg
       61 gttttgatca ccggggcgag cagtggcatt gggctagccc tttgcggtcg actgctggca
      121 gaagacgatg acctccacct gtgtttggcg tgtaggaacc tgagcaaagc aagagctgtt
      181 cgagataccc tgctggcctc tcacccctcc gccgaagtca gcatcgtgca gatggatgtc
      241 agcagcctgc agtcggtggt ccggggtgca gaggaagtca agcaaaagtt tcaaagatta
      301 gactacttat atctgaatgc tggaatcctg cctaatccac aattcaacct caaggcattt
      361 ttctgcggca tcttttcaag aaatgtgatt catatgttca ccacagcgga aggaattttg
      421 acccagaatg actcggtcac tgccgaccgg ttgcaggagg tgtttgaaac caatctctct
      481 tgccacttta ttctgattcg ggaactggaa ccacttctct tgcatgcgga caacccctct
      541 cagctcatct ggacgtcctc tcgcaatgca nagaaggcta acttcagcct ggaggacatn
      601 cagcactcca tagggcccgg accctacagc tctttccaat atgctaccga cctcctgaat
      661 gtcgctttga acangaatnt caaccagaag ggtctgtatt ccagtcgcat gtgcccaggc
      721 gtcgtgatga ccaatatgac gtatggaatc ttgcctccct tttatctgga cgtgctccta
      781 cccatgatgg tgctccttcg cttctttggt aatgcgctta ctgggacacc gtacaac
//
```

FIGURE 52, cont.

**FIGURE 53. Mouse Gene with Similarity to *YLR100w***

```
LOCUS       3319971      334 aa                          14-JUL-1998
DEFINITION  17-beta-hydroxysteroid dehydrogenase type 7.
ACCESSION   3319971
PID         g3319971
DBSOURCE    EMBL: locus MMY15733, accession Y15733
KEYWORDS    .
SOURCE      house mouse.
  ORGANISM  Mus musculus
            Eukaryota; Metazoa; Chordata; Vertebrata; Mammalia; Eutheria;
            Rodentia; Sciurognathi; Muridae; Murinae; Mus.
REFERENCE   1  (residues 1 to 334)
  AUTHORS   Nokelainen,P., Peltoketo,H., Vihko,R. and Vihko,P.
  TITLE     Expression cloning of a novel estrogenic mouse 17
            beta-hydroxysteroid dehydrogenase/17-ketosteroid reductase
            (m17HSD7), previously described as a prolactin receptor-associated
            protein (PRAP) in rat
  JOURNAL   Mol. Endocrinol. 12 (7), 1048-1059 (1998)
  MEDLINE   98322544
REFERENCE   2  (residues 1 to 334)
  AUTHORS   Nokelainen,P.A.
  TITLE     Direct Submission
  JOURNAL   Submitted (27-NOV-1997) P.A. Nokelainen, University of Oulu,
            Biocenter Oulu, WHO Collaborating Centre for Research on
            Reproductive Health Department of Clinical Chemistry, Kajaanintie
            50, FIN-90220 Oulu, FINLAND
FEATURES             Location/Qualifiers
     source          1..334
                     /organism="Mus musculus"
                     /strain="BALB/c"
                     /db_xref="taxon:10090"
                     /tissue_type="mammary gland"
                     /cell_type="epithelial cell derived from mammary gland of
                     a pregnant mouse"
                     /clone_lib="cDNA library prepared from poly(A)-enriched
                     RNA isolated from HC11 cell line"
                     /clone="m17HSD7.1"
                     /clone="m17HSD7.2"
     Protein         1..334
                     /product="17-beta-hydroxysteroid dehydrogenase type 7"
     CDS             1..334
                     /gene="HSD17B7"
                     /db_xref="SPTREMBL:O88736"
                     /coded_by="Y15733:64..1068"
ORIGIN
        1 mrkvvlitga ssgiglalcg rllaedddlh lclacrnlsk aravrdtlla shpsaevsiv
       61 qmdvsslqsv vrgaeevkqk fqrldylyln agilpnpqfn lkaffcgifs rnvihmftta
      121 egiltqndsv tadglqevfe tnlfghfili releplicha dnpsqliwts srnakkanfs
      181 lediqhskgp epyssskyat dllnvalnrn fnqkglyssv mcpgvvmtnm tygilppfiw
      241 tlllpimwll rffvnaltvt pyngaealvw lfhqkpesln pltkyasats gfgtnyvtgq
      301 kmdidedtae kfyevllele krvrttvqks dhps
//
```

FIGURE 54. *YER034w* DNA Sequence

Sequence contains 559bp of 5' promoter sequence.
Symbols: 1 to: 1117 from: chr5.gcg ck: 9036, 221286 to: 222402
Chromosome V Sequence
Nature 387:78-81 [97313264] (1997) The nucleotide sequence of Saccharomyces cerevisiae chromosome V.
Dietrich, F. S., Mulligan, J., Hennessy, K., Yelton, M. A., Allen, E., Araujo, R., Aviles, E., Berno, A., Brennan, T., Carpenter, J., Chen, . . .

gcgseq.tmp.6597 Length: 1117 March 26, 1999 16:54 Type: N Check: 5026 ..

```
   1  TGATGAAATA TTCCAGTTAT GCGTGTGCGT CTTGTGATGC AGATCCTTTT
  51  GGGCAAAAAC AGTTGGTTTG TGCGAAAACG CAAGGTAATA AATAGGCTTA
 101  AAGGAACTAA AAAAAAAAAA AGGAAAATAA CCAGCTAAGA TTTAAGGTAC
 151  AAGAAAGCGG TTGCACCTCA AGTAATGATA GTTATTAAAC CTTGGATTGG
 201  ACCAGATGTT TAAAATTGTT TTCAATAGTA GATTTGCAGT CGTAAATGCG
 251  TTCTCAGCAA TATCATATTG TGTTTATGAA GTATTACCAA ACGGGTAGAA
 301  GAACGGTTTA AGAGAATATG TCCGGATAAA GCGATCAGGA GAAAAGCTTA
 351  AAACCCAAAG TGGTCAATCT GCAGCCCATT TAGGCACTCT GCATTTAACC
 401  GATACCCGGA TTGAAGAAAG CTGGCGGGTG TATGGGTGAA GGAGAAGAAA
 451  GGAAGTGATT AGGAGAAACC TCATGGAGAT GAGCACATGC TACAACTAAT
 501  AACGTTATTC TACTTAAAAC GAGCAAAACA AAAAAAAAAA CAAGACAATT
 551  GAAAACGCAA TGGATGCATT CAGCTTAAAG AAGGATAATC GAAAAAAATT
 601  TCAAGATAAA CAGAAATTGA AAAGAAAACA TGCCACACCC AGTGATAGAA
 651  AGTACCGGCT ATTGAACCGC CAAAAAGAAG AGAAAGCTAC CACAGAGGAG
 701  AAAGATCAAG ACCAAGAACA GCCCGCCCTG AAGTCAAACG AGGACAGGTA
 751  CTATGAGGAC CCGGTACTCG AGGACCCGCA TTCTGCAGTC GCCAATGCAG
 801  AGTTGAACAA GGTGCTAAAA GACGTCCTCA AAAATCGGCT CCAGCAGAAC
 851  GACGACGCCA CAGCCGTCAA TAATGTTGCT AATAAAGATA CTTTGAAAAT
 901  CAAAGACCTC AAGCAGATGA ATACGGATGA GCTCAATCGT TGGCTCGGAC
 951  GGCAGAATAC AACATCGGCT ATAACAGCGG CTGAGCCCGA ATCATTAGTC
1001  GTTCCCATTC ACGTACAAGG TGATCATGAT CGTGCGGGCA AGAAGATCAG
1051  TGCCCCTTCG ACCGATCTAC CGGAAGAACT AGAGACCGAT CAGGATTTCC
1101  TTGATGGACT GCTCTAA
```

FIGURE 55. *YER034w* Protein Sequence

Nature 387:78-81 [97313264] (1997) The nucleotide sequence of Saccharomyces cerevisiae chromosome V.

Dietrich, F. S., Mulligan, J., Hennessy, K., Yelton, M. A., Allen, E., Araujo, R., Aviles, E., Berno, A., Brennan, T., Carpenter, J., Chen, E., Cherry, J. M., Chung, E., Duncan, M., Guzman, E., Hartzell, G., et al.

YER034W Length: 185 March 26, 1999 16:55 Type: P Check: 3501 ..

```
  1  MDAFSLKKDN RKKFQDKQKL KRKHATPSDR KYRLLNRQKE EKATTEEKDQ

 51  DQEQPALKSN EDRYYEDPVL EDPHSAVANA ELNKVLKDVL KNRLQQNDDA

101  TAVNNVANKD TLKIKDLKQM NTDELNRWLG RQNTTSAITA AEPESLVVPI

151  HVQGDHDRAG KKISAPSTDL PEELETDQDF LDGLL
```

FIGURE 56. *YKL077w* DNA Sequence

Sequence contains 1200bp of 5' promoter sequence.
Symbols: 1 to: 2379 from: chr11.gcg ck: 9298, 289895 to: 292273
Chromosome XI Sequence
Nature 387:98-102 [97313270] (1997) The nucleotide sequence of Saccharomyces cerevisiae chromosome XV.
Dujon, B., Albermann, K., Aldea, M., Alexandraki, D., Ansorge, W., Arino, J., Benes, V., Bohn, C., Bolotin-Fukuhara, M., Bordonne, R., . . .

gcgseq.tmp.4920 Length: 2379 March 26, 1999 16:48 Type: N Check: 4118 ..

```
   1 GAAAGGAAGC TATAGTAATG GGGCTTCAGG AACTTTATGA ATTGGGTGCT
  51 CTTGACACTC GTGGAAAGAT AACTAAACGG GGTCAACAAA TGGCTCTGTT
 101 ACCGCTACAA CCGCATTTAA GTAGTGTCTT AATTAAAGCC AGTGAAGTCG
 151 GATGTTTGAG TCAGGTCATT GATATCGTCT CTTGCCTTAG TGTGGAAAAT
 201 TTACTGTTGA ATCCGTCACC AGAAGAAAGA GATGAGGTGA ACGAGCGTCG
 251 TTTGTCCTTA TGCAACGCTG GTAAAAGGTA TGGTGACCTT ATCATGCTGA
 301 AAGAGCTTTT TGATATCTAT TTCTACGAAC TAGGGAAAAG TCAAGATGCA
 351 AGCTCTGAAA GAAATGATTG GTGTAAAGGA TTGTGTATTT CGATACGTGG
 401 GTTTAAAAAT GTAATTCGTG TCAGAGACCA GTTAAGAGTT TATTGTAAGC
 451 GTTTGTTTTC TTCAATCAGT GAAGAGGATG AAGAATCCAA AAAGATTGGT
 501 GAAGATGGCG AGCTAATTTC GAAAATTTTA AAGTGTTTCT TAACTGGGTT
 551 TATCAAGAAT ACAGCTATAG GGATGCCAGA CAGGTCTTAT AGAACTGTTT
 601 CCACTGGAGA GCCGATAAGC ATTCATCCAT CATCTATGCT ATTTATGAAT
 651 AAAAGCTGCC CCGGTATAAT GTACACGGAG TATGTCTTTA CTACGAAGGG
 701 ATATGCCAGA AATGTTAGTA GGATTGAACT TTCATGGTTA CAAGAAGTTG
 751 TCACTAATGC AGCCGCTGTA GCAAAGCAAA AAGTTTCTGA TTCAAAATAA
 801 GTCACCTACT CTTAGCGCAT TTTTATTGTA TATAAAGGCA TTTAATGTAA
 851 TTTATAGAGC ATTATAAATC GTAACAACTA CTGCAGTATG AGTTTCATGG
 901 ATTCATTTCT CAATATCTTA TGAATATACA CAGGTATATA TGTATATTCA
 951 TGTTAAACGC CTTTCGAATT GTTCGTTGGC TTTTTTTGTG AAATTATCTC
1001 GGGAAAAGGG CGAAATTATA TTATTTTGCC GTTGACATTT TGAAAAGGAA
1051 TAAAAGATCA TGAAAAAAAT AAGAAAGGCA ATTCGACGCA TTTCTCTCAG
1101 CAAGCTATTC TTTACTTTTG AAGAACAAAA TATTTTAGCA AAAAGGTTAA
1151 GACAATATAG TCGGAAGCAG TTCTGCGGGA TCTGAAGGAA TTGCGGAATA
1201 ATGAGATTTC ACGATAGTAT ACTTATCTTC TTTTCTTTGG CATCGCTTTA
1251 TCAACATGTT CATGGTGCAA GACAAGTCGT TCGTCCAAAG GAGAAAATGA
1301 CTACTTCAGA AGAAGTTAAA CCTTGGTTAC GTACGGTTTA TGGAAGTCAA
1351 AAAGAATTAG TCACTCCTAC GGTCATTGCC GGTGTCACTT TTTCTGAAAA
1401 ACCAGAAGAA ACACCAAATC CATTGAAACC TTGGGTATCT TTAGAGCATG
1451 ATGGTAGGCC AAAAAACCATT AAACCAGAAA TCAACAAAGG TCGAACCAAG
1501 AAGGGAAGAC CTGATTACTC AACTTACTTC AAAACGGTAA GTTCCCACAC
1551 ATATTCTTAT GAAGAATTGA AGGCTCACAA TATGGGCCCT AATGAAGTTT
1601 TTGTAGAAGA AGAGTATATT GATGAAGATG ACACCTACGT CTCCCTGAAT
1651 CCTATTGTCA GATGTACTCC TAATCTTTAC TTCAATAAAG GTCTAGCAAA
1701 GGATATCCGC AGTGAGCCAT TTTGTACCCC TTATGAGAAT TCTAGATGGA
1751 AGGTTGACAA GACTTACTTC GTTACTTGGT ATACAAGATT TTTTACAGAT
1801 GAGAATTCCG GTAAAGTTGC TGATAAGGTT CGTGTTCATT TGTCCTATGT
1851 TAAAGAAAAC CCCGTAGAGA AGGGCAATTA TAAAAGAGAT ATCCCTGCAA
1901 CTTTTTTCTC TTCCGAATGG ATTGATAATG ACAACGGTCT AATGCCGGTT
1951 GAGGTCAGAG ATGAATGGCT GCAGGACCAA TTTGATCGTA GGATCGTTGT
2001 ATCAGTTCAG CCAATATACA TATCAGATGA AGATTTCGAT CCACTACAAT
2051 ACGGTATTTT ATTATACATC ACTAAGGGTT CAAAAGTGTT TAAGCCTACT
2101 AAGGAGCAAC TGGCTTTAGA CGATGCAGGT ATAACAAATG ATCAGTGGTA
```

2151 TTATGTTGCA TTATCTATCC CTACTGTCGT GGTGGTATTT TTCGTCTTCA
2201 TGTACTTTTT CTTATATGTC AACGGGAAAA ACAGAGATTT CACAGATGTT
2251 ACTAGAAAAG CTTTAAACAA GAAACGCCGT GTTTTGGGTA AGTTCTCGGA
2301 GATGAAGAAA TTCAAAAACA TGAAAAATCA CAAGTACACC GAATTGCCAT
2351 CTTATAAGAA AACCAGTAAA CAAAATTAG

FIGURE 56, cont.

FIGURE 57. *YKL077w* Protein Sequence

Nature 387:98-102 [97313270] (1997) The nucleotide sequence of Saccharomyces cerevisiae chromosome XV.

Dujon, B., Albermann, K., Aldea, M., Alexandraki, D., Ansorge, W., Arino, J., Benes, V., Bohn, C., Bolotin-Fukuhara, M., Bordonne, R., Boyer, J., Camasses, A., Casamayor, A., Casas, C., Cheret, G., et al.

YKL077W Length: 392 March 26, 1999 16:50 Type: P Check: 1732 ..

```
  1 MRFHDSILIF FSLASLYQHV HGARQVVRPK EKMTTSEEVK PWLRTVYGSQ
 51 KELVTPTVIA GVTFSEKPEE TPNPLKPWVS LEHDGRPKTI KPEINKGRTK
101 KGRPDYSTYF KTVSSHTYSY EELKAHNMGP NEVFVEEEYI DEDDTYVSLN
151 PIVRCTPNLY FNKGLAKDIR SEPFCTPYEN SRWKVDKTYF VTWYTRFFTD
201 ENSGKVADKV RVHLSYVKEN PVEKGNYKRD IPATFFSSEW IDNDNGLMPV
251 EVRDEWLQDQ FDRRIVVSVQ PIYISDEDFD PLQYGILLYI TKGSKVFKPT
301 KEQLALDDAG ITNDQWYYVA LSIPTVVVVF FVFMYFFLYV NGKNRDFTDV
351 TRKALNKKRR VLGKFSEMKK FKNMKNHKYT ELPSYKKTSK QN
```

FIGURE 58. *YGR046w* DNA Sequence

Sequence contains 599bp of 5' promoter sequence.
Symbols: 1 to: 1757 from: chr7.gcg ck: 9962, 584290 to: 586046
Chromosome VII Sequence
Nature 387:81-84 [97313265] (1997) The nucleotide sequence of
Saccharomyces cerevisiae chromosome VII.
Tettelin, H., Agostoni Carbone, M. L., Albermann, K., Albers, M.,
Arroyo, J., Backes, U., Barreiros, T., Bertani, I., Bjourson, A. J., . . .

gcgseq.tmp.228 Length: 1757 March 26, 1999 16:44 Type: N Check: 9449 ..

| | | | | | |
|---|---|---|---|---|---|
| 1 | TCTCACTCCG | GCGGCCATTT | TACGTGACGA | AGCATCCCTT | ACAACAGAAA |
| 51 | GAAGAAAAAA | GATATGCCGC | TTTGCGGTTT | CTTTCTGGCA | ATGTATGCAC |
| 101 | TCATAATGCT | ACTCGTTTAC | CCACTATCCC | TGTCCAAACT | AAAGAGGGAG |
| 151 | GAAAGCACTT | TTTGCATTTA | CACATCGTAG | ATTATAAAAT | GATCGTTAAC |
| 201 | AGGCGCTTGT | GATTTTGAAT | TTAAGAAATG | TGGACTAGAG | AAGTCTTAAA |
| 251 | TCGCCAATGC | TGTACCAGAC | TCTCTATAGC | ATCTAAACAC | GAAATTCAAC |
| 301 | TGTTATCTTA | GTTTTTCACT | TACCAGTAGC | GCGCTTGTTA | TTCCCACGTT |
| 351 | ATTATTTGCC | CCCACATCAT | AGGTCAAGTG | ACCTTCTCTT | ACCCGACATG |
| 401 | AATAAAGAAA | AGAAAAGAAA | TCATACCCTT | CAGCCTGTTT | AGCCATAAAT |
| 451 | AGTAAAGAGT | AGATGTTTCG | ACGGACTAAA | TAATGTGAAA | AAGGTTCTAA |
| 501 | AACCTTCAAA | ACAATTAAAC | TTGAGAAACG | TTGCTATAGG | ATTGAGCTAA |
| 551 | TAATTTGAAT | TAATAGGAGC | TGCTTTTTAC | TTTGATATAT | CCTGAAGTTA |
| 601 | TGTTACGAGT | TTCTGAAAAT | GGTCTACGGT | TTCTGCTGAA | ATGCCATTCA |
| 651 | ACGAACGTAA | GCATGTTTAA | TAGGCTTCTG | AGTACTCAAA | TAAAGGAGGG |
| 701 | GAGAAGTTCC | ATAGATGATG | CTGGCATTAT | CCCCGATGGA | ACTATTAACG |
| 751 | AAAGGCCGAA | TCACTACATC | GAGGGAATTA | CTAAAGGCAG | TGATCTGGAC |
| 801 | CTCTTGGAAA | AAGGTATAAG | AAAAACTGAC | GAAATGACTT | CCAATTTTAC |
| 851 | AAATTATATG | TACAAGTTTC | ACAGATTGCC | CCCCAACTAT | GGAAGTAACC |
| 901 | AGCTCATTAC | TATCGATAAG | GAACTTCAAA | AGGAACTGGA | TGGGGTAATG |
| 951 | TCATCCTTCA | AAGCTCCGTG | CCGGTTTGTA | TTTGGTTACG | GCTCAGGAGT |
| 1001 | TTTCGAACAA | GCGGGATATT | CCAAAAGTCA | TAGCAAACCT | CAAATCGATA |
| 1051 | TAATCTTGGG | CGTCACATAT | CCATCACATT | TTCACTCTAT | TAATATGAGG |
| 1101 | CAGAATCCGC | AACATTATTC | AAGTTTGAAA | TACTTCGGTT | CCGAGTTCGT |
| 1151 | GTCTAAATTT | CAACAGATCG | GCGCAGGCGT | ATATTTTAAT | CCATTTGCAA |
| 1201 | ATATAAATGG | ACACGACGTA | AAATATGGGG | TGGTTTCTAT | GGAAACACTT |
| 1251 | TTAAAGGACA | TAGCTACTTG | GAATACATTC | TATTTAGCAG | GACGACTACA |
| 1301 | AAAGCCTGTA | AAAATATTGA | AGAATGATTT | GAGAGTGCAA | TATTGGAACC |
| 1351 | AATTAAACTT | AAAAGCTGCA | GCTACTTTGG | CCAAACATTA | CACCTTAGAG |
| 1401 | AAAAATAACA | ATAAGTTTGA | CGAATTCCAA | TTTTACAAGG | AGATCACTGC |
| 1451 | CTTAAGTTAT | GCAGGTGATA | TTAGATACAA | ACTGGGTGGA | GAAAATCCCG |
| 1501 | ACAAAGTTAA | CAACATTGTT | ACCAAAAACT | TTGAAAGATT | TCAAGAGTAT |
| 1551 | TACAAGCCGA | TTTACAAAGA | AGTGGTCCTA | AATGATTCAT | TTTATCTTCC |
| 1601 | AAAAGGGTTC | ACATTAAAGA | ATACTCAGAG | ACTTTTGCTC | AGCCGTATTA |
| 1651 | GTAAATCAAG | TGCATTACAA | ACTATTAAAG | GTGTTTTCAC | AGCTGGAATC |
| 1701 | ACAAAGTCAA | TTAAGTATGC | TTGGGCCAAA | AAACTAAAAT | CGATGAGGAG |
| 1751 | AAGCTAG | | | | |

FIGURE 59. *YGR046w* Protein Sequence

Nature 387:81-84 [97313265] (1997) The nucleotide sequence of Saccharomyces cerevisiae chromosome VII.

Tettelin, H., Agostoni Carbone, M. L., Albermann, K., Albers, M., Arroyo, J., Backes, U., Barreiros, T., Bertani, I., Bjourson, A. J., Bruckner, M., Bruschi, C. V., Carignani, G., Castagnoli, L., Cerdan, et al.

YGR046W Length: 385 March 26, 1999 16:46 Type: P Check: 4137 ..

1 MLRVSENGLR FLLKCHSTNV SMFNRLLSTQ IKEGRSSIDD AGIIPDGTIN

51 ERPNHYIEGI TKGSDLDLLE KGIRKTDEMT SNFTNYMYKF HRLPPNYGSN

101 QLITIDKELQ KELDGVMSSF KAPCRFVPGY GSGVFEQAGY SKSHSKPQID

151 IILGVTYPSH FHSINMRQNP QHYSSLKYFG SEFVSKFQQI GAGVYFNPFA

201 NINGHDVKYG VVSMETLLKD IATWNTFYLA GRLQKPVKIL KNDLRVQYWN

251 QLNLKAAATL AKHYTLEKNN NKFDEFQFYK EITALSYAGD IRYKLGGENP

301 DKVNNIVTKN FERFQEYYKP IYKEVVLNDS FYLPKGFTLK NTQRLLLSRI

351 SKSSALQTIK GVFTAGITKS IKYAWAKKLK SMRRS

FIGURE 60. *YJR041c* DNA Sequence

This sequence includes 1000bp of 5' promoter sequence.
Symbols: 1 to: 4525 from: chr10.gcg /rev ck: 4711, 509927 to: 514451
Chromosome X Sequence
EMBO J. 15:2031-2049 [8641269] (1996) Complete nucleotide sequence of Saccharomyces cerevisiae chromosome X.
Galibert, F., Alexandraki, D., Baur, A., Boles, E., Chalwatzis, N., Chuat, J. C., Coster, F., Cziepluch, C., De Haan, M., Domdey, H., . . .

gcgseq.tmp.25123 Length: 4525 March 26, 1999 11:33 Type: N Check: 4481 ..

```
   1 TACCTGCTGT AGAATCCTTC ACTGAAAACA CTTGTTCAAT ATATTCTTCA
  51 TCTGGTTCAC CGTCTGATCT ATTAATCCAG TTTAGCAATG ACTCAATAAA
 101 CTCTGATCTG TTCTCCTCTA CATCCTGACC ATCTAATATG AAGTACATTG
 151 TCCTCAGACA GTTTAAAACG GTTAAAGATT CTTCCAACTC ATAAAATCGG
 201 TTCACTCTTC CATCCTGATC CTTGACTCTA CCAATAAACA CTTCCAATTC
 251 ATTCAGAATC GCCTCCATGG CCAGATTTAC TGTTGCATTA TGCTCCTTCG
 301 CGAAATTAGA ATTAACAACT CCAATCGTTG GTACATTAAA CACTCTGTCA
 351 TCACCTAAAT CACGGTAAAT TTCAAATAAA CCTGATACGT ATGCAGAAAA
 401 CTCTTTGCTG GTATCTAATC TAGGAATTCT AACAGGATAA AGCTTATATT
 451 TATCTTTTGC AGTTATGAAT GCCATATTTT GGTAAGAAAG TGGCCCCAGC
 501 TTGAACTTTA AAGGCATCTT GTCGCCATTT TTTTCAATCG GTTGATCATT
 551 TACAGTCATA GGGACCAGGA TAGCCCCGCT GACTGGGTCC CTTTTATATA
 601 GTTGTTCTTC TTCATCGGTC TTGTTATTAC TAAGTTGCGC CGTTCCGTCG
 651 TCCAAAAAAT CAAATTGATC GACGTCCATA AGTAATCGAT TTGAATCATC
 701 GATTGTCATA TCTGATAATT GCGTTCTGGC TCACGCTTAT TGACTCAACT
 751 CAAGACCGTA AGTTCAATGT TTTCTATACA ACTACAATTT GTACAAGGCT
 801 TGACTTCCAT CCAACTAAAA AACCTCTCCG TCGTGCGCGA TCTGAAAAAT
 851 TTCACTTAGC TCATCTCAAA ATGATCGCTA AGAGGGCACT TGGTCACAAC
 901 TACAGAATTG TTTACTAGCA TAGGAACATC TCTGTCTAAG ATTTAGCTTG
 951 CCATCAATTA TCTTTGGAAA AACAGAGAGT ATACTGCACT TTTTGATAAT
1001 ATGGGTGATC TTACAGAAGA ACTATCTATC CCAGACAATG CCCAAGATTT
1051 GTCGAAATTA CTACGTTCGA CGAGCACAAA ACCCCATCAA ATTGCCGAGA
1101 TAGTTTCAAA ATTTGATAAA TTAGAAACCT ACTTTCCAAA AAAAGAAATT
1151 TTCGTCTTAG ATTTACTCAT TGATAGGCTC AACAATGGAA ATTTGGATGA
1201 TTTTAAGACC AGTGAACATA CTTGGATAAT TTTCACGAGA TTATTAGATG
1251 CTATTAATGA TCCAATTTCG ATAAAAAAAC TACTCAAAAA ATTGAAGACT
1301 GTGCCTGTAA TGATAAGAAC ATTTTTCCTT TGGCCTAAAG ACAAATTACT
1351 TACACGTAGC GTTTCGTTTA TAAAAGCATT TTTTGCGATT AATGACTACT
1401 TGATTGTCAA TTTTTCTGTT GAAGAGTCTT TTCAACTTTT AGAACATGCC
1451 ATAAATGGAT TAAGTTCGTG CCCGACGACT GACTTTGCGC TTTCATACTT
1501 GCAAGATGCC TGCAATCTAA CTCATGTTGA CAATATTACT ACAACGGATA
1551 ACAAAATTGC TACTTGTTAC TGCAAGCATA TGCTACTACC AAGTTTAAGA
1601 TATTTCGCAC AGACCAAAAA TTCTGCATCT TCAAACCAAT CCTTCATTCG
1651 TCTATCTCAT TTTATGGGAA AGTTCCTTTT ACAACCACGC ATAGATTACA
1701 TGAAATTAAA TAAAAAGTTT GTCCAAGAGA ATGCGTCCGA AATTACCGAC
1751 GATATGGCTT ATTATTATTT TGCCACTTTC GTCACTTTCT TATCAAAAGA
1801 CAATTTTGCT CAACTAGAAG TCATCTTTAC AATTTTAGGT GCCAAGAAAC
1851 CTAGTTTAGA ATGCAGATTT CTGAATCTTT TATCGGAATC GAAGAAAACC
1901 GTATCTCAAG AGTTCCTTGA AGCATTATTG CTTGAAATGT TAGCGTCGAC
1951 TGATGAATCT GGAGTGTTAT CATTAATACC AATTATCCTT AAATTGGATA
2001 TCGAGGTTGC TATTAAACAT ATTTTTCGGT TACTTGAATT GATTCAGCTC
2051 GAAAATTTGA ACGATCCTCT CTTTTCCTCT CATATTTGGG ATTTAATAAT
2101 CCAATCACAC GCTAACGCAA GGGAATTATC AGATTTTTTT GCCAAAATAA
```

```
2151 ATGAGTACTG TTCCAGAAAA GGACCCGATT CCTATTTTTT GATAAATCAT
2201 CCTGCATATG TCAAGTCTAT AACGAAGCAA TTGTTCACTT TATCTTCTTT
2251 ACAATGGAAA AATCTATTGC AAGCTTTACT TGACCAAGTC AATCACGATT
2301 CCACCAACAG GGTTCCTTTA TATTTAATAC GCATATGCTT GGAGGGACTA
2351 TCAGAGGGCG CATCGCGCGC AACTCTCGAT GAGGTAAAGC CTATTTTATC
2401 TCAAGTATTT ACTTTGGAAT CATTTAATAA CAGTCTTCAA TGGGACCTAA
2451 AGTATCATAT AATGGAAGTC TACGATGATA TTGTCCCTGC AGAGGAACTA
2501 GAAAAAATCG ATTACGTGTT ATCTTCTAAT ATTTTTGATA CTACATCGGC
2551 TGATGTTGAA GAACTGTTCT TTTATTGCTT CAAATTGAGA GAATATATTT
2601 CGTTCGATCT TTCTGATGCA AAAAAAAAAT TCATGAGGCA CTTTGAAATC
2651 CTTGACGAAG AAAGAAAGTC AAACTTATCA TACTCTGTTG TGTCCAAATT
2701 TGCAACATTA GTAAACAACA ACTTTACAAG AGAACAAATT TCTTCTTTAA
2751 TTGATTCATT ACTATTGAAC TCGACAAATT TATCTTCGTT ATTAAAAAAT
2801 GATGACATTT TTGAGGAGAC AAATATCACG TACGCTTTAA TAAACAAGCT
2851 TGCTTCATCA TACCATCAAA CCTTCGCTCT AGAAGCTTTG ATTCAAATTC
2901 CTATCCAATG CATCAACAAA AACGTTAGAG TGGCTCTCAT TAACAATCTA
2951 ACATGCGAAT CATTTTGCCT TGATTCCGCT ACTAGAGAAT GCCTCCTTCA
3001 TTTATTGTCA AGCCCGACCT TCAAGAGCAA CATTGAAACA AATTTCTACG
3051 AATTATGTGA GAAAACAATA ATGAGCCCCG AAATGGCCAT TTCAGAGACA
3101 GGTGATGAAA AAAAGGAAAT AGAAGACAAA ATATCTATTT TCGAAAAAGT
3151 TTGGACTAAT CATCTGTCAC AGGCAAAGGA GCCTGTGAGT GAGAAGTTCT
3201 TAGAATCTGG TTACGATATC GTTAAACAGT CAATGTCATT GTCCAATGGT
3251 GATAGCAAAC TAATTATCGC CGGGTTTACT ATCGCAAAAT TTTTGAAACC
3301 AGATAACAAG CATAGAGATA TACAAGGTAT GGCAATTAGC TATGCTGTTA
3351 AAATTTTGGA AAACTACTCT GAAAATTTTG AATCTGAAAC AATTCCCCTT
3401 TTCAGAATAT CAATGTCTAC ATTGTACAAG ATTATAACGA CCGGACAAGG
3451 CGATATTTCT AAGCATAAAT CGAGAATTCT GGATATATTT TCCAAAATTA
3501 TGCTTCGATA TCATTCTAAA AAAGTGTACC ATGCGCCAGA AGAACAGGAA
3551 ATGTTTTTGG TTCATTCACT CCTTACAGAA AACAAGTTGG AGTATATTTT
3601 TGCAGAGTAC TTAAATATTG AGCATACAGA TAAGTGCGAT TCTGCCTTGG
3651 GGTTCTGCTT GGAAGAAAGT CTTAAACAAG GTCCTGATGC GTTTAACCGC
3701 CTGCTCTGGA ACAGTGCTAA ATCGTTTTCC ACCATTAGCC AACCTTGTGC
3751 TGAAAAATTT GTGAGAGTTT TTATCATAAT GTCAAAAAGG ATTGCAAGAG
3801 ACAATAACCT TGGTCATCAC CTATTTGTGA TAGCTTTACT TGAAGCCTAC
3851 ACCTATTGTG ATATAGAAAA ATTTGGCTAC AAGTCATACT TGCTACTGTT
3901 CAATGCTATC AAGGAGTTCT TAGTATCGAA ACCATGGCTA TTCAGCCAAT
3951 ACTGTATTGA AATGCTGCTT CCTTTCTGTT TAAAAACTCT CGCTTTTATA
4001 GTAAACCATG AGTCAACGGA TGAAATCAAT GAAGGCTTTA TTAACATCAT
4051 CGAAGTGATA GATCATATGC TATTAGTTCA CAGGTTTAAA TTTTCCAATC
4101 GTCACCATTT GTTTAACTCC GTTCTTTGCC AGATACTAGA AATAATAGCA
4151 ATTCATGATG GTACATTGTG TGCAAATTCA GCAGACGCCG TAGCCAGACT
4201 AATAACGAAC TACTGCGAGC CTTATAATGT ATCAAACGCT CAAAATGGGC
4251 AGAAAAATAA CTTAAGCTCA AAGATAAGTT TGATAAAGCA GTCCATCAGA
4301 AAAAATGTAC TTGTGGTTCT AACGAAATAT ATACAGTTGT CTATTACGAC
4351 GCAGTTCAGT TTAAACATAA AAAAGAGTCT GCAGCCCGGT ATTCATGCGA
4401 TTTTTGATAT ATTATCTCAG AACGAGTTGA ATCAATTGAA CGCTTTCCTT
4451 GACACACCTG GGAAACAATA TTTCAAAGCA CTTTACCTCC AATACAAAAA
4501 GGTTGGTAAA TGGCGCGAAG ATTAA
```

FIGURE 60, cont.

Figure 61:
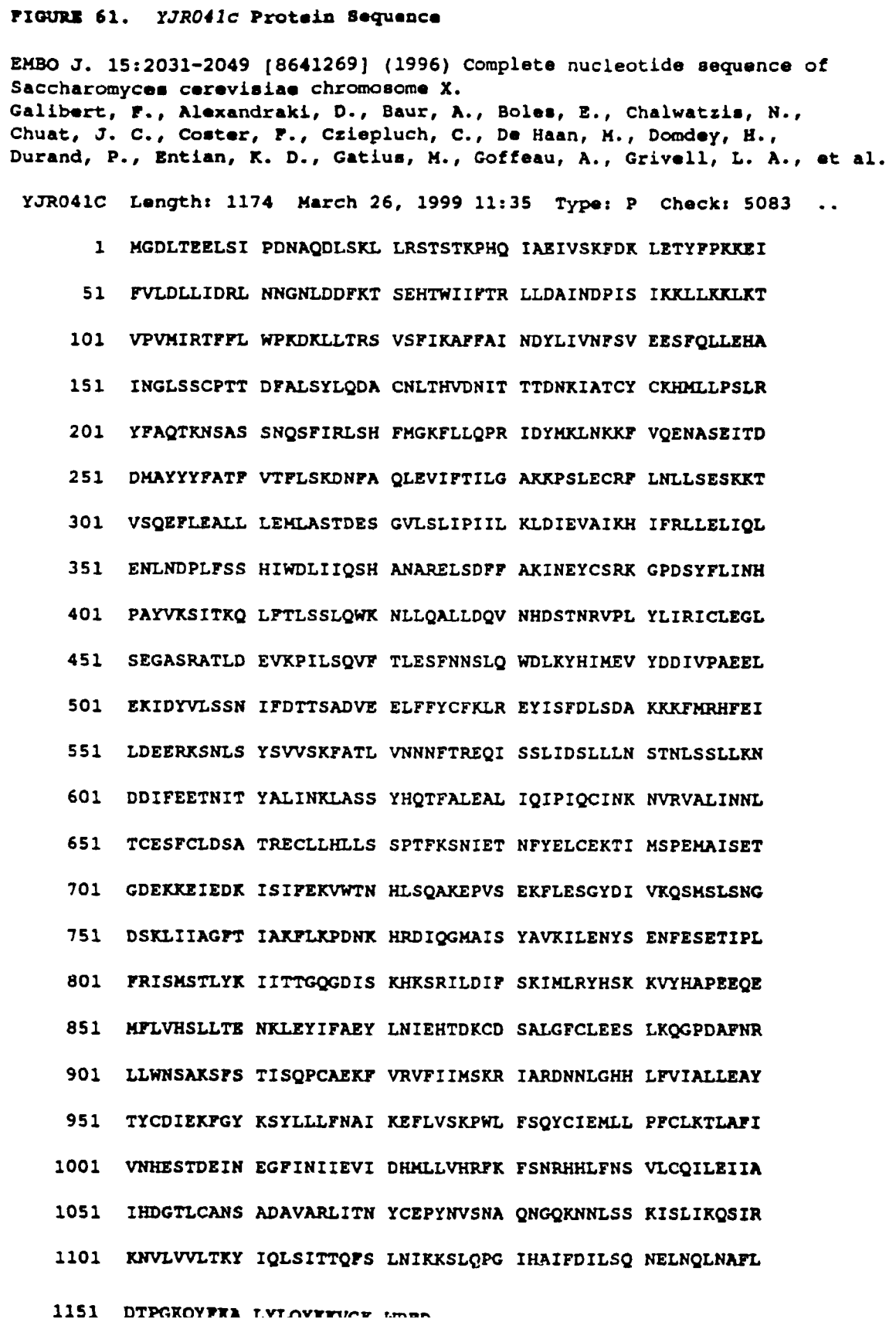

FIGURE 61. *YJR041c* Protein Sequence

EMBO J. 15:2031-2049 [8641269] (1996) Complete nucleotide sequence of Saccharomyces cerevisiae chromosome X.
Galibert, F., Alexandraki, D., Baur, A., Boles, E., Chalwatzis, N., Chuat, J. C., Coster, F., Cziepluch, C., De Haan, M., Domdey, H., Durand, P., Entian, K. D., Gatius, M., Goffeau, A., Grivell, L. A., et al.

YJR041C Length: 1174 March 26, 1999 11:35 Type: P Check: 5083 ..

```
   1  MGDLTEELSI PDNAQDLSKL LRSTSTKPHQ IAEIVSKFDK LETYFPKKEI
  51  FVLDLLIDRL NNGNLDDFKT SEHTWIIFTR LLDAINDPIS IKKLLKKLKT
 101  VPVMIRTFFL WPKDKLLTRS VSFIKAFFAI NDYLIVNFSV EESFQLLEHA
 151  INGLSSCPTT DFALSYLQDA CNLTHVDNIT TTDNKIATCY CKHMLLPSLR
 201  YFAQTKNSAS SNQSFIRLSH FMGKFLLQPR IDYMKLNKKF VQENASEITD
 251  DMAYYYFATF VTFLSKDNFA QLEVIFTILG AKKPSLECRF LNLLSESKKT
 301  VSQEFLEALL LEMLASTDES GVLSLIPIIL KLDIEVAIKH IFRLLELIQL
 351  ENLNDPLFSS HIWDLIIQSH ANARELSDFF AKINEYCSRK GPDSYFLINH
 401  PAYVKSITKQ LFTLSSLQWK NLLQALLDQV NHDSTNRVPL YLIRICLEGL
 451  SEGASRATLD EVKPILSQVF TLESFNNSLQ WDLKYHIMEV YDDIVPAEEL
 501  EKIDYVLSSN IFDTTSADVE ELFFYCFKLR EYISFDLSDA KKKFMRHFEI
 551  LDEERKSNLS YSVVSKFATL VNNNFTREQI SSLIDSLLLN STNLSSLLKN
 601  DDIFEETNIT YALINKLASS YHQTFALEAL IQIPIQCINK NVRVALINNL
 651  TCESFCLDSA TRECLLHLLS SPTFKSNIET NFYELCEKTI MSPEMAISET
 701  GDEKKEIEDK ISIFEKVWTN HLSQAKEPVS EKFLESGYDI VKQSMSLSNG
 751  DSKLIIAGFT IAKFLKPDNK HRDIQGMAIS YAVKILENYS ENFESETIPL
 801  FRISMSTLYK IITTGQGDIS KHKSRILDIF SKIMLRYHSK KVYHAPEEQE
 851  MFLVHSLLTE NKLEYIFAEY LNIEHTDKCD SALGFCLEES LKQGPDAFNR
 901  LLWNSAKSFS TISQPCAEKF VRVFIIMSKR IARDNNLGHH LFVIALLEAY
 951  TYCDIEKFGY KSYLLLFNAI KEFLVSKPWL FSQYCIEMLL PFCLKTLAFI
1001  VNHESTDEIN EGFINIIEVI DHMLLVHRFK FSNRHHLFNS VLCQILEIIA
1051  IHDGTLCANS ADAVARLITN YCEPYNVSNA QNGQKNNLSS KISLIKQSIR
1101  KNVLVVLTKY IQLSITTQFS LNIKKSLQPG IHAIFDILSQ NELNQLNAFL
1151  DTPGKQYFKA LYLQYKWVGK WDPD
```

FIGURE 62. *HES1* DNA Sequence

DNA sequence includes 1089bp 5' promoter sequence.
Symbols: 1 to: 2394 from: chr15.gcg ck: 9129, 780903 to: 783296
Chromosome XV Sequence
Nature 387:98-102 [97313270] (1997) The nucleotide sequence of Saccharomyces cerevisiae chromosome XV.
Dujon, B., Albermann, K., Aldea, M., Alexandraki, D., Ansorge, W., Arino, J., Benes, V., Bohn, C., Bolotin-Fukuhara, M., Bordonne, R., . . .

gcgseq.tmp.10515 Length: 2394 March 26, 1999 14:35 Type: N Check: 4842 ..

```
   1 CATGGCTGGA GGAAAGATTC CTATTGTAGG AATTGTGGCA TGTTTACAGC
  51 CGGAGATGGG GATAGGATTT CGTGGAGGTC TACCATGGAG GTTGCCCAGT
 101 GAAATGAAGT ATTTCAGACA GGTCACTTCA TTGACGAAAG ATCCAAACAA
 151 AAAAAATGCT TTGATAATGG GAAGGAAGAC ATGGGAATCC ATACCGCCCA
 201 AGTTTCGCCC ACTGCCCAAT AGAATGAATG TCATTATATC GAGAAGCTTC
 251 AAGGACGATT TTGTCCACGA TAAAGAGAGA TCAATAGTCC AAAGTAATTC
 301 ATTGGCAAAC GCAATAATGA ACCTAGAAAG CAATTTTAAG GAGCATCTGG
 351 AAAGAATCTA CGTGATTGGG GGTGGCGAAG TTTATAGTCA AATCTTCTCC
 401 ATTACAGATC ATTGGCTCAT CACGAAAATA AATCCATTAG ATAAAAACGC
 451 AACTCCTGCA ATGGACACTT TCCTTGATGC GAAGAAATTG GAAGAAGTAT
 501 TTAGCGAGCA AGATCCGGCC CAGCTGAAAG AATTTCTTCC CCCTAAAGTA
 551 GAGTTGCCCG AAACAGACTG TGATCAACGC TACTCGCTGG AAGAAAAAGG
 601 TTATTGCTTC GAATTCACTC TATACAATCG TAAATGAAAC CTCTCCGCCC
 651 GTATATTTTT TTTAATATGT TAAATAGTGA TAGAACTGAT AAGCCTCATT
 701 TTCTTTTATT GGGCTCCAAG ACGCGAACTG TTCGTAGGGT AACCGTTTGA
 751 CACCTAAACG ACCTTTCAGC CTCACCTGCA GTATTTCTTC AACAACGCCT
 801 GTCGCTATGT TAAATAATAG CAATCGTTTG TGATCACCAT TGTCGAATTT
 851 GACGCGCTTA AACAAAAACC ATTGTTTTGG CCTCGTTCCC TGCATTCAAC
 901 AAAAGAGCAA GGTATGCCGT CAAACAGTCG TTAAAAGAGA AGGTTTATAA
 951 ACTATCTTGT TTTGTACTTT GCTGTCCCGG ATCCAGTTGG GTCTTCTTTT
1001 CAACCTGTCT GAGTCCGATC TTTCTTTCCC TACTTGAAGC TCCATATATC
1051 TAAGTCATCT AAGTGTATCC TGCTAGATTA CAAACGAAAA TGTCTCAACA
1101 CGCAAGCTCA TCTTCTTGGA CTTCTTTTTT GAAATCGATA AGTTCGTTCA
1151 ACGGAGATCT ATCGTCTTTG TCTGCACCAC CGTTTATTCT TTCTCCCACT
1201 TCCTTAACAG AGTTTTCTCA GTATTGGGCT GAACATCCAG CTTTATTTCT
1251 GGAGCCTTCG TTGATTGATG GTGAAAACTA CAAAGATCAC TGTCCCTTTG
1301 ACCCAAATGT GGAATCAAAG GAAGTGGCGC AGATGTTGGC GGTTGTTAGG
1351 TGGTTTATTT CTACTTTGAG ATCTCAATAC TGCTCTAGAA GCGAATCGAT
1401 GGGTTCTGAA AAGAAGCCTT TGAACCCATT CTTGGGTGAG GTATTTGTTG
1451 GAAAGTGGAA AAATGATGAG CATCCAGAGT TTGGTGAAAC GGTTCTTTTA
1501 AGTGAGCAAG TTTCACATCA TCCACCTATG ACAGCATTTT CGATTTTTAA
1551 TGAAAAAAAT GATGTTTCTG TTCAAGGATA CAATCAAATT AAAACTGGTT
1601 TTACCAAAAC ATTGACGCTA ACGGTCAAAC CATACGGGCA TGTCATTTTG
1651 AAGATTAAAG ATGAGACCTA CCTGATTACA ACCCCGCCTT TGCATATCGA
1701 AGGTATTTTA GTCGCTTCTC CATTTGTTGA ATTAGGAGGC AGGTCATTCA
1751 TACAGTCATC AAATGGTATG TTATGTGTTA TAGAATTTTC AGGAAGGGGG
1801 TATTTCACAG GGAAGAAGAA CTCCTTTAAG GCAAGAATTT ACAGAAGCCC
1851 ACAAGAGCAT AGTCATAAAG AAAATGCGCT ATACCTAATC TCTGGCCAAT
1901 GGTCAGGTGT TTCAACAATT ATAAAAAAAG ACTCGCAAGT TTCACATCAG
1951 TTTTACGATT CATCGGAAAC TCCTACTGAA CATTTATTAG TTAAGCCAAT
2001 CGAAGAACAA CATCCTCTGG AAAGTAGGAG GGCATGGAAG GATGTGGCAG
2051 AAGCAATCAG ACAAGGAAAT ATTAGTATGA TAAAAAAGAC TAAGGAAGAA
2101 CTAGAAAATA AGCAAAGAGC CTTGAGAGAA CAAGAACGCG TAAAAGGTGT
```

```
2151  GGAATGGCAA AGAAGATGGT TCAAACAAGT GGACTACATG AATGAAAATA
2201  CATCAAATGA TGTAGAGAAA GCAAGTGAAG ATGATGCCTT TAGGAAATTG
2251  GCGTCCAAAC TGCAGCTTTC TGTGAAAAAT GTGCCAAGTG GGACATTGAT
2301  TGGCGGCAAA GATGATAAGA AAGATGTTTC AACCGCATTG CATTGGAGGT
2351  TTGATAAAAA TTTGTGGATG AGGGAGAACG AAATTACTAT ATAA
```

FIGURE 62, cont.

FIGURE 63. *HES1* Protein Sequence

Nature 387:98-102 [97313270] (1997) The nucleotide sequence of Saccharomyces cerevisiae chromosome XV.

Dujon, B., Albermann, K., Aldea, M., Alexandraki, D., Ansorge, W., Arino, J., Benes, V., Bohn, C., Bolotin-Fukuhara, M., Bordonne, R., Boyer, J., Camasses, A., Casamayor, A., Casas, C., Cheret, G., et al.

YOR237W Length: 434 March 26, 1999 14:37 Type: P Check: 7501 ..

```
  1 MSQHASSSSW TSFLKSISSF NGDLSSLSAP PFILSPTSLT EFSQYWAEHP
 51 ALFLEPSLID GENYKDHCPF DPNVESKEVA QMLAVVRWFI STLRSQYCSR
101 SESMGSEKKP LNPFLGEVFV GKWKNDEHPE FGETVLLSEQ VSHHPPMTAF
151 SIFNEKNDVS VQGYNQIKTG FTKTLTLTVK PYGHVILKIK DETYLITTPP
201 LHIEGILVAS PFVELGGRSF IQSSNGMLCV IEFSGRGYFT GKKNSFKARI
251 YRSPQEHSHK ENALYLISGQ WSGVSTIIKK DSQVSHQFYD SSETPTEHLL
301 VKPIEEQHPL ESRRAWKDVA EAIRQGNISM IKKTKEELEN KQRALREQER
351 VKGVEWQRRW FKQVDYMNEN TSNDVEKASE DDAFRKLASK LQLSVKNVPS
401 GTLIGGKDDK KDVSTALHWR FDKNLWMREN EITI
```

**FIGURE 65. Rat Gene with Similarity to *YLR100w***

```
LOCUS       1397235         334 aa                              04-FEB-1999
DEFINITION  ovarian-specific protein.
ACCESSION   1397235
PID         g1397235
DBSOURCE    locus RNU44803 accession U448031
KEYWORDS    .
SOURCE      Norway rat.
  ORGANISM  Rattus norvegicus
            Eukaryotae; mitochondrial eukaryotes; Metazoa; Chordata;
            Vertebrata; Eutheria; Rodentia; Sciurognathi; Myomorpha; Muridae;
            Murinae; Rattus.
REFERENCE   1  (residues 1 to 334)
  AUTHORS   Duan,W.R., Linzer,D.I.H. and Gibori,G.
  TITLE     Cloning and characterization of an ovarian-specific protein that
            associates with the short form of the prolactin receptor
  JOURNAL   J. Biol. Chem. 271 (26), 15602-15607 (1996)
  MEDLINE   96279080
REFERENCE   2  (residues 1 to 334)
  AUTHORS   Gibori,G. and Duan,W.R.
  TITLE     Direct Submission
  JOURNAL   Submitted (05-JAN-1996) Geula Gibori, Department of Physiology,
            University of Illinois at Chicago, Chicago, IL 60612, USA
COMMENT     Method: conceptual translation.
FEATURES             Location/Qualifiers
     source          1..334
                     /organism="Rattus norvegicus"
                     /strain="Sprague-Dawley"
                     /db_xref="taxon:10116"
                     /sex="female"
                     /tissue_type="corpus luteum"
                     /dev_stage="pregnant"
                     /cell_type="luteal"
     Protein         1..334
                     /product="ovarian-specific protein"
     CDS             1..334
                     /note="The protein can associate with the short form of
                     prolactin receptor in the rat corpus luteum."
                     /coded_by="U44803:15..1019"
ORIGIN
        1 mrkvvlitga ssgiglalcg rllaedddlh lclacrnlsk agavrdalla shpsaevsiv
       61 qmdvsnlqsv vrgaeevkrr fqrldylyln agimpnpqln lkaffcgifs rnvihmfsta
      121 eglltqndki tadgfqevfe tnlfghfili releplichs dnpsqliwts srnakksnfs
      181 lediqhakgq epyssskyat dllnvalnrn fnqkglyssv tcpgvvmtnl tygilppfvw
      241 tlllpviwll rffahaftvt pyngaealvw lfhqkpesln pltkylsgtt glgtnyvkgq
      301 kmdvdedtae kfyktllele kqvritiqks dhhs
```

FIGURE 66. *DAK1* DNA Sequence

This sequence contains 1200bp of 5' promoter sequence.
Symbols: 1 to: 2955 from: chr13.gcg ck: 8335, 132275 to: 135229

Chromosome XIII Sequence
Nature 387:90-93 [97313268] (1997) The nucleotide sequence of Saccharomyces cerevisiae chromosome XIII.
Bowman, S., Churcher, C., Badcock, K., Brown, D., Chillingworth, T., Connor, R., Dedman, K., Devlin, K., Gentles, S., Hamlin, N., Hunt, S., .

gcgseq.tmp.16080 Length: 2955 March 31, 1999 09:57 Type: N Check: 5254 ..

```
   1 TAATATAAAT ACTAGTCGTT AGATGATAGT TGCTTCTTAT TCCGAAAATG
  51 AGTATGGAAG TGTTGCATAT GATAGGGCGG CTACAGTGAT GGTAAACATA
 101 AGATACTTTA GCGGGAAATT AGCAACTGGA AGTTAAATTA TCTAGACATA
 151 AGTGTGGCGG TCACGCTGAA CGCAGGAGAT CGGATAGATT GATAAGCTGA
 201 TCAAGAACAT TGATCGGTTT GTTGTTTAAA GAATGGTTTT TGAAAACGTT
 251 TGACCAGTTG CTTCTCCCAG ACGCTTACCG ATATGATGAT AAAGATAATA
 301 TCTTCAATTG AATACCCCGT GGATCAGCAC GAATAACAGA AAAAAAGGGT
 351 GAAATTCACC GTAAGCATGA TACGCACTAC GTTCTTCTTA CCTTTGCCAA
 401 CGTGTTGTCT TTGACGTACG TAATTATGGG AGATCGTTGA TGATTAGCCC
 451 CAGCTCACTT TCTTCTTAAT GACTGACCCG CTACTATCAA AATTAAGGTG
 501 TCAAATATCA TGATGAATGA GGTCTCTAGG CGACTCAATT ATACATCTTT
 551 TAGAGATTTT TTTACTACTT GCAGATAATT TCTCAAGGGA TTAGATTCAA
 601 ATCTGGCTTG TCAATTACGC CCTTTTCAAG CTCATCAAAT TGCGTATGTC
 651 ATTCATGCTT CCATTAGGAA CCATAGAAGC ATGGCTGAAA TGGCAATATA
 701 CGGCTTCCCA ATTTCAACTC TAAAGTAATG GCGGTCGAAT TTAATCTATA
 751 TTTTACAGTT TTATACGTAC TTTAAAAGCA ATCAGTAAAC ACCTCTGGTG
 801 CTATTCAAGG GTTTTTTGCC TTTATTTGTT ACTGTCAATT GTCTGGCGCT
 851 GTGATAAAAA ACAAGGCATA AAGCTCCCCC GTCATGAACA TTAAGACTCG
 901 CTAGACGAGA GAGTGAAATA TAATGCATTT CCTGATTTAA ATGCGCTACA
 951 AACATGGTGT AAATCTGGCC CGGAGTGAGT GCTTGCCAAT TTGGCTTCTA
1001 AGGGAGAAAG ATCAAACCAC TCCCAATTGC GTCATTTTGA AAGAGTGGCC
1051 ACCTCGCGAG CGTCTGTCGA ACTAACTGAT GAATAAATAT ATAAGGAGAA
1101 AATCACTTCA ACTTCGCTAC AAGTAGTCAC TATTTGTAGC AACTGTAAAC
1151 GAACACATCA AAGAATAAGA TTACATTCTA TATCTAAGAC TAAATTTTAA
1201 ATGTCCGCTA AATCGTTTGA AGTCACAGAT CCAGTCAATT CAAGTCTCAA
1251 AGGGTTTGCC CTTGCTAACC CCTCCATTAC GCTGGTCCCT GAAGAAAAAA
1301 TTCTCTTCAG AAAGACCGAT TCCGACAAGA TCGCATTAAT TTCTGGTGGT
1351 GGTAGTGGAC ATGAACCTAC ACACGCCGGT TTCATTGGTA AGGGTATGTT
1401 GAGTGGCGCC GTGGTTGGCG AAATTTTTGC ATCCCCTTCA ACAAAACAGA
1451 TTTTAAATGC AATCCGTTTA GTCAATGAAA ATGCGTCTGG CGTTTTATTG
1501 ATTGTGAAGA ACTACACAGG TGATGTTTTG CATTTTGGTC TGTCCGCTGA
1551 GAGAGCAAGA GCCTTGGGTA TTAACTGCCG CGTTGCTGTC ATAGGTGATG
1601 ATGTTGCAGT TGGCAGAGAA AAGGGTGGTA TGGTTGGTAG AAGAGCATTG
1651 GCAGGTACCG TTTTGGTTCA TAAGATTGTA GGTGCCTTCG CAGAAGAATA
1701 TTCTAGTAAG TATGGCTTAG ACGGTACAGC TAAAGTGGCT AAAATTATCA
1751 ACGACAATTT GGTGACCATT GGATCTTCTT TAGACCATTG TAAAGTTCCT
1801 GGCAGGAAAT TCGAAAGTGA ATTAAACGAA AAACAAATGG AATTGGGTAT
1851 GGGTATTCAT AACGAACCTG GTGTGAAAGT TTTAGACCCT ATTCCTTCTA
1901 CCGAAGACTT GATCTCCAAG TATATGCTAC CAAAACTATT GGATCCAAAC
1951 GATAAGGATA GAGCTTTTGT AAAGTTTGAT GAAGATGATG AAGTTGTCTT
2001 GTTAGTTAAC AATCTCGGCG GTGTTTCTAA TTTTGTTATT AGTTCTATCA
2051 CTTCCAAAAC TACGGATTTC TTAAAGGAAA ATTACAACAT AACCCCGGTT
2101 CAAACAATTG CTGGCACATT GATGACCTCC TTCAATGGTA ATGGGTTCAG
2151 TATCACATTA CTAAACGCCA CTAAGGCTAC AAAGGCTTTG CAATCTGATT
2201 TTGAGGAGAT CAAATCAGTA CTAGACTTGT TGAACGCATT TACGAACGCA
2251 CCGGGCTGGC CAATTGCAGA TTTTGAAAAG ACTTCTGCCC CATCTGTTAA
2301 CGATGACTTG TTACATAATG AAGTAACAGC AAAGGCCGTC GGTACCTATG
2351 ACTTTGACAA GTTTGCTGAG TGGATGAAGA GTGGTGCTGA ACAAGTTATC
```

```
2401  AAGAGCGAAC CGCACATTAC GGAACTAGAC AATCAAGTTG GTGATGGTGA
2451  TTGTGGTTAC ACTTTAGTGG CAGGAGTTAA AGGCATCACC GAAAACCTTG
2501  ACAAGCTGTC GAAGGACTCA TTATCTCAGG CGGTTGCCCA AATTTCAGAT
2551  TTCATTGAAG GCTCAATGGG AGGTACTTCT GGTGGTTTAT ATTCTATTCT
2601  TTTGTCGGGT TTTTCACACG GATTAATTCA GGTTTGTAAA TCAAAGGATG
2651  AACCCGTCAC TAAGGAAATT GTGGCTAAGT CACTCGGAAT TGCATTGGAT
2701  ACTTTATACA AATATACAAA GGCAAGGAAG GGATCATCCA CCATGATTGA
2751  TGCTTTAGAA CCATTCGTTA AAGAATTTAC TGCATCTAAG GATTTCAATA
2801  AGGCGGTAAA AGCTGCAGAG GAAGGTGCTA AATCCACTGC TACATTCGAG
2851  GCCAAATTTG GCAGAGCTTC GTATGTCGGC GATTCATCTC AAGTAGAAGA
2901  TCCTGGTGCA GTAGGCCTAT GTGAGTTTTT GAAGGGGGTT CAAAGCGCCT
2951  TGTAA
```

FIGURE 66, cont.

**FIGURE 67. *DAK1* Protein Sequence**

Nature 387:90-93 [97313268] (1997) The nucleotide sequence of Saccharomyces cerevisiae chromosome XIII.

Bowman, S., Churcher, C., Badcock, K., Brown, D., Chillingworth, T., Connor, R., Dedman, K., Devlin, K., Gentles, S., Hamlin, N., Hunt, S., Jagels, K., Lye, G., Moule, S., Odell, C., Pearson, D., Rajandream, et al.

YML070W Length: 584 March 31, 1999 09:58 Type: P Check: 167 ..

```
  1 MSAKSFEVTD PVNSSLKGFA LANPSITLVP EEKILFRKTD SDKIALISGG
 51 GSGHEPTHAG FIGKGMLSGA VVGEIFASPS TKQILNAIRL VNENASGVLL
101 IVKNYTGDVL HFGLSAERAR ALGINCRVAV IGDDVAVGRE KGGMVGRRAL
151 AGTVLVHKIV GAFAEEYSSK YGLDGTAKVA KIINDNLVTI GSSLDHCKVP
201 GRKFESELNE KQMELGMGIH NEPGVKVLDP IPSTEDLISK YMLPKLLDPN
251 DKDRAFVKFD EDDEVVLLVN NLGGVSNFVI SSITSKTTDF LKENYNITPV
301 QTIAGTLMTS FNGNGFSITL LNATKATKAL QSDFEEIKSV LDLLNAFTNA
351 PGWPIADFEK TSAPSVNDDL LHNEVTAKAV GTYDFDKFAE WMKSGAEQVI
401 KSEPHITELD NQVGDGDCGY TLVAGVKGIT ENLDKLSKDS LSQAVAQISD
451 FIEGSMGGTS GGLYSILLSG FSHGLIQVCK SKDEPVTKEI VAKSLGIALD
501 TLYKYTKARK GSSTMIDALE PFVKEFTASK DFNKAVKAAE EGAKSTATFE
551 AKFGRASYVG DSSQVEDPGA VGLCEFLKGV QSAL
```

FIGURE 68. *PGU1* DNA Sequence

DNA sequence includes 1200bp of 5' promoter sequence.
Symbols: 1 to: 2286 from: chr10.gcg ck: 4711, 721304 to: 723589
Chromosome X Sequence
EMBO J. 15:2031-2049 [8641269] (1996) Complete nucleotide sequence of Saccharomyces cerevisiae chromosome X.
Galibert, F., Alexandraki, D., Baur, A., Boles, E., Chalwatzis, N., Chuat, J. C., Coster, F., Cziepluch, C., De Haan, M., Domdey, H., . .

gcgseq.tmp.30022 Length: 2286 March 31, 1999 09:20 Type: N Check: 4618 ..

```
   1 ATGATTCTGA CGACCCTTTG ATAGTGGCAA TGATCAAAAA GAAAAAAAAA
  51 AGATAAGACG GTAGTGTGAA GATGACATAT AGCGCTACTC TATACTCGTC
 101 CAACTTCGAA AATAATATGT GGTCGTTGGT ACGTTCAGAT AAGAGAATAC
 151 ATCTCGCGCG TACGCATAAT TGTGGTCTAA AAAACCGCTG AAATTTTCTC
 201 AATACTGAAT AGAATCACGC TACTACGACA AGACTCGGTT ACTGTGCCTA
 251 AAATAATCCT GTGATAAACG AGTTATGTTA AACGCAGTAC AGGGGTTAAA
 301 GGGCATTGAG TTTTTGTGAG TGGAAATGCC CCCGTTATAG CTTCCAGTTT
 351 AATTACAAAT TATCAATTTA AGCAAATATA ACTGGAGGAT TGGGGAGGCG
 401 ACTAAAAATG GCTACCACGC TATTAGACAT ACAACATTGA GTATTTTATG
 451 TAATTTTGTT ACTGCTAGCA CGGCCATGCA ATTGGCAACT GAAAGCTATC
 501 TGACAACTTA AATGATTCTT AAAACAATGA CGACTATAAT CTTCTCTAAG
 551 AAGTTTCATA TCCATCTTCC TCATTATTCA GTTTCTTTTT CCTCTTGAAA
 601 GTATCGTAAA GAACAACGTC TTCACATTAG CTATTAGAAG ACCATTGAAC
 651 TACCGGATAT GAGTAAGAGT GATCTTGCCG GAGAGATAAT AGCTGCACAA
 701 AGGCCAAGGA TTAGATTAAT GGGTGCATTG TACGAAAAAA AATAGTTTAC
 751 AGTCATTTAT TCGCAATAAA TCAATTTTTT TTTCAAAAAA TATGTAAGTC
 801 TGATAAAAAA TTCTTCACTG AAGAGAGATG CTTACATTCT AATTCTTGAA
 851 TAAAAGACTC TCTAACGCTG TGAATTCTCT TTAGCTGTAA CGGAAACAGA
 901 GAGTTATTCC GTAGTCACTG AATTTTTTTT TTTTGACGCT ATTATTTAAA
 951 ACCTAGGATA TCCGTCCCAT ACAAAACGGC CACGAGTTTC AATCCCAGAA
1001 TGTACGAGTT ATAATTCTCC TAGATGCATG ATACTCGTGC ATTCGTTTAA
1051 CAATCATACC AATTTCCCAT TTTCGGGATA TTAAACATGA ACATACTTTT
1101 TTACTGTGAG AATGTGGTTT CACAATTATT CCATACAGGT ATAAAAAACGC
1151 ACAGAACTTC AAACGGGAAG ACTATCTACC CACATTGATG GACAAACGCA
1201 ATGATTTCTG CTAATTCATT ACTTATTTCC ACTTTGTGCG CTTTTGCGAT
1251 CGCAACACCT TTGTCAAAAA GAGATTCCTG TACCCTAACA GGATCTTCTT
1301 TGTCTTCACT CTCAACCGTG AAAAAATGTA GCAGCATCGT TATTAAAGAC
1351 TTAACTGTCC CAGCTGGACA GACTTTAGAT TTAACTGGGT TAAGCAGTGG
1401 TACTACTGTT ACGTTTGAAG GCACAACCAC ATTTCAGTAC AAGGAATGGA
1451 GCGGCCCTTT AATTTCAATC TCAGGGTCTA AAATCAGCGT TGTTGGTGCT
1501 TCGGGACATA CCATTGATGG TCAAGGAGCA AAATGGTGGG ATGGCTTAGG
1551 TGATAGCGGT AAAGTCAAAC CGAAGTTTGT AAAGTTGGCG TTGACGGGAA
1601 CATCTAAGGT CACCGGATTG AATATTAAAA ATGCTCCACA CCAAGTCTTC
1651 AGCATCAATA AATGTTCAGA TTTAACCATC AGCGACATAA CAATTGATAT
1701 CAGAGACGGT GATTCGGCTG GTGGTCATAA TACGGATGGG TTTGATGTTG
1751 GTAGTTCTAG TAACGTCTTA ATTCAAGGAT GTACTGTTTA TAATCAGGAT
1801 GACTGTATTG CTGTGAATTC CGGTTCAACT ATTAAATTTA TGAACAACTA
1851 CTGCTACAAT GGCCATGGTA TTTCTGTAGG TTCTGTTGGT GGCCGTTCTG
1901 ATAATACAGT CAATGGTTTC TGGGCTGAAA ATAACCATGT TATCAACTCT
1951 GACAACGGGT TGAGAATAAA AACCGTAGAA GGTGCGACAG GCACAGTCAC
2001 TAATGTCAAC TTTATCAGTA ATAAAATTAG CGGCATAAAA AGTTATGGTA
2051 TTGTTATCGA AGGCGATTAT TTGAATAGTA AGACTACTGG AACTGCTACA
2101 GGTGGCGTTC CCATTTCGAA TTTAGTAATG AAGGATATCA CCGGGAGCGT
2151 GAACTCCACA GCGAAGAGGG TTAAAATTTT GGTGAAAAAC GCTACTAACT
2201 GGCAATGGTC TGGGGTGTCA ATTACCGGTG GTTCTTCCTA TTCTGGATGT
2251 TCTGGAATCC CATCTGGATC TGGTGCAAGC TGTTAA
```

FIGURE 69. *PGU1* Protein Sequence

EMBO J. 15:2031-2049 [8641269] (1996) Complete nucleotide sequence of Saccharomyces cerevisiae chromosome X.

Galibert, F., Alexandraki, D., Baur, A., Boles, E., Chalwatzis, N., Chuat, J. C., Coster, F., Cziepluch, C., De Haan, M., Domdey, H., Durand, P., Entian, K. D., Gatius, M., Goffeau, A., Grivell, L. A., et al.

YJR153W Length: 361 March 31, 1999 09:55 Type: P Check: 9795

```
  1 MISANSLLIS TLCAFAIATP LSKRDSCTLT GSSLSSLSTV KKCSSIVIKD
 51 LTVPAGQTLD LTGLSSGTTV TFEGTTTFQY KEWSGPLISI SGSKISVVGA
101 SGHTIDGQGA KWWDGLGDSG KVKPKFVKLA LTGTSKVTGL NIKNAPHQVF
151 SINKCSDLTI SDITIDIRDG DSAGGHNTDG FDVGSSSNVL IQGCTVYNQD
201 DCIAVNSGST IKFMNNYCYN GHGISVGSVG GRSDNTVNGF WAENNHVINS
251 DNGLRIKTVE GATGTVTNVN FISNKISGIK SYGIVIEGDY LNSKTTGTAT
301 GGVPISNLVM KDITGSVNST AKRVKILVKN ATNWQWSGVS ITGGSSYSGC
351 SGIPSGSGAS C
```

FIGURE 70. *STE18* DNA Sequence

This sequence contains 600bp of 5' promoter sequence.
Symbols: 1 to: 933 from: chr10.gcg ck: 4711, 585156 to: 586088

Chromosome X Sequence
EMBO J. 15:2031-2049 [8641269] (1996) Complete nucleotide sequence of Saccharomyces cerevisiae chromosome X.
Galibert, F., Alexandraki, D., Baur, A., Boles, E., Chalwatzis, N., Chuat, J. C., Coster, F., Cziepluch, C., De Haan, M., Domdey, H., . .

gcgseq.tmp.6719 Length: 933 March 31, 1999 10:01 Type: N Check: 8833 ..

```
  1 TTCGTTTCTG TCTTGTCTCC CGCTGTTACC TAATAACTTC ATGTGATCTG
 51 CTCCCCCTTC TCGTTAAATA CCACCTTTTC ATCAACCCCG TAGGGCGCGA
101 CACGTCTAAA ATATTAACCT CTGAATACTT ATTGGGTCAA AATGAATGTT
151 GATAACTTTC CTTTACAAAA AAAAAACTAA TAGAGTATAT GCATTTCGGT
201 AGTGAAATAT TCGTTAATGC TAATATGCTC AGTAGTGATC CTAGATTACC
251 AGTTTTACTG CAGCCATCGT ACAATTTTGG AACGAGTATA AAGAGAGAAA
301 TTAAAAACGA CAAGAAATAT TCGTACTAGC TTCTCTTCCG GCTTGATGAC
351 AGTCTTAATA TCATCTGCAA CTCTTGAAAT CTTGCTTTAT AGTCAAAATT
401 TACGTACGCT TTTCACTATA TAATATGATT TGTCAATGTG ATGAGTGAAT
451 GTCTCCCTGT TACCCGGTTT TCATGTTGAT TTTTGTTTCA GGCTCTAAAT
501 GTTTGATGCA ATATTTAACA AGGAGAACAG AAATGTTTTG TGACAGCACC
551 TGTCAATTTT AGGATAGTAG CAATCGCAAA CGTTCTCAAT AATTCTAAGA
601 ATGACATCAG TTCAAAACTC TCCACGCTTA CAACAACCTC AGGAACAGCA
651 ACAGCAACAG CAACAGCTTT CCTTAAAGAT AAAACAATTG AAGTTAAAAA
701 GAATCAACGA ACTTAACAAT AAACTGAGGA AAGAACTCAG CCGTGAAAGA
751 ATTACTGCTT CAAATGCATG TCTTACAATA ATAAACTATA CCTCGAATAC
801 AAAAGATTAT ACATTACCAG AACTATGGGG CTACCCCGTA GCAGGATCAA
851 ATCATTTTAT AGAGGGTTTG AAAAATGCTC AAAAAAATAG CCAAATGTCA
901 AACTCAAATA GTGTTTGTTG TACGCTTATG TAA
```

**FIGURE 71. *STE18* Protein Sequence**

EMBO J. 15:2031-2049 [8641269] (1996) Complete nucleotide sequence of Saccharomyces cerevisiae chromosome X.

Galibert, F., Alexandraki, D., Baur, A., Boles, E., Chalwatzis, N., Chuat, J. C., Coster, F., Cziepluch, C., De Haan, M., Domdey, H., Durand, P., Entian, K. D., Gatius, M., Goffeau, A., Grivell, L. A., et al.

YJR086W Length: 110 March 31, 1999 10:02 Type: P Check: 6859

```
  1 MTSVQNSPRL QQPQEQQQQQ QQLSLKIKQL KLKRINELNN KLRKELSRER

 51 ITASNACLTI INYTSNTKDY TLPELWGYPV AGSNHFIEGL KNAQKNSQMS

101 NSNSVCCTLM
```

FIGURE 72. *YGL198w* DNA Sequence

This sequence contains 989bp of 5' promoter sequence.
Symbols: 1 to: 1775 from: chr7.gcg ck: 9962, 122605 to: 124379

Chromosome VII Sequence
Nature 387:81-84 [97313265] (1997) The nucleotide sequence of Saccharomyces cerevisiae chromosome VII.
Tettelin, H., Agostoni Carbone, M. L., Albermann, K., Albers, M., Arroyo, J., Backes, U., Barreiros, T., Bertani, I., Bjourson, A. J., gcgseq.tmp.32650 Length: 1775 March 31, 1999 10:03 Type: N Check: 2850

```
   1 GAGAATTATT CGCGACTTCA GGTTATCCAA TCGTGTATGT AATCGTATGT
  51 AGGCAAAAGT AAATAGATAT GAACTACATT TTCCTGCTTT ACTTAGACTA
 101 GAGATGTGAC CTCAAAGAAT CTTCTCAAGT AGTATATCTG GAAAAGAGAG
 151 TTTGCAATAA CGACGCCCAA TTGGAAGATG GACCACCATT TAACACGATC
 201 GTTGGTCGAC TCTGCAGTAT TTCTATGCGT CCTTTCTCTA ATAACAATAT
 251 AACTTTGTTC GTCCTTGACT TCCCTGGTTA ATTTGGACAA CTTTCTGACA
 301 GCACTATCCA ATGTATTGGT GTTTGGGTCG TCCAAATCCA CATATACCAC
 351 CCCATGAATG TTGAAAGTCA CGTCTTTTGT CTCGATACCG GTGTTCTCGT
 401 TCAAGAAACA GTATTGGAAA TGTCCCTTGT ATGGAGCAGA CAATGTGATT
 451 TCACCGTGCG ACGTGTCCCT AACCGTTTTC AAAACTTCAT GTCTTTCCGG
 501 CCCGTAGATG ATAAAGTCAC CAGTCAGCTG GCTACTGGAT TGAGGGTTTC
 551 TATCACCGAA CTGGAACGAA ATGGAGAGCT CGTCACCCTT ACTCAAGTCT
 601 TCGAAGAAGC ATCTACGGCC ATAAGCTGGA AGAAGGACAT TATGGGCGGA
 651 CGCCGAGAAG AACAGGAAGC AAGCAATGAC AAACTTAGTA GCAAATGAGG
 701 CCATCCTTAT GCGTGTGTAT TTTTGTGCGG AGGGATACTA TTAAGATTGC
 751 AGTTTCACCA AGTATAGCTT TTTATTTCAT TATAAGTTTC GTGTCAAAAT
 801 GTTTAAGCGA CCCGATCTCT CAGGCTGTTT TGCACGACTT TTCTGACTTT
 851 CCTCGCGTCT TTTTTCATGA AAATTGGATT ACCCGGAGTG ATGATTTTCT
 901 CACAGTGATT TTTCGTCCCC TTTTACAATA GCAAATGAAG CTGTTTTAGC
 951 AATATTTGTA GAAAGATATG TCACAAGAGG GCAGGCAAAA TGTCATACGG
1001 AAGAGAAGAC ACTACGATTG AGCCCGACTT CATAGAACCA GATGCACCTT
1051 TGGCTGCTTC CGGGGGTGTT GCTGACAACA TAGGCGGAAC TATGCAGAAT
1101 TCAGGCAGCA GAGGGACGCT CGACGAGACT GTGCTGCAAA CACTAAAGCG
1151 AGATGTGGTG GAGATTAATT CCAGACTGAA ACAAGTGGTA TACCCGCATT
1201 TCCCCTCATT CTTTAGCCCC TCTGATGACG GGATAGGGGC GGCTGATAAC
1251 GACATTTCAG CCAATTGCGA CCTGTGGGCG CCCCTTGCGT TTATCATATT
1301 GTATTCTCTA TTTGTATCGC ATGCGCGGTC GCTGTTCTCG AGCCTATTTG
1351 TGTCTAGTTG GTTCATTTTG CTGGTGATGG CATTGCATCT GAGACTCACC
1401 AAGCCACACC AGAGGGTGTC GCTGATTTCG TACATCTCCA TTTCCGGGTA
1451 TTGCTTATTC CCACAAGTGC TGAATGCCTT AGTCTCGCAG ATACTACTTC
1501 CATTGGCCTA CCATATTGGA AAGCAAAATC GCTGGATTGT GAGGGTCCTG
1551 TCGCTCGTGA AACTGGTGGT CATGGCGCTG TGCCTGATGT GGTCTGTGGC
1601 CGCCGTTTCG TGGGTTACCA AGAGCAAGAC CATTATCGAG ATATACCTCT
1651 GGCACTCTGT CTTTTTTGGC ATGGCTGGTT GTCAACTATT TTATAACACT
1701 AGTTACATAT GTATAAAACC CAATATTCAT GGACATAGAA TTGCCTATCT
1751 CGCGAGCCAC GGCAGAAAGT TCTGA
```

FIGURE 73. ***YGL198w* Protein Sequence**

Nature 387:81-84 [97313265] (1997) The nucleotide sequence of Saccharomyces cerevisiae chromosome VII.

Tettelin, H., Agostoni Carbone, M. L., Albermann, K., Albers, M., Arroyo, J., Backes, U., Barreiros, T., Bertani, I., Bjourson, A. J., Bruckner, M., Bruschi, C. V., Carignani, G., Castagnoli, L., Cerdan, et al.

YGL198W Length: 261 March 31, 1999 10:05 Type: P Check: 1705

```
  1 MSYGREDTTI EPDFIEPDAP LAASGGVADN IGGTMQNSGS RGTLDETVLQ
 51 TLKRDVVEIN SRLKQVVYPH FPSFFSPSDD GIGAADNDIS ANCDLWAPLA
101 FIILYSLFVS HARSLFSSLF VSSWFILLVM ALHLRLTKPH QRVSLISYIS
151 ISGYCLFPQV LNALVSQILL PLAYHIGKQN RWIVRVLSLV KLVVMALCLM
201 WSVAAVSWVT KSKTIIEIYL WHSVFFGMAG CQLFYNTSYI CIKPNIHGHR
251 IAYLASHGRK F
```

METHODS FOR THE IDENTIFICATION OF INHIBITORS OF AN ISOPRENOID METABOLIC PATHWAY

This application is a continuation of application Ser. No. 09/540,806, filed on Mar. 31, 2000, now abandoned, which in turn claims benefit, under 35 U.S.C. § 119(e), to U.S. provisional Patent Application No. 60/127,223, filed on Mar. 31, 1999, both of which are incorporated by reference in their entireties.

TECHNICAL FIELD OF THE INVENTION

The present invention relates to methods of identifying genes whose expression is indicative of activation of a particular biochemical or metabolic pathway or a common set of biological reactions or functions in a cell ("regulon indicator genes") The present invention provides an example of such an indicator gene. The present invention also relates to methods of partially characterizing a gene of unknown function by determining which biological pathways, reactions or functions its expression is associated with, thereby placing the gene within a functional genetic group or "regulon". These partially characterized genes may be used to identify desirable therapeutic targets of biological pathways of interest ("regulon target genes") The present invention provides examples of such target genes. Methods for identifying effectors (activators and inhibitors) of regulon target genes are provided. The present invention also provides examples of regulon target gene inhibitors.

BACKGROUND OF THE INVENTION

The sequencing of the *S. cerevisiae* genome marked the first complete, ordered set of genes from a eukaryotic organism, and revealed the presence of over 6,000 genes on 16 chromosomes (Mewes et al., 1997, Goffeau et al., 1996). The DNA sequence revealed the presence of 6275 known and hypothetical open reading frames (ORFs) encoding putative proteins longer than 99 amino acids in length. Based upon codon usage, which can serve as a predictor of whether or not an ORF is actually expressed, there are currently thought to be 6222 expressed ORFs (Cherry et al., 1997).

The sequence of the roughly 6,000 ORFs in the yeast genome is compiled in the *Saccharomyces* Genome Database (SGD). The SGD provides Internet access to the complete genomic sequence of *S. cerevisiae*, ORFs, and the putative polypeptides encoded by these ORFs. The SGD can be accessed via the World Wide Web at Stanford's website for *Saccharomyces* and at the Munich Information Center for Protein Sequences, *Saccharomyces cerevisiae* group. A gazetteer and genetic and physical maps of *S. cerevisiae* is found in Mewes et al., 1997 (incorporated herein by reference). References therein also contain the sequence of each chromosome of *S. cerevisiae* (incorporated herein by reference).

Having the complete DNA sequence of yeast available creates an opportunity to take a collectivist, rather than a reductionist, view on biology. We have developed a new technology that enables the simultaneous measurement of gene expression across an entire genome. The GENOME REPORTER MATRIX™ system (GRM) is a matrix of units comprising living yeast cells, the cells in each unit containing one yeast reporter fusion (GRM construct) representative of essentially every known hypothetical ORF of *S. cerevisiae*. See U.S. Pat. Nos. 5,569,588 and 5,777,888. A GRM construct comprises the promoter, 5' upstream untranslated region and generally, the first four amino acids from one of each hypothetical ORF fused to a gene encoding an easily assayed reporter, such as green fluorescent protein (GFP), luciferin, or β-galactosidase. The GRM constructs are able to reveal changes in transcription for each hypothetical in response to specific stimuli. In addition, the GRM constructs are able to reveal changes in mRNA splicing, translation and protein stability in those cases in which the N-terminus of the protein is sufficient for regulation.

The GRM provides an unprecedented view into the compensatory changes a cell makes in the face of a changing environment. Such environmental changes may be in the form of pH, salinity, temperature, osmotic pressure, nutrient availability, as well as biochemical perturbations caused by xenobiotics, pharmaceutical compounds and mutation. Identifying the compensatory changes a cell makes in response to exposure to a chemical can provide insight into the biological target of the chemical. For example, treatment of the GRM with the cholesterol-lowering drug lovastatin causes the cells to become depleted for sterols and non-sterol isoprenoids. The yeast cells respond by significantly up-regulating the genes encoding sterol biosynthetic enzymes and thus synthesizing more of the enzymes that make sterols. One may identify those genes that are involved in sterol biosynthesis or in related metabolic pathways by assaying the GRM. Because natural selection operates on a selected outcome rather than on a particular molecular mechanism, gene expression profiling strategies that detect regulatory changes through several molecular mechanisms contribute to a fuller view of how regulatory circuits have evolved.

An understanding of the regulatory circuits of yeast serves two purposes. On the one hand, yeast is an ideal model system for eukaryotic cells, including mammalian cells. Therefore, an understanding of the metabolic pathways of yeast can be used to design or discover drugs for use in plants and animals, including humans. On the other hand, yeast possess certain metabolic pathways and genes which are unique to yeast. An understanding of the differences between yeast and higher eukaryotes will permit the design and discovery of antifungal drugs that target genes and metabolic pathways specific to yeast. See U.S. Ser. No. 60/127,272, filed concurrently herewith.

Yeast cells are eukaryotic and have many pathways that are similar or identical to those of mammalian cells. However, because yeast cells are unicellular, they are easier to manipulate experimentally and the results of such manipulations are easier to determine. Thus, yeast serves as an ideal model system for eukaryotic cells, including mammalian cells. The deduced protein sequences of the yeast genome display a significant amount of sequence identity with mammalian proteins. About one-third of the yeast ORFs, when aligned with their mammalian counterparts, produce a P-value score of less than $1\times10^{-10}$ (Botstein et al., 1997). This number may in fact be a significant underestimate because the alignments were done with GENBANK® entries that make up only about 10–20% of the unique human protein sequences thought to exist.

The evolutionary conservation between yeast and humans is not limited to sequence identity. The list of human genes that can functionally substitute for their yeast counterparts is extensive. For example, H-Ras (Kataoka et al., 1985), HMG-CoA reductase (Basson et al., 1988) and the heme A:farnesyltransferase (Glerum and Tzagoloff, 1994) have been shown to functionally replace their yeast counterparts. Researchers have utilized this evolutionary conservation to clone mammalian genes through their ability to complement the corresponding yeast mutants. Two examples include CDC2 (Lee and Nurse, 1987) and CDK2 (Elledge and Spottswood, 1991).

Functional conservation between yeast and humans may be best illustrated by the notable lack of antifungal therapeutic agents available for safely treating systemic infections in humans. Antifungal agents certainly exist, but they are characterized by profound side effects likely caused by inhibition of the mammalian counterparts of the yeast target. L659,699, lovastatin, and zaragozic acid inhibit different steps in the yeast sterol pathway (G-COA synthase, HMG-CoA reductase, and squalene synthase, respectively). These inhibitors are also potent inhibitors of the corresponding mammalian enzymes (Correll and Edwards, 1994). In addition, we have found that in experiments with over 100 pharmaceutical agents used to treat a variety of distinct clinical indications in mammals, approximately 80% produced significant changes in gene expression in the GRM, indicating that there is substantial overlap in drug specificity between mammalian and yeast systems.

Yeast also contain genes that encode proteins that do not have plant and/or animal homologs. These non-homologous genes may be used as targets for the design and discovery of highly specific antifungal agents for use in plants and animals, including humans. The GRM may be used to identify genes that are expressed in particular metabolic pathways. Non-homologous genes in a pathway of interest may be used as targets for design and discovery of antifungal agents, for instance. See, e.g., U.S. Ser. No. 60/127,272, filed concurrently herewith.

One metabolic pathway of interest for identification of both homologous and non-homologous genes is the pathway for synthesis of isoprenoids. Eukaryotic cells utilize a group of structurally related compounds, the isoprenoids, for a vast array of cellular processes. These processes include structural composition of the lipid bilayer, electron transport during respiration, protein glycosylation, tRNA modification, and protein prenylation. All isoprenoids are synthesized via a pathway known variously as the isoprenoid pathway, mevalonate pathway, or sterol biosynthetic pathway. Although the bulk end product of the pathway is sterols, there are several branches of the pathway that lead to non-sterol isoprenoids. Due to the involvement of isoprenoids in a variety of physiologically and medically important processes, a comprehensive understanding of the regulation of this pathway would offer many scientific and practical benefits.

The regulation of the isoprenoid biosynthetic pathway is known to be complex in all eukaryotic organisms examined, including *S. cerevisiae*. The overriding principle for the regulation of this pathway is multiple levels of feedback inhibition. This feedback regulation is keyed to multiple intermediates and appears to act at numerous steps of the pathway, involving changes in transcription, translation and protein stability. Additionally, the availability of molecular oxygen, required for sterol and heme biosynthesis, also regulates the expression of genes at key steps of the pathway The emerging picture is that the isoprenoid pathway has numerous points of regulation that act to control overall flux through the pathway as well as the relative flux through various branches of the pathway.

Given the complexity of the isoprenoid pathway, it can be difficult to understand the regulation of any one step of this pathway, unless it is viewed within the context of the entire pathway. Thus, the GRM is ideal for understanding the regulation of the isoprenoid pathway because one may observe the regulation of all the yeast genes involved in the isoprenoid pathway at one time by using the GRM. In addition, analysis of the gene expression provided by the GRM (preferably using software described below) may provide information about which particular genes in the isoprenoid pathway are important regulatory genes in the pathway, those which are important indicator genes of the isoprenoid pathway, and those which are suitable targets to regulate isoprenoid synthesis.

Today we have the luxury of reflecting upon the wealth of information that has come from decades of research into the cell biology and genetics of yeast. Still, less than 20% of the hypothetical ORFs discovered by the yeast genome project had been previously identified through basic research (Goffeau et al., 1996). Additionally, 25% of the yeast ORFs with obvious human homologs have no known function (Botstein et al., 1997). The situation will likely be the same when the human genome sequence is completed.

Several research groups have created software programs that enable the comparison of both chemical and genetic expression profiles to identify related gene expression response patterns, as shown, for example, in FIG. 38. In addition, expression changes of individual genes in response to any given treatment can often be accessed through hypertext links. Currently, our software will: 1) normalize expression data; 2) rank changes in individual gene's expression relative to a particular treatment; 3) rank similarities between genomic expression profiles as a result of a chemical or genetic treatment; and 4) determine the correlation coefficient for an individual gene's expression relative to that of all other genes to identify regulons, or groups of genes that share the same regulatory programs. See U.S. application Ser. No. 09/076,668, now pending; Eisen et al. (1998); and Tamayo et al (1999).

The ability to assign ORFs to functional groups based upon their expression patterns will provide valuable information pertaining to the function of proteins from model organisms as well as their mammalian counterparts. Analysis of genomic expression patterns may also reveal upstream regulatory sequences, including promoters, with great utility for regulated or constituitive expression of recombinant genes. Such regulated sequences can be used for making reporter constructs for any selected process intrinsic to a given genome.

These functional genomics studies will provide a great deal of information that can implicate yeast genes, as well as their mammalian counterparts, in a variety of cellular functions. Associations of particular genes with specific biological pathways will be made by virtue of the genes' patterns of regulation under numerous conditions.

One particular problem in the prior art has been identifying genes whose expression is representative of a specific biological (e.g., metabolic) pathway. One would like to be able to measure the expression of a gene or its encoded protein to indicate the effect of a particular treatment on a specific pathway. Thus, there is a need for various pathway indicator genes for the various metabolic pathways.

A second problem in the prior art has been identifying genes and their encoded proteins which can be efficient targets within a specific biochemical pathway or set of associated pathways. Once good targets have been identified, pharmaceutical compounds and treatments may be designed or discovered to regulate the expression or activity of the target gene or protein.

SUMMARY OF THE INVENTION

The instant invention addresses the above problems by providing a method using genomic arrays, such as the GRM or hybridization arrays, for identifying indicator genes that are specific for particular biochemical pathways and sensitive to perturbations of these pathways. The instant invention provides one such gene, HES1, which is an indicator for the isoprenoid metabolic pathway. The invention provides the polynucleotide sequence of HES1 and vectors and host cells comprising this sequence. The invention also provides a method of producing HES1 recombinantly. The invention further provides methods of using HES1 as a specific indicator of the state of the isoprenoid pathway to identify compounds that regulate that pathway.

The instant invention also provides a method for identifying targets for one or more biochemical pathways of interest using the GRM or other types of genomic arrays, such as hybridization arrays. The instant invention also provides a number of ORFs and their encoded proteins which are targets for lipid metabolism, yeast morphology, RNA metabolism and growth control. These ORFs include YMR134w, YER034w, YJL105w, YKL077w, YGR046w, YJR041c, YER044c and YLR100w and their encoded proteins.

The invention provides the polynucleotide sequences of these ORFs and vectors and host cells comprising these ORFs for use in methods of identifying, designing and discovering highly specific anti-target agents. Specific anti-target agents include antisense nucleic acid molecules that target YMR134w, YER034w, YJL105w, YKL077w, YGR046w, YJR041c, YER044c and YLR100w and ribozymes that cleave RNAs encoded by these ORFs. The invention also provides a methods of recombinantly producing the protein encoded by these ORFs for use as a target in methods of identifying, designing and discovering highly specific antifungal agents and for producing antibodies directed against the encoded protein. Specific anti-target agents include antibodies that bind to the protein encoded by YMR134w, YER034w, YJL105w, YKL077w, YGR046w, YJR041c, YER044c and YLR100w and small organic molecules that bind to and inhibit proteins encoded by these ORFs.

BRIEF DESCRIPTION OF THE DRAWINGS

FIG. 1. Summary of Characteristics for YJL105w.

FIG. 5. Summary of Characteristics for YMR134w.

FIG. 7. Treatments Causing Highest Expression of YMR134w. YMR134w is induced most significantly by inhibitors of the isprenoid biosynthetic pathway.

FIG. 8. Database Searches with YMR134w. Database searches with YMR134w did not reveal any apparent mammalian counterparts.

FIG. 9. Summary of Characteristics for YER044c.

FIG. 11. Treatments Causing Highest Expression of YER044c. YER044c is induced most significantly by inhibitors of the isprenoid biosynthetic pathway FIG. 12. Database Searches with YER044c. Database searches with YER044c reveal numerous mammalian expressed-sequence tag (EST) apparent counterparts.

FIG. 13. Comparison of the YER044c Predicted Protein Sequence (SEQ ID NO:1) with Mouse and Human EST Translations. Amino acid residues 23 to 136 of SEQ ID NO:1 (SEQ ID NO:4) have 35% identity to amino acid residues 93 to 434 of the Mouse EST Translation (SEQ ID NO:2). Amino acid residues 23 to 116 of SEQ ID NO:1 (SEQ ID NO:5) have 35% identity to amino acid residues 112 to 393 of the Human EST Translation (SEQ ID NO:3).

FIG. 14. Comparison of the YER044c Predicted Protein Sequence (SEQ ID NO:1) with a Rat EST Translation. Amino acid residues 23 to 136 of SEQ ID NO:1 (SEQ ID NO:4) have 35% identity to amino acid residues 63 to 404 of the Rat EST Translation (SEQ ID NO:8).

FIG. 15. Summary of Characteristics for YLR100w.

FIG. 17. Treatments Causing Highest Expression of YLR100w. YLR100w is induced most significantly by inhibitors of isprenoid biosynthesis and a mutation in the gene encoding Erg11p.

FIG. 18. Database Searches with YLR100w. Database searches with YLR100w reveal numerous mammalian expressed-sequence tag (EST) apparent counterparts.

FIG. 19. Alignment of the amino acid sequence of YLR100w (SEQ ID NO:7) to Mammalian ESTs (SEQ ID NOs:6, 9, and 10, respectively).

FIG. 20. Summary of Characteristics for YER034w.

FIG. 23. Summary of Characteristics for YKL077w.

FIG. 25. Expression Correlation of YKL077w. Expression of the YKL077w gene correlates with that of genes involved in cell wall integrity and cytoskeletal reorganization.

FIG. 26. Database Searches with YKL077w. Database searches with YKL077w did not reveal any apparent mammalian counterparts.

FIG. 27. Summary of Characteristics for YGR046w.

FIG. 29. Expression Correlation of YGR046w. Expression of the YGR046w gene is correlated to other genes involved in growth control.

FIG. 30. Treatments Causing the Most Significant Changes in Expression of YGR046w. Expression of YGR046w is sensitive to agents that perturb mitochondrial function, create oxidative stress and disrupt the cytoskeleton.

FIG. 31. Summary of Characteristics for YJR041c.

FIG. 33. Expression Correlation of YJR041c. Expression of YJR041c is correlated to genes involved in RNA metabolism including RNA polymerase I and II transcription, mRNA splicing and turnover and ribosome function.

FIG. 34. Database Searches with YJR041c. Database searches with YJR041c did not reveal any apparent mammalian counterparts.

FIG. 35. Summary of Characteristics for HES1.

FIG. 36. Expression Correlation of HES1.

FIG. 37. Treatments that Induce the HES1 Reporter. Inhibitors of the isoprenoid biosynthetic pathway cause a significant induction of the HES1 reporter.

FIG. 39. YJL105w DNA Sequence (SEQ ID NO:11).

FIG. 40. YJL105w Protein Sequence (SEQ ID NO:12).

FIG. 41. YMR134w DNA Sequence (SEQ ID NO:13).

FIG. 42. YMR134w Protein Sequence (SEQ ID NO:14).

FIG. 43. YER044c DNA Sequence (SEQ ID NO:15).

FIG. 44. YER044c Protein Sequence (SEQ ID NO:1).

FIG. 45. Mouse EST with Similarity to YER044c. The mouse EST (GenBank Accession No. AI386195) and the primer listed in the figure are SEQ ID NOs: 17 and 16, respectively.

FIG. 46. Human EST with Similarity to YER044c. The human EST (GenBank Accession No. W28235) and the primers listed in the figure are SEQ ID NOs: 21, 18, 19, and 20, respectively.

FIG. 47. Rat EST (GenBank Accession No. AI172515; SEQ ID NO:22) with Similarity to YER044c.

FIG. 48. YLR100w DNA Sequence (SEQ ID NO:23).

FIG. 49. YLR100w Protein Sequence (SEQ ID NO:7).

FIG. 50. Human EST with Similarity to YLR100w. The human EST (GenBank Accession No. R92053) and the primer listed in the figure are SEQ ID NOs:25 and 24, respectively.

FIG. 51. Mouse EST with Similarity to YLR100w. The mouse EST (GenBank Accession No. R92053), the oligo (dT) primer, the adaptor, and the custom primers listed in the figure are SEQ ID NOs: 30, 26, 27, 28, and 29, respectively.

FIG. 52. Mouse EST with Similarity to YLR100w. The mouse EST (GenBank Accession No. AI52381), the oligo (dT) primer, the adaptor, and the custom primers listed in the figure are SEQ ID NOs: 31, 26, 27, 28, and 29, respectively.

FIG. 53. Mouse Gene (SEQ ID NO:32) with Similarity to YLR100w.

FIG. 54. YER034w DNA Sequence (SEQ ID NO:33).

FIG. 55. YER034w Protein Sequence (SEQ ID NO:34).

FIG. 56. YKL077w DNA Sequence (SEQ ID NO:35).

FIG. 57. YKL077w Protein Sequence (SEQ ID NO:36).

FIG. 58. YGR046w DNA Sequence (SEQ ID NO:37).

FIG. 59. YGR046w Protein Sequence (SEQ ID NO:38).

FIG. 60. YJR041c DNA Sequence (SEQ ID NO:39).

FIG. 61. YJR041c Protein Sequence (SEQ ID NO:40).

FIG. 62. HES1 DNA Sequence (SEQ ID NO:41).

FIG. 63. HES1 Protein Sequence (SEQ ID NO:42).

FIG. 65. Rat Gene (GenBank Accession No. 1397235; SEQ ID NO:43) with Similarity to YLR100w.

FIG. 66. DAK1 DNA Sequence (SEQ ID NO:44).

FIG. 67. DAK1 Protein Sequence (SEQ ID NO:45).

FIG. 68. PGU1 DNA Sequence (SEQ ID NO:46).

FIG. 69. PGU1 Protein Sequence (SEQ ID NO:49).

FIG. 70. STE18 DNA Sequence (SEQ ID NO:47).

FIG. 71. STE18 Protein Sequence (SEQ ID NO:48).

FIG. 72. YGL198w DNA Sequence (SEQ ID NO:50).

FIG. 73. YGL198w Protein Sequence (SEQ ID NO:51).

DETAILED DESCRIPTION OF THE INVENTION

Definitions and General Techniques

Figure 2:
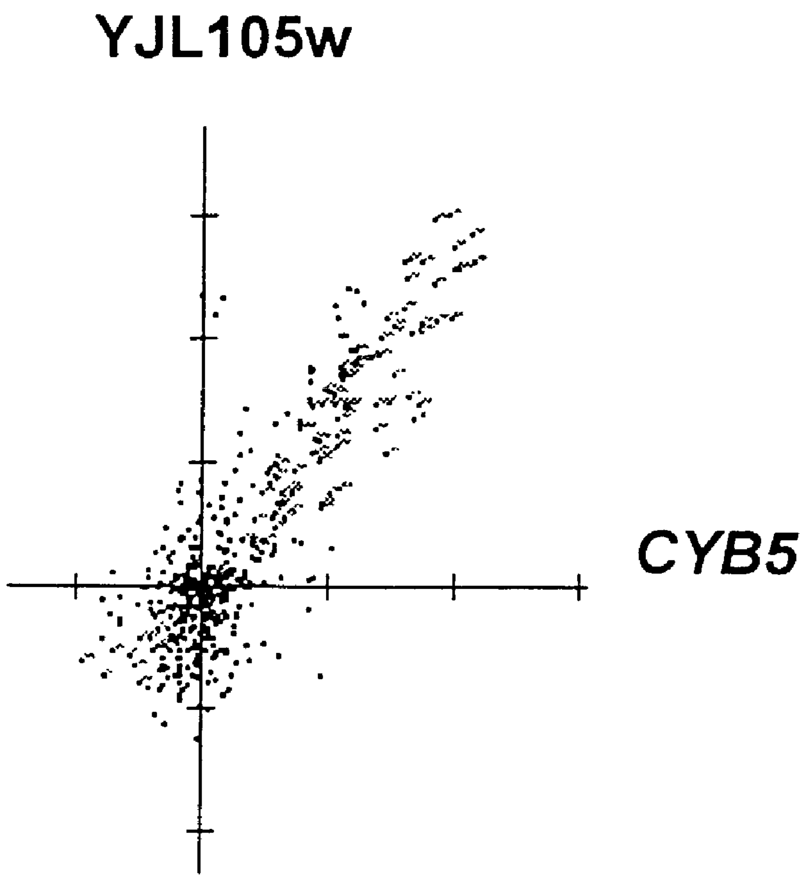
FIG. 2. Plot of changes in expression of YJL105w and CYB5 in response to different chemical treatments. Each point represents the expression changes in a given chemical treatment. The fitness of the points to a line provides an indication of the level of coordinate gene expression. CYB5 functions in sterol biosynthesis through its activation of the Erg11p NADPH-cytochrome P-450 reductase FIG. 3 Regulated Expression of YJL105w. YJL105w is significantly induced by isoprenoid biosynthetic inhibitors and mutations in HMG-CoA synthase (hmgs). "Log Ratio" refers to the natural log ratio of treated/untreated expression values FIG. 4. Effects of lovastatin on wild-type and YJL105w knockout yeast strains. 10 μl of a 25 mg/ml solution of lovastatin (250 μg) in ethanol was applied to a sterile drug disk on a lawn of yeast ($5\times10^6$ cells, ABY363). The plates were incubated overnight at 30° C.

Unless otherwise defined, all technical and scientific terms used herein have the meaning as commonly understood by one of ordinary skill in the art to which this invention belongs. The practice of the present invention employs, unless otherwise indicated, conventional techniques of chemistry, molecular biology, microbiology, recombinant DNA, genetics and immunology. See, e.g., Maniatis et al., 1982; Sambrook et al., 1989; Ausubel et al., 1992; Glover, 1985; Anand, 1992; Guthrie and Fink, 1991 (which are incorporated herein by reference).

A "regulon" is a group of genes that are coordinately regulated in response to a number of different stimuli, e.g., treatment with chemical compounds or mutations The member genes of a regulon comprise a functional unit by which a cell is able to adapt to a changing environment. The regulation of these genes that led to their categorization could be at the level of transcription, mRNA stability, splicing, translation or protein stability. The mode of regulation of each member gene of a given regulon need not be the same.

Genes are categorized into separate regulons based upon changes in gene expression. In order to efficiently and accurately group genes into functional groups, it is necessary to observe each gene's expression change. Since many genes function in specialized roles, it is necessary to measure global gene expression under as diverse a variety of conditions as possible. Therefore, the database of expression profiles used in this invention was made from a diverse collection of chemicals and mutant strains of yeast In general, the greater the number of diverse stimuli which cause the genes of a regulon to exhibit coordinate expression and the higher the correlation coefficient, the more confident one will be that the regulon is a robust indicator of the pathway or process of interest.

A "regulon indicator gene" (RIG) is a gene whose expression changes when a particular regulon or biochemical pathway or cellular process is activated or repressed. Although a RIG's expression may correlate with a particular biochemical pathway, the RIG does not necessarily have to be a part of the biochemical pathway for which it is an indicator. A RIG may comprise the entire gene, the 5' region of the gene including the promoter and/or enhancer and all or a part of the coding region, or a fragment, conservatively modified variant or homolog thereof which retains the indicator function of the RIG. A RIG may be coordinately expressed with a particular biological pathway, such that when the pathway is activated the RIG is more highly expressed and when the pathway is repressed the RIG's expression is repressed as well. However, the invention also encompasses RIGs in which there is an inverse correlation with a particular pathway. In this case, activation of a pathway would lead to a repression of RIG expression, while repression of a pathway would lead to activation of RIG expression. A RIG may be coordinately expressed with a particular biological pathway, such that when the pathway is activated the RIG is more highly expressed. However, the invention also encompasses RIGs in which there is an inverse correlation with a particular pathway. In this case, activation of a pathway would lead to a repression of RIG expression. Furthermore, the invention also encompasses RIGs which are not necessarily part of the regulon, pathway or process for which they are indicators. In this case, expression of RIGs may be activated or repressed specifically in response to perturbations of a regulon, pathway or process even though the RIG itself may only be indirectly related or have no apparent relationship in function to the regulon, pathway or process.

In a preferred embodiment, a RIG is specific to a particular pathway, wherein its expression changes most significantly when a particular pathway is activated or repressed. Such a highly specific regulon indicator gene cannot always be found for a pathway of interest. In such cases, more than one RIG can be identified that, when their expression patterns are taken together, correlate with specificity to the pathway of interest. Thus, in another preferred embodiment, a plurality of RIGs is identified wherein the coordinated expression pattern of the plurality of RIGs is specific to a particular biological pathway. In this preferred embodiment, expression of each member of the plurality of RIGs may independently increase or decrease when the biological pathway of interest is activated or repressed.

In another preferred embodiment, a RIG is highly sensitive to changes in activation or repression of a pathway, such that even a small perturbation in regulation of a pathway results in a change in RIG expression. In a further preferred embodiment, a RIG has a large dynamic range, and is highly induced or repressed upon the corresponding perturbation of the pathway to which it is correlated.

In another preferred embodiment, a RIG does not contain sequences that are problematic for maintaining on plasmids when introduced into host cells. Such sequences that may be problematic include centromeric sequences or sites that are particularly susceptible to recombination.

A "target gene" or "regulon target gene" is a gene whose function is desirable to modulate. A target gene may consist of the entire gene, the 5' region comprising the promoter and/or enhancer and all or a part of the coding region, or a fragment, conservatively modified variant or homolog thereof which retains the function of the target gene. In general, a target gene encodes a protein which is a part of the biological (e.g., metabolic or biochemical) pathway or process whose modulation would result in a desired outcome. In a preferred embodiment, a target gene is a control point in such a pathway. In one more preferred embodiment, a target gene is a control point that is relatively "upstream" in the metabolic pathway. "Upstream" means that the target gene is involved in one of the first steps of the metabolic pathway or process. In another more preferred embodiment, a target gene is a control point that is relatively "downstream" but specific to a biological pathway or a branch of that pathway or process. "Downstream" means that the target gene is involved in one of the later steps of the pathway or process.

A "target" or "target protein" is a protein whose expression or activity is to be modulated. A target may consist of the entire protein or a fragment, mutein, derivative or homolog thereof which retains the function of the target. In general, a target is a protein included within a biological pathway wherein it is desired to modulate the process which the protein is involved in. In a preferred embodiment, a target is a control point in such a biological pathway. In a more preferred embodiment, a target is a control point that is relatively "upstream" in the biological pathway. "Upstream" means that the target is involved in one of the first steps of the pathway In another more preferred embodiment, a target is a control point that is relatively "downstream" but specific to a biological pathway or a branch of that pathway. "Downstream" means that the target is involved in one of the later steps of the pathway.

A "target-dependent reporter gene" is a gene whose expression is altered in a cell in which the target gene has been altered or inactivated compared to the cell which expresses the normal target gene. The expression of the target-dependent reporter gene may increase or decrease in a cell harboring an altered or inactivated target gene, depending upon the identity of the gene. If expression of the target-dependent reporter gene increases in the cell harboring the altered or inactivated target gene, then a potential inhibitor of the regulon target gene will increase expression of the target-dependent reporter gene, and if expression of the target-dependent reporter gene decreases in the cell, then a potential inhibitor of the regulon target gene will decrease expression of the target-dependent reporter gene.

By "pathway" is meant any biological, e.g., metabolic or biochemical, set of concerted reactions which occur in response to a particular signal or stimulus in a cell The isoprenoid pathway is one example of such a pathway. Other pathways include, without limitation, amino acid and protein synthesis, lipid synthesis, protein and lipid glycosylation, protein modification, DNA synthesis and repair, RNA transcription, phospholipid synthesis, nucleotide synthesis, and energy generation and storage (e.g., glycolysis, citric acid cycle, oxidative phosphorylation, gluconeogenesis, pentose phosphate pathway, fatty acid metabolism, glycogen and disaccharide metabolism, amino acid degradation and the urea cycle), signal transduction and growth control.

By "process" is meant any biological reaction or set of reactions that occurs within a cell or organism that occurs in response to a stimulus or signal, or that occurs during growth, homeostasis, development, differentiation or death of the cell or organism.

An "isolated" protein or polypeptide is one that has been separated from naturally associated components that accompany it in its native state. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A monomeric protein is "substantially pure," "substantially homogeneous" or "substantially purified" when at least about 60 to 75% of a sample exhibits a single polypeptide sequence. A substantially pure protein will typically comprise about 60 to 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

A *S. cerevisiae* protein has "homology" or is "homologous" to a protein from another organism if the encoded amino acid sequence of the yeast protein has a similar sequence to the encoded amino acid sequence of a protein of a different organism. Alternatively, a *S. cerevisiae* protein may have homology or be homologous to another *S. cerevisiae* protein if the two proteins have similar amino acid sequences. Although two proteins are said to be "homologous," this does not imply that there is necessarily an evolutionary relationship between the proteins. Instead, the term "homologous" is defined to mean that the two proteins have similar amino acid sequences. In addition, although in many cases proteins with similar amino acid sequences will have similar functions, the term "homologous" does not imply that the proteins must be functionally similar to each other.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity) In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al.,1994, and [Henikoff et al., 1992, herein incorporated by reference).

The following six groups each contain amino acids that are conservative substitutions for one another:

1) Alanine (A), Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Valine (V), and
6) Phenylalanine (F), Tyrosine (Y), Tryptophan (W).

Sequence homology for polypeptides, which is also referred to as sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof.

A preferred algorithm when comparing a *S. cerevisiae* sequence to a database containing a large number of sequences from different organisms is the computer program BLAST, especially blastp or tblastn (Altschul et al., 1997, herein incorporated by reference). Preferred parameters for blastp are:

| | |
|---|---|
| Expectation value: | 10 (default) |
| Filter | seg (default) |
| Cost to open a gap: | 11 (default) |
| Cost to extend a gap: | 1 (default |
| Max. alignments: | 100 (default) |
| Word size: | 11 (default) |
| No of descriptions: | 100 (default) |
| Substitution Matrix: | BLOSUM62 |

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms using a *S. cerevisiae* query sequence, it is preferable to compare amino acid sequences. Comparison of amino acid sequences is preferred to comparing nucleotide sequences because *S. cerevisiae* has significantly different codon usage compared to mammalian or plant codon usage.

Database searching using amino acid sequences can be measured by algorithms other than blastp known in the art. For instance, polypeptide sequences can be compared using Fasta, a program in GCG Version 6.1. Fasta provides alignments and percent sequence identity of the regions of the best overlap between the query and search sequences (Pearson, 1990, herein incorporated by reference). For example, percent sequence identity between amino acid sequences can be determined using Fasta with its default parameters (a word size of 2 and the PAM250 scoring matrix), as provided in GCG Version 6.1, herein incorporated by reference.

The invention envisions two general types of polypeptide "homologs." Type 1 homologs are strong homologs. A comparison of two polypeptides that are Type 1 homologs would result in a blastp score of less than $1\times10^{-40}$, using the blastp algorithm and the parameters listed above. The lower the blastp score, that is, the closer it is to zero, the better the match between the polypeptide sequences For instance, yeast lanosterol demethylase, which is a common target of antifungal agents, as discussed above, has a Type 1 homolog in humans. The probability score (e.g., blastp score) is dependent upon the size of the database. Comparison of yeast and human lanosterol demethylases produces a blastp score of $1\times10^{-86}$.

Type 2 homologs are weaker homologs. A comparison of two polypeptides that are Type 2 homologs would result in a blastp score of between $1\ 10^{-40}$ and $1\times10^{-10}$, using the Blast algorithm and the parameters listed above. One having ordinary skill in the art will recognize that other algorithms can be used to determine weak or strong homology.

The terms "no substantial homology" or "no human (or mammalian, vertebrate, amphibian, fish, insect or plant) homolog" refers to a yeast polypeptide sequence which exhibits no substantial sequence identity with a polypeptide sequence from human, non-human mammals, other vertebrates, insects or plants. A comparison of two polypeptides which have no substantial homology to one another would result in a blastp score of greater than $1\times10^{-10}$, using the Blast algorithm and the parameters listed above. One having ordinary skill in the art will recognize that other algorithms can be used to determine whether two polypeptides demonstrate no substantial homology to each other.

A polypeptide "fragment," "portion" or "segment" refers to a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

A polypeptide "mutein" refers to a polypeptide whose sequence contains substitutions, insertions or deletions of one or more amino acids compared to the amino acid sequence of the native or wild type protein. A mutein has at least 50% sequence homology to the wild type protein, preferred is 60% sequence homology, more preferred is 70% sequence homology. Most preferred are muteins having 80%, 90% or 95% sequence homology to the wild type protein, in which sequence homology is measured by any common sequence analysis algorithm, such as Gap or Bestfit.

A "derivative" refers to polypeptides or fragments thereof that are substantially homologous in primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See Ausubel et al., 1992, hereby incorporated by reference.

The term "fusion protein" refers to polypeptides comprising polypeptides or fragments coupled to heterologous amino acid sequences. Fusion proteins are useful because they can be constructed to contain two or more desired functional elements from two or more different proteins. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, or genomic sequences with which it is naturally associated. The term embraces a nucleic acid or polynucleotide that has been removed from its naturally occurring environment. The term "isolated" or "substantially pure" also can be used in reference to recombinant or cloned DNA isolates, chemically synthesized polynucleotide analogs, or polynucleotide analogs that are biologically synthesized by heterologous systems.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using Fasta, a program in GCG Version 6.1. Fasta provides alignments and percent sequence identity of the regions of the best overlap between the query and search sequences (Pearson, 1990, herein incorporated by reference). For instance, percent sequence identity between nucleic acid sequences can be determined using Fasta with its default parameters (a word size of 6 and the NOPAMfactor for the scoring matrix) as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases, as measured by any well-known algorithm of sequence identity, such as Fasta, as discussed above.

Alternatively, substantial homology or similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity—preferably at least about 65%, more preferably at least about 75%, and most preferably at least about 90%—over a stretch of at least about 14 nucleotides. See, e.g., Kanehisa, 1984, herein incorporated by reference.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., page 9.5 1, hereby incorporated by reference.

The $T_m$ for a particular DNA-DNA hybrid can be estimated by the formula.

$$T_m=81.5° \text{ C.}+16.6(\log_{10}[Na^+])+0.41 \text{ (fraction } G+C)-0.63 \text{ (\% formamide)}-(600/l) \text{ where l is the length of the hybrid in base pairs.}$$

The $T_m$ for a particular RNA-RNA hybrid can be estimated by the formula $$T_m=79.8° \text{ C.}+18.5(\log_{10}[Na^+])+0.58\text{(fraction } G+C)+11.8 \text{ (fraction } G+C)^2-0.35 \text{ (\% formamide)}-(820/l).$$

The $T_m$ for a particular RNA-DNA hybrid can be estimated by the formula.

$$T_m=79\ 8° \text{ C.}+18.5(\log_{10}[Na^+])+0.58 \text{ (fraction } G+C)+11.8 \text{ (fraction } G+C)^2-0.50 \text{ (\% formamide)}-(820/l).$$

In general, the $T_m$ decreases by 1–1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10–15° C. would be subtracted from the calculated $T_m$ of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours. Another example of stringent hybridization conditions is 6×SSC at 68° C. for at least ten hours. An example of low stringency hybridization conditions for hybridization of complementary nucleic acid sequences having more than 100 complementary residues on a filter in a Southern or northern blot or for screening a library is 6×SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6×SSC), or keeping the hybridization temperature and salt concentration constant (e.g. 42° C. and 6×SSC) and varying the formamide concentration from 50% to 0%. Hybridization buffers may also include blocking agents to lower background. These agents are well-known in the art. See Sambrook et al., pages 8.46 and 9.46–9.58, herein incorporated by reference Wash conditions also can be altered to change stringency conditions. An example of stringent wash conditions is a 0.2×SSC wash at 65° C. for 15 minutes (see Sambrook et al., for SSC buffer). Often the high stringency wash is preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, signal-to-noise ratio of 2× or higher than that observed for an unrelated probe in the particular hybridization assay indicates detection of a specific hybridization.

As defined herein, nucleic acids that do not hybridize to each other under stringent conditions are still substantially homologous to one another if they encode polypeptides that are substantially identical to each other. This occurs, for example, when a nucleic acid is created synthetically or recombinantly using a high codon degeneracy as permitted by the redundancy of the genetic code.

The polynucleotides of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e g, alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Conservatively modified variations" or "conservatively modified variants" of a particular nucleic acid sequence refers to nucleic acids that encode identical or essentially identical amino acid sequences or DNA sequences where no amino acid sequence is encoded. Due to the degeneracy of the genetic code, a large number of functionally identical nucleic acids encode any given polypeptide sequence. When a nucleic acid sequence is changed at one or more positions with no corresponding change in the amino acid sequence which it encodes, that mutation is called a "silent mutation."

Thus, one species of a conservatively modified variation according to this invention is a silent mutation. Accordingly, every nucleic acid sequence herein which encodes a polypeptide also describes every possible silent mutation or variation.

Furthermore, one of skill in the art will recognize that individual substitutions, deletions, additions and the like, which alter, add or delete a single amino acid or a small percentage of amino acids (less than 5%, more typically less than 1%) in an encoded sequence are "conservatively modified variations" or "conservatively modified variants" where the alterations result in the substitution of one amino acid with a chemically similar amino acid. Conservative substitution tables providing functionally similar amino acids are well known in the art.

The term "antibody" refers to a polypeptide encoded by an immunoglobulin gene, genes, or fragments thereof The immunoglobulin genes include the kappa, lambda, alpha, gamma, delta, epsilon and mu constant regions, as well as a myriad of immunoglobulin variable regions. Light chains are classified as either kappa or lambda. Heavy chains are classified as gamma, mu, alpha, delta, or epsilon, which in turn define the immunoglobulin classes IgG, IgM, IgA, IgD and IgE, respectively.

Antibodies exist for example, as intact immunoglobulins or as a number of well-characterized fragments produced by digestion with various peptidases. For example, trypsin digests an antibody below the disulfide linkages in the hinge region to produce $F(ab)'_2$, a dimer of Fab which itself is a light chain joined to a $V_H$-$C_H1$ by a disulfide bond The $F(ab)'_2$ may be reduced under mild conditions to break the disulfide linkage in the hinge region thereby converting the $F(ab)'_2$ dimer to a Fab' monomer. The Fab' monomer is essentially an Fab with part of the hinge region. See Paul (1993) (incorporated herein by reference), for a detailed description of epitopes, antibodies and antibody fragments. One of skill in the art recognizes that such Fab' fragments may be synthesized de novo either chemically or using recombinant DNA technology. Thus, as used herein, the term antibody includes antibody fragments produced by the modification of whole antibodies or those synthesized de novo. The term antibody also includes single-chain antibodies, which generally consist of the variable domain of a heavy chain linked to the variable domain of a light chain. The production of single-chain antibodies is well known in the art (see, e.g., U.S. Pat. No. 5,359,046) The antibodies of the present invention are optionally derived from libraries of recombinant antibodies in phage or similar vectors (see, e.g., Huse et al. (1989); Ward et al. (1989); Vaughan et al. (1996) which are incorporated herein by reference)

As used herein, "epitope" refers to an antigenic determinant of a polypeptide, i e., a region of a polypeptide that provokes an immunological response in a host This region need not comprise consecutive amino acids. The term epitope is also known in the art as "antigenic determinant." An epitope may comprise as few as three amino acids in a spatial conformation which is unique to the immune system of the host. Generally, an epitope consists of at least five such amino acids, and more usually consists of at least 8–10 such amino acids. Methods for determining the spatial conformation of such amino acids are known in the art.

Methods for Analyzing ORF Gene Expression

The cell's ability to monitor its own biochemical ecology may be considered as a fully integrated multi-dimensional set of specific biochemical assays. The data from each individual assay manifests itself either directly or indirectly in the change in expression of a single gene or small set of genes. The individual components of the assaying capabilities of the cell may be extracted by measuring the changes in global gene expression in response to a controlled experimental challenge.

The measurement of global gene expression may be done by a number of different methods. One technique is that of hybridization to nucleic acid arrays on solid surfaces, such as "gene chips" (Fodor et al., 1991). Another method uses a reporter construct in the GRM or an equivalent matrix comprising living cells, preferably eukaryotic cells, and more preferably yeast, insect, plant, avian, fish or mammalian cultured cells. Other methods include SAGE.

DNA Chip Technology

One method for determining comprehensive gene expression profiles is DNA gene chip technology ( see, e.g., Fodor et al., 1991). A DNA gene chip can be made comprising a large number of immobilized single-stranded nucleic acids, each of which hybridizes specifically to a gene or its mRNA, representing a particular genome or a significant subset thereof Messenger RNA molecules extracted from a cell or cDNA molecules converted from such mRNA molecules can be labeled. The labeling can be accomplished, for example, radioisotopically or fluorescently by methods well known in the art. These mRNA or cDNA molecules are rendered single-stranded and then allowed to hybridize to the immobilized single-stranded nucleic acids on the gene chip. A computer equipped with a scanner then determines the extent of hybridization, thereby quantitating the amount of mRNA produced for any given gene or genetic sequence.

Profiles of gene expression generated under different conditions or in response to different stimuli such as treatment with chemical compounds are produced by treating cells with a compound, isolating the mRNA the cells, optionally producing cDNA and then hybridizing the single-stranded nucleic acids on the gene chip as discussed above. Preferably, software is used to correlate the expression of each gene on the hybridization chip relative to other genes under different conditions or in response to different treatments (see below).

Promoter elements from genes of interest that respond to an input signal can then be isolated and operatively linked to a reporter gene described above by recombinant DNA techniques well known in the art for further characterization.

GENOME REPORTER MATRIX™ system Technology

An alternative method to DNA gene chip technology is the use of a GENOME REPORTER MATRIX™ system (GRM), or an equivalent thereof. The description below of the generation of gene expression profiles utilizing the Genome Reporter Matrix™ has been described essentially in U.S. Pat. Nos. 5,569,888 and 5,777,888, both of which are incorporated herein by reference.

The promoter (and optionally, 5' upstream regulatory elements and/or 5' upstream untranslated sequences) of an ORF or a gene from a cellular genome (preferably a eukaryotic genome) is fused to a reporter gene creating a transcriptional and/or translational fusion of the promoter to the reporter gene. In a preferred embodiment, the genome is that of *S. cerevisiae*. The promoter and optional additional sequences comprise all the regulatory elements necessary for transcriptional (and optionally translational) control of an attached coding sequence. The reporter gene can be any gene that, when expressed in a suitable host, encodes a product that can be detected by a quantitative assay. Any suitable assay may be used, including but not limited to enzymatic, colorimetric, fluorescence or other spectrographic assays, fluorescent activated cell sorting assay and immunological assays. Examples of suitable reporter genes include, inter alia, green fluorescent protein (GFP), β-lactamase, lacZ, invertase, membrane bound proteins (e.g., CD2, CD4, CD8, the influenza hemagglutinin protein, and others well known in the art) to which high affinity antibodies directed to them exist or can be made routinely, fusion protein comprising membrane bound protein appropriately fused to an antigen tag domain (e.g., hemagglutinin or Myc and others well known in the art). In a preferred embodiment, the reporter protein is GFP from the jellyfish *Aequorea victoria*. GFP is a naturally fluorescing protein that does not require the addition of any exogenous substrates for activity. The ability to measure GFP fluorescence in intact living cells makes it an ideal reporter protein for the GRM or an equivalent matrix comprising living cells.

In a preferred embodiment, reporter constructs comprise the 5' region of the ORF comprising the promoter of the ORF and other expression regulatory sequences, and generally the first four codons of the ORF fused in-frame to the green fluorescent protein. In a more preferred embodiment, approximately 1200 base-pairs of 5' regulatory sequence are included in each fusion. Only 228 yeast ORFs (3.5%) possess introns Of these 228 intron-containing ORFs, all but four contain only one intron In these ORFs, fusions are created two to four codons past (3' to) the splice junction. Therefore, these fusions must undergo splicing in order to create a functional reporter fusion.

Each reporter is assembled in an episomal yeast shuttle vector (either CEN or 2μ plasmid) or on a yeast integrating vector for subsequent insertion into the chromosomal DNA In a preferred embodiment, the gene reporter constructs are built using a yeast multicopy vector. A multicopy vector is chosen to facilitate easy transfer of the reporter constructs to many different yeast strain backgrounds. In addition, the vector replicates at an average of 10 to 20 copies per cell, providing added sensitivity for detecting genes that are expressed at a low level. In principle, introducing additional copies of a gene's regulatory region could, through titration of regulatory proteins, disrupt a response of interest. However, in practice this appears not to occur, and efforts to successfully exploit such titration effects have required much higher copy number vectors and have been largely unsuccessful. In another preferred embodiment, the reporter constructs are maintained on episomal plasmids in yeast.

In one embodiment, a plurality (all or a significant subset) of the resulting approximately 6,000 reporter constructs is transformed into a strain of yeast. The resulting strains constitute one embodiment of the Genome Reporter Matrix™. See Example 1.

Profiles are produced by arraying wild type or mutant cells carrying the reporter fusion genes in growth media containing different drugs and chemical compounds and measuring changes in expression of the reporter gene by the appropriate assay (see below). In a preferred embodiment, where the reporter gene is GFP, measurement of changes in expression are done by measuring the amount of green light produced by the cells over time with an automated fluorescence scanner. Alternatively, the drugs or chemical compounds may be added to the yeast cells after they have been arrayed onto growth media and then measuring changes in reporter gene expression by the appropriate assay.

Figure 64:
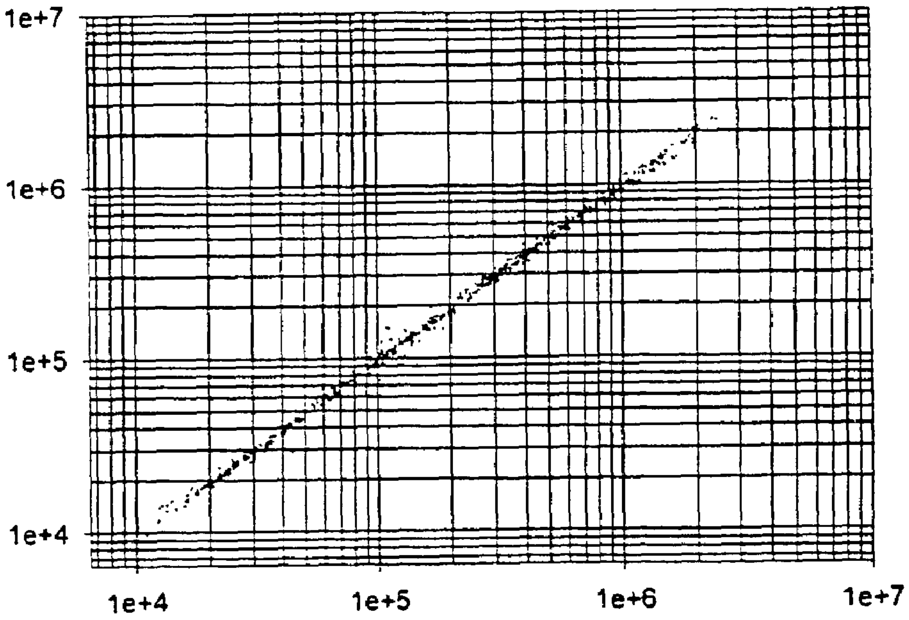
FIG. 64. Reproducibility of the Genome Reporter Matrix™ Fluorescence from 864 independent untreated reporter-harboring yeast strains was plotted against the corresponding clones of an independent control array.

Over 93% of the reporters are detectable over background on rich medium. The reproducibility of individual reporters is high, with expression generally varying by less than 10%. In contrast, hybridization experiments have proven unreliable for effects of less than a factor of two. FIG. 64 depicts expression data of the GRM from two independent experiments plotted against each other.

In a preferred embodiment, the GRM is used to obtain gene expression information from a genome. The GRM is preferred to hybridization-based methods of profiling for several reasons. First, because the promoter-reporter fusions include the first four amino acids of the native gene product, the response profiles are composites of both transcriptional and translational effects. The importance of being able to monitor both levels of response is underscored by the experience with bacterial antibiotics. Those antibiotics that work at the translational level have a greater therapeutic performance than those affecting transcription. Because hybridization-based methods can reveal only effects on transcription, profiling with the GRM provides a more complete view of the full spectrum of biological effects induced by exposure to drugs or compounds.

Second, the GRM permits profiling of gene expression changes in living cells, which permits one to easily measure the kinetics of changes in gene response profiles in the same population of cells following exposure to different drugs and chemical agents. Thus, by collecting multiple data sets over time, one can identify the genes that make up primary and secondary responses.

Third, hybridization-based methods require relatively sophisticated molecular procedures to produce labeled cDNA, followed by a 14 hour hybridization of labeled cDNA probes to target DNA arrays on slides or chips. The GRM requires only that being able to produce arrays of colonies and measure emitted light. These procedures are easier to scale up in an industrial setting than are sophisticated molecular biology methods, rendering data that is more straightforward to produce and more reproducible in nature.

Gene Expression Profiles

Using the reporter construct, gene chip technology or another method for obtaining genome-wide gene expression, the gene expression profile of yeast genes can be obtained. In a preferred embodiment, either the GRM or gene chip technology is used In a more preferred embodiment, the GRM is treated with a number of pharmaceutical compounds and the resulting expression of the reporter constructs is analyzed. Generally, for each pharmaceutical compound, the expression of the reporter constructs are analyzed in the presence of the vehicle for the pharmaceutical compound alone and is compared to the expression of the reporter constructs in the presence of the pharmaceutical compound. Changes in expression of the reporter constructs in the absence and presence of the pharmaceutical compound is obtained either by subtracting the baseline level of expression from the level after treatment or dividing the baseline level of expression from the level after treatment. By looking at a large number of reporter constructs, one can assign yeast ORFs to functional groups based upon their expression patterns in response to various pharmaceutical compounds. These functional groups may provide valuable information as to the function of the yeast proteins as well as their human, non-human mammalian, avian, fish, insect and plant counterparts.

Preferably, software is used to correlate the expression of each gene in the GRM or on the DNA chip relative to other genes under different conditions and in response to different pharmaceutical compounds. In one preferred embodiment, the software is capable of producing a correlation coefficient for each gene's expression relative to every other gene across all expression profiles in a database. Such analysis reveals groups of genes that exhibit coordinate regulation (regulons) See, e.g., U.S. Ser. No 09/076,668, now pending; Eisen et al. (1998); and Tamayo et al. (1999).

In a preferred embodiment, a gene of unknown function may be placed into a functional genetic group by the following steps.

a) generating a gene expression profile for Gene X, a gene of unknown function;

b) comparing the gene expression profile of Gene X with expression profiles of a plurality of other genes in a database of compiled gene expression profiles to generate expression correlation coefficients;

c) identifying based on their expression correlation coefficients a set of genes comprising Gene X that are coordinately expressed;

d) determining if the genes whose expression is most highly correlated with that of Gene X belong to a gene regulon involved in a known biological pathway, or a common set of biological reactions or functions; and e) optionally testing the effect on Gene X expression of at least one altered condition or treatment known to affect the function to which Gene X hs been ascribed.

If Gene X expression is coordinate with expression of the regulon, then Gene X is placed in the regulon.

Methods to Identify Potential RIGs

A GRM (or an equivalent) is chemically treated with a large number of compounds. Regulons are identified as groups of genes that are coordinately regulated in response to genetic mutations, treatment with compounds or different environmental conditions In a preferred embodiment, regulons are identified using correlation coefficients assembled by software that does clustering analysis, such as that described in U.S. Ser. No. 09/076,668, now pending; Eisen et al. (1998); and Tamayo et al. (1999). In a preferred embodiment, genes that constitute a regulon have a correlation coefficient of greater than 0.5. In a more preferred embodiment, genes that constitute a regulon have a correlation coefficient of at least 0.6 or 0.7. In a further preferred embodiment, genes that constitute a regulon have a correlation coefficient of at least 0.8 or 0.9. The correlation coefficient may be measured by any method of obtaining correlation coefficients, including, without limitation, the method described in U.S. patent application Ser. No. 09/076,668, now pending or in Eisen et al. (1998)

Once a group of genes has been grouped into a regulon, one can identify potential regulon indicator genes (RIGs), which may or may not be a member of the regulon, pathway or process with the regulon, pathway, or process for which they are an indicator. RIGs may be either characterized or uncharacterized genes provided they have certain characteristics. Preferred characteristic include one or more of the following: 1) its expression profile is sensitive to one or more stimuli; 2) its expression profile exhibits a large dynamic range in response to one or more stimuli; 3) its expression profile exhibits a rapid kinetic response to one or more stimuli; 4) its expression profile is specific to a known biological pathway or a common set of biological reactions or functions; 5) the regulon indicator gene does not contain sequences that are problematic for maintaining on plasmids when introduced into host cells. Most preferably, their expression is relatively specific for a particular biochemical pathway or cellular condition, highly sensitive to small changes in activation of a biochemical pathway or cellular condition and exhibit a wide dynamic range of expression so that the RIG is easier to assay.

A "large dynamic range" is one in which the response in gene expression in response to a stimulus is at least four-fold over basal levels of expression in the absence of the stimulus. A response may be either an increase or a decrease in gene expression. In a preferred embodiment, the response is at least ten-fold over basal levels. In a more preferred embodiment, the response is at least twenty-fold over basal levels In an even more preferred embodiment, the response is at least 100-fold over basal levels.

A "rapid kinetic response" is one in which the response occurs in the same time period as the doubling time of the organism after stimulation with the stimulus In a preferred embodiment, the response occurs less than 10 minutes. In a more preferred embodiment, the response occurs in less than one minute A "stimulus" or "stimuli" is a chemical compound, a genetic mutation, or a change in the environment of the cell, including, without limitation, a change in pH, temperature, osmotic pressure, salinity, light, gas concentration or partial pressure (e g $O_2$, $CO_2$, CO or NO).

In order to determine whether a potential RIG is specific for a particular biochemical pathway or cellular condition, expression of the potential RIG is examined under all conditions in the expression database. A desirable RIG is one whose expression is selectively induced or repressed by chemicals or mutations that are known to affect the process in question. Likewise, a desirable RIG's expression is not influenced by chemicals or mutations that are known not to affect the process in question This analysis provides information regarding whether the RIG participates in additional cellular processes or biochemical pathways. When a potential RIG is not a member of a target regulon, pathway or process, specificity is measured by analyzing expression under all conditions under which the potential RIG is activated or repressed to determine if similar conditions elicit similar responses.

Most preferably, a single RIG may be identified to be highly specific to a particular pathway, i.e., wherein its expression changes only when a particular pathway is activated or repressed, but not when other pathways are likewise regulated. Such a highly specific regulon indicator gene cannot always be found for a pathway of interest In such cases, however, more than one RIG may be identified whose coordinate expression patterns correlate with high specificity to a pathway of interest. Preferably, the coordinate expression of two RIGs provides such specificity. However, the present invention is not limited by the number of RIGs identified and used simultaneously as regulated pathway indicators. Expression of each member of a plurality of RIGs may independently increase or decrease when the biological pathway of interest is activated or repressed.

In order to determine whether a potential RIG is highly indicative of activation of a particular pathway, the gene will be activated or repressed to an expression level at least 2-fold higher or lower (if the gene is repressed) than when the pathway is not activated. In a preferred embodiment, the gene is activated or repressed to an expression level at least 10-fold higher or lower than the unactivated pathway In a more preferred embodiment, the gene is activated or repressed to an expression level at least 20-fold higher or lower than the unactivated pathway. The expression level may be represented as a natural log ratio of treated/untreated expression values. See FIG. 37, for example. In a preferred embodiment, the natural log ratio of a RIG is greater than 1, more preferably greater than 2.5, and even more preferably greater than 4.0 when the pathway or process is activated.

In order to determine the dynamic range of a potential RIG, the expression of the RIG is assessed by examining its expression in response to all the treatments and mutations in the database. In a preferred embodiment, there is a high level of change in RIG expression for small changes in activation of the pathway.

In one embodiment of the invention, expression of a regulon indicator gene correlates with the expression of at least one known gene in a group of coordinately expressed genes or provide a measure of the function of a biological process of interest. The RIG is identified by a method comprising the steps of:

- a) comparing gene expression profiles of a plurality of genes in the database to generate expression correlation coefficients;
- b) identifying based on their relative expression correlation coefficients a set of genes that are coordinately expressed;
- c) selecting a set of genes from b) which comprises one or more genes known to function in a particular biological pathway, or a common set of biological reactions or functions;
- d) selecting a member of the set of c) having one or more of the following characteristics:
    - 1) its expression profile is sensitive to one or more stimuli;
    - 2) its expression profile exhibits a large dynamic range in response to one or more stimuli;
    - 3) its expression profile exhibits a rapid kinetic response to one or more stimuli;
    - 4) its expression profile is specific to a known biological pathway or a common set of biological reactions or functions;
    - 5) the regulon indicator gene does not contain sequences that are problematic for maintaining on plasmids when introduced into host cells.

The RIG may also be co-regulated with one or more genes in the group of coordinately expressed genes of c) above. In addition, the RIG may control the expression of at least one other gene in the group of coordinately expressed genes of c) above. The RIG may be a gene of previously unknown function.

In another embodiment, the invention provides a method for identifying a regulon indicator gene in a database of compiled gene expression profiles, wherein expression of the regulon indicator gene provides a measure of the function of a biological pathway or process of interest. The method comprises the steps of:

a) examining exemplary expression profiles in response to one or more chemical or genetic treatments which target the pathway or process of interest to generate reporter sensitivity data;

b) selecting a set of genes from a) which comprises one or more genes most significantly affected in response to the treatment or treatments; and c) selecting at least one gene from b) whose expression profile is maximized for its specificity and sensitivity to the treatment or class of treatments in a) compared to its sensitivity to all other treatments in the database.

The regulon indicator gene may be co-regulated with one or more genes in the set of genes of a) or the regulon indicator gene, upon expression, controls the expression of at least one other gene in the in the set of genes of a).

Methods to Identify Potential Target Genes and Targets

A regulon is identified as described above under "Methods to Identify Potential RIGs." In a preferred embodiment, a regulon will contain both characterized and uncharacterized genes. In many cases, the characterized genes will have a common function or will be part of the same biochemical pathway. For instance, a regulon of the isoprenoid pathway will contain characterized genes involved in sterol biosynthesis. Uncharacterized genes will then be analyzed in terms of whether they are likely to be part of the same biochemical pathway as the characterized genes. The sequence of uncharacterized genes will be compared to the sequence of genes of known function to determine if the uncharacterized genes or their gene products have any motifs common to characterized genes.

For instance, uncharacterized genes will be examined for domains indicating enzymatic functions, including, without limitation, kinase, protease and phosphorylase activities Similarly, uncharacterized genes will be examined for domains indicating that they might be transcription factors, including, without limitation, zinc finger, PHD, steroid-binding and helix-loop-helix regions. Other domains of interest include lipid-binding and ATP-binding domains. Uncharacterized genes will also be examined for sequence similarities to secreted factors and receptors. In a preferred embodiment, target genes and their encoded target proteins are previously uncharacterized, highly correlated with a particular regulon containing genes for a specific pathway or process, and that appear to be an enzyme, secreted factor, receptor or transcription factor.

In a preferred embodiment, a novel regulon target gene may be selected from a database of compiled gene expression profiles. The target gene is selected comprising the steps of:

- a) comparing gene expression profiles of a plurality of genes in the database to generate expression correlation coefficients;
- b) identifying based on their expression correlation coefficients a set of genes that are coordinately expressed;
- c) selecting from b) a set of genes comprising one or more genes of unknown function and one or more genes known to function in a particular biological pathway, or a common set of biological reactions or functions of interest;
- d) selecting from the set of c) at least one gene of unknown function, Gene X, as a novel regulon target gene; wherein Gene X is a gene whose expression profile closely correlates to the expression profiles of the one or more genes of the set of c) known to function in the particular biological pathway, or common set of biological reactions or functions of interest.

The method may further comprise the step of generating individual correlation coefficients between the gene expression profile of Gene X and a plurality of genes in the database to assess the selectivity of Gene X as a novel regulon target gene. The method may further comprise the step of determining whether the protein encoded by Gene X exhibits substantial homology to a human, non-human mammal, avian, amphibian, fish, insect or plant protein, including, without limitation, the step of hybridizing Gene X to genomic DNA from human, non-human mammal, avian, amphibian, fish, insect or plant cells or tissue under low stringency conditions, comparing the DNA sequence of Gene X to the DNA sequences from other organisms, or obtaining an amino acid sequence encoded by Gene X and comparing it to amino acid sequences from other organisms. The DNA or amino acid sequences from other organisms may be contained within a database and the DNA or amino acid sequence encoded by Gene X may compared to the DNA or amino acid sequences from other organisms using a computer algorithm such as blastp, tblastn or another algorithm that utilizes string alignments. The method for identifying a target may further comprise the steps of:

a) disrupting the function of Gene X or its homolog in a yeast cell; and b) identifying whether the function of Gene X is essential for yeast germination, vegetative growth, pseudohyphal or hyphal growth.

In another embodiment of the invention, genes that are regulated by regulon target genes of yeast or its mammalian homolog may be identified. The method comprises the steps of a) overexpressing the target gene in host cells of a matrix comprising a plurality of units of cells, the cells in each unit containing a reporter gene operably linked to an expression control sequence derived from a gene of a selected organism; and b) identifying genes that are either induced or repressed by overexpression of the target gene.

In a preferred embodiment, the target gene is selected from the group consisting of YMR134w, YER034w, YJL105w, YKL077w, YGR046w, YJR041c, YER044c and YLR100w and their mammalian homologs.

Methods for Constructing Mutant Yeast Strains

Once a potential target has been identified, one may disrupt the gene to determine the effect of inhibiting the gene's activity has on the phenotype of the yeast cell. There are a number of methods well known in the art by which a person can disrupt a particular gene in yeast. One of skill in the art can disrupt an entire gene and create a null allele, in which no portion of the gene is expressed. One may also produce and express an allele comprising a portion of the gene which is not sufficient for gene function This may be done by inserting a nonsense codon into the sequence of the gene such that translation of the mutant mRNA transcript ends prematurely. One may also produce and express alleles containing point mutations, individually or in combination, that reduce or abolish gene function.

There are a number of different strategies for creating conditional alleles of genes. Broadly, an allele can be conditional for function or expression. An example of an allele that is conditional for function is a temperature sensitive mutation where the gene product is functional at one temperature but non-functional at another, e.g., due to misfolding or mislocalization. One of ordinary skill in the art may produce mutant alleles which may have only one or a few altered nucleotides but which encode inactive or temperature-sensitive proteins. Temperature-sensitive mutant yeast strains express a functional protein at permissive temperatures but do not express a functional protein at non-permissive temperatures.

An example of an allele that is conditional for expression is a chimeric gene where a regulated promoter controls the expression of the gene. Under one condition the gene is expressed and under another it is not. One may replace or alter the endogenous promoter of the gene with a heterologous or altered promoter that can be activated only under certain conditions. These conditional mutants only express the gene under defined experimental conditions. In a preferred embodiment, the gene is under the control of a regulated promoter where the gene may be expressed at higher or lower levels depending upon the degree of activation of the promoter. For instance, a gene under the control of a regulated promoter may be expressed at any level between 0 and 100% of wild type expression, such as at 10%, 20%, 50% or 80% of its wild type level. The gene may also be expressed at levels above its usual wild type expression (overexpression). All of these methods are well known in the art. For example, see Stark (1998), Garfinkel et al., (1998), and Lawrence and Rothstein, (1991), herein incorporated by reference.

One having ordinary skill in the art also may decrease expression of a gene without disrupting or mutating the gene. For instance, one may decrease the expression of a gene by transforming yeast with an antisense molecule or ribozyme under the control of a regulated or constitutive promoter (see Nasr et al., 1995, herein incorporated by reference). One may introduce an antisense construct operably linked to an inducible promoter into *S. cerevisiae* to study the function of a conditional allele (see Nasr et al supra). One problem that may be encountered, however, is that many antisense molecules do not work well in yeast, for reasons that are, as yet, unclear (see Atkins et al., 1994 and Olsson et al., 1997).

One may also decrease gene expression by inserting a sequence by homologous recombination into or next to the gene of interest wherein the sequence targets the mRNA or the protein for degradation. For instance, one can introduce a construct that encodes ubiquitin such that a ubiquitin fusion protein is produced. This protein will be likely to have a shorter half-life than the wildtype protein. See, e.g., Johnson et al. (1992), herein incorporated by reference.

In a preferred mode, a gene of interest is completely disrupted in order to ensure that there is no residual function of the gene. One can disrupt a gene by "classical" or PCR-based methods. The "classical" method of gene knockout is described by Rothstein (1991), herein incorporated by reference. However, it is preferable to use a PCR-based deletion method because it is faster and less labor intensive.

A preferred method to delete a gene is a one-step, polymerase chain reaction (PCR) based gene deletion method (Rothstein, 1991). Gene specific primer pairs are designed for PCR amplification of the plasmid pFA6a-KanMX4 (Wach et al., 1994), which teachings are herein incorporated by reference. The 3' ends of the upstream and downstream gene specific primers have been designed to include 18 basepairs (bp) and 19 bp, respectively, of nucleotide homology flanking the KanMX gene of the plasmid pFA6a-KanMX4 template. All of the gene specific primer pairs contain these complementary sequences, such that the same plasmid pFA6a-KanMX4 template can be used for all of the first round PCR reactions. At their 5' ends, the primers each have gene specific sequence homologies. The upstream primer contains a nucleotide sequence which includes the start codon of the gene to be knocked out and the sequence immediately upstream of the start codon. The downstream primer contains a nucleotide sequence which includes the stop codon of the gene and the sequence immediately downstream of the stop codon. For each set of primers, the sequences of the gene are derived from the 5' and 3' ends of the target DNA sequence.

The upstream and downstream primers are then used to amplify the pFA6a-KanMX4 by PCR using standard conditions for PCR. Hybridization conditions for specific gene-specific primers can be experimentally determined, or estimated by a number of formulas. One such formula is $T_m$=81.5+16.6 ($\log_{10}$[$Na^+$])+0.41 (fraction G+C)−(600/*N*). See Sambrook et al. pages 11.46–11.47. The products of the first round PCR reactions are DNA molecules containing the KanMX marker (conferring resistance to the drug G-418 in *S. cerevisiae*) flanked on both ends by 18 bp of gene specific sequences.

The gene specific flanking sequences are extended during the second round PCR reactions The sequences of the two gene specific PCR primers are derived from the 45 bp immediately upstream (including the start codon) and the 45 bp immediately downstream (including the stop codon) of each gene. Thus, following the second round of PCR the product contains the KanMX marker flanked by 45 bp of gene specific sequences corresponding to the sequences flanking the gene's ORF. The PCR products are purified by an isopropanol precipitation, and shipped with the analytical primers (see below) to the consortium members on dry ice. The precipitated PCR products are resuspended in TE buffer (10 mM Tris-HCl [pH 7.6], 1 mM EDTA).

The various mutations are constructed in two related *Saccharomyces cerevisiae* strains, BY4741 (MATα his3 Δ1 leu2 Δ0 met15 Δ0 ura3 Δ0) and BY4743 (MATα/MATα his3Δ1/his3Δ1 leu2Δ0/leu2Δ0 LYS2/lys2Δ0 met15Δ0/MET15 ura3Δ0/ura3Δ0) (Brachmann et al., 1998). Both of these strains are transformed with the PCR products by the lithium acetate method as described by Ito et al., 1983, and Schiestl and Gietz, 1989, herein incorporated by reference. The flanking, gene-specific yeast sequences target the integration event by homologous recombination to the desired locus (FIG. 1). Transformants are selected on rich medium (YPD) which contains G-418 (Geneticin, Life Technologies, Inc.) as described by Guthrie and Fink, 1991, herein incorporated by reference. Ideally, independent mutations are isolated in the haploid (BY4741) and the diploid (BY4743) strains. The heterozygous mutant diploid strain is then sporulated, and subjected to tetrad analysis (Sherman, 1991; Sherman and Wakem, 1991, herein incorporated by reference). This allows for the isolation of the mutation in a MATα haploid strain. The two independently isolated MATα and MATα haploid strains are then mated to create a homozygous mutant diploid strain.

Methods to Characterize Yeast Gene Function

One of skill in the art will recognize that a number of methods can be used to characterize the function of a yeast gene. In general, the preferred strategy depends upon the assumptions made regarding the function of the gene. For example, if one creates a conditional allele of the gene, then one can engineer a mutant strain wherein the wildtype allele has been replaced by a conditional allele. See, e.g., Stark (1998) The strain is constructed and propagated under the permissive condition, and then the strain is switched to the non-permissive (or restrictive) condition and effects upon the cell's phenotype is monitored. This can be done in a haploid cell, or in a diploid cell as either a homozygous or heterozygous mutant.

A preferred method of characterizing the function of a gene is to knockout the gene completely and then analyze the knockout yeast strain by tetrad analysis This method is preferred because one does not need to be able to engineer a conditional allele Furthermore, as the knockout is a null allele, one is assured that it is the null phenotype that is assessed, rather than a phenotype resulting from a potentially hypomorphic conditional allele. In addition, a complete knockout of the gene can be constructed in a diploid strain where the potentially essential function of the gene is complemented by the second copy of the gene.

Once the knockout has been constructed as a heterozygous mutant, the effects of the mutation is assessed in the haploid spores. Tetrad analysis of the haploid spores allows for the genetic characterization of a mutation because one can determine the effect of the homozygous gene linked to the knockout marker (G-418 resistance).

Figure 22:
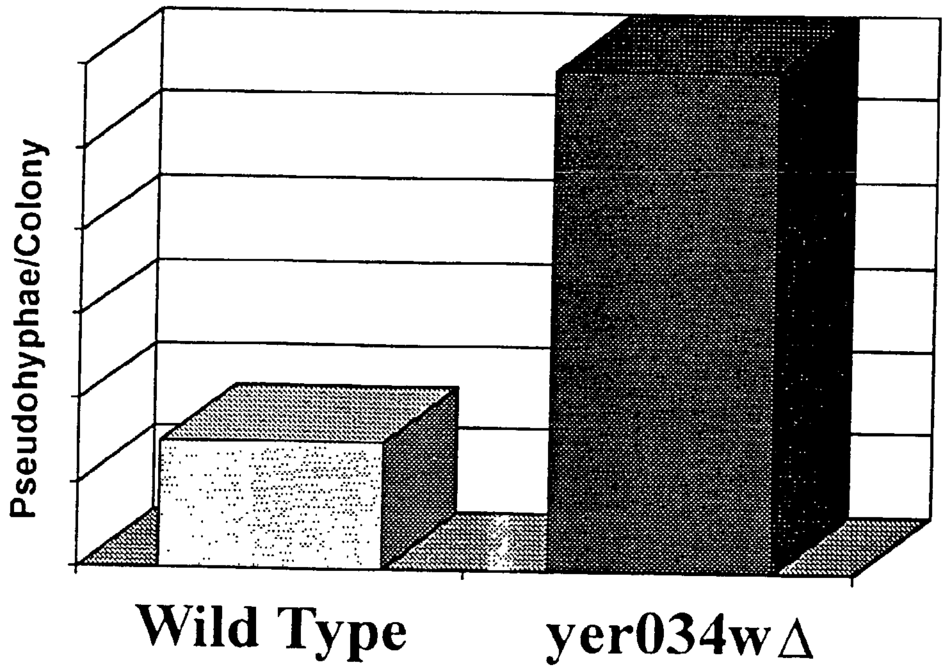
FIG. 22. Mutation of the YER034w Gene Leads to Increased Pseudohyphal Growth. Cells were plated onto low nitrogen plates (0.5% agarose, 2% glucose, 0.34% yeast nitrogen base without amino acids and ammonium sulfate, 0.05 mM ammonium sulfate, 20 μg/ml uracil, 30 μg/ml leucine, and 5 μg/ml histidine) and incubated for four days at 25° C. Bar height represents the average number of hyphal projections per colony (n=20)

Any of a number of different tests can be performed to determine the effect of knocking out the selected target gene. For instance, one can determine whether the yeast cell is more or less responsive to various pharmaceutical compounds (e.g., see FIG. 4), pH, salinity, osmotic pressure, temperature or nutritional conditions. One can determine whether the knockout results in a different observable phenotype (e.g., see FIG. 22). In addition, yeast cells can be tested for their ability to mate, sporulate and bud relative to a wild type control. Thus, these tests may provide important information regarding the function of the target gene.

Methods to Identify Potential Homologs in Other Organisms

Once a gene has been identified as a potential target, one can determine whether the gene from yeast has homologs in other organisms, such as humans, non-human mammals, other vertebrates such as fish, insects, plants, or other fungi.

One method of determining whether an *S. cerevisiae* gene has homologs is by the use of low stringency hybridization and washing. In general, genomic DNA or cDNA libraries can be screened using probes derived from the target *S. cerevisiae* gene using methods known in the art. See above and pages 8.46–8.49 and 9 46–9.58 of Sambrook et al., 1989, herein incorporated by reference. Preferably, genomic DNA libraries are screened because cDNA libraries generally will not contain all the mRNA species an organism can make. Genomic DNA libraries from a variety of different organisms, such as plants, fungi, insects, and various mammalian species are commercially available and can be screened. This method is useful for determining whether there are homologs in organisms whose DNA sequences have not been characterized extensively.

A second method of determining whether an *S. cerevisiae* gene has homologs is through the use of degenerate PCR. In this method, degenerate oligonucleotides that encode short amino acid sequences of the *S. cerevisiae* gene are made Methods of preparing degenerate oligonucleotides and using them in PCR to isolate uncloned genes are well known in the art (see Sambrook, pages 14.7–14.8, and Crawley et al., 1997, pages 4.2.1–4.2.5, herein incorporated by reference).

The most preferred method is to compare the sequence of the *S. cerevisiae* gene to sequences from other organism. Either the nucleotide sequence of the gene or its encoded amino acid sequence is compared to the sequences from other organisms. Preferably, the encoded amino acid sequence of the yeast gene is compared to amino acid sequences from other organisms. The sequence of the yeast gene can be compared by a number of different algorithms well known in the art. In general, computer programs designed for sequence analysis are used for the purpose of comparing the sequence of interest to a large database of other sequences. Any computer program designed for the purpose of sequence comparison can be used in this method. Some computer programs, such as Fasta, produce results that are typically presented as "% sequence identity." Other computer programs, such as blastp, produce results presented as "p-values." Preferably, the target gene sequence will be compared to other sequences using the blastp algorithm.

Nucleotide and amino acid sequences of target genes may be compared to vertebrate sequences, including human and non-human mammalian sequences, as well as plant and insect sequences using any one of the large number of programs known in the art for comparing nucleotide and amino acid sequences to sequences in a database. Examples of such programs are Fasta and blastp, discussed above. Examples of databases which can be searched include GENBANK®-EMBL, SWISSPROT®, DDBJ, GENESEQ® and EST databases, as well as databases containing combinations of these databases.

As a further characterization, any potential homologs from other organisms can be assessed for their ability to functionally complement the yeast mutant. This can be achieved by first cloning the homolog into a *S. cerevisiae* expression vector by standard methods. This plasmid can then be transformed into the heterozygous mutant diploid strain. Upon sporulation and tetrad dissection the ability of the homolog to complement the yeast function is determined by whether or not the haploid spores complements the yeast knockout and restores the wildtype function of the haploid spore. The ability of the homolog to complement the yeast mutant would indicate shared function(s) and suggest that the homolog may be part of a similar pathway in the other organism.

Nucleic Acids, Vectors and Production of Recombinant Polypeptides

The present invention provides nucleic acids and recombinant DNA vectors which comprise *S. cerevisiae* RIG and target gene DNA sequences. Specifically, vectors comprising all or portions of the DNA sequence of HES1, YMR134w, YER034w, YJL105w, YKL077w, YGR046w, YJR041c, YER044c and YLR100w are provided. The vectors of this invention also include those comprising DNA sequences which hybridize under stringent conditions to the HES1, YMR134w, YER034w, YJL105w, YKL077w, YGR046w, YJR041c, YER044c and YLR100w gene sequences, and conservatively modified variations thereof.

The nucleic acids of this invention include single-stranded and double-stranded DNA, RNA, oligonucleotides, antisense molecules, or hybrids thereof and may be isolated from biological sources or synthesized chemically or by recombinant DNA methodology. The nucleic acids, recombinant DNA molecules and vectors of this invention may be present in transformed or transfected cells, cell lysates, or in partially purified or substantially pure forms.

DNA sequences may be expressed by operatively linking them to an expression control sequence in an appropriate expression vector and employing that expression vector to transform an appropriate unicellular host. Expression control sequences are sequences which control the transcription, post-transcriptional events and translation of DNA sequences. Such operative linking of a DNA sequence of this invention to an expression control sequence, of course, includes, if not already part of the DNA sequence, the provision of a translation initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences.

Useful expression vectors for bacterial hosts include bacterial plasmids, such as those from *E. coli*, including, pBLUESCRIPT® pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, λGT10 and λGT11, and other phages, e.g., M13 and filamentous single stranded phage DNA. In yeast, vectors include Yeast Integrating plasmids (e.g., YIp5) and Yeast Replicating plasmids (the YRp and YEp series plasmids), Yeast centromere plasmids (the YCp series plasmids), pGPD-2, 2μ plasmids and derivatives thereof, and improved shuttle vectors such as those described in Gietz and Sugino, *Gene,* 74, pp. 527–34 (1988) (YIplac, YEplac and YCplac). Expression in mammalian cells can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL 941.

In addition, any of a wide variety of expression control sequences—sequences that control the expression of a DNA sequence when operatively linked to it—may be used in these vectors to express the DNA sequences of this invention. Such useful expression control sequences include the expression control sequences associated with structural genes of the foregoing expression vectors Expression control sequences that control transcription include, e.g., promoters, enhancers and transcription termination sites. Expression control sequences that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct expression of the polypeptide to particular cellular compartments, and sequences in the 5' and 3' untranslated regions that modify the rate or efficiency of translation Examples of useful expression control sequences include, for example, the early and late promoters of SV40 or adenovirus, the lac system, the trp system, the TAC or TRC system, the T3 and T7 promoters, the major operator and promoter regions of phage lambda, the control regions of fd coat protein, the promoter for 3-phosphoglycerate kinase or other glycolytic enzymes, the promoters of acid phosphatase, e.g, Pho5, the promoters of the yeast α-mating system, the GAL1 or GAL10 promoters, and other constitutive and inducible promoter sequences known to control the expression of genes of prokaryotic or eukaryotic cells or their viruses, and various combinations thereof. See, e.g., *The Molecular Biology of the Yeast Saccharomyces* (eds. Strathern, Jones and Broach) Cold Spring Harbor Lab., Cold Spring Harbor, N.Y. for details on yeast molecular biology in general and on yeast expression systems (pp. 181–209) (incorporated herein by reference)).

DNA vector design for transfection into mammalian cells should include appropriate sequences to promote expression of the gene of interest, including: appropriate transcription initiation, termination and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. A great number of expression control sequences—constitutive, inducible and/or tissue-specific—are known in the art and may be utilized. For eukaryotic cells, expression control sequences typically include a promoter, an enhancer derived from immunoglobulin genes, SV40, cytomegalovirus, etc., and a polyadenylation sequence which may include splice donor and acceptor sites Substantial progress in the development of mammalian cell expression systems has been made in the last decade and many aspects of the system are well characterized.

Preferred DNA vectors also include a marker gene and means for amplifying the copy number of the gene of interest. DNA vectors may also comprise stabilizing sequences (e.g., ori- or ARS-like sequences and telomere-like sequences), or may alternatively be designed to favor directed or non-directed integration into the host cell genome. In a preferred embodiment, DNA sequences of this invention are inserted in frame into an expression vector that allows high level expression of an RNA which encodes a fusion protein comprising encoded DNA sequence of interest.

Of course, not all vectors and expression control sequences will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered.

In selecting an expression control sequence, a variety of factors should also be considered. These include, for example, the relative strength of the sequence, its controllability, and its compatibility with the DNA sequence of this invention, particularly with regard to potential secondary structures. Unicellular hosts should be selected by consideration of their compatibility with the chosen vector, the toxicity of the product coded for by the DNA sequences of this invention, their secretion characteristics, their ability to fold the polypeptide correctly, their fermentation or culture requirements, and the ease of purification from them of the products coded for by the DNA sequences of this invention.

Within these parameters, one of skill in the art may select various vector/expression control sequence/host combinations that will express the DNA sequences of this invention in fermentation or in other large scale cultures.

Given the strategies described herein, one of skill in the art can construct a variety of vectors and nucleic acid molecules comprising functionally equivalent nucleic acids. DNA cloning and sequencing methods are well known to those of skill in the art and are described in an assortment of laboratory manuals, including Sambrook et al, supra, 1989; and Ausubel et al., 1994 Supplement. Product information from manufacturers of biological, chemical and immunological reagents also provide useful information.

The recombinant DNA molecules and more particularly, the expression vectors of this invention may be used to express the RIG and target genes from *S. cerevisiae* as recombinant polypeptides in a heterologous host cell. The polypeptides of this invention may be full-length or less than full-length polypeptide fragments recombinantly expressed from the DNA sequences according to this invention. Such polypeptides include variants and muteins having biological activity. The polypeptides of this invention may be soluble, or may be engineered to be membrane- or substrate-bound using techniques well known in the art.

Particular details of the transfection, expression and purification of recombinant proteins are well documented and are understood by those of skill in the art. Further details on the various technical aspects of each of the steps used in recombinant production of foreign genes in mammalian cell expression systems can be found in a number of texts and laboratory manuals in the art. See, e.g., Ausubel et al., 1989, herein incorporated by reference.

Transformation and other methods of introducing nucleic acids into a host cell (e.g., transfection, electroporation, liposome delivery, membrane fusion techniques, high velocity DNA-coated pellets, viral infection and protoplast fusion) can be accomplished by a variety of methods which are well known in the art (see, for instance, Ausubel, supra, and Sambrook, supra). Bacterial, yeast, plant or mammalian cells are transformed or transfected with an expression vector, such as a plasmid, a cosmid, or the like, wherein the expression vector comprises the DNA of interest. Alternatively, the cells may be infected by a viral expression vector comprising the DNA or RNA of interest. Depending upon the host cell, vector, and method of transformation used, transient or stable expression of the polypeptide will be constitutive or inducible. One having ordinary skill in the art will be able to decide whether to express a polypeptide transiently or stably, and whether to express the protein constitutively or inducibly.

A wide variety of unicellular host cells are useful in expressing the DNA sequences of this invention. These hosts may include well known eukaryotic and prokaryotic hosts, such as strains of *E. coli, Pseudomonas, Bacillus, Streptomyces*, fungi, yeast, insect cells such as *Spodoptera frugiperda* (SF9), animal cells such as CHO, BHK, MDCK and various murine cells, e.g., 3T3 and WEHI cells, African green monkey cells such as COS 1, COS 7, BSC 1, BSC 40, and BMT 10, and human cells such as VERO, WI38, and HeLa cells, as well as plant cells in tissue culture.

Expression of recombinant DNA molecules according to this invention may involve post-translational modification of a resultant polypeptide by the host cell. For example, in mammalian cells expression might include, among other things, glycosylation, lipidation or phosphorylation of a polypeptide, or cleavage of a signal sequence to produce a "mature" protein. Accordingly, the polypeptide expression products of this invention encompass full-length polypeptides and modifications or derivatives thereof, such as glycosylated versions of such polypeptides, mature proteins and polypeptides retaining a signal peptide. The present invention also provides for biologically active fragments of the polypeptides. Sequence analysis or genetic manipulation may identify those domains responsible for the function of the protein in yeast. Thus, the invention encompasses the production of biologically active fragments The invention also encompasses fragments of the polypeptides which would be valuable as antigens for the production of antibodies, or as competitors for antibody binding.

The polypeptides of this invention may be fused to other molecules, such as genetic, enzymatic or chemical or immunological markers such as epitope tags. Fusion partners include, inter alia, myc, hemagglutinin (HA), GST, immunoglobulins, β-galactosidase, biotin trpE, protein A, β-lactamase, α amylase, maltose binding protein, alcohol dehydrogenase, polyhistidine (for example, six histidine at the amino and/or carboxyl terminus of the polypeptide), lacZ, green fluorescent protein (GFP), yeast α mating factor, GAL4 transcription activation or DNA binding domain, luciferase, and serum proteins such as ovalbumin, albumin and the constant domain of IgG. See, e.g., Godowski et al., 1988, and Ausubel et al., supra. Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques such as those described in Merrifield, 1963, herein incorporated by reference, or produced by chemical cross-linking Tagged fusion proteins permit easy localization, screening and specific binding via the epitope or enzyme tag. See Ausubel, 1991, Chapter 16. Some tags allow the protein of interest to be displayed on the surface of a phagemid, such as M13, which is useful for panning agents that may bind to the desired protein targets. Thus, fusion proteins are useful for screening potential agents using the proteins encoded by the target genes.

One advantage of fusion proteins is that an epitope or enzyme tag can simplify purification. These fusion proteins may be purified, often in a single step, by affinity chromatography For example, a $His^6$ tagged protein can be purified on a Ni affinity column and a GST fusion protein can be purified on a glutathione affinity column Similarly, a fusion protein comprising the Fc domain of IgG can be purified on a Protein A or Protein G column and a fusion protein comprising an epitope tag such as myc can be purified using an immunoaffinity column containing an anti-c-myc antibody It is preferable that the epitope tag be separated from the protein encoded by the target gene by an enzymatic cleavage site that can be cleaved after purification. A second advantage of fusion proteins is that the epitope tag can be used to bind the fusion protein to a plate or column through an affinity linkage for screening targets.

In addition, fusion proteins comprising the constant domain of IgG or other serum proteins can increase a protein's half-life in circulation for use therapeutically. Fusion proteins comprising a targeting domain can be used to direct the protein to a particular cellular compartment or tissue target in order to increase the efficacy of the functional domain. See, e.g., U.S. Pat. No. 5,668,255, which discloses a fusion protein containing a domain which binds to an animal cell coupled to a translocation domain of a toxin protein. Fusion proteins may also be useful for improving antigenicity of a protein target. Examples of making and using fusion proteins are found in U.S. Pat. Nos. 5,225,538, 5,821,047, and 5,783,398, which are hereby incorporated by reference.

Production of Polypeptide Fragments, Derivatives and Muteins and Biological Assays Thereof Fragments, derivatives and muteins of polypeptides encoded by the RIG and target genes can be produced recombinantly or chemically, as discussed above. One can produce fragments of a polypeptide encoding a target gene by truncating the DNA encoding the target gene and then expressing it recombinantly. Alternatively, one can produce a fragment by chemically synthesizing a portion of the full-length polypeptide. One may also produce a fragment by enzymatically cleaving the polypeptide. Methods of producing polypeptide fragments are well-known in the art (see, eg., Sambrook et al. and Ausubel et al. supra).

One may produce muteins of a polypeptide encoded by a target gene by introducing mutations into the DNA sequence of the gene and then expressing it recombinantly These mutations may be targeted, in which particular encoded amino acids are altered, or may be untargeted, in which random encoded amino acids within the polypeptide are altered. Muteins with random amino acid alterations can be screened for a particular biological activity. Methods of producing muteins with targeted or random amino acid alterations are well known in the art, see e.g., Sambrook et al., Ausubel et al., supra, and U.S. Pat. No. 5,223,408, herein incorporated by reference. Production of polypeptide derivatives are well known in the art, see above.

There are a number of methods known in the art to determine whether fragments, muteins and derivatives of polypeptides encoded by a target gene has the same, enhanced or decreased biological activity as the wild type polypeptide. One of the simplest assays involves determining whether the fragment, mutein or derivative can complement the gene function in a cell which does not contain the target gene. For instance, one can introduce a DNA encoding a fragment or mutein of a polypeptide encoded by a gene into a mutant yeast strain which has the gene of interest deleted (see above under "Methods of Producing Mutant Yeast Strains"). If introduction of the DNA encoding the fragment or mutein permits the mutant yeast strain to regain its wildtype phenotype, then the fragment or mutein is biologically active, and complements the deleted gene.

In one type of screening assay, the target gene or a fragment thereof can be used as the "bait" in a two-hybrid screen to identify molecules that physically interact with the target gene. See Chien et al. (1991).

In addition, one may generate genome expression profiles of yeast strains to characterize the gene's function. In order to generate such profiles, a non-functional or conditional allele of the gene in a yeast strain must be produced. The conditional or non-functional allele may be constructed by any technique known in the art, including deleting the gene as described above, making a temperature-sensitive allele of the gene or operably linking the gene to an inducible promoter for regulated expression. If the yeast strain contains a non-functional allele, a genome expression profile of the mutant strain is compared to a wild type strain. If the yeast strain contains a conditional allele, the yeast strain is first grown under the permissive condition to permit expression of the functional product of the target1 gene. Then, the yeast strain is shifted to the nonpermissive condition, in which the product of the target gene is not made or is non-functional. The genome expression profile of the yeast strain under the nonpermissive condition may be compared to the same yeast strain grown under permissive conditions or a wildtype yeast strain. Structure-function studies can be performed wherein a library of mutant forms of the gene is screened for the ability to complement the knock-out mutant strain.

Fragments, muteins and derivatives may also be microinjected into a mutant yeast strain in which the gene of interest is deleted to determine whether the introduction of the fragment, mutein or derivative can complement the genetic defect. Similarly, fragments, muteins and derivatives may be microinjected into other cell types in which the homologous gene has been deleted.

Finally, if a particular biochemical activity of a polypeptide encoded by a target gene is known, this activity can be measured for fragments, muteins or derivatives of the polypeptide. For instance, if a target gene encodes a kinase, one could measure the kinase activity of the wild type polypeptide and compare it to the activity of a fragment, mutein or derivative.

Production of Antibodies

The polypeptides encoded by the target genes of this invention may be used to elicit polyclonal or monoclonal antibodies which bind to the target gene product or a homolog from another species using a variety of techniques well known to those of skill in the art. Alternatively, peptides corresponding to specific regions of the polypeptide encoded by the target gene may be synthesized and used to create immunological reagents according to well known methods.

Antibodies directed against the polypeptides of this invention are immunoglobulin molecules or portions thereof that are immunologically reactive with the polypeptide of the present invention. It should be understood that the antibodies of this invention include antibodies immunologically reactive with fusion proteins.

Antibodies directed against a polypeptide encoded by a target gene may be generated by immunization of a mammalian host. Such antibodies may be polyclonal or monoclonal. Preferably they are monoclonal. Methods to produce polyclonal and monoclonal antibodies are well known to those of skill in the art. For a review of such methods, see Harlow and Lane (1988), Yelton et al (1981), and Ausubel et al. (1989) herein incorporated by reference. Determination of immunoreactivity with a polypeptide encoded by an target gene may be made by any of several methods well known in the art, including by immunoblot assay and ELISA.

Monoclonal antibodies with affinities of $10^{-8}$ $M^{-1}$ or preferably $10^{-9}$ to $10^{-10}$ $M^{-1}$ or stronger are typically made by standard procedures as described, e.g., in Harlow and Lane, 1988 or Goding, 1986. Briefly, appropriate animals are selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350, 3,996,345; 4,277,437; 4,275,149 and 4,366,241, herein incorporated by reference. Also, recombinant immunoglobulins may be produced (see U.S. Pat. No. 4,816,567, herein incorporated by reference)

An antibody of this invention may also be a hybrid molecule formed from immunoglobulin sequences from different species (e.g., mouse and human) or from portions of immunoglobulin light and heavy chain sequences from the same species An antibody may be a single-chain antibody or a humanized antibody. It may be a molecule that has multiple binding specificities, such as a bifunctional antibody prepared by any one of a number of techniques known to those of skill in the art including the production of hybrid hybridomas, disulfide exchange, chemical cross-linking, addition of peptide linkers between two monoclonal antibodies, the introduction of two sets of immunoglobulin heavy and light chains into a particular cell line, and so forth.

The antibodies of this invention may also be human monoclonal antibodies, for example those produced by immortalized human cells, by SCID-hu mice or other non-human animals capable of producing "human" antibodies, or by the expression of cloned human immunoglobulin genes. The preparation of humanized antibodies is taught by U.S. Pat. Nos. 5,777,085 and 5,789,554, herein incorporated by reference.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Therapeutic Methods Using Nucleic Acids Encoding Target Genes

Once a target gene has been identified in *S. cerevisiae*, the gene and its nucleotide sequence can be exploited in a number of ways depending upon the nature of the target gene. One method is to use the primary sequence of the target gene itself. For instance, antisense oligonucleotides can be produced which are complementary to the mRNA of the target gene. Antisense oligonucleotides can be used to inhibit transcription or translation of a target yeast gene. Production of antisense oligonucleotides effective for therapeutic use is well-known in the art, see Agrawal et al., 1998, Lavrovsky et al., 1997, and Crooke, 1998, herein incorporated by reference. Antisense oligonucleotides are often produced using derivatized or modified nucleotides in order to increase half-life or bioavailability.

The primary sequence of the target gene can also be used to design ribozymes that can target and cleave specific target gene sequences. There are a number of different types of ribozymes. Most synthetic ribozymes are generally hammerhead, *Tetrahymena* and hairpin ribozymes. Methods of designing and using ribozymes to cleave specific RNA species are known in the art, see Zhao et al., 1998, Larovsky et al., 1997, and Eckstein, 1997, herein incorporated by reference. Although hammerhead ribozymes are generally ineffective in yeast (Castanotto et al., 1998), other types of ribozymes may be effective in yeast, and hammerhead and other types of ribozymes are effective in other organisms.

As discussed above, one can use target yeast genes to identify homologous genes in plants and animals, including humans. Therefore, one can design ribozymes and antisense molecules to these genes from plants and animals, including humans Methods Using Neutralizing Antibodies to Proteins Encoded by Target Genes The protein encoded by the target gene can be used to elicit neutralizing antibodies for use as inhibit the function of the target protein. An antibody may be an especially good inhibitor if the target gene of interest encodes a protein which is expressed on the cell surface, such as an integral membrane protein. Although polyclonal antibodies may be made, monoclonal antibodies are preferred. Monoclonal antibodies can be screened individually in order to isolate those that are neutralizing or inhibitory for the protein encoded by the target gene. Monoclonal antibodies also may be screened for inhibition of a particular function of a protein. For instance, if it is known that the target gene in yeast encodes an enzyme, one can identify antibodies that inhibit the enzymatic activity. Alternatively, if the specific function of a target gene is unknown, one can measure inhibition of the protein by determining the genome expression profile for yeast cells contacted with the neutralizing antibody. Similarly, one can screen antibodies which are directed against animal, plant or human proteins for inhibition of the protein's activity in appropriate cells.

Monoclonal antibodies which inhibit a target protein in vitro may be humanized for therapeutic use using methods well-known in the art, see, e.g., U.S. Pat. Nos. 5,777,085 and 5,789,554, herein incorporated by reference. Monoclonal antibodies may also be engineered as single-chain antibodies using methods well-known in the art for therapeutic use, see, e.g., U.S. Pat. Nos. 5,091,513, 5,587,418, and 5,608,039, herein incorporated by reference.

Neutralizing antibodies may also be used diagnostically. For instance, the binding site of a neutralizing antibody to the protein encoded by the target gene can be used to help identify domains that are required for the protein's activity The information about the critical domains of a target protein can be used to design inhibitors that bind to the critical domains of the target protein. In addition, neutralizing antibodies can be used to validate whether a potential inhibitor of an target protein inhibits the protein in in vitro assays.

Methods of Identifying Functional Attributes of the Target

Once a target gene in yeast is identified, the GRM (or an equivalent) is used to help identify critical functional attributes of the gene. In order to determine the particular transcripts a target gene modifies, one overexpresses the target gene in the cells of the GRM. One may also overexpress a conditional allele of the gene in the cells of the GRM. Then, one identifies a subset of genes that are either induced or repressed by overexpression of the target gene. Methods for processing data using the GRM are also disclosed in U.S. Pat. Nos. 5,569,588 and 5,777,888; see also U.S. patent application Ser. No. 09/076,668, now pending. Once the genes that are regulated by a target gene are identified, one can use this information in a number of ways to identify potential inhibitors or activators of the target protein. Alternatively, one may determine the genome expression profile of a cell that has a mutation in a target gene, or a cell that has the endogenous target gene replaced either with an altered allele or with the counterpart gene from another species. Similarly, plant and animal GRMs, including human GRMs, overexpressing target genes can be used in the same way to identify potential inhibitors or activators of the target protein in these organisms.

Another method for isolating a potential inhibitors or activators of a target gene is to use information obtained from the "two-hybrid system" to identify and clone genes encoding proteins that interact with the polypeptide encoded by the target gene (see, e g., Chien et al.,1991, incorporated herein by reference). The amino acid sequences of the polypeptides identified by the two-hybrid system can be used to design inhibitory peptides to the target protein. The "two-hybrid" system using libraries of the appropriate species can also be used to identify and clone genes encoding proteins that interact with the polypeptide encoded by the target genes.

Methods of Using Target Proteins

Recombinantly expressed target proteins or functional fragments thereof can be used to screen libraries of natural, semisynthetic or synthetic compounds. Particularly useful types of libraries include combinatorial small organic molecule libraries, phage display libraries, and combinatorial peptide libraries. Methods of determining whether components of the library bind to a particular polypeptide are well known in the art. In general, the polypeptide target is attached to solid support surface by non-specific or specific binding. Specific binding can be accomplished using an antibody which recognizes the protein that is bound to a solid support, such as a plate or column. Alternatively, specific binding may be through an epitope tag, such as GST binding to a glutathione-coated solid support, or IgG fusion protein binding to a Protein A solid support. Alternatively, the recombinantly expressed protein or fragments thereof may be expressed on the surface of phage, such as M13 A library in mobile phase is incubated under conditions to promote specific binding between the target and a compound. Compounds which bind to the target can then be identified. Alternately, the library is attached to a solid support and the polypeptide target is in the mobile phase.

Binding between a compound and target can be determined by a number of methods. The binding can be identified by such techniques as competitive ELISAs or RIAs, for example, wherein the binding of a compound to a target will prevent an antibody to the target from binding. These methods are well-known in the art, see, e.g., Harlow and Lane, supra. Another method is to use a BIACORE® device to measure interactions between a target and a compound using methods provided by the manufacturer. A preferred method is automated high throughput screening, see, e.g., Burbaum et al., 1997, and Schullek et al., 1997, herein incorporated by reference.

Once a compound that binds to a target is identified, one then determines whether the compound inhibits the activity of the target. If a biological function for the target protein is known, one could determine whether the compound inhibited the biological activity of the protein. For instance, if it is known that the target protein is an enzyme, one can measure the inhibition of enzymatic activity in the presence of the potential inhibitor.

In a preferred embodiment, the target gene is selected from YMR134w, YER034w, YJL105w, YKL077w, YGR046w, YJR041c, YER044c and YLR100w and their mammalian homologs.

Another embodiment of the invention is to use the recombinantly expressed protein for rational drug design. The structure of the recombinant protein may be determined using x-ray crystallography or nuclear magnetic resonance (NMR). Alternatively, one could use computer modeling to determine the structure of the protein. The structure can be used in rational drug design to design potential inhibitory compounds of the target (see, e.g., Clackson, Mattos et al., Hubbard, Cunningham et al., Kubinyi, Kleinberg et al., all herein incorporated by reference).

In another embodiment, potential inhibitors of a regulon target gene can be identified by the following steps:

a) creating a host cell in which the target gene has been altered or inactivated by mutation;

b) comparing gene expression profiles in the mutated host cell to those in a host cell which expresses the normal target gene;

c) identifying one or more potential target-dependent reporter genes whose expression is altered in the host cell in which the target gene has been altered or inactivated compared to the host cell which expresses the normal target gene; and d) screening one or more compounds for their effects on expression of the target-dependent reporter gene.

If expression of the target-dependent reporter gene increases in the host cell harboring an altered or inactivated target gene, then a potential inhibitor of the regulon target gene will increase expression of the target-dependent reporter gene, and if expression of the target-dependent reporter gene decreases in the host cell harboring an altered or inactivated target gene, then a potential inhibitor of the regulon target gene will decrease expression of the target-dependent reporter gene.

The method may further comprise the step, performed before step d), of assessing the specificity of a potential target-dependent reporter gene by comparing gene expression profiles the potential target-dependent reporter gene to a plurality of genes in a database of compiled gene expression profiles to generate individual expression correlation coefficients wherein a target-dependent reporter gene whose expression correlates with the expression of the regulon target gene and with a minimal number or no other gene is selected over one whose expression correlates with a greater number of genes based on expression correlation coefficients. The method may also encompass upstream sequences that control expression of the target-dependent reporter genes fused to a heterologous coding sequence, and the fusion is used to screen compounds for potential inhibitors of the regulon target gene, as discussed above.

In a preferred embodiment, the target gene is selected from YMR134w, YER034w, YJL105w, YKL077w, YGR046w, YJR041c, YER044c and YLR100w and their mammalian homologs.

Pharmaceutical Applications

Compounds that bind to target proteins or regulate target gene expression can be tested in yeast cell systems and heterologous host cell systems (e.g., human cells) to verify that they do not have undesirable side effects. In addition, the yeast GRM can be used to make sure that the compounds do not adversely alter gene transcription (e.g., in an undesirable way). Of course, certain changes in gene expression may be inevitable and many of these will not be deleterious to the patient or host organism. Once lead compounds have been identified, these compounds can be refined further via rational drug design and other standard pharmaceutical techniques.

The compounds of this invention may be formulated into pharmaceutical compositions and administered in vivo at an effective dose to treat a particular disease or condition. Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the compounds of this invention, including isolated and purified forms, their salts or pharmaceutically acceptable derivatives thereof, may be accomplished using any conventionally accepted mode of administration.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration The compounds of this invention may, for example, be placed into sterile, isotonic formulations with or without cofactors which stimulate uptake or stability. The formulation is preferably liquid, or may be lyophilized powder. For example, the inhibitors may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP)

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Alternatively, the composition may be pressurized and contain a compressed gas, such as nitrogen or a liquified gas propellant. The liquified propellant medium and indeed the total composition is preferably such that the active ingredient does not dissolve therein to any substantial extent Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required Ophthalmic formulation, ear drops, eye ointments, powders and solutions are also contemplated as being within the scope of this invention.

The pharmaceutical compositions of this invention may also be administered using microspheres, microparticulate delivery systems or other sustained release formulations placed in, near, or otherwise in communication with affected tissues or the bloodstream. Suitable examples of sustained release carriers include semipermeable polymer matrices in the form of shaped articles such as suppositories or microcapsules Implantable or microcapsular sustained release matrices include polylactides (U.S. Pat. No. 3,773,319; EP 58,481), copolymers of L-glutamic acid and gamma ethyl-L-glutamate (Sidman et al., 1985); poly(2-hydroxyethyl-methacrylate) or ethylene vinyl acetate (Langer et al., 1981, Langer, 1982)

The compounds of this invention may also be attached to liposomes, which may optionally contain other agents to aid in targeting or administration of the compositions to the desired treatment site. Attachment of the compounds to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., 1992), herein incorporated by reference.

Liposomes containing pharmaceutical compounds may be prepared by well-known methods (See, e.g. DE 3,218,121; Epstein et al., 1985, Hwang et al.,1980; U.S. Pat. Nos. 4,485,045 and 4,544,545). Ordinarily the liposomes are of the small (about 200–800 Angstroms) unilamellar type in which the lipid content is greater than about 30 mol. % cholesterol. The proportion of cholesterol is selected to control the optimal rate of MAG derivative and inhibitor release.

The compositions also will preferably include conventional pharmaceutically acceptable carriers well known in the art (see, e.g., Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations The compositions are preferably in the form of a unit dose and will usually be administered one or more times a day.

EXAMPLE 1

Preparation of the Genome Report Matrix™

Construction of Reporter Gene Fusions (Method 1)

The regulatory region of each yeast gene was cloned into one of two vectors, pAB1 or pAB2. The vector pAB1 was constructed in the following manner: First, the polymerase chain reaction (PCR) was used to amplify the transcriptional terminator region from the gene PGK1 using the oligonucleotides 5P-PGKTERM (5'-GATTGAATTCAATTGAAATCGATAG-3'; SEQ ID NO:52) and 3P-PGKTERM (5'-CCGAGGCGCCGAATTTTCGAGTTAT-3'; SEQ ID NO:53). The amplified fragment consists of the 263 base-pair region immediately downstream of the PGK1 stop codon, and contains an EcoRI site at the 5' end and a NarI site at the 3' end. These restriction sites were engineered into the two PCR primers (underlined sequences). The terminator was then cloned into YIplac211 that had been linearized with EcoRI and NarI, yielding pAB34. Next, the coding region of the green fluorescent protein (GFP) from *Aequoria victoria* was amplified by PCR using the oligonucleotides 5P-GFP-ORF (5'-CATGTCTAGAGGAGAAGAACTTTTC-3'; SEQ ID NO:54) and 3P-GFP-ORF (5'-CGCGAATTCCTATTTGTATAGTTCA-3'; SEQ ID NO:55). Again, these oligonucleotides contain engineered XbaI and EcoRI sites at the 5' and 3' ends, respectively (underlined). This fragment was cloned into pAB34, linearized with XbaI and EcoRI, to produce pAB35. Finally, the GFP-PGK terminator fragment was moved into the episomal vector YEplac195 (9) as an XbaI/NarI fragment, thereby producing pAB1.

The vector pAB2 is pAB1 with an altered multiple cloning site (MCS). The new MCS contains 8 basepair recognition sites for three restriction enzymes. These larger 8 base-pair recognition sites occur less frequently throughout the yeast genome than the 6 base-pair sites present in the MCS of pAB1. Thus, the utilization of restriction enzymes that recognize 8 base-pair sequences to clone the various regulatory regions (engineered into the PCR primers used to amplify the regions) would minimize the occurrence of those sites within the regions themselves. To construct pAB2, pAB1 was linearized with XbaI and SphI, dropping out the existing MCS, and an adapter containing the new MCS was ligated in. The adapter was made by hybridizing two oligonucleotides, 8Cutter (5'-CGGCGCGCCGCGGCCGCATGGCCGGCCAAT-3'; SEQ ID NO:56) and 8CutEnd (5'-CTAGATTGGCCGGCCATGCGGCCGCGGCGCGCCGCATG-3'; SEQ ID NO:57). This adapter has sites for the restriction enzymes FseI, NotI, and AscI (underlined).

The promoter regions were cloned utilizing PCR of genomic DNA prepared from a strain derived from S288c; JRY147 (MATa SUC2 mal mel gal2 CUP1) The promoter-specific primers were designed such that the proximal primer spanned the start codon of the specific gene and included a few (usually four) codons derived from the gene. The position of the distal primer was determined on a case-by-case basis depending on the distance to, and orientation of, the neighboring open reading frame (ORF) and the restriction sites present. Where the upstream ORF was positioned in a divergent orientation and within 1,200 base-pairs, the size of the promoter fragment amplified was adjusted such that all nucleotides up to, but not including, the start codon of the upstream ORF were present. In cases where the upstream ORF was situated in the same orientation, the amplified fragment was designed to extend into the coding region but not so as to include the start codon. Both primers had restriction enzyme recognition sites engineered into the ends to allow the subsequent cloning of the PCR fragment into pAB1, or pAB2.

Construction of Reporter Gene Fusions (Method 2)

In another method for constructing genome reporter constructs, a vector comprising a marker gene having an amber mutation and a supF tRNA gene which suppresses the amber mutation is used as the parent vector.

A plasmid cloning vector was constructed which comprises a mutant β-lactamase gene with an amber mutation and a supF tRNA gene. Downstream of the supF tRNA gene there is a "stuffer" DNA fragment which is flanked by BsmBI restriction sites. The BsmBI restriction enzyme cuts outside of its six base pair recognition sequence (see, e.g., New England Biolabs 96/97 Catalog, p. 23) and creates a four nucleotide 5' overhang. When the plasmid cloning vector is digested with BsmBI, the enzyme cleaved within the stuffer DNA and within the adjoining tRNA gene and deleted the four 3' terminal nucleotides of the gene. The deleted supF tRNA gene encodes a tRNA which cannot fold correctly and is non-functional, i.e., it could not suppress the amber mutation in the mutant β-lactamase gene (β-lactamase (amber)). Downstream from the stuffer DNA fragment is the coding region of a modified green fluorescent protein ("GFP") gene.

The stuffer DNA was excised from the vector by digestion with BsmBI. The double-stranded DNA at the supF-stuffer fragment junction, produced by BsmBI digestion, is shown below. The tRNA gene sequences are indicated in bold:

```
                                         (SEQ ID NO:58)
 5' ..supF..TC          CCCCGGAGACGTC..stuffer..
          ..AGGGGG         CCTCTGCAG..5'
             BsmBI
```

The 3' terminal sequence of the supF gene necessary for proper function is TCCCCCACCA (SEQ ID NO:59). The vector, once cleaved with BsmBI, lacks the supF tRNA ACCA terminal nucleotides if the overhangs self-anneals during re-circularization of the plasmid in the absence of insert.

A DNA insert containing the upstream regulatory sequence from a yeast ORF was generated as a PCR fragment. Two oligonucleotides were designed to flank the DNA insert sequences of interest on a template DNA and anneal to opposite strands of the template DNA. These oligonucleotides also contained a sequence at their respective 5' ends that, when converted into a 5' overhang (in the double-stranded PCR fragment generated using the oligonucleotides), is complementary to the overhangs on the cloning vector generated by BsmBI endonucleolytic cleavage.

Oligonucleotide #1 comprises the 5' terminal sequence: 5° CCCCACCA . . . . The remaining nucleotides 3' to this sequence were designed to anneal to sequences at one end of the DNA insert of choice, in this Example, to one of a multitude of yeast expression control sequences.

As highlighted in bold above, oligonucleotide #1 comprises the base pairs needed to restore the wild-type 3' terminal end of the supF tRNA gene. These base pairs are located immediately 3' to the sequence that allows the insert to anneal to the overhang in the BsmBI-digested pAB4 vector.

Oligonucleotide #2 comprises the 5' terminal sequence: 5' TCCTG . . . . The remaining nucleotides 3' to this sequence were designed to anneal to sequences at the other end of the DNA insert of choice, in this Example, to one of a variety of yeast expression control sequences which may be used according to this invention.

The DNA template (*S. cerevisiae* genomic DNA) and the two oligonucleotides were annealed and the hybrids were amplified by polymerase chain reaction using KLENTAQ™ polymerase and PCR buffer according to the manufacturer's instructions (Clonetech). Briefly, 15 ng *S. cerevisiae* genomic DNA served as template DNA in a 1 μl PCR reaction containing 0.2 mM dNTPs, PCR buffer, KLENTAQ™ polymerase, and 1 μl of an 8 μM solution containing the primer pairs. The PCR reaction mixture was subjected to the following steps: a) 94° C. for 3 min; b) 94° C. for 15 sec; c) 52° C. for 30 sec; d) 72° C. for 1 min, 45 sec; and e) 4° C. indefinitely. Steps b) through d) were repeated for a total of 30 cycles. The PCR amplification product was purified away from other components of the reaction by standard methods.

To generate the desired 5' overhangs on the ends of the PCR amplification product, the PCR fragment was treated with DNA polymerase I in the presence of dTTP and dCTP. Under these conditions, DNA polymerase I fills in 3' overhangs with its 5' to 3' polymerase activity and also generates 5' overhangs with its 3' to 5' exonucleolytic activity, which, in the presence of excess dTTP and dCTP, removes nucleotides in a 3' to 5' direction until a thymidine or a cytosine, respectively, is removed and then replaced.

The overhangs generated by this reaction are:

a) At the 5' end (supF tRNA restoring end) of the DNA insert:

```
5' CCCCACCA..        becomes   5' CCCCACCA..
       GGGGTGGT..                       TGGT..
```

b) At the 3' end of the DNA insert joined to the GFP coding sequence):

```
5' CAGGA..       becomes      5' C
   GTCCT..                       GTCCT..
```

This DNA insert, now comprising 5' overhangs compatible with one of each of the ends of the BsmBI-cleaved pAB4 vector, was used as substrate in a standard ligation reaction with the BsmBI-cleaved pAB4 vector. The resulting ligation mixture was used to transform competent *E. coli* cells. The cells were plated on agar plates in the presence of ampicillin.

Colonies that grew in the presence of ampicillin were producing functional β-lactamase enzyme and each harbored the desired recombinant DNA molecule, having a DNA insert with a yeast expression control sequence inserted upstream of the modified GFP coding region. The supF gene on vectors which re-ligated without a DNA insert did not express a functional supF tRNA and did not make functional β-lactamase. Thus, they were not found in transformed host cells grown on ampicillin.

Construction of Yeast Strains

Strain ABY11 (MATa leu2Δ1 ura3-52) of *S. cerevisiae* was used. ABY11 is derived from S288c. GRM arrays were grown at 30° C. on solid casamino acid medium (Difco) with 2% glucose and 0.5% UltraPure Agarose (Gibco BRL) The medium was supplemented with additional amino acids and adenine (Sigma) at the following concentrations: adenine and tryptophan at 30 μg/ml; histidine, methionine, and tyrosine at 20 μg/ml; leucine and lysine at 40 μg/ml. Stock solutions of the supplements were made at 100× concentrations in water. Yeast cells were transformed with the reporter plasmids prepared by Method 1 or Method 2 (above) by the lithium acetate method (Ito et al., 1983, and Schiestl and Gietz, 1989).

Determinations of Reporter Gene Expression Levels

Solutions of test compounds were added directly to the yeast strains or were coated on plates prior to addition of the yeast strains. The individual strains comprising the GRM were maintained as independent colonies (and cultures) in a 96-well format, in medium selecting for the URA3-containing reporter plasmid. Prior to each experiment, fresh dilutions of the reporter-containing strains were inoculated and grown overnight at 30° C. A Hamilton MicroLab 4200, a multichannel gantry robot equipped with a custom pin tool device capable of dispensing 50 nanoliter volumes in a highly reproducible manner, was used to array the matrix of yeast strains in a uniform manner onto solid agar growth media at a density of 1536 reporter strains per 110 $cm^2$ plate. Fifty nanoliters of yeast liquid cultures arrayed onto solid medium by the Hamilton MicroLab 4200 results in colony-to-colony signal reproducibility of less than 5% variation. Once arrayed, each plate was grown at 30° C. for 18 hours or at 25° C. for 24 hours.

The level of fluorescence expressed from each reporter gene fusion was determined using a Molecular Dynamics Fluorimager SI. AIS image analysis software (Imaging Research, Ontario Calif.) was used to quantitate the fluorescence of each colony in the images Generally, the drug treatments were performed at several concentrations, with the analysis based upon the concentration producing the most informative expression profile.

EXAMPLE 2

Identification of HES1 as a Regulon Indicator Gene

The effects of Simvastatin on the GENOME REPORTER MATRIX™ system were tested at a concentration of 20 μg/ml. The HES1 reporter gene construct was induced by a natural log ratio of 4.2 (treated/untreated), indicating that the HES1 reporter had an excellent signal to noise ratio induction in response to Simvastatin. The HES1 gene encodes a protein with a significant amount of similarity with oxysterol binding proteins and has been implicated in isoprenoid metabolism (FIG. 35). Analysis of gene expression data with the GENOME REPORTER MATRIX™ system revealed that HES1 expression is highly correlated with the expression of genes encoding enzymes of the isoprenoid biosynthetic pathway (FIG. 36).

The specificity of the HES1 reporter for inhibitors of ergosterol biosynthesis was tested in silico. The expression of the HES1 reporter was examined in data from 710 experimental treatments of the GENOME REPORTER MATRIX™ system. Basal levels of HES1 reporter gene expression were 0.1 units. Units are defined as an arbitrary fluorescent value that has been normalized such that a value of 1.0 equals the mean reporter fluorescent level of all members of the GENOME REPORTER MATRIX™ system in a given experiment. All treatments (a total of 51) that induced HES1 reporter gene levels to 0.5 units or greater were treatments known to inhibit ergosterol biosynthesis, indicating a high degree of specificity for this pathway (FIG. 37).

The utility of the HES1 reporter gene in a high-throughput screen was tested by incubating a yeast strain harboring the HES1 reporter in a 384-well array containing various concentraions of ergosterol biosynthesis inhibitors (Econazole and Simvastatin) and nonspecific drugs (Flucytosine and Nifedipine). Cells were grown to mid-log phase at 30° C. in casamino acids medium (0 67% yeast nitrogen base, 2% glucose, 2% casamino acids). Cell density was adjusted prior to incubation in various concentrations of drug Arrays were incubated at 30° C. for 24 hrs prior to imaging. The HES1 reporter was found to be specifically induced by Econazole and Simvastatin but not by Flucytosine or Nifedipine.

To further test the viability of this indicator gene in a high-throughput screen, the regulation of the HES1 reporter was tested in two different strain backgrounds ABY11 (MATa leu2Δ1 ura3-52) is a wild-type strain. ABY140 (MATa his3Δ1 leu2Δ0 met15Δ0 pdr5::KanMX ura3Δ0 yor1::KanMX) is a strain containing mutations in two multidrug resistance genes Induction of the HES1 reporter gene in ABY140 was found to be more sensitive to Simvastain and Econazole but not to Flucytosine or Nifedipine when compared to ABY11.

The ABY140 [HES1] strain was used to screen approximately 16,800 chemicals from a combinatorial chemistry library. One percent of these chemicals induced the HES1 indicator gene. Twenty-four of these chemical were further tested in a secondary screen for the ability to induce four additional indicator (also referred to as reporter) genes whose expression are also coordinately regulated with genes encoding ergosterol biosynthetic enzymes. Eight of these twenty-four chemicals also induced these reporter genes, suggesting that these chemicals interfere with ergosterol biosynthesis This example reveals how a high quality promoter sequence identified from systematic genome expression data can be employed with a significant degree of confidence to identify chemicals with a desired biological activity.

The DNA and amino acid sequence of HES1 is shown in FIGS. 62 and 63, respectively.

EXAMPLE 3

Identification of YJL105w as a Target Gene

YJL105w was a previously uncharacterized ORF which contains a PHD finger suggesting that it functions as a transcription factor (FIG. 1) Gene expression correlation coefficients were calculated for 1532 reporter constructs including known genes involved in sterol biosynthesis. Several uncharacterized genes, including YJL105w, were found to have highly correlated gene expression with genes encoding sterol biosynthetic enzymes. YJL105w expression correlated very well (0.83) with expression of CYB5, a gene involved in ergosterol biosynthesis (FIG. 2). Cyb5p is thought to be an electron donor for sterol modifying enzymes (Mitchell A. G., Martin C E, *J. Biol. Chem.*, 1995, 270(50):29766–72). Expression of YJL105w was induced considerably by drugs that inhibit sterol biosynthesis as well as by a mutation in the gene encoding HMG-CoA Synthase (FIG. 3). The YJL105w reporter construct comprises 1200 base-pairs of DNA sequence 5' to the ATG start codon and thus, contains sequence information sufficient to confer the observed regulated expression.

Figure 4:
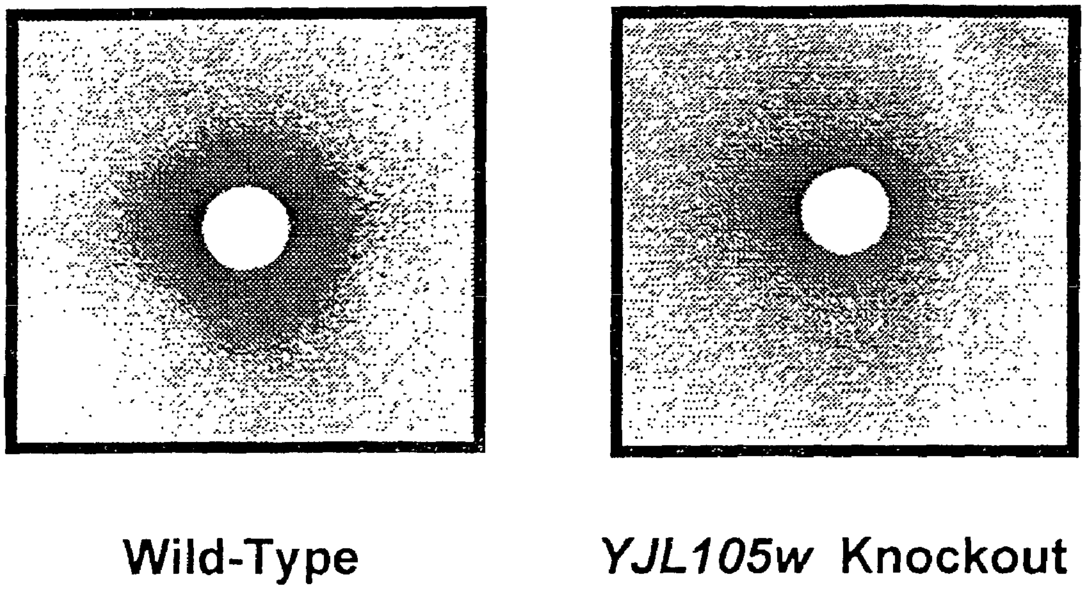

To test whether YJL105w has a role in isoprenoid metabolism, a yjl105w mutant where the entire ORF was replaced with the kanamycin resistance gene was constructed. Approximately $5\times10^6$ cells of the yjl105w mutant strain and a wild-type control strain (ABY363, MATα his3Δ1 leu2Δ0 lys2Δ0 ura3Δ0) were plated onto separate non-selective agar plates. The sterol biosynthetic inhibitor lovastatin (250 μg) was applied to a sterile disk on each lawn and the cells were allowed to grow overnight at 30° C. The yjl105w mutant strain was found to be significantly more resistant to lovastatin treatment, further implicating this ORF in lipid metabolism (FIG. 4).

YJL105w appears to be fungal-specific since no apparent mammalian counterparts were found. Although YJL105w is not an essential gene, it could provide utility for constructing strains for specific applications. For instance, the resistance to lovastatin conferred by a yjl105w mutant could result from an elevated flux through the isoprenoid biosynthetic pathway. Such a condition may result from an altered composition of the cell's lipid bilayer that triggers the induction of synthesis of isoprenoid biosynthetic enzymes and/or reduces the cell's permeability to lovastatin. In either of these cases, a strain defective for YJL105w could be useful for constructing strains that could grow under extreme situations, such as in industrial applications. Examples of extreme conditions include growth at high or low temperatures (>35° C. or <20° C.) or in osmotically stressful conditions or in the presence of amphipathic solutes. Alternatively, the resistance to lovastatin in the yjl105w mutant could result from decreased expression of membrane transporters or channels that allow entry of foreign compounds (xenobiotics). In this case, overexpression of YJL105w could produce a highly permeablized strain that would have numerous applications where entry of compounds into a cell is limited by permeability or availability of compounds. A mammalian counterpart of this ORF, if found, could be useful as a diagnostic marker for people with high serum cholesterol levels. Individuals that have mutations, null or weak (hypomorphic) alleles, might be expected to have a higher rate of sterol synthesis.

The DNA and protein sequences of YJL105w are depicted in FIGS. 39 and 40, respectively.

EXAMPLE 4

Identification of YMR134w as a Target Gene

Figure 6:
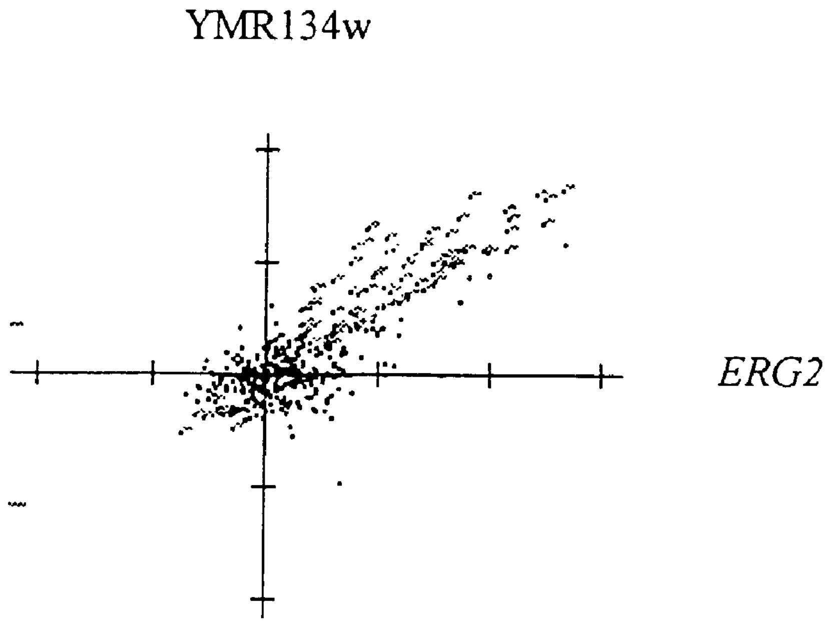
FIG. 6. Plot of changes in expression of YMR134w and ERG2 in response to different chemical treatments. Each point represents the expression changes in a given chemical treatment. The fitness of the points to a line provides an indication of the level of coordinate gene expression. ERG2 encodes sterol isomerase.

YMR134w is an ORF that had been suggested previously to be involved in iron metabolism (FIG. 5). Among 1532 reporter constructs, YMR134w expression was found to be highly correlated with the expression of ERG2 (FIG. 6) and is therefore likely to be involved in lipid metabolism. The YMR134w reporter construct was found to be highly induced by various statins (inhibitors of HMG-CoA reductase) and azole compounds (inhibitors of lanosterol 14-alpha demethylase, ERG11) (FIG. 7). The YMR134w reporter construct comprises 1200 base-pairs of DNA sequence 5' to the ATG start codon and thus, contains sequence information sufficient to confer the observed regulated expression A database search for YMR134w-related protein sequences revealed a weak similarity to human vascular endothelial growth factor receptor (FIG. 8).

The DNA and protein sequences of YMR134w are depicted in FIGS. 41 and 42, respectively

EXAMPLE 5

Identification of YER044c as a Target Gene

Figure 10:
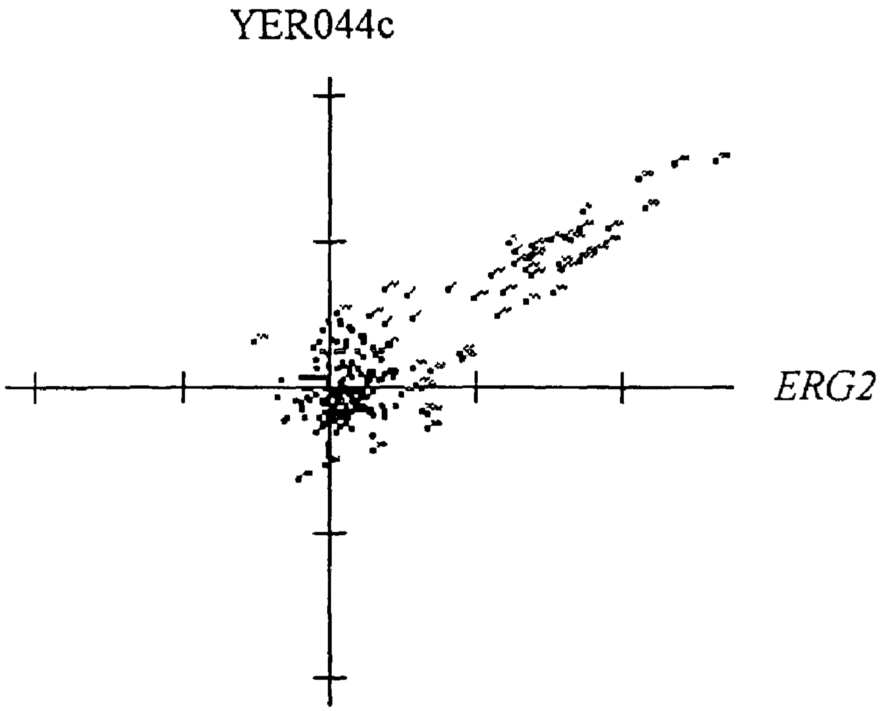
FIG. 10. Plot of changes in expression of YER044c and ERG2 in response to different chemical treatments. Each point represents the expression changes in a given chemical treatment. The fitness of the points to a line provides an indication of the level of coordinate gene expression.
Figure 16:
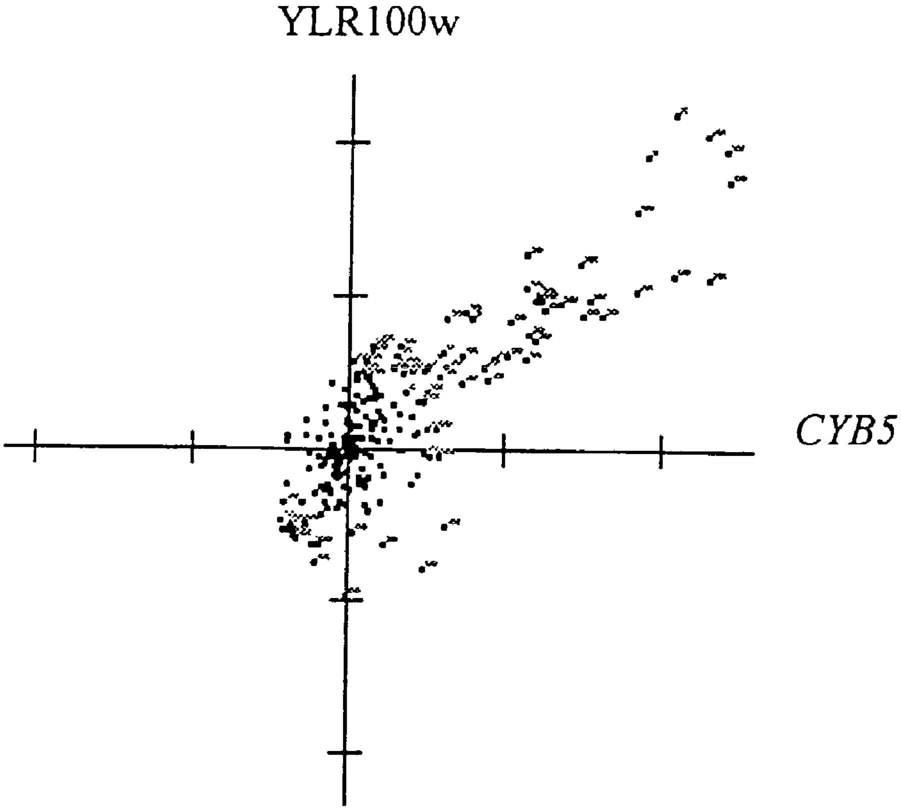
FIG. 16 Plot of changes in expression of YLR100w and CYB5 in response to different chemical treatments. Each point represents the expression changes in a given chemical treatment. The fitness of the points to a line provides an indication of the level of coordinate gene expression.

YER044c was a previously uncharacterized yeast ORF with one predicted transmembrane domain (FIG. 9). YER044c expression is significantly correlated with the expression of ERG2 (0.82, FIG. 10). Statins, azoles and a deletion mutant of the ERG11 gene each induce expression of the YER044c reporter construct most significantly in 498 treatments of the GRM (FIG. 11) The YER044c reporter construct comprises 1200 base-pairs of DNA sequence 5' to the ATG start codon and thus contains sequence information sufficient to confer the observed regulated expression. DNA and proteins sequence database comparisons with the predicted protein sequence of YER044c revealed an apparent *Schizosaccharomyces pombe* counterpart and numerous mammalian EST apparent counterparts (FIGS. 12–14)

The DNA and protein sequences of YER044c are depicted in FIGS. 43 and 44 respectively. The apparent mouse, human and rat EST counterparts of YER044c are depicted in FIGS. 45–47, respectively.

EXAMPLE 6

Identification of YLR100w as a Target Gene

YLR100w was a previously uncharacterized yeast ORF (FIG. 15). Expression of YLR100w correlated significantly (0.82) with CYB5 in the GRM composed of 6036 reporter constructs in 706 experimental treatments. The correlation of expression of YLR100w to the expression of CYB5 implied a role of YLR100w in lipid metabolism. Expression of the YLR100w reporter was induced significantly by statins, azoles and in a yeast erg11 mutant consistent with a role of YLR100w in lipid metabolism (FIG. 17). Searches of DNA and protein sequence databases for similar sequences revealed a GENBANK® entry for a 17-beta-hydroxysteroid dehydrogenase mouse cDNA (FIG. 18).

The sequence of the mouse cDNA is shown in FIG. 53. Given the protein sequence similarity (FIG. 19) and the fact that yeast is not known to synthesize steroid hormones, it is conceivable that the mouse cDNA encodes a protein with another role in lipid metabolism. In this case, the mammalian protein could have utility as a pharmacological target to modulate lipid metabolism. Another GENBANK® entry was found for a rat ovarian specific protein with significant similarity to YLR100w. The sequence of the rat protein is shown in FIG. 65. Two mouse ESTs were found to be significantly similar to YLR100w. The sequence of the two mouse ESTs are shown in FIGS. 51 and 52. A human EST was found that was similar to YLR100w, but to a lesser extent than the two mouse ESTs.

The DNA and protein sequences of YLR100w are depicted in FIGS. 48 and 49, respectively. The sequence of the human EST is shown in FIG. 50.

EXAMPLE 7

Identification of YER034w as a Target Gene

Figure 21:
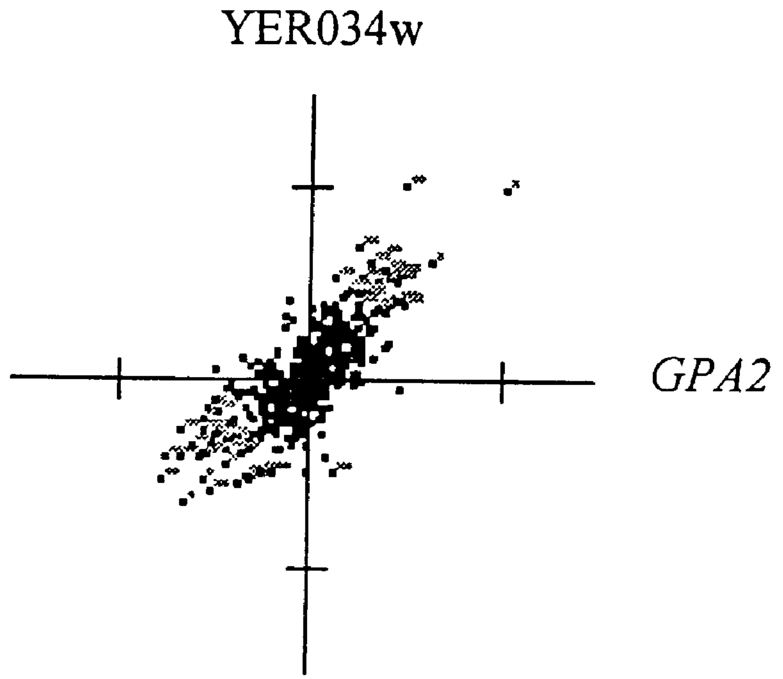
FIG. 21. Plot of changes in expression of YER034w and GPA2 in response to different chemical treatments. Each point represents the expression changes in a given chemical treatment. The fitness of the points to a line provides an indication of the level of coordinate gene expression. Gpa2p, encoded by GPA2, is the alpha subunit of a trimer G-protein involved in pseudohyphal growth.

YER034w is a yeast ORF that had been shown previously not to be essential for cell viability (FIG. 20). Expression of the YER034w reporter construct was found to be correlated (0.75) with the expression of a GPA2 reporter construct in a GRM composed of 1532 reporters treated under 498 experimental conditions (FIG. 21). GPA2 encodes the alpha subunit of a trimeric G protein involved in pseudohyphal differentiation (Lorentz, M. C. and Heitman, J. *EMBO J.* 1997 16:7008–7018) This correlation suggested that YER034w had a role in the pseudohyphal growth and could represent a new antifungal target To test this hypothesis, a diploid homozygous yer034w knockout strain was purchased from Research Genetics (Huntsville, Ala.). Wild-type cells (ABY13, MATα/MATalpha his3Δ1/his3Δ1 leu2Δ0/leu2Δ0 met15Δ0/MET15 LYS2/lys2Δ0 ura3Δ0/ura3Δ0) and the homozygous yer034w knockout strain were plated onto low nitrogen plates to stimulate pseudohyphal differentiation. After four days at 25° C., plates were examined under a microscope. The yer034w knockout strain had undergone significantly more differentiation than the wild-type control both in terms of numbers of projections per colony (FIG. 22) and the size of the hyphae. This result implicated YER034w in the dimorphic transition of cells from yeast to pseudohyphae. The ability of fungi to undergo this morphological transition has been suggested to be a critical aspect of fungal pathogenicity. A search for related mammalian protein sequences did not identify any obvious counterparts suggesting that this protein is fungal-specific and may be an amenable antifungal target.

The DNA and protein sequences of YER034w are depicted in FIGS. 54 and 55, respectively.

EXAMPLE 8

Identification of YKL0774w as a Target Gene

Figure 24:
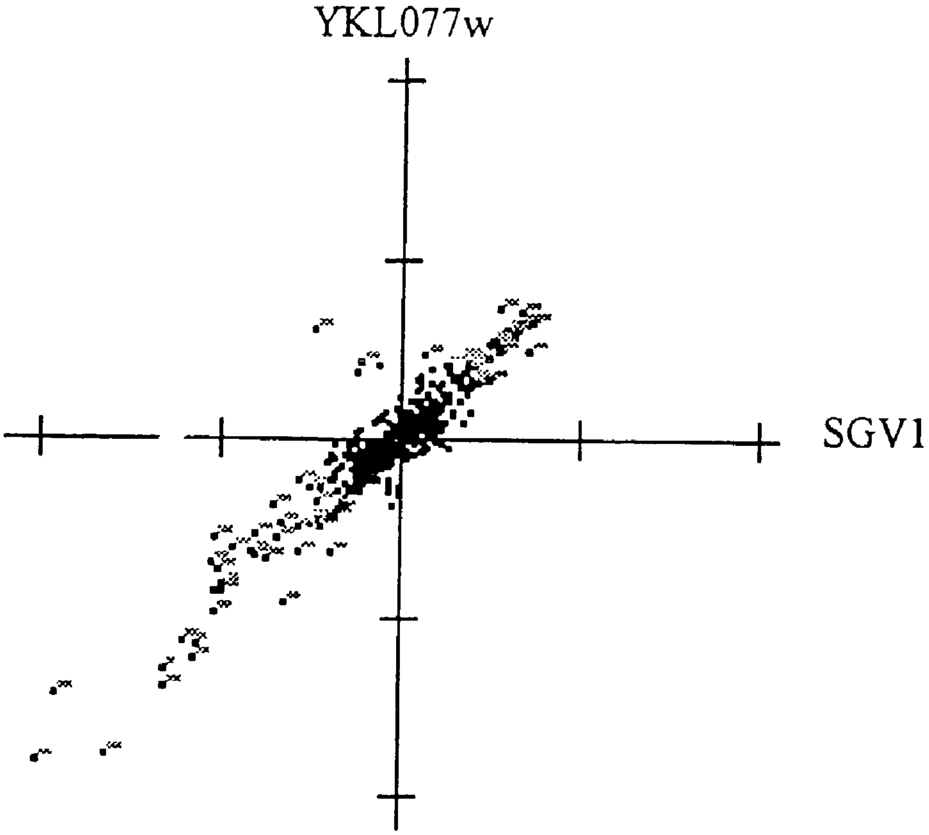
FIG. 24. Plot of changes in expression of YKL077w and SGV1 in response to different chemical treatments. Each point represents the expression changes in a given chemical treatment. The fitness of the points to a line provides an indication of the level of coordinate gene expression. SGV1 is a Cdc28p-related protein kinase that is essential for yeast viability.

YKL077w was a previously uncharacterized ORF with one predicted transmembrane domain (FIG. 23). Expression of the YKL077w reporter construct was found to be correlated (0.92) with the expression of a SGV1 reporter construct in a GRM composed of 1532 reporters treated under 498 experimental conditions (FIG. 24) Sgv1p is a Cdc28p-related protein kinase that is essential for cell viability. In addition to Sgv1p expression, YKL077w expression correlated highly (>0 8) with PKC1 and RHO1 (FIG. 25), genes involved in cell wall integrity and cytoskeletal reorganization. Database searches with the predicted protein sequence of YKL077w did not identify apparent mammalian counterparts (FIG. 26). YKL077w could represent an antifungal target given the lack of a mammalian homolog and its proposed involvement in cellular structure and/or proliferation. Nevertheless, in the event a mammalian counterpart is discovered, it could represent an anti-proliferative target as well.

The DNA and protein sequences of YKL077w are depicted in FIGS. 56 and 57, respectively.

EXAMPLE 9

Identification of YGR046w as a Target Gene

Figure 28:
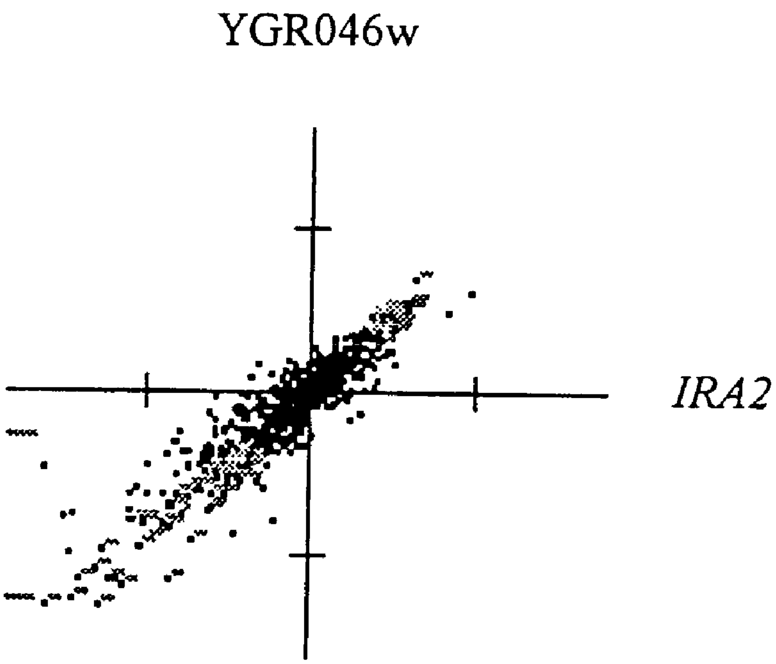
FIG. 28. Plot of changes in expression of YGR046w and IRA2 in response to different chemical treatments. Each point represents the expression changes in a given chemical treatment. The fitness of the points to a line provides an indication of the level of coordinate gene expression. IRA2 encodes a GTPase-activating protein for Ras1p and Ras2p.

YGR046w was a previously uncharacterized yeast ORF that has been shown to be essential for viability (FIG. 27). Expression of YGR046w correlated significantly (0.90) with IRA2 in the GRM composed of 6036 reporter constructs in 706 experimental treatments (FIG. 28). Ira2p is a GTPase activating protein (GAP) for Ras1p and Ras2p In addition to IRA2 expression, YGR046w expression correlated very well (>0.77) with the expression of known genes involved cell proliferation functions (FIG. 29). The expression of YGR046w was found to be most sensitive to agents that disrupt mitochondrial function, create oxidative stress and disrupt the cytoskeleton (FIG. 30).

Given its proposed involvement in cell proliferation, YGR046w could represent a target for modulation of cell growth. A search of protein and DNA sequence databases did not reveal any apparent mammalian homologs. Nevertheless, if such a sequence is identified, it may represent an anti-proliferative mammalian target.

The DNA and protein sequences of YGR046w are depicted in FIGS. 58 and 59, respectively

EXAMPLE 10

Identification of YJR041c as a Target Gene

Figure 32:
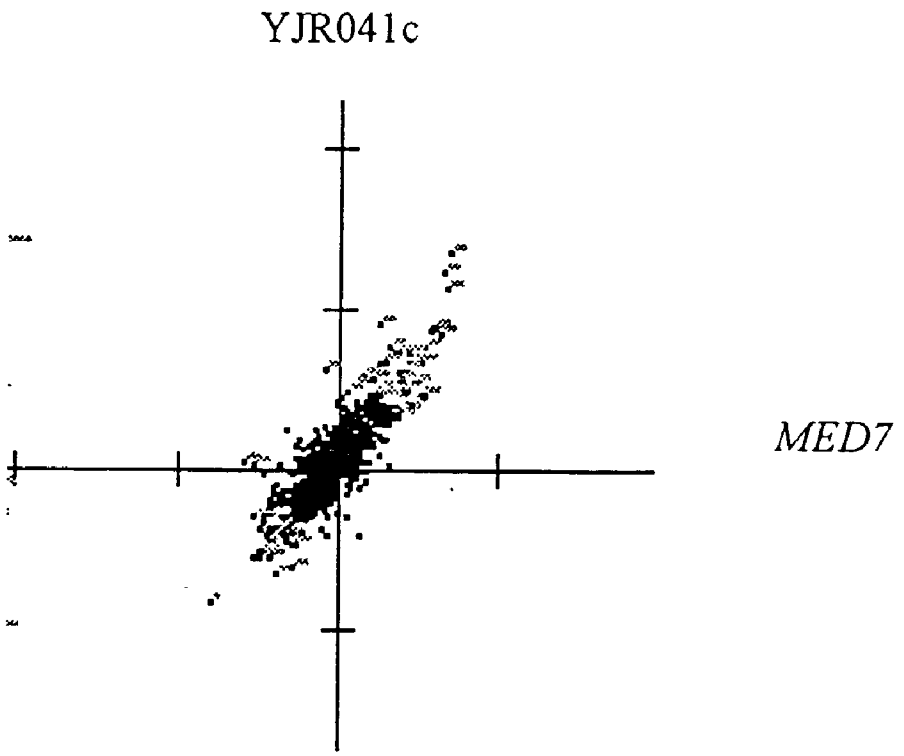
FIG. 32. Plot of changes in expression of YJR041c and MED7 in response to different chemical treatments. Each point represents the expression changes in a given chemical treatment. The fitness of the points to a line provides an indication of the level of coordinate gene expression. MED7 is a component of the mediator complex involved in RNA Polymerase II transcription.
Figure 38:
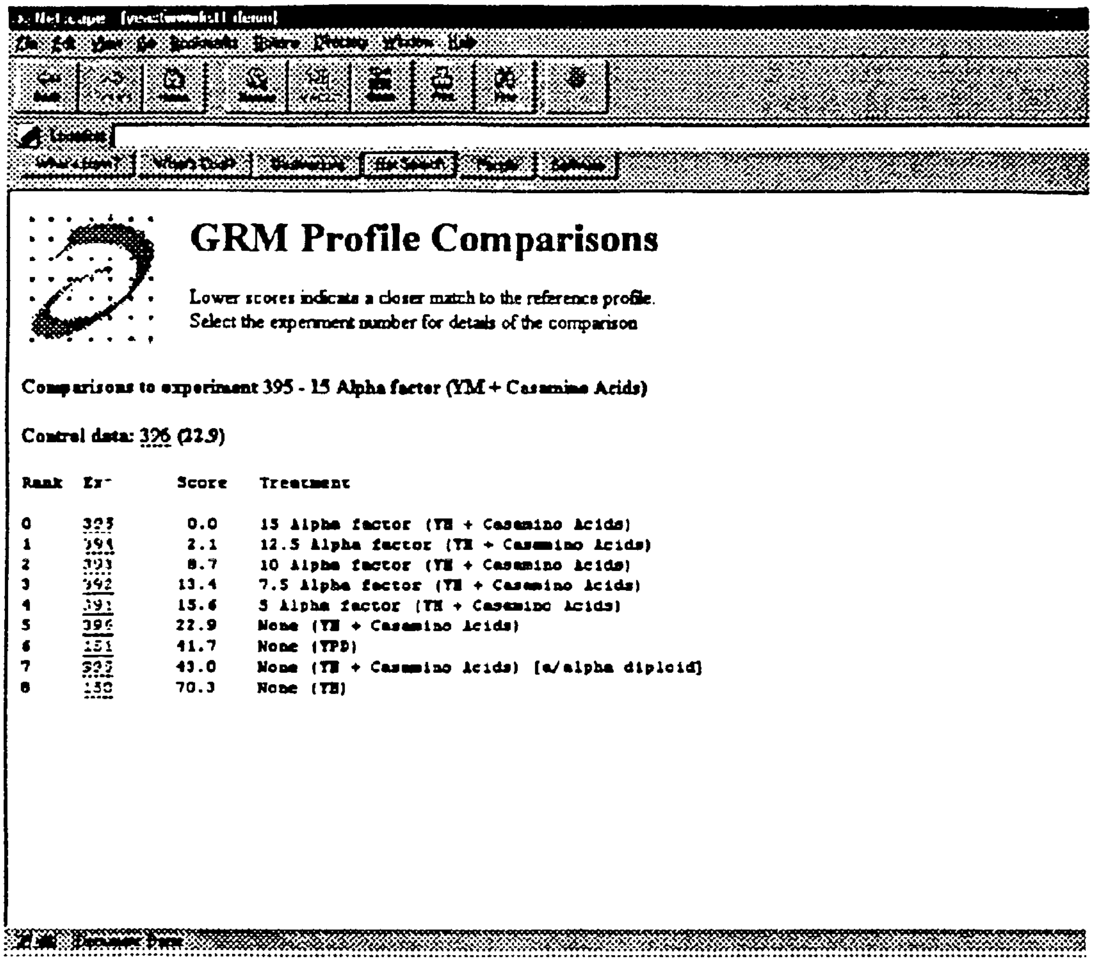
FIG. 38. Browser Interface of Acacia's Expression Software.

Mutant strains defective for YJR041c have been shown previously to display a severe growth defect, but no function for YJR041c was known (FIG. 31). Expression of YJR041c correlated significantly (0.83) with MED7 in the GRM composed of 6036 reporter constructs in 706 experimental treatments (FIG. 32). Med7p encodes a component of the mediator complex involved in RNA polymerase II transcription YJR041c expression was also found to correlate significantly (>0.71) with several genes involved in different aspects of RNA metabolism. These processes include RNA polymerase I and II transcription, mRNA splicing, RNA turnover and ribosome function (FIG. 33).

Database searches for related sequence identified similar sequences from *Schizosaccharomyces pombe* (FIG. 34). No obvious mammalian counterparts were identified suggesting that YJR041c is a fungal-specific protein. Given these factors, YJR041c could represent an attractive target for antifungal therapy. In the event a mammalian counterpart is identified, it also could represent a target with utility for modulating cell proliferation.

The DNA and protein sequences of YJR041c are shown in FIGS. 60 and 61, respectively.

EXAMPLE 11

Screening Assay Using the Genome Reporter Matrix™ to Identify Target Inhibitors

A mutant or conditional allele of target yeast gene is produced as discussed above. The allele may be conditional either for function or expression. For instance, the conditional allele may be a temperature-sensitive allele of the target gene or the target gene may be operably linked to an inducible promoter for regulated expression. In a preferred embodiment, the target gene is operably linked to an inducible promoter that permits expression anywhere between 0% and 500% of wild type expression. The target gene of interest is transfected and expressed in yeast cells of the GRM that have a functional deletion of the target gene of interest. The level of expression of the conditional allele is varied between 0% and 500% of wild type expression, and the expression of the reporter constructs of the GRM is measured in response to the expression of the target gene. The expression of the reporter constructs is then correlated to the expression of the target gene. Thus, one can identify a subset of genes that are either induced or repressed by overexpression of the target gene.

The yeast strains containing the subset of genes whose expression is dependent upon overexpression, and thus the function of the essential gene, are then used to screen compounds that are potential target inhibitors. The yeast strains are incubated with the compounds. If a reporter gene in a particular yeast strain is induced by overexpression of the target gene, then potential inhibitors are screened for the ability to downregulate the reporter gene. Conversely, if a reporter gene is repressed by overexpression of the target gene, then potential inhibitors are screened for the ability to upregulate the reporter gene. Potential inhibitors are screened for the ability to appropriately upregulate and downregulate a number of the genes whose expression is dependent upon expression or overexpression of the target gene. When potential target inhibitors are identified, these candidate compounds are tested for their ability to inhibit the pathway that the target gene is part of For instance, if the target gene is YER034w, then the inhibitor may be tested for antifungal activity.

If a target gene has a plant or animal counterpart, one may express the plant or animal counterpart in a yeast strain lacking the target gene to see if the plant or animal counterpart can functionally substitute for the yeast gene. If it can, then the plant or animal counterpart can be used in the above example to screen for potential targets for either a plant or animal inhibitor. This is especially useful if the target gene has a mammalian counterpart. Similarly, even if a plant, animal or mammalian counterpart has not been identified, potential inhibitors may be tested for their ability to inhibit the pathway that the target gene is part of, if that pathway is shared by yeast and higher eukaryotes.

EXAMPLE 12

Simultaneous Tracking of Multiple Reporters as Regulon Indicator Genes

Figure 74:
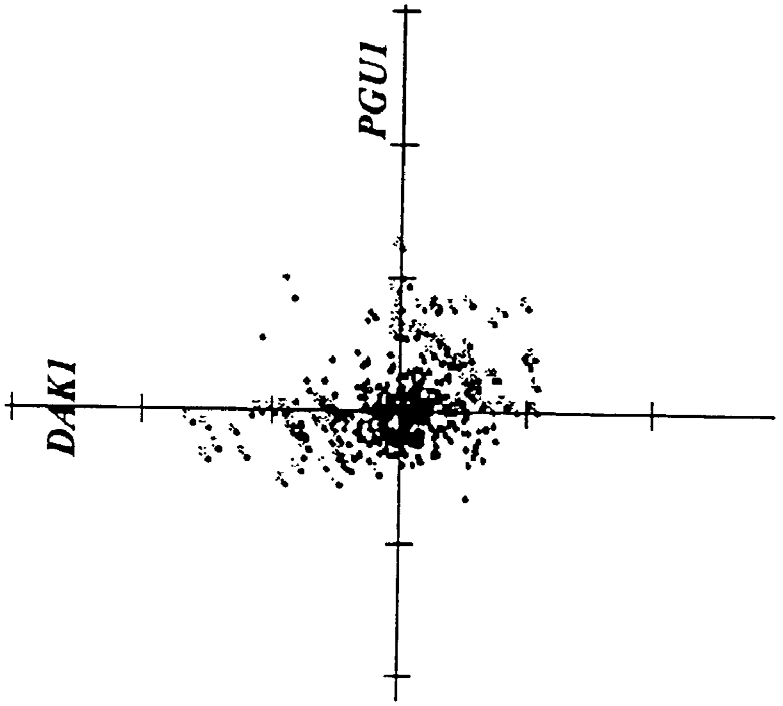
FIG. 74. Each dot on the 4-quadrant plot represents a treatment affecting the reporters affecting DAK1 and PGU1. Treatments are plotted as to whether DAK1 was up-regulated (above x-axis) or down-regulated (below x-axis) and whether PGU1 was up-regulated (right of the y-axis) or down-regulated (left of the y-axis) Thus, conditions where both reporters are up-regulated are in the upper right quadrant. Each division on the graph represents one natural log ratio change relative to controls. The hog1 knock-out profile is indicated at the lower right. Thus, simultaneously measuring induction of PGU1 above 2 natural log ratios and repression of DAK1 below one natural ratio specifically indicates Hog1p pathway inactivation.

The effects of inactivating an osmotic stress pathway were tested by deleting a pathway component (Hog1p stress-activated protein kinase). Using the hog1 knock-out profile as model, multiple RIGs that would specifically indicate pathway inhibitors were identified and tested in silico by examining all conditions in which selected RIGs were activated or repressed. It was determined that simultaneously monitoring up-regulation of PGU1 and down-regulation of DAK1 gave good specificity for pathway inactivation as determined by the separation of the hog1 knock-out profile from all other conditions in which these two reporters were affected (FIG. 74). In this example, RIGs were not part of the target regulon but were chosen empirically based on behavior under all conditions.

Figure 75:
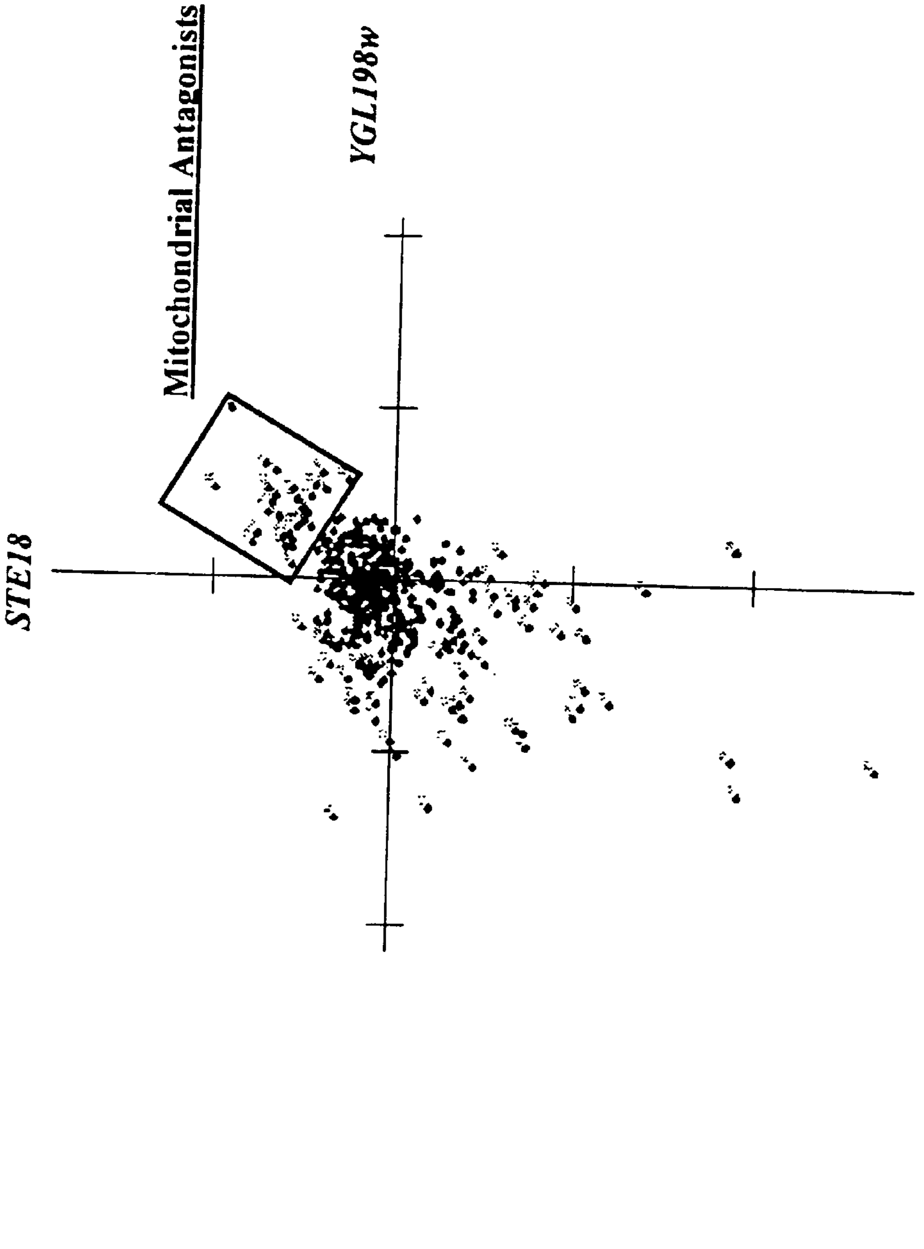
FIG. 75. The plot description is the same as for FIG. 74. The subset of treatments that target mitochondrial function form a distinct group in the upper right quadrant (within rectangle). Thus, simultaneously measuring induction of YGL198w and STE18 should specifically indicate perturbations of the mitochondria.

Similarly, 2 RIGs were identified that could specifically indicate mitochondrial inactivation by comparing the behavior these RIGs in the subset of treatments that target mitochondria with all treatments that affect these RIGs. It was determined that simultaneously measuring up-regulation of 2 RIGs (STE18 and YGL198w) provides good specificity for mitochondrial perturbations as determined by the separation of this subset of common treatments from all other conditions that affect these RIGs (FIG. 75).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Agrawal, S. et al. (1997). *Pharmacology & Therapeutics*, 76, pp. 151–60.

Altschul, S F et al (1997). *Nucleic Acids Res.*, 25, pp. 3389–402.

Atkins, D. et al. (1994). *Biological Chemistry*, 375, 721–29.

Ausubel et al (1989) *Current Protocols in Molecular Biology* (New York: John Wiley & Sons) Updated annually including 1991, 1992, 1993 and 1994

Basson, M E et al. (1988). *Molecular And Cellular Biology*, 8, pp. 3797–3808.

Botstein, D. et al. (1997). *Science*, 277, pp. 1259–60.

Brachmann, C. B. et al. (1998). *Yeast*, 14, pp. 115–32.

Burbaum, J et al (1997) *Current Opinion in Chemical Biology*, 1, pp. 72–8.

Castanotto, D. et al. (1998). *Antisense & Nucleic Acid Drug Development*, 8, pp. 1–13.

Cherry, J. M, Ball, C., Weng, S., Juvik, G., Schmidt, R., Adler, C., Dunn, B., Dwight, S, Riles, L., Mortimer, R. K., and Botstein, D. 1997. "Genetic and physical maps of *Saccharomyces cerevisiae.*" *Nature* 387:67–73.

Chien et al. (1991). *Proc. Natl. Acad. Sci. U.S.A.*, 88(21), pp. 9578–82.

Clackson, T. (1998) *Curr. Opin. Struct. Biol.*, 8, 451–8.

Correll, C. C., and Edwards, P. A. 1994. "Mevalonic acid-dependent degradation of 3-hydroxy-3-methylglutaryl-coenzyme A reductase in vivo and in vitro." *J. Biol Chem.* 269:633–638.

Crooke, S. (1998). *Biotechnology and Genetic Engineering Reviews*, 15, pp. 121–57.

Cunningham, B. C. et al. (1997) *Curr. Opin. Struct. Biol.*, 7, 457–62.

Duzgunes et al., (1992) *J. Cell. Biochem*. Abst. Suppl. 16E 77.

Eckstein, F. (1997). *Ciba Foundation Symposium*, pp. 207–17

Eisen, M. B. et al. (1998). *Proc. Natl. Acad. Sci. U.S.A.*, 95, 14863–14868.

Elledge S. J., and Spottswood M. R. 1991. "A new human p34 protein kinase, CDK2, identified by complementation of a cdc28 mutation in *Saccharomyces cerevisiae*, is a homolog of *Xenopus* Eg1." *EMBO J.* 10:2653–2659.

Epstein et al (1985) *Proc Natl. Acad Sci. U.S.A.*, 82, pp. 3688–92.

Fodor et al. *Science* (1991) 251, 767–773

Garfinkel, D. J. et al. (1998). *Methods in Microbiology*, 26, pp. 101–118.

Gietz, R. D., Schiestl, R. H., Willems, A. R., and Woods, R. A. 1995. "Studies on the transformation of intact yeast cells by the LiAc/SS-DNA/PEG procedure." *Yeast* 11:355–360.

Gietz, R. D , and A. Sugino. 1988. New yeast-*Escherichia coli* shuttle vectors constructed with in vitro mutagenized yeast genes lacking six-base pair restriction sites. *Gene.* 74: 527–34.

Glerum D. M., Tzagoloff A. (1994). "Isolation of a human cDNA for heme A:farnesyltransferase by functional complementation of a yeast cox10 mutant" *Proc Natl Acad Sci USA* 91:8452–8456.

Goffeau, A. et al. (1996). *Science*, 274, pp. 546–67.

Guthrie, C. et al. (1991). *Methods Enzymol*., pp. 1–863.

Harlow and Lane (1988), *Antibodies, A Laboratory Manual.*

Henikoff, S. and Henikoff, J. G. (1992). *Proc. Natl. Acad Sci. USA* 89, pp. 10915–9.

Hubbard, R. E. (1997). *Curr. Opin. Biotechnol.*, 8, 696–700.

Huse et al. (1989). *Science*, 246, pp. 1275–81.

Hwang et al. (1980) *Proc Natl. Acad. Sci. U.S.A.*, 77, pp. 4030–34.

Ito, H. et al. (1983). *J Bacteriol.*, 153, pp. 163–68.

Johnson, E et al (1992). *The EMBO Journal*, 11, pp. 497–505.

Kataoka T, Powers S, Cameron S, Fasano O, Goldfarb M, Broach J, and Wigler M. (1985) "Functional homology of mammalian and yeast RAS genes." *Cell* 40:19–26.

Kleinberg, M. L. et al (1995). *Am. J. Health Syst. Pharm.*, 52, 1323–36.

Kubinyi, H. (1995). *Pharmazie*, 50, 647–62.

Langer et al. (1981). *J. Biomed. Mater. Res.*, 15, pp. 167–277.

Langer (1982) *Chem. Tech.*, 12, pp. 98–105.

Lavrovsky, Y et al. (1997). *Biochemical and Molecular Medicine*, 62, pp. 11–22.

Lawrence and Rothstein (1991). *Methods in Enzymology*, Volume 194.

Lee M G, Nurse P. 1987. "Complementation used to clone a human homologue of the fission yeast cell cycle control gene cdc2." *Nature* 327:31–35.

Maniatis et al. (1989) *Molecular Cloning: A Laboratory Manual* (Cold Spring Harbor, N.Y. Cold Spring Harbor Laboratory Press).

Mattos, C et al (1996). *Nature Biotechnol.*, 14, 595–9.

Mewes, H W et al (1997). *Nature*, 387, pp. 7–65.

Nasr, F et al. (1995). *Molecular & General Genetics*, 249, pp. 51–57.

Olsson, L et al. (1997). *Applied and Environmental Microbiology*, 63, pp. 2366–71.

Paul, W E., ed., (1993) (New York: Raven Press) *Fundamental Immunolgy*, Third Edition.

Pearson et al. (1994) *Methods in Molecular Biolog*, 24, pp. 307–31.

Pearson (1990). *Methods in Enzymology*, 183, pp. 63–98.

Rothstein, R. (1991) *Methods Enzymol.* 194, pp. 281–301.

Sambrook, J. et al. (1989). *Molecular Cloning: A Laboratory Manual* (Cold Spring Harbor, N.Y. Cold Spring Harbor Laboratory Press).

Schiestl, R H et al. (1989). *Curr. Genet.*, 16, pp. 339–46.

Schullek, J et al. (1997). *Analytical Biochemistry*, 246, pp. 20–29.

Sherman, F. et al (1991). Mapping yeast genes. *Methods Enzymol.*, 194, pp. 38–57

Sherman. F (1991) Getting started with yeast. *Methods Enzymol.*, 194, pp. 3–21.

Sidman et al. (1985). *Biopolymers*, 22, pp. 547–56.

Stark (1998). *Methods in Microbiology*, 26, pp. 83–100.

Tamayo, P. et al. (1999). *Proc. Natl. Acad. Sci. U.S.A.* 96, pp. 2907–2912.

Vaughan et al (1996) *Nature Biotech.*, 14, pp. 309–14.

Wach, A et al (1994) *Yeast* 10, pp. 1793–1808.

Ward et al. (1989). *Nature*, 341, pp. 544–46.

Yelton, D. E. et al. (1981). *Ann. Rev. of Biochem.*, 50, pp. 657–80.

Zhao et al. (1998) *Mol Cell. Neurosci;* 11, 92–97.

We claim:

1. A method for determining whether a compound is an inhibitor of an isoprenoid metabolic pathway in a cell, comprising the steps of:

a) determining the effect of said compound on the expression level in said cell of a HES1 gene or a homolog thereof that is able to functionally complement a mutant of said HES1 gene;

b) identifying said compound as an inhibitor of said isoprenoid metabolic pathway if said compound induces expression of said HES1 gene or said homolog.

2. The method of claim 1, wherein the cell is a cell of yeast strain ABY140.

3. The method of claim 1, wherein the cell is a cell of yeast strain ABY11.

4. The method of claim 1, wherein the isoprenoid metabolic pathway is a sterol synthesis pathway.

5. The method of claim 1, wherein said one or more compounds are from a combinatorial chemistry library.

6. The method of claim 1, wherein said compound is identified as an inhibitor in step b) if said compound alters the expression level of said HES1 gene by at least a log ratio of 1, said log ratio being a natural log of a ratio of expression level of the HES1 gene in said cell treated with said compound to expression level of the HES1 gene in a cell of the same type as said cell but not treated with said compound.

7. The method of claim 1, wherein said compound is identified as an inhibitor in step b) if said compound alters the expression level of said HES1 gene by at least a log ratio of 2, said log ratio being a natural log of a ratio of expression level of the HES1 gene in said cell treated with said compound to expression level of the HES1 gene in a cell of the same type as said cell but not treated with said compound.

8. The method of claim 1, wherein said compound is identified as an inhibitor in step b) if said compound alters the expression level of said HES1 gene by at least a log ratio of 3, said log ratio being a natural log of a ratio of expression level of the HES1 gene in said cell treated with said compound to expression level of the HES1 gene in a cell of the same type as said cell but not treated with said compound.

9. The method of claim 1, wherein said compound is identified as an inhibitor in step b) if said compound alters the expression level of said HES1 gene by at least a log ratio of 4, said log ratio being a natural log of a ratio of expression level of the HES1 gene in said cell treated with said compound to expression level of the HES1 gene in a cell of the same type as said cell but not treated with said compound.

10. The method of claim 1, wherein said step a) is carried out using a GENOME REPORTER MATRIX™, said GENOME REPORTER MATRIX™ comprising a yeast strain which comprises a HES1 gene reporter construct.

11. The method of claim 10, wherein said HES1 gene reporter construct comprises a gene encoding a protein selected from the group consisting of green fluorescent protein (GFP), β-lactamase, lacZ, invertase, CD2, CD4, CD8, the influenza hemagglutinin protein, hemagglutinin and Myc.

12. A method for determining whether a compound is an inhibitor of an isoprenoid metabolic pathway, comprising the steps of:

a) measuring an expression level in a first cell of a cell type of a HES1 gene or a homolog thereof in that is able to functionally complement a mutant of said HES1 gene, said first cell being treated with said compound;

b) comparing said expression level measured in step a) with an expression level of said HES1 gene or said homolog measured in a second cell of said cell type, said second cell not being treated with said compound;

c) identifying said compound as an inhibitor of the isoprenoid metabolic pathway if said expression level of said HES1 gene or said homolog measured in said first cell is increased in comparison to said expression level of said HES1 gene or said homolog measured in said second cell.

13. The method of claim 12, wherein said cell type is yeast strain ABY140.

14. The method of claim 12, wherein said cell type is yeast strain ABY11.

15. The method of claim 12, wherein the isoprenoid metabolic pathway is a sterol synthesis pathway.

16. The method of claim 12, wherein said compound is from a combinatorial chemistry library.

17. The method of claim 12, wherein said compound is identified as an inhibitor in step c) if said compound alters the expression level of said HES1 gene by at least a log ratio of 1, said log ratio being a natural log of a ratio of expression level of the HES1 gene in said first cell to expression level of the HES1 gene in said second cell.

18. The method of claim 12, wherein said compound is identified as an inhibitor in step c) if said compound alters the expression level of said HES1 gene by at least a log ratio of 2, said log ratio being a natural log of a ratio of expression level of the HES1 gene in said first cell to expression level of the HES1 gene in said second cell.

19. The method of claim 12, wherein said compound is identified as an inhibitor in step c) if said compound alters the expression level of said HES1 gene by at least a log ratio of 3, said log ratio being a natural log of a ratio of expression level of the HES1 gene in said first cell to expression level of the HES1 gene in said second cell.

20. The method of claim 12, wherein said compound is identified as an inhibitor in step c) if said compound alters the expression level of said HES1 gene by at least a log ratio of 4, said log ratio being a natural log of a ratio of expression level of the HES1 gene in said first cell to expression level of the HES1 gene in said second cell.

21. The method of claim 12, wherein said expression levels are measured using a GENOME REPORTER MATRIX™, said GENOME REPORTER MATRIX™ comprising a yeast strain which comprises a HES1 gene reporter construct.

22. The method of claim 21, wherein said HES1 gene reporter construct comprises a gene encoding a protein selected from the group consisting of green fluorescent protein (GFP), β-lactamase, lacZ, invertase, CD2, CD4, CD8, the influenza hemagglutinin protein, hemagglutinin and Myc.

* * * * *

SEQUENCE LISTING

<160> NUMBER OF SEQ ID NOS: 59

<210> SEQ ID NO 1
<211> LENGTH: 148
<212> TYPE: PRT
<213> ORGANISM: Saccharomyces cerevisiae

<400> SEQUENCE: 1

```
Met Phe Ser Leu Gln Asp Val Ile Thr Thr Thr Lys Thr Thr Leu Ala
1               5                   10                  15

Ala Met Pro Lys Gly Tyr Leu Pro Lys Trp Leu Leu Phe Ile Ser Ile
            20                  25                  30

Val Ser Val Phe Asn Ser Ile Gln Thr Tyr Val Ser Gly Leu Glu Leu
        35                  40                  45

Thr Arg Lys Val Tyr Glu Arg Lys Pro Thr Glu Thr Thr His Leu Ser
    50                  55                  60

Ala Arg Thr Phe Gly Thr Trp Thr Phe Ile Ser Cys Val Ile Arg Phe
65                  70                  75                  80

Tyr Gly Ala Met Tyr Leu Asn Glu Pro His Ile Phe Glu Leu Val Phe
                85                  90                  95

Met Ser Tyr Met Val Ala Leu Phe His Phe Gly Ser Glu Leu Leu Ile
            100                 105                 110

Phe Arg Thr Cys Lys Leu Gly Lys Gly Phe Met Gly Pro Leu Val Val
        115                 120                 125

Ser Thr Thr Ser Leu Val Trp Met Tyr Lys Gln Arg Glu Tyr Tyr Thr
    130                 135                 140

Gly Val Ala Trp
145
```

<210> SEQ ID NO 2
<211> LENGTH: 114
<212> TYPE: PRT
<213> ORGANISM: Mus musculus

<400> SEQUENCE: 2

```
Leu Arg Ser Trp Leu Val Met Val Ser Ile Ile Ala Met Gly Asn Thr
1               5                   10                  15

Leu Gln Ser Phe Arg Asp His Thr Phe Leu Tyr Glu Lys Leu Tyr Thr
            20                  25                  30

Gly Lys Pro Asn Leu Val Asn Gly Leu Gln Ala Arg Thr Phe Gly Ile
        35                  40                  45

Trp Thr Leu Leu Ser Ser Val Ile Arg Cys Leu Cys Ala Ile Asp Ile
    50                  55                  60

His Asn Lys Thr Leu Tyr His Ile Thr Leu Trp Thr Phe Leu Leu Ala
65                  70                  75                  80

Leu Gly His Phe Leu Ser Glu Leu Phe Val Tyr Gly Thr Ala Ala Pro
                85                  90                  95

Thr Ile Gly Val Leu Ala Pro Leu Met Val Ala Ser Phe Ser Ile Leu
            100                 105                 110

Gly Met
```

<210> SEQ ID NO 3
<211> LENGTH: 94
<212> TYPE: PRT
<213> ORGANISM: Homo sapiens

-continued

<400> SEQUENCE: 3

Leu Arg Ser Trp Leu Val Met Val Ser Ile Ile Ala Met Gly Asn Thr
1               5                   10                  15

Leu Gln Ser Phe Arg Asp His Thr Phe Leu Tyr Glu Lys Leu Tyr Thr
            20                  25                  30

Gly Lys Pro Asn Leu Val Asn Gly Leu Gln Ala Arg Thr Phe Gly Ile
        35                  40                  45

Trp Thr Leu Leu Ser Ser Val Ile Arg Cys Leu Cys Ala Ile Asp Ile
    50                  55                  60

His Asn Lys Thr Leu Tyr His Ile Thr Leu Trp Thr Phe Leu Leu Ala
65                  70                  75                  80

Leu Gly His Phe Leu Ser Glu Leu Phe Val Leu Trp Asn Cys
                85                  90

<210> SEQ ID NO 4
<211> LENGTH: 114
<212> TYPE: PRT
<213> ORGANISM: Saccharomyces cerevisiae

<400> SEQUENCE: 4

Leu Pro Lys Trp Leu Leu Phe Ile Ser Ile Val Ser Val Phe Asn Ser
1               5                   10                  15

Ile Gln Thr Tyr Val Ser Gly Leu Glu Leu Thr Arg Lys Val Tyr Glu
            20                  25                  30

Arg Lys Pro Thr Glu Thr Thr His Leu Ser Ala Arg Thr Phe Gly Thr
        35                  40                  45

Trp Thr Phe Ile Ser Cys Val Ile Arg Phe Tyr Gly Ala Met Tyr Leu
    50                  55                  60

Asn Glu Pro His Ile Phe Glu Leu Val Phe Met Ser Tyr Met Val Ala
65                  70                  75                  80

Leu Phe His Phe Gly Ser Glu Leu Leu Ile Phe Arg Thr Cys Lys Leu
                85                  90                  95

Gly Lys Gly Phe Met Gly Pro Leu Val Val Ser Thr Thr Ser Leu Val
            100                 105                 110

Trp Met

<210> SEQ ID NO 5
<211> LENGTH: 94
<212> TYPE: PRT
<213> ORGANISM: Saccharomyces cerevisiae

<400> SEQUENCE: 5

Leu Pro Lys Trp Leu Leu Phe Ile Ser Ile Val Ser Val Phe Asn Ser
1               5                   10                  15

Ile Gln Thr Tyr Val Ser Gly Leu Glu Leu Thr Arg Lys Val Tyr Glu
            20                  25                  30

Arg Lys Pro Thr Glu Thr Thr His Leu Ser Ala Arg Thr Phe Gly Thr
        35                  40                  45

Trp Thr Phe Ile Ser Cys Val Ile Arg Phe Tyr Gly Ala Met Tyr Leu
    50                  55                  60

Asn Glu Pro His Ile Phe Glu Leu Val Phe Met Ser Tyr Met Val Ala
65                  70                  75                  80

Leu Phe His Phe Gly Ser Glu Leu Leu Ile Phe Arg Thr Cys
                85                  90

-continued

<210> SEQ ID NO 6
<211> LENGTH: 215
<212> TYPE: PRT
<213> ORGANISM: Mus musculus
<220> FEATURE:
<221> NAME/KEY: misc_feature
<223> OTHER INFORMATION: Xaa = any amino acid

<400> SEQUENCE: 6

```
Arg Lys Val Val Leu Ile Thr Gly Ala Ser Ser Gly Ile Gly Leu Ala
1               5                   10                  15

Leu Cys Gly Arg Leu Leu Ala Glu Asp Asp Asp Leu His Leu Cys Leu
            20                  25                  30

Ala Cys Arg Asn Leu Ser Lys Ala Arg Ala Val Arg Asp Thr Leu Leu
        35                  40                  45

Ala Ser His Pro Ser Ala Glu Val Ser Ile Val Gln Met Asp Val Ser
    50                  55                  60

Ser Leu Gln Ser Val Val Arg Gly Ala Glu Glu Val Lys Gln Lys Phe
65                  70                  75                  80

Gln Arg Leu Asp Tyr Leu Tyr Leu Asn Ala Gly Ile Leu Pro Asn Pro
                85                  90                  95

Gln Phe Asn Leu Lys Ala Phe Phe Cys Gly Ile Phe Ser Arg Asn Val
            100                 105                 110

Ile His Met Phe Thr Thr Ala Glu Gly Ile Leu Thr Gln Asn Asp Ser
        115                 120                 125

Val Thr Ala Asp Gly Leu Gln Glu Val Phe Glu Thr Asn Leu Phe Gly
    130                 135                 140

His Phe Ile Leu Ile Arg Glu Leu Glu Pro Leu Leu Cys His Ala Asp
145                 150                 155                 160

Asn Pro Ser Gln Leu Ile Trp Thr Ser Ser Arg Asn Ala Lys Lys Ala
                165                 170                 175

Asn Phe Ser Leu Glu Asp Ile Gln His Ser Lys Gly Pro Glu Pro Tyr
            180                 185                 190

Ser Ser Phe Gln Tyr Ala Thr Asp Leu Leu Asn Val Ala Xaa Asn Arg
        195                 200                 205

Glu Phe Lys Pro Glu Gly Leu
    210                 215
```

<210> SEQ ID NO 7
<211> LENGTH: 347
<212> TYPE: PRT
<213> ORGANISM: Saccharomyces cerevisiae

<400> SEQUENCE: 7

```
Met Asn Arg Lys Val Ala Ile Val Thr Gly Thr Asn Ser Asn Leu Gly
1               5                   10                  15

Leu Asn Ile Val Phe Arg Leu Ile Glu Thr Glu Asp Thr Asn Val Arg
            20                  25                  30

Leu Thr Ile Val Val Thr Ser Arg Thr Leu Pro Arg Val Gln Glu Val
        35                  40                  45

Ile Asn Gln Ile Lys Asp Phe Tyr Asn Lys Ser Gly Arg Val Glu Asp
    50                  55                  60

Leu Glu Ile Asp Phe Asp Tyr Leu Leu Val Asp Phe Thr Asn Met Val
65                  70                  75                  80

Ser Val Leu Asn Ala Tyr Tyr Asp Ile Asn Lys Lys Tyr Arg Ala Ile
                85                  90                  95
Asn Tyr Leu Phe Val Asn Ala Ala Gln Gly Ile Phe Asp Gly Ile Asp
            100                 105                 110
```

-continued

Trp Ile Gly Ala Val Lys Glu Val Phe Thr Asn Pro Leu Glu Ala Val
115 120 125

Thr Asn Pro Thr Tyr Lys Ile Gln Leu Val Gly Val Lys Ser Lys Asp
130 135 140

Asp Met Gly Leu Ile Phe Gln Ala Asn Val Phe Gly Pro Tyr Tyr Phe
145 150 155 160

Ile Ser Lys Ile Leu Pro Gln Leu Thr Arg Gly Lys Ala Tyr Ile Val
165 170 175

Trp Ile Ser Ser Ile Met Ser Asp Pro Lys Tyr Leu Ser Leu Asn Asp
180 185 190

Ile Glu Leu Leu Lys Thr Asn Ala Ser Tyr Glu Gly Ser Lys Arg Leu
195 200 205

Val Asp Leu Leu His Leu Ala Thr Tyr Lys Asp Leu Lys Lys Leu Gly
210 215 220

Ile Asn Gln Tyr Val Val Gln Pro Gly Ile Phe Thr Ser His Ser Phe
225 230 235 240

Ser Glu Tyr Leu Asn Phe Phe Thr Tyr Phe Gly Met Leu Cys Leu Phe
245 250 255

Tyr Leu Ala Arg Leu Leu Gly Ser Pro Trp His Asn Ile Asp Gly Tyr
260 265 270

Lys Ala Ala Asn Ala Pro Val Tyr Val Thr Arg Leu Ala Asn Pro Asn
275 280 285

Phe Glu Lys Gln Asp Val Lys Tyr Gly Ser Ala Thr Ser Arg Asp Gly
290 295 300

Met Pro Tyr Ile Lys Thr Gln Glu Ile Asp Pro Thr Gly Met Ser Asp
305 310 315 320

Val Phe Ala Tyr Ile Gln Lys Lys Lys Leu Glu Trp Asp Glu Lys Leu
325 330 335

Lys Asp Gln Ile Val Glu Thr Arg Thr Pro Ile
340 345

<210> SEQ ID NO 8
<211> LENGTH: 114
<212> TYPE: PRT
<213> ORGANISM: Rattus sp.

<400> SEQUENCE: 8

Leu Arg Ser Trp Leu Val Met Val Ser Ile Ile Ala Met Gly Asn Thr
1 5 10 15

Leu Gln Ser Phe Arg Asp His Thr Phe Leu Tyr Glu Lys Leu Tyr Thr
20 25 30

Gly Lys Pro Asn Leu Val Asn Gly Leu Gln Ala Arg Thr Phe Gly Ile
35 40 45

Trp Thr Leu Leu Ser Ser Val Ile Arg Cys Leu Cys Ala Ile Asp Ile
50 55 60

His Asn Lys Thr Leu Tyr His Ile Thr Leu Trp Thr Phe Leu Leu Ala
65 70 75 80

Leu Gly His Phe Leu Ser Glu Leu Phe Val Phe Gly Thr Ala Ala Pro
85 90 95

Thr Val Gly Val Leu Ala Pro Leu Met Val Ala Ser Phe Ser Ile Leu
100 105 110

Gly Met

-continued

```
<210> SEQ ID NO 9
<211> LENGTH: 243
<212> TYPE: PRT
<213> ORGANISM: Mus musculus
<220> FEATURE:
<221> NAME/KEY: misc_feature
<223> OTHER INFORMATION: Xaa = any amino acid

<400> SEQUENCE: 9

Arg Lys Val Val Leu Ile Thr Gly Ala Ser Ser Gly Ile Gly Leu Ala
1               5                   10                  15

Leu Cys Gly Arg Leu Leu Ala Glu Asp Asp Asp Leu His Leu Cys Leu
            20                  25                  30

Ala Cys Arg Asn Leu Ser Lys Ala Arg Ala Val Arg Asp Thr Leu Leu
        35                  40                  45

Ala Ser His Pro Ser Ala Glu Val Ser Ile Val Gln Met Asp Val Ser
    50                  55                  60

Ser Leu Gln Ser Val Val Arg Gly Ala Glu Glu Val Lys Gln Lys Phe
65                  70                  75                  80

Gln Arg Leu Asp Tyr Leu Tyr Leu Asn Ala Gly Ile Leu Pro Asn Pro
                85                  90                  95

Gln Phe Asn Leu Lys Ala Phe Phe Cys Gly Ile Phe Ser Arg Asn Val
            100                 105                 110

Ile His Met Phe Thr Thr Ala Glu Gly Ile Leu Thr Gln Asn Asp Ser
        115                 120                 125

Val Thr Ala Asp Arg Leu Gln Glu Val Phe Glu Thr Asn Leu Ser Cys
    130                 135                 140

His Phe Ile Leu Leu Ile Arg Glu Leu Pro Leu Leu Leu His Ala Asn
145                 150                 155                 160

Asp Pro Ser Gln Leu Ile Trp Thr Ser Ser Arg Asn Ala Xaa Lys Ala
                165                 170                 175

Asn Phe Ser Leu Glu Asp Xaa Gln His Ser Ile Gly Pro Gly Pro Tyr
            180                 185                 190

Ser Ser Phe Gln Tyr Ala Thr Asp Leu Leu Asn Val Ala Leu Asn Xaa
        195                 200                 205

Asn Xaa Asn Gln Lys Gly Leu Tyr Ser Ser Arg Met Cys Pro Gly Val
    210                 215                 220

Val Met Thr Asn Met Thr Tyr Gly Ile Leu Pro Pro Phe Tyr Leu Asp
225                 230                 235                 240

Val Leu Leu


<210> SEQ ID NO 10
<211> LENGTH: 78
<212> TYPE: PRT
<213> ORGANISM: Homo sapiens

<400> SEQUENCE: 10

Phe Glu Thr Asn Val Phe Gly His Phe Ile Leu Ile Arg Glu Leu Glu
1               5                   10                  15

Pro Leu Leu Cys His Ser Asp Asn Pro Ser Gln Leu Ile Trp Thr Ser
            20                  25                  30

Ser Arg Ser Ala Arg Lys Ser Asn Phe Ser Leu Glu Asp Phe Gln His
        35                  40                  45

Ser Lys Gly Pro Glu Pro Tyr Ser Ser Ser Lys Tyr Ala Thr Asp Leu
    50                  55                  60

Leu Ser Val Ala Leu Asn Arg Asn Asn Val Ala Cys Pro Gly
65                  70                  75
```

-continued

<210> SEQ ID NO 11
<211> LENGTH: 2883
<212> TYPE: DNA
<213> ORGANISM: Saccharomyces cerevisiae

<400> SEQUENCE: 11
tggaaaagct cactgtgagg ttccttggag ccaatagtaa tacagcacaa tccaaggaaa 60
aatctggcct atatgcaagg aaggagagat agtcaaaagc attctttccc ctagaagttg 120
gtgcatatat ggcatcgtta aaacatatta cccccaaaat ttcttctcta aacgatgtgc 180
ttggcctttg ttttggtttt tgatgtcggt cgtttgaggc cccttgcgga aaatcgagat 240
cgccgaatgg cacgcgaggg aagggaaata aggtttaaag gcactgaaac aataggcaag 300
aagtaggcga gagccgacat acgagactaa tgtgtccgcg tttctaaggc cacttttcaa 360
tgaaacggat attgatatgc tagtaaaagg acgagctcaa gagcgaaaat ataagtaaag 420
aattcgagtg cacttgtctc catgcagcaa gatttcatat gagtcttttt tatcttttta 480
ctttttacat tacacgatat gcactttatg aaaatttaac gaggttggaa gccggataat 540
caaccaaaat caggcacgaa ggcacactcg tatatgcatg ttgttgaaac tctgttacgc 600
tgaactaaca atcacacatg tagaggtcac cgggaaaagt tgcgaccccca tggaaggtcg 660 atctcttcgt ttggctttgc ttggctggcg gcattgcgct tcttcgctta tacccgtctc 720
ttgacgctcg agctcgttca ttgagatacc tttattcttg cacattttct ggcttttttc 780
gctactcggg tacatgtaat catgcacaca gaaggtgctg tagggtgaaa gttcctttgt 840
gctgtcgttt gtttttaatg ccaaactttc tggtgatcaa taaccacctc tttttccttc 900
aggaaacctt attattgttc ttggatagta ctaggaagta tataaggaac ctcgattttg 960
gtattgcacg gctatacaca tctaagaaac tttgtataaa aggtggctac cctattcata 1020
gcttgatatc aataggccat ctcatcactt tttattgaaa aggaaaggag ggaaatatat 1080
ctgattcaaa ttacttgttt gcttctcttt aagacaaaag catagataat ttcagcgtgg 1140
aacgccggaa taagattggt accctcgtca gaaagttaca aataccgctt catcttcaaa 1200
atgacttcac cggaatcact atcttctcgt catatcaggc aaggaaggac atacacaacc 1260
acagacaagg tcatatcgcg gtcgtcgtcg tactcatcta atagttcaat gtctaaagat 1320
tacggcgatc acacaccctt gtccgtcagc agtgcagctt cagagacatt accctcacct 1380
cagtatatgc cgataaggac attcaataca atgcctacag ctggcccaac gcctttacat 1440
ttatttcaaa atgacagggg cattttcaac catcattctt catcaggctc atcaaaaacg 1500
gcatcaacaa ataaaagagg aatagcagca gcagtagcat tggcaactgc tgccaccata 1560
ccatttccac tgaaaaaaca gaatcaagat gataattcca aggtctcggt aacacacaat 1620
gaatcatcga aagaaaataa aattacaccc tccatgagag cagaagataa caaacctaaa 1680
aatggttgca tctgcggttc aagtgactcc aaggatgagt tgtttataca gtgtaacaaa 1740
tgtaaaacgt ggcagcacaa gttatgttat gctttcaaaa aatcagatcc aataaaaaga 1800
gattttgttt gcaaaagatg tgacagtgat acgaaagtgc aggttaatca agtaaaacca 1860
atgatattcc ctagaaaaat gggagatgag cgattatttc aattttcatc catagtgaca 1920
acttcagcat cgaacacaaa tcagcatcaa cagtctgtga ataacataga ggaacagccc 1980
aagaaacgtc aacttcatta taccgcccca acaactgaaa atagcaatag tatacggaaa 2040
aaattgaggc aagaaaaact ggtagtatca agccactttc tgaagccact actgaatgag 2100
gtaagttctt ccaatgacac ggaattcaaa gcaataacaa tatcagagta taaggacaaa 2160

-continued

```
tatgttaaga tgtttattga taaccattat gatgacgatt gggttgtttg ttctaactgg   2220

gaaagctcaa ggtcagctga catcgaggta agaaaatcat caaatgaaag agattttgga   2280

gtcttcgctg cagattcttg tgttaaaggt gagctaattc aagaatattt gggcaaaatt   2340

gattttcaaa aaaattatca gacagatcca aataatgact atcgtttgat gggaacgaca   2400

aaacctaaag tactttttca tccacattgg cctttatata tagactctcg agaaacaggc   2460

ggattaacaa gatacataag acggagttgt gagcccaatg tggaactagt aacggtaaga   2520

ccgcttgacg aaaaaccaag aggagataat gattgtagag ttaaatttgt tttaagggct   2580

ataagagata ttcgtaaggg agaagagata agcgtagaat ggcaatggga tttgagaaat   2640

cctatttggg agataataaa tgcatctaaa gatttggatt ccctaccgga tcccgacaag   2700

ttctggttga tggggtcaat aaagactatt ttaacaaatt gtgattgtgc atgtgggtac   2760

ttgggccata attgtccaat aactaaaatc aaaaactttt ctgaagaatt catgaggaat   2820

acgaaggaat ccctatctaa taaatcttac tttaatacaa taatgcacaa ctgtaagcca   2880

taa                                                                 2883
```

```
<210> SEQ ID NO 12
<211> LENGTH: 560
<212> TYPE: PRT
<213> ORGANISM: Saccharomyces cerevisiae

<400> SEQUENCE: 12

Met Thr Ser Pro Glu Ser Leu Ser Ser Arg His Ile Arg Gln Gly Arg
1               5                   10                  15

Thr Tyr Thr Thr Thr Asp Lys Val Ile Ser Arg Ser Ser Ser Tyr Ser
            20                  25                  30

Ser Asn Ser Ser Met Ser Lys Asp Tyr Gly Asp His Thr Pro Leu Ser
        35                  40                  45

Val Ser Ser Ala Ala Ser Glu Thr Leu Pro Ser Pro Gln Tyr Met Pro
    50                  55                  60

Ile Arg Thr Phe Asn Thr Met Pro Thr Ala Gly Pro Thr Pro Leu His
65                  70                  75                  80

Leu Phe Gln Asn Asp Arg Gly Ile Phe Asn His His Ser Ser Ser Gly
                85                  90                  95

Ser Ser Lys Thr Ala Ser Thr Asn Lys Arg Gly Ile Ala Ala Ala Val
            100                 105                 110

Ala Leu Ala Thr Ala Ala Thr Ile Pro Phe Pro Leu Lys Lys Gln Asn
        115                 120                 125

Gln Asp Asp Asn Ser Lys Val Ser Val Thr His Asn Glu Ser Ser Lys
    130                 135                 140

Glu Asn Lys Ile Thr Pro Ser Met Arg Ala Glu Asp Asn Lys Pro Lys
145                 150                 155                 160

Asn Gly Cys Ile Cys Gly Ser Ser Asp Ser Lys Asp Glu Leu Phe Ile
                165                 170                 175

Gln Cys Asn Lys Cys Lys Thr Trp Gln His Lys Leu Cys Tyr Ala Phe
            180                 185                 190

Lys Lys Ser Asp Pro Ile Lys Arg Asp Phe Val Cys Lys Arg Cys Asp
        195                 200                 205

Ser Asp Thr Lys Val Gln Val Asn Gln Val Lys Pro Met Ile Phe Pro
    210                 215                 220

Arg Lys Met Gly Asp Glu Arg Leu Phe Gln Phe Ser Ser Ile Val Thr
225                 230                 235                 240
```

-continued

```
Thr Ser Ala Ser Asn Thr Asn Gln His Gln Gln Ser Val Asn Asn Ile
                245                 250                 255

Glu Glu Gln Pro Lys Lys Arg Gln Leu His Tyr Thr Ala Pro Thr Thr
            260                 265                 270

Glu Asn Ser Asn Ser Ile Arg Lys Lys Leu Arg Gln Glu Lys Leu Val
        275                 280                 285

Val Ser Ser His Phe Leu Lys Pro Leu Leu Asn Glu Val Ser Ser Ser
    290                 295                 300

Asn Asp Thr Glu Phe Lys Ala Ile Thr Ile Ser Glu Tyr Lys Asp Lys
305                 310                 315                 320

Tyr Val Lys Met Phe Ile Asp Asn His Tyr Asp Asp Asp Trp Val Val
                325                 330                 335

Cys Ser Asn Trp Glu Ser Ser Arg Ser Ala Asp Ile Glu Val Arg Lys
            340                 345                 350

Ser Ser Asn Glu Arg Asp Phe Gly Val Phe Ala Ala Asp Ser Cys Val
        355                 360                 365

Lys Gly Glu Leu Ile Gln Glu Tyr Leu Gly Lys Ile Asp Phe Gln Lys
    370                 375                 380

Asn Tyr Gln Thr Asp Pro Asn Asn Asp Tyr Arg Leu Met Gly Thr Thr
385                 390                 395                 400

Lys Pro Lys Val Leu Phe His Pro His Trp Pro Leu Tyr Ile Asp Ser
                405                 410                 415

Arg Glu Thr Gly Gly Leu Thr Arg Tyr Ile Arg Arg Ser Cys Glu Pro
            420                 425                 430

Asn Val Glu Leu Val Thr Val Arg Pro Leu Asp Glu Lys Pro Arg Gly
        435                 440                 445

Asp Asn Asp Cys Arg Val Lys Phe Val Leu Arg Ala Ile Arg Asp Ile
    450                 455                 460

Arg Lys Gly Glu Glu Ile Ser Val Glu Trp Gln Trp Asp Leu Arg Asn
465                 470                 475                 480

Pro Ile Trp Glu Ile Ile Asn Ala Ser Lys Asp Leu Asp Ser Leu Pro
                485                 490                 495

Asp Pro Asp Lys Phe Trp Leu Met Gly Ser Ile Lys Thr Ile Leu Thr
            500                 505                 510

Asn Cys Asp Cys Ala Cys Gly Tyr Leu Gly His Asn Cys Pro Ile Thr
        515                 520                 525

Lys Ile Lys Asn Phe Ser Glu Glu Phe Met Arg Asn Thr Lys Glu Ser
    530                 535                 540

Leu Ser Asn Lys Ser Tyr Phe Asn Thr Ile Met His Asn Cys Lys Pro
545                 550                 555                 560


<210> SEQ ID NO 13
<211> LENGTH: 1914
<212> TYPE: DNA
<213> ORGANISM: Saccharomyces cerevisiae

<400> SEQUENCE: 13

tacaataaca agccaggtgc aaggcaataa taacggtaca aaggtctgtt tcacagaagg      60

tccaaaagtt agtagctaca caaatccgaa cacgcaattt caaactcaaa acatgattat     120

ggatttcagt caacgttatc aggaagaatc tgaaagagag tcaaataatc gttcaaatat     180

aactttacca cacgacagca ttcaaatagc tcaacaaata tggccaaaca cggatttaaa     240

tgtagtacaa tcttcacaag acctcaacac tccaatggct acgcaaactg ttttgggtcg     300

tcctgagtcg ctaattgtac agccattgga ggtttctcaa tctccaccaa acactaccaa     360
```

-continued

```
ctgccttcct aatgcagaaa acaaaaagaa aaaagtcgac accacttctg attttacttc    420
aagaaaggag attgctctgt gtaaaactgg tttattagaa actattcata taccaaagga    480
aagggaaagt cagatgcaaa gcgtcactgg tttagatgca acaccaacga ttatatggag    540
ccccgggaaa gacaacacgg cgaagaaaaa taccagtaat aagaaaaata ttgatgataa    600
actaacaaac ccccaaaaat ctggaaatac acataccccct gatagaaata aagaagtgct    660
acctaacggc acacttaatg aaacgaggaa agaagcatcg ccaagcgaag gattaacgat    720
aagagttaaa aacgttaatc ggaatgcgtc aagaaaaata tctaagcggc taatcaagga    780
aaagttgaaa gacgaagaat tcatgaaatg ggtatgtatg catttgcaag aaactgagct    840
gtttccccct cttatccact cattttctct gacttgacaa agaaatacta actaacaact    900
tttgccacta caaatatgaa tgaaaaggtt aataaggttg aaacggttct caataaaatg    960
ttcgaaaagt gaacccttttt tttgcaattc ctttttacac tagccacgaa gtaaaatgga   1020
aaagtaaacc cgagtttcgg caatatcgct aagcaagaag agcaagctcg tttaagtaag   1080
cctttatgaa aaaaaaacaa aatataaagc attataaaaa ttgaatcaca tcgcaaatct   1140
gcaatatact tggaagtgtt tatagcaaag tgtggtatag aaaaagaacc aaaggccggt   1200
atgtcgttaa aggataggta tctaaatctc gaattaaaat taataaataa actacaggag   1260
ttgccatatg ttcatcaatt tatccatgat cgaataagtg gtaggataac tctctttttg   1320
atagtggttg gtacgcttgc attttttaac gaactgtata taacgatcga aatgagtctt   1380
ctacaaaaga acacatcaga agaactagag cgtggaagaa tcgatgaaag tctgaagctt   1440
catcggatgt tggtgagtga tgaatatcac ggtaaagaat acaaagacga gaaaagcggt   1500
attgttattg aagagttcga agatcgcgat aagtttttg caaaacctgt gtttgtatca    1560
gaattggatg tcgaatgtaa tgttattgta gatgggaaag aacttctgtc caccccatta   1620
aaatttcatg ttgaattttc tccagaggat tatgaaaatg aaaaaagacc tgagtttggt   1680
actaccttgc gtgtattgag gctgagactt taccactact ttaaagattg cgaaatatat   1740
cgcgatataa ttaagaatga gggcggtgaa ggggcaagaa agtttacgat ttccaacggt   1800
gtcaaaattt acaatcataa agatgaacta ctgccattga atatcgatga tgttcaatta   1860
tgtttcctga agattgatac gggaaacacg ataaaatgcg aattcatact atga          1914
```

<210> SEQ ID NO 14
<211> LENGTH: 237
<212> TYPE: PRT
<213> ORGANISM: Saccharomyces cerevisiae

<400> SEQUENCE: 14

```
Met Ser Leu Lys Asp Arg Tyr Leu Asn Leu Glu Leu Lys Leu Ile Asn
1               5                   10                  15

Lys Leu Gln Glu Leu Pro Tyr Val His Gln Phe Ile His Asp Arg Ile
            20                  25                  30

Ser Gly Arg Ile Thr Leu Phe Leu Ile Val Val Gly Thr Leu Ala Phe
        35                  40                  45

Phe Asn Glu Leu Tyr Ile Thr Ile Glu Met Ser Leu Leu Gln Lys Asn
    50                  55                  60

Thr Ser Glu Glu Leu Glu Arg Gly Arg Ile Asp Glu Ser Leu Lys Leu
65                  70                  75                  80

His Arg Met Leu Val Ser Asp Glu Tyr His Gly Lys Glu Tyr Lys Asp
                85                  90                  95
```

-continued

```
Glu Lys Ser Gly Ile Val Ile Glu Glu Phe Glu Asp Arg Asp Lys Phe
            100                 105                 110

Phe Ala Lys Pro Val Phe Val Ser Glu Leu Asp Val Glu Cys Asn Val
        115                 120                 125

Ile Val Asp Gly Lys Glu Leu Leu Ser Thr Pro Leu Lys Phe His Val
    130                 135                 140

Glu Phe Ser Pro Glu Asp Tyr Glu Asn Glu Lys Arg Pro Glu Phe Gly
145                 150                 155                 160

Thr Thr Leu Arg Val Leu Arg Leu Arg Leu Tyr His Tyr Phe Lys Asp
                165                 170                 175

Cys Glu Ile Tyr Arg Asp Ile Ile Lys Asn Glu Gly Gly Glu Gly Ala
            180                 185                 190

Arg Lys Phe Thr Ile Ser Asn Gly Val Lys Ile Tyr Asn His Lys Asp
        195                 200                 205

Glu Leu Leu Pro Leu Asn Ile Asp Asp Val Gln Leu Cys Phe Leu Lys
    210                 215                 220

Ile Asp Thr Gly Asn Thr Ile Lys Cys Glu Phe Ile Leu
225                 230                 235


<210> SEQ ID NO 15
<211> LENGTH: 1647
<212> TYPE: DNA
<213> ORGANISM: Saccharomyces cerevisiae

<400> SEQUENCE: 15

aacactccaa atcttgttag tttctcatta ttcgcatcgc atagattctg attcttcttt     60

taagaggaca ctgatagacg ttcatgtttt caatttcatc gccaagtttc tgtttaatag    120

aattttattg aagaagaacc aaaacgatcc aaaatggctt caaaactttt acgaccaggg    180

agatggcaaa catttatgtg ataaagttga ctacaagcgc ttgtgttcgt tgcattttac    240

ccttatttac tctattatta acattcaact catcaaaatc aagacaaacc aaacatttga    300

accgcagata ttaaaatacg tatctgttct gaaattaatt gaacacatac ttatcatcat    360

cgaaagtctg atacatgtac ttattagatt tgtatcgaag cataaactaa tatgcatcaa    420

ccggaaaaag gcgtactgtc gagtatacct cgaaagagaa ttgagtttga agaaaaccta    480

cttaaagaac ttttacagtg taataagcgg tgtcccagaa aaagagttag gggtctatt     540

gaaaatactc aagatagtta ttctatcatt gctcgagaca tttgaaagca ttgaatggca    600

gcacttaaaa cctttcctgg aaaaatttcc ggctcatgaa atatcgcttc agaagaaaag    660

gaaatatata caggcggcct tattaattac tgccgaaaga aatttgatag cgcgctttcg    720

attgtcaaga tggttcaatg agacagaaaa catttaattt ttcttttgca gtaggaggcg    780

cattataaaa cacaaaaata tcgaaagctc tttcatttcg gggacaacaa cttcagttga    840

aaattacagt gaacacaaca tcttccccaa cagacctaca ttaaaacgct tcttccggac    900

ttgcccatga ttaacctaat cttatacgaa ctgaattaaa ctttacggta ttaccgatag    960

gaaacttcta ttttatgatt ttttcgttcg gggacggaac gaacaggaaa caaaaaaaaa   1020

ggtacgatcc attgtattct ctacccccgt atataaaact aagctgaaca agcctgttgt   1080

tttgctttac tattgctact atttttgacg taaacgcatt gactaatttc aggtttttat   1140

attcttgaca ctagctagac catagtatcg aaggattcaa atacactaaa gtatcagata   1200

atgttcagcc tacaagacgt aataactaca accaagacca ccttggcagc aatgccaaaa   1260

ggttacttac caaaatggtt acttttcatt tccattgtat cagtcttcaa ttctatccag   1320
```

-continued

```
acttacgttt ctggtttaga attgacacgt aaagtctacg aaagaaaacc cactgaaaca   1380

acccatttga gtgcaagaac tttcggtact tggaccttta tttcctgtgt tatcagattc   1440

tatggggcta tgtacttgaa tgaaccacac attttcgaat tggtcttcat gtcttatatg   1500

gttgccctat tccacttcgg ctctgaatta ttgatcttta gaacttgtaa gttgggaaag   1560

ggattcatgg gtccattggt tgtctcaacc acctctttgg tttggatgta caaacaaaga   1620

gaatactaca ctggtgttgc ttggtaa                                       1647
```

<210> SEQ ID NO 16
<211> LENGTH: 55
<212> TYPE: DNA
<213> ORGANISM: Artificial
<220> FEATURE:
<223> OTHER INFORMATION: PCR Primer

<400> SEQUENCE: 16

```
tgttaccaat ctgaagtggg agcggccgcg tttttttttt tttttttttt ttttt          55
```

<210> SEQ ID NO 17
<211> LENGTH: 455
<212> TYPE: DNA
<213> ORGANISM: Mus musculus
<220> FEATURE:
<221> NAME/KEY: misc_feature
<223> OTHER INFORMATION: n = a, t, g, or c

<400> SEQUENCE: 17

```
tgcggatgct gctgatactg ctgcagtagt actggatcgt caggcagagc gccctctctt     60

ggaggggagt catgagccgc ttcctgaatg tgttacgaag ctggctggtt atggtgtcca    120

ttatagccat ggggaacaca ctccagagct tccgagacca cacttttctc tacgagaagc    180

tctacactgg caagccaaac cttgtgaatg gcctccaagc ccggaccttt gggatctgga    240

cgctgctctc atcagtgatt cgctgcctct gtgccattga catccacaac aaaacactct    300

atcacatcac actgtggaca ttcctcctcg ccctgngaca cttcctctca gagttgtttg    360

tatttggaac agcagctccc acagttggtg tgctggcacc cctgatggta gcaagtttct    420

caatcctggg catgctggtc gggctcccgt accta                              455
```

<210> SEQ ID NO 18
<211> LENGTH: 28
<212> TYPE: DNA
<213> ORGANISM: Artificial
<220> FEATURE:
<223> OTHER INFORMATION: PCR Primer

<400> SEQUENCE: 18

```
cttttgagca agttcagcct ggttaagt                                       28
```

<210> SEQ ID NO 19
<211> LENGTH: 32
<212> TYPE: DNA
<213> ORGANISM: Artificial
<220> FEATURE:
<223> OTHER INFORMATION: PCR Primer

<400> SEQUENCE: 19

```
gaggtggctt atgagtattt cttccagggt aa                                   32
```

-continued

<210> SEQ ID NO 20
<211> LENGTH: 20
<212> TYPE: DNA
<213> ORGANISM: Artificial
<220> FEATURE:
<223> OTHER INFORMATION: PCR Primer

<400> SEQUENCE: 20
gggtaaaaag caaaagaatt 20

<210> SEQ ID NO 21
<211> LENGTH: 839
<212> TYPE: DNA
<213> ORGANISM: Homo sapiens
<220> FEATURE:
<221> NAME/KEY: misc_feature
<223> OTHER INFORMATION: n = a, t, g, or c

<400> SEQUENCE: 21
gnnnnnngnn nnnnnnnnnt tnttgagnac cgcagtngca gcagcagcag ccgctgncgc 60
aaacaagccc tcccacgttt gaggggagtc atgagccgtt tcctgaatgt gttaagaagt 120
tggctggtta tggtgtccat catagccatg gggaacacgc tgcagagctt ccgagaccac 180
acttttctct atgaaaagct ctacactggc aagccaaacc ttgtgaatgg cctccaagct 240
cggacctttg ggatctggac gctgctctca tcagtgattc gctgcctctg tgccattgac 300
attcacaaca agacgctcta tcacatcaca ctctggacct tcctccttgc cctggggcat 360
ttcctctctg agttgtttgt cttatggaac tgcagctccc acgattggng tcctggcanc 420
cctgatggtg gnaagtttct ccatcctggg tattgtggtc ggctccngta ttttagaagt 480
agaaccagtt ccagacagaa gaagagaact gaggcagaat atcaacccca gggtggatca 540
antgggttac aagtggttna aaannnnnnn nnnnnnnnnc nnnntnntnt naannnnnnn 600
nnnnnnnnnn nnnnnnnnna nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnnnn nnnnnnnnnn nnnnnnnnc 839

<210> SEQ ID NO 22
<211> LENGTH: 475
<212> TYPE: DNA
<213> ORGANISM: Rattus sp.
<220> FEATURE:
<221> NAME/KEY: misc_feature
<223> OTHER INFORMATION: n = a, t, g, or c

<400> SEQUENCE: 22
tttttttttt tttttttctg tctggatact ggttctgctt ctaggtaccg gagcccaact 60
agcataccca ggattgagaa acttgctacc atcaagggtg ccagcacacc aactgtggga 120
gccgctgttc caaatacaaa caactccgag aggaagtgtc ccagggcaag gaggaatgtc 180
cacagtgtga tgtgatagag tgttttgttg tggatgtcaa tggcacagag gcagcgaatc 240
actgaagaga gcagcgtcca gatcccaaag gtccgggctt ggaggccatt cacaaggttt 300
ggtttgccag tgtanagctt ttcatanaga aaagtgtggt ctcggaagct ctggagcgtg 360
ttncccatgg ctatgatgga caccataacc agccagcttc gtagcacatt caggaagcgg 420
ctcatgactc ccctcaaaga gagggcgctc tgcctgaccc tcgtgccgaa ttctt 475

-continued

<210> SEQ ID NO 23
<211> LENGTH: 1844
<212> TYPE: DNA
<213> ORGANISM: Saccharomyces cerevisiae

<400> SEQUENCE: 23

```
acgtacaaaa aagagcacgc tgctttattt atacttttgt gccacaagaa tgatcaacat     60
caacataaat atcaactagt atctgcaaca catctgctcc acggaactaa acccgttgag    120
cagtgccccg tggaaacgta aactatcgca aattgggatt aacaagccaa aaacagccaa    180
gcaagattca cgaaaccgcg cctcgtttgg accccgaagg cccatttaac ggccggccgt    240
tacaagcaag atcggcagag caaaccactc cccagcacca cagcacatca ctgcacgagc    300
aacaataact agaacatggc agatagcgag gatacctctg tgatcctgca gggcatcgac    360
acaatcaaca gcgtggaggg cctggaagaa gatggttacc tcagcgacga ggacacgtca    420
ctcagcaacg agctcgcaga tgcacagcgt caatgggaag agtcgctgca acagttgaac    480
aagctgctca actgggtcct gctgccccctg ctgggcaagt atataggtag gagaatggcc    540
aagactctat ggagtaggtt cattgaacac tttgtataag tgtttgttgt ttatgtatcc    600
gcatatagca gttataacag ataaatggca cttttcgcac acccgttgtt ttatctccga    660
tagtacgtgg gcctttattt atggtcgttt aacgaaagaa cggcatcttg aattgagcag    720
gtatttaaaa gataggacga gaaacaagca catgatctgt gtcgaaaaaa agtagcaaag    780
agaaaaagta ggaggatagg atgaacagga aagtagctat cgtaacgggt actaatagta    840
atcttggtct gaacattgtg ttccgtctga ttgaaactga ggacaccaat gtcagattga    900
ccattgtggt gacttctaga acgcttcctc gagtgcagga ggtgattaac cagattaaag    960
atttttacaa caaatcaggc cgtgtagagg atttggaaat agactttgat tatctgttgg   1020
tggacttcac caacatggtg agtgtcttga acgcatatta cgacatcaac aaaaagtaca   1080
gggcgataaa ctaccttttc gtgaatgctg cgcaaggtat ctttgacggt atagattgga   1140
tcggagcggt caaggaggtt ttcaccaatc cattggaggc agtgacaaat ccgacataca   1200
agatacaact ggtgggcgtc aagtctaaag atgacatggg gcttattttc caggccaatg   1260
tgtttggtcc gtactacttt atcagtaaaa ttctgcctca attgaccagg ggaaaggctt   1320
atattgtttg gatttcgagt attatgtccg atcctaagta tctttcgttg aacgatattg   1380
aactactaaa gacaaatgcc tcttatgagg gctccaagcg tttagttgat ttactgcatt   1440
tggccaccta caaagacttg aaaaagctgg gcataaatca gtatgtagtt caaccgggca   1500
tatttacaag ccattccttc tccgaatatt tgaatttttt cacctatttc ggcatgctat   1560
gcttgttcta tttggccagg ctgttggggt ctccatggca caatattgat ggttataaag   1620
ctgccaatgc cccagtatac gtaactagat tggccaatcc aaactttgag aaacaagacg   1680
taaaatacgg ttctgctacc tctagggatg gtatgccata tatcaagacg caggaaatag   1740
accctactgg aatgtctgat gtcttcgctt atatacagaa gaagaaactg gaatgggacg   1800
agaaactgaa agatcaaatt gttgaaacta gaacccccat ttaa                    1844
```

<210> SEQ ID NO 24
<211> LENGTH: 43
<212> TYPE: DNA
<213> ORGANISM: Artificial
<220> FEATURE:
<223> OTHER INFORMATION: PCR Primer -continued

<400> SEQUENCE: 24
aactggaaga attaattaaa gatctttttt tttttttttt ttt 43

<210> SEQ ID NO 25
<211> LENGTH: 454
<212> TYPE: DNA
<213> ORGANISM: Homo sapiens
<220> FEATURE:
<221> NAME/KEY: misc_feature
<223> OTHER INFORMATION: n = a, t, g, or c

<400> SEQUENCE: 25
tttgagacca atgtctttgg ccattttatc ctgattcggg aactggagcc tctcctctgt 60
cacagtgaca atccatctca gctcatctgg acatcatctc gcagtgcaag gaaatctaat 120
ttcagcctcg aggacttcca gcacagcaaa ggcaaggaac cctacagctc ttccaaatat 180
gccactgacc ttttgagtgt ggctttgaac aggaacttca accagcaggg tctctattcc 240
aatgtggcct gtccaggtac agcattgacc aatttgacat atggaattct gcctccgttt 300
atatggacgc tgttggatgc cggcaatatt gctacttcgc ttttttggca aatggcattc 360
actttggaca ccatataatg ggaacaggaa gntatgggta tgggnttttc ccaccaaaag 420
gctggaatcn tttcaatcct ctggatccaa atat 454

<210> SEQ ID NO 26
<211> LENGTH: 25
<212> TYPE: DNA
<213> ORGANISM: Artificial
<220> FEATURE:
<223> OTHER INFORMATION: PCR Primer

<400> SEQUENCE: 26
atgtggcctt tttttttttt ttttt 25

<210> SEQ ID NO 27
<211> LENGTH: 14
<212> TYPE: DNA
<213> ORGANISM: Artificial
<220> FEATURE:
<223> OTHER INFORMATION: PCR Primer

<400> SEQUENCE: 27
tgttggccta ctgg 14

<210> SEQ ID NO 28
<211> LENGTH: 20
<212> TYPE: DNA
<213> ORGANISM: Artificial
<220> FEATURE:
<223> OTHER INFORMATION: PCR Primer

<400> SEQUENCE: 28
cttctgctct aaaagctgcg 20

<210> SEQ ID NO 29
<211> LENGTH: 20
<212> TYPE: DNA
<213> ORGANISM: Artificial
<220> FEATURE:
<223> OTHER INFORMATION: PCR Primer

<400> SEQUENCE: 29
cgacctgcag ctcgagcaca 20

-continued

<210> SEQ ID NO 30
<211> LENGTH: 1039
<212> TYPE: DNA
<213> ORGANISM: Mus musculus
<220> FEATURE:
<221> NAME/KEY: misc_feature
<223> OTHER INFORMATION: n = a, t, g, or c

<400> SEQUENCE: 30

```
ggctaagaga accccggtgc agttctactt cggtgcaggg cgtggaagat gcggaaggtg     60

gttttgatca ccggggcgag cagtggcatt gggctagccc tttgcggtcg actgctggca    120

gaagacgatg acctccacct gtgtttggcg tgtaggaacc tgagcaaagc aagagctgtt    180

cgagataccc tgctggcctc tcacccctcc gccgaagtca gcatcgtgca gatggatgtc    240

agcagcctgc agtcggtggt ccggggtgca gaggaagtca agcaaaagtt tcaaagatta    300

gactacttat atctgaatgc tggaatcctg cctaatccac aattcaacct caaggcattt    360

ttctgcggca tcttttcaag aaatgtgatt catatgttca ccacagcgga aggaattttg    420

acccagaatg actcggtcac tgccgacggg ttgcaggagg tgtttgaaac caatctcttt    480

ggccacttta ttctgattcg ggaactggaa ccacttctct gccatgccga caacccctct    540

cagctcatct ggacgtcctc tcgcaatgca aagaaggcta acttcagcct ggaggacata    600

cagcacttca aaggcccgga accctacagc tctttccaat atgctaccga cctcctgaat    660

gtggctntga acagggaatt caaaccagaa ggtctggtat tcagtggtga ttgccgaggg    720

cgtctgatga ccaatatgac gtatggaaat ttgccttcct ttatcctgac cgtggttcta    780

cccttaagtg ggctccttcg cttttttgaa aatgccctca cctgggaccc cgtaccactg    840

atcaaaagct ctgggtgtgt ttctttcaca tataaccgga ggcttttatt ctttgaccaa    900

atacgcgagc tccaccttgg tagtgggact atataccgac cggtcccacg aatgcactca    960

tttaacacct tgtcaaaact ttttatagtt ttacctgttg tgataacgtg gtgntacccc   1020

cttcgtantt gnaataccc                                                1039
```

<210> SEQ ID NO 31
<211> LENGTH: 837
<212> TYPE: DNA
<213> ORGANISM: Mus musculus
<220> FEATURE:
<221> NAME/KEY: misc_feature
<223> OTHER INFORMATION: n = a, t, g, or c

<400> SEQUENCE: 31

```
ggctaagaga accccggtgc agttctactt cggtgcaggg cgtggaagat gcggaaggtg     60

gttttgatca ccggggcgag cagtggcatt gggctagccc tttgcggtcg actgctggca    120

gaagacgatg acctccacct gtgtttggcg tgtaggaacc tgagcaaagc aagagctgtt    180

cgagataccc tgctggcctc tcacccctcc gccgaagtca gcatcgtgca gatggatgtc    240

agcagcctgc agtcggtggt ccggggtgca gaggaagtca agcaaaagtt tcaaagatta    300

gactacttat atctgaatgc tggaatcctg cctaatccac aattcaacct caaggcattt    360

ttctgcggca tcttttcaag aaatgtgatt catatgttca ccacagcgga aggaattttg    420

acccagaatg actcggtcac tgccgaccgg ttgcaggagg tgtttgaaac caatctctct    480

tgccacttta ttctgattcg ggaactggaa ccacttctct tgcatgcgga caacccctct    540

cagctcatct ggacgtcctc tcgcaatgca nagaaggcta acttcagcct ggaggacatn    600

cagcactcca tagggcccgg accctacagc tctttccaat atgctaccga cctcctgaat    660
```

-continued

```
gtggctttga acangaatnt caaccagaag ggtctgtatt ccagtcgcat gtgcccaggc    720

gtcgtgatga ccaatatgac gtatggaatc ttgcctccct tttatctgga cgtgctccta    780

cccatgatgg tgctccttcg cttctttggt aatgcgctta ctgggacacc gtacaac       837


<210> SEQ ID NO 32
<211> LENGTH: 334
<212> TYPE: PRT
<213> ORGANISM: Mus musculus

<400> SEQUENCE: 32

Met Arg Lys Val Val Leu Ile Thr Gly Ala Ser Ser Gly Ile Gly Leu
1               5                   10                  15

Ala Leu Cys Gly Arg Leu Leu Ala Glu Asp Asp Asp Leu His Leu Cys
            20                  25                  30

Leu Ala Cys Arg Asn Leu Ser Lys Ala Arg Ala Val Arg Asp Thr Leu
        35                  40                  45

Leu Ala Ser His Pro Ser Ala Glu Val Ser Ile Val Gln Met Asp Val
    50                  55                  60

Ser Ser Leu Gln Ser Val Val Arg Gly Ala Glu Glu Val Lys Gln Lys
65                  70                  75                  80

Phe Gln Arg Leu Asp Tyr Leu Tyr Leu Asn Ala Gly Ile Leu Pro Asn
                85                  90                  95

Pro Gln Phe Asn Leu Lys Ala Phe Phe Cys Gly Ile Phe Ser Arg Asn
            100                 105                 110

Val Ile His Met Phe Thr Thr Ala Glu Gly Ile Leu Thr Gln Asn Asp
        115                 120                 125

Ser Val Thr Ala Asp Gly Leu Gln Glu Val Phe Glu Thr Asn Leu Phe
    130                 135                 140

Gly His Phe Ile Leu Ile Arg Glu Leu Glu Pro Leu Leu Cys His Ala
145                 150                 155                 160

Asp Asn Pro Ser Gln Leu Ile Trp Thr Ser Ser Arg Asn Ala Lys Lys
                165                 170                 175

Ala Asn Phe Ser Leu Glu Asp Ile Gln His Ser Lys Gly Pro Glu Pro
            180                 185                 190

Tyr Ser Ser Ser Lys Tyr Ala Thr Asp Leu Leu Asn Val Ala Leu Asn
        195                 200                 205

Arg Asn Phe Asn Gln Lys Gly Leu Tyr Ser Ser Val Met Cys Pro Gly
    210                 215                 220

Val Val Met Thr Asn Met Thr Tyr Gly Ile Leu Pro Pro Phe Ile Trp
225                 230                 235                 240

Thr Leu Leu Leu Pro Ile Met Trp Leu Leu Arg Phe Phe Val Asn Ala
                245                 250                 255

Leu Thr Val Thr Pro Tyr Asn Gly Ala Glu Ala Leu Val Trp Leu Phe
            260                 265                 270

His Gln Lys Pro Glu Ser Leu Asn Pro Leu Thr Lys Tyr Ala Ser Ala
        275                 280                 285

Thr Ser Gly Phe Gly Thr Asn Tyr Val Thr Gly Gln Lys Met Asp Ile
    290                 295                 300

Asp Glu Asp Thr Ala Glu Lys Phe Tyr Glu Val Leu Leu Glu Leu Glu
305                 310                 315                 320

Lys Arg Val Arg Thr Thr Val Gln Lys Ser Asp His Pro Ser
                325                 330
```

-continued

<210> SEQ ID NO 33
<211> LENGTH: 1117
<212> TYPE: DNA
<213> ORGANISM: Saccharomyces cerevisiae

<400> SEQUENCE: 33

```
tgatgaaata ttccagttat gcgtgtgcgt cttgtgatgc agatcctttt gggcaaaaac     60

agttggtttg tgcgaaaacg caaggtaata aataggctta aaggaactaa aaaaaaaaaa    120

aggaaaataa ccagctaaga tttaaggtac aagaaagcgg ttgcacctca agtaatgata    180

gttattaaac cttggattgg accagatgtt taaaattgtt ttcaatagta gatttgcagt    240

cgtaaatgcg ttctcagcaa tatcatattg tgtttatgaa gtattaccaa acgggtagaa    300

gaacggttta agagaatatg tccggataaa gcgatcagga gaaaagctta aaacccaaag    360

tggtcaatct gcagcccatt taggcactct gcatttaacc gatacccgga ttgaagaaag    420

ctggcgggtg tatgggtgaa ggagaagaaa ggaagtgatt aggagaaacc tcatggagat    480

gagcacatgc tacaactaat aacgttattc tacttaaaac gagcaaaaca aaaaaaaaaa    540

caagacaatt gaaaacgcaa tggatgcatt cagcttaaag aaggataatc gaaaaaaatt    600

tcaagataaa cagaaattga aaagaaaaca tgccacaccc agtgatagaa agtaccggct    660

attgaaccgc caaaaagaag agaaagctac cacagaggag aaagatcaag accaagaaca    720

gcccgccctg aagtcaaacg aggacaggta ctatgaggac ccggtactcg aggacccgca    780

ttctgcagtc gccaatgcag agttgaacaa ggtgctaaaa gacgtcctca aaaatcggct    840

ccagcagaac gacgacgcca cagccgtcaa taatgttgct aataaagata ctttgaaaat    900

caaagacctc aagcagatga atacggatga gctcaatcgt tggctcggac ggcagaatac    960

aacatcggct ataacagcgg ctgagcccga atcattagtc gttcccattc acgtacaagg   1020

tgatcatgat cgtgcgggca agaagatcag tgccccttcg accgatctac cggaagaact   1080

agagaccgat caggatttcc ttgatggact gctctaa                            1117
```

<210> SEQ ID NO 34
<211> LENGTH: 185
<212> TYPE: PRT
<213> ORGANISM: Saccharomyces cerevisiae

<400> SEQUENCE: 34

```
Met Asp Ala Phe Ser Leu Lys Lys Asp Asn Arg Lys Lys Phe Gln Asp
1               5                   10                  15

Lys Gln Lys Leu Lys Arg Lys His Ala Thr Pro Ser Asp Arg Lys Tyr
            20                  25                  30

Arg Leu Leu Asn Arg Gln Lys Glu Glu Lys Ala Thr Thr Glu Glu Lys
        35                  40                  45

Asp Gln Asp Gln Glu Gln Pro Ala Leu Lys Ser Asn Glu Asp Arg Tyr
    50                  55                  60

Tyr Glu Asp Pro Val Leu Glu Asp Pro His Ser Ala Val Ala Asn Ala
65                  70                  75                  80

Glu Leu Asn Lys Val Leu Lys Asp Val Leu Lys Asn Arg Leu Gln Gln
                85                  90                  95

Asn Asp Asp Ala Thr Ala Val Asn Asn Val Ala Asn Lys Asp Thr Leu
            100                 105                 110

Lys Ile Lys Asp Leu Lys Gln Met Asn Thr Asp Glu Leu Asn Arg Trp
        115                 120                 125

Leu Gly Arg Gln Asn Thr Thr Ser Ala Ile Thr Ala Ala Glu Pro Glu
    130                 135                 140
```

-continued

```
Ser Leu Val Val Pro Ile His Val Gln Gly Asp His Asp Arg Ala Gly
145                 150                 155                 160

Lys Lys Ile Ser Ala Pro Ser Thr Asp Leu Pro Glu Glu Leu Glu Thr
                165                 170                 175

Asp Gln Asp Phe Leu Asp Gly Leu Leu
            180                 185
```

<210> SEQ ID NO 35
<211> LENGTH: 2379
<212> TYPE: DNA
<213> ORGANISM: Saccharomyces cerevisiae

<400> SEQUENCE: 35

```
gaaaggaagc tatagtaatg gggcttcagg aactttatga attgggtgct cttgacactc     60

gtggaaagat aactaaacgg ggtcaacaaa tggctctgtt accgctacaa ccgcatttaa    120

gtagtgtctt aattaaagcc agtgaagtcg gatgtttgag tcaggtcatt gatatcgtct    180

cttgccttag tgtggaaaat ttactgttga atccgtcacc agaagaaaga gatgaggtga    240

acgagcgtcg tttgtcctta tgcaacgctg gtaaaaggta tggtgacctt atcatgctga    300

aagagctttt tgatatctat ttctacgaac tagggaaaag tcaagatgca agctctgaaa    360

gaaatgattg gtgtaaagga ttgtgtattt cgatacgtgg gtttaaaaat gtaattcgtg    420

tcagagacca gttaagagtt tattgtaagc gtttgttttc ttcaatcagt gaagaggatg    480

aagaatccaa aaagattggt gaagatggcg agctaatttc gaaaatttta aagtgtttct    540

taactgggtt tatcaagaat acagctatag ggatgccaga caggtcttat agaactgttt    600

ccactggaga gccgataagc attcatccat catctatgct atttatgaat aaaagctgcc    660

ccggtataat gtacacggag tatgtcttta ctacgaaggg atatgccaga aatgttagta    720

ggattgaact ttcatggtta caagaagttg tcactaatgc agccgctgta gcaaagcaaa    780

aagtttctga ttcaaaataa gtcacctact cttagcgcat ttttattgta tataaaggca    840

tttaatgtaa tttatagagc attataaatc gtaacaacta ctgcagtatg agtttcatgg    900

attcatttct caatatctta tgaatataca caggtatata tgtatattca tgttaaacgc    960

ctttcgaatt gttcgttggc tttttttgtg aaattatctc gggaaaaggg cgaaattata   1020

ttattttgcc gttgacattt tgaaaaggaa taaaagatca tgaaaaaaat aagaaaggca   1080

attcgacgca tttctctcag caagctattc tttacttttg aagaacaaaa tattttagca   1140

aaaaggttaa gacaatatag tcggaagcag ttctgcggga tctgaaggaa ttgcggaata   1200

atgagatttc acgatagtat acttatcttc ttttctttgg catcgcttta tcaacatgtt   1260

catggtgcaa gacaagtcgt tcgtccaaag gagaaaatga ctacttcaga agaagttaaa   1320

ccttggttac gtacggttta tggaagtcaa aaagaattag tcactcctac ggtcattgcc   1380

ggtgtcactt tttctgaaaa accagaagaa acaccaaatc cattgaaacc ttgggtatct   1440

ttagagcatg atggtaggcc aaaaaccatt aaaccagaaa tcaacaaagg tcgaaccaag   1500

aagggaagac ctgattactc aacttacttc aaaacggtaa gttcccacac atattcttat   1560

gaagaattga aggctcacaa tatgggccct aatgaagttt ttgtagaaga agagtatatt   1620

gatgaagatg acacctacgt ctccctgaat cctattgtca gatgtactcc taatctttac   1680

ttcaataaag gtctagcaaa ggatatccgc agtgagccat tttgtacccc ttatgagaat   1740

tctagatgga aggttgacaa gacttacttc gttacttggt atacaagatt ttttacagat   1800

gagaattccg gtaaagttgc tgataaggtt cgtgttcatt tgtcctatgt taaagaaaac   1860
```

-continued

```
cccgtagaga agggcaatta taaaagagat atccctgcaa ctttttctc ttccgaatgg   1920

attgataatg acaacggtct aatgccggtt gaggtcagag atgaatggct gcaggaccaa   1980

tttgatcgta ggatcgttgt atcagttcag ccaatataca tatcagatga agatttcgat   2040

ccactacaat acggtatttt attatacatc actaagggtt caaaagtgtt taagcctact   2100

aaggagcaac tggctttaga cgatgcaggt ataacaaatg atcagtggta ttatgttgca   2160

ttatctatcc ctactgtcgt ggtggtattt ttcgtcttca tgtacttttt cttatatgtc   2220

aacgggaaaa acagagattt cacagatgtt actagaaaag ctttaaacaa gaaacgccgt   2280

gttttgggta agttctcgga gatgaagaaa ttcaaaaaca tgaaaaatca caagtacacc   2340

gaattgccat cttataagaa aaccagtaaa caaaattag                         2379
```

<210> SEQ ID NO 36
<211> LENGTH: 392
<212> TYPE: PRT
<213> ORGANISM: Saccharomyces cerevisiae

<400> SEQUENCE: 36

```
Met Arg Phe His Asp Ser Ile Leu Ile Phe Phe Ser Leu Ala Ser Leu
1               5                   10                  15

Tyr Gln His Val His Gly Ala Arg Gln Val Val Arg Pro Lys Glu Lys
            20                  25                  30

Met Thr Thr Ser Glu Glu Val Lys Pro Trp Leu Arg Thr Val Tyr Gly
        35                  40                  45

Ser Gln Lys Glu Leu Val Thr Pro Thr Val Ile Ala Gly Val Thr Phe
    50                  55                  60

Ser Glu Lys Pro Glu Glu Thr Pro Asn Pro Leu Lys Pro Trp Val Ser
65                  70                  75                  80

Leu Glu His Asp Gly Arg Pro Lys Thr Ile Lys Pro Glu Ile Asn Lys
                85                  90                  95

Gly Arg Thr Lys Lys Gly Arg Pro Asp Tyr Ser Thr Tyr Phe Lys Thr
            100                 105                 110

Val Ser Ser His Thr Tyr Ser Tyr Glu Glu Leu Lys Ala His Asn Met
        115                 120                 125

Gly Pro Asn Glu Val Phe Val Glu Glu Glu Tyr Ile Asp Glu Asp Asp
    130                 135                 140

Thr Tyr Val Ser Leu Asn Pro Ile Val Arg Cys Thr Pro Asn Leu Tyr
145                 150                 155                 160

Phe Asn Lys Gly Leu Ala Lys Asp Ile Arg Ser Glu Pro Phe Cys Thr
                165                 170                 175

Pro Tyr Glu Asn Ser Arg Trp Lys Val Asp Lys Thr Tyr Phe Val Thr
            180                 185                 190

Trp Tyr Thr Arg Phe Phe Thr Asp Glu Asn Ser Gly Lys Val Ala Asp
        195                 200                 205

Lys Val Arg Val His Leu Ser Tyr Val Lys Glu Asn Pro Val Glu Lys
    210                 215                 220

Gly Asn Tyr Lys Arg Asp Ile Pro Ala Thr Phe Phe Ser Ser Glu Trp
225                 230                 235                 240

Ile Asp Asn Asp Asn Gly Leu Met Pro Val Glu Val Arg Asp Glu Trp
                245                 250                 255

Leu Gln Asp Gln Phe Asp Arg Arg Ile Val Val Ser Val Gln Pro Ile
            260                 265                 270

Tyr Ile Ser Asp Glu Asp Phe Asp Pro Leu Gln Tyr Gly Ile Leu Leu
        275                 280                 285
```

-continued

```
Tyr Ile Thr Lys Gly Ser Lys Val Phe Lys Pro Thr Lys Glu Gln Leu
    290                 295                 300

Ala Leu Asp Asp Ala Gly Ile Thr Asn Asp Gln Trp Tyr Tyr Val Ala
305                 310                 315                 320

Leu Ser Ile Pro Thr Val Val Val Val Phe Phe Val Phe Met Tyr Phe
                325                 330                 335

Phe Leu Tyr Val Asn Gly Lys Asn Arg Asp Phe Thr Asp Val Thr Arg
            340                 345                 350

Lys Ala Leu Asn Lys Lys Arg Arg Val Leu Gly Lys Phe Ser Glu Met
        355                 360                 365

Lys Lys Phe Lys Asn Met Lys Asn His Lys Tyr Thr Glu Leu Pro Ser
    370                 375                 380

Tyr Lys Lys Thr Ser Lys Gln Asn
385                 390
```

<210> SEQ ID NO 37
<211> LENGTH: 1757
<212> TYPE: DNA
<213> ORGANISM: Saccharomyces cerevisiae

<400> SEQUENCE: 37

```
tctcactccg gcggccattt tacgtgacga agcatccctt acaacagaaa gaagaaaaaa     60

gatatgccgc tttgcggttt ctttctggca atgtatgcac tcataatgct actcgtttac    120

ccactatccc tgtccaaact aaagagggag gaaagcactt tttgcattta cacatcgtag    180

attataaaat gatcgttaac aggcgcttgt gattttgaat ttaagaaatg tggactagag    240

aagtcttaaa tcgccaatgc tgtaccagac tctctatagc atctaaacac gaaattcaac    300

tgttatctta gtttttcact taccagtagc gcgcttgtta ttcccacgtt attatttgcc    360

cccacatcat aggtcaagtg accttctctt acccgacatg aataaagaaa agaaaagaaa    420

tcataccctt cagcctgttt agccataaat agtaaagagt agatgtttcg acggactaaa    480

taatgtgaaa aaggttctaa aaccttcaaa acaattaaac ttgagaaacg ttgctatagg    540

attgagctaa taatttgaat taataggagc tgctttttac tttgatatat cctgaagtta    600

tgttacgagt ttctgaaaat ggtctacggt ttctgctgaa atgccattca acgaacgtaa    660

gcatgtttaa taggcttctg agtactcaaa taaaggaggg gagaagttcc atagatgatg    720

ctggcattat ccccgatgga actattaacg aaaggccgaa tcactacatc gagggaatta    780

ctaaaggcag tgatctggac ctcttggaaa aaggtataag aaaaactgac gaaatgactt    840

ccaattttac aaattatatg tacaagtttc acagattgcc ccccaactat ggaagtaacc    900

agctcattac tatcgataag gaacttcaaa aggaactgga tggggtaatg tcatccttca    960

aagctccgtg ccggtttgta tttggttacg gctcaggagt tttcgaacaa gcgggatatt   1020

ccaaaagtca tagcaaacct caaatcgata taatcttggg cgtcacatat ccatcacatt   1080

ttcactctat taatatgagg cagaatccgc aacattattc aagtttgaaa tacttcggtt   1140

ccgagttcgt gtctaaattt caacagatcg gcgcaggcgt atattttaat ccatttgcaa   1200

atataaatgg acacgacgta aaatatgggg tggtttctat ggaaacactt ttaaaggaca   1260

tagctacttg gaatacattc tatttagcag gacgactaca aaagcctgta aaaatattga   1320

agaatgattt gagagtgcaa tattggaacc aattaaactt aaaagctgca gctactttgg   1380

ccaaacatta caccttagag aaaaataaca ataagtttga cgaattccaa ttttacaagg   1440

agatcactgc cttaagttat gcaggtgata ttagatacaa actgggtgga gaaaatcccg   1500
```

-continued acaaagttaa caacattgtt accaaaaact ttgaaagatt tcaagagtat tacaagccga 1560
tttacaaaga agtggtccta aatgattcat tttatcttcc aaaagggttc acattaaaga 1620
atactcagag acttttgctc agccgtatta gtaaatcaag tgcattacaa actattaaag 1680
gtgttttcac agctggaatc acaaagtcaa ttaagtatgc ttgggccaaa aaactaaaat 1740
cgatgaggag aagctag 1757

<210> SEQ ID NO 38
<211> LENGTH: 385
<212> TYPE: PRT
<213> ORGANISM: Saccharomyces cerevisiae

<400> SEQUENCE: 38

Met Leu Arg Val Ser Glu Asn Gly Leu Arg Phe Leu Leu Lys Cys His
1 5 10 15

Ser Thr Asn Val Ser Met Phe Asn Arg Leu Leu Ser Thr Gln Ile Lys
20 25 30

Glu Gly Arg Ser Ser Ile Asp Asp Ala Gly Ile Ile Pro Asp Gly Thr
35 40 45

Ile Asn Glu Arg Pro Asn His Tyr Ile Glu Gly Ile Thr Lys Gly Ser
50 55 60

Asp Leu Asp Leu Leu Glu Lys Gly Ile Arg Lys Thr Asp Glu Met Thr
65 70 75 80

Ser Asn Phe Thr Asn Tyr Met Tyr Lys Phe His Arg Leu Pro Pro Asn
85 90 95

Tyr Gly Ser Asn Gln Leu Ile Thr Ile Asp Lys Glu Leu Gln Lys Glu
100 105 110

Leu Asp Gly Val Met Ser Ser Phe Lys Ala Pro Cys Arg Phe Val Phe
115 120 125

Gly Tyr Gly Ser Gly Val Phe Glu Gln Ala Gly Tyr Ser Lys Ser His
130 135 140

Ser Lys Pro Gln Ile Asp Ile Ile Leu Gly Val Thr Tyr Pro Ser His
145 150 155 160

Phe His Ser Ile Asn Met Arg Gln Asn Pro Gln His Tyr Ser Ser Leu
165 170 175

Lys Tyr Phe Gly Ser Glu Phe Val Ser Lys Phe Gln Gln Ile Gly Ala
180 185 190

Gly Val Tyr Phe Asn Pro Phe Ala Asn Ile Asn Gly His Asp Val Lys
195 200 205

Tyr Gly Val Val Ser Met Glu Thr Leu Leu Lys Asp Ile Ala Thr Trp
210 215 220

Asn Thr Phe Tyr Leu Ala Gly Arg Leu Gln Lys Pro Val Lys Ile Leu
225 230 235 240

Lys Asn Asp Leu Arg Val Gln Tyr Trp Asn Gln Leu Asn Leu Lys Ala
245 250 255

Ala Ala Thr Leu Ala Lys His Tyr Thr Leu Glu Lys Asn Asn Asn Lys
260 265 270

Phe Asp Glu Phe Gln Phe Tyr Lys Glu Ile Thr Ala Leu Ser Tyr Ala
275 280 285

Gly Asp Ile Arg Tyr Lys Leu Gly Gly Glu Asn Pro Asp Lys Val Asn
290 295 300

Asn Ile Val Thr Lys Asn Phe Glu Arg Phe Gln Glu Tyr Tyr Lys Pro
305 310 315 320

-continued

```
Ile Tyr Lys Glu Val Val Leu Asn Asp Ser Phe Tyr Leu Pro Lys Gly
                325                 330                 335

Phe Thr Leu Lys Asn Thr Gln Arg Leu Leu Leu Ser Arg Ile Ser Lys
            340                 345                 350

Ser Ser Ala Leu Gln Thr Ile Lys Gly Val Phe Thr Ala Gly Ile Thr
        355                 360                 365

Lys Ser Ile Lys Tyr Ala Trp Ala Lys Lys Leu Lys Ser Met Arg Arg
    370                 375                 380

Ser
385
```

<210> SEQ ID NO 39
<211> LENGTH: 4525
<212> TYPE: DNA
<213> ORGANISM: Saccharomyces cerevisiae

<400> SEQUENCE: 39

```
tacctgctgt agaatccttc actgaaaaca cttgttcaat atattcttca tctggttcac     60

cgtctgatct attaatccag tttagcaatg actcaataaa ctctgatctg ttctcctcta    120

catcctgacc atctaatatg aagtacattg tcctcagaca gtttaaaacg gttaaagatt    180

cttccaactc ataaaatcgg ttcactcttc catcctgatc cttgactcta ccaataaaca    240

cttccaattc attcagaatc gcctccatgg ccagatttac tgttgcatta tgctccttcg    300

cgaaattaga attaacaact ccaatcgttg gtacattaaa cactctgtca tcacctaaat    360

cacggtaaat ttcaaataaa cctgatacgt atgcagaaaa ctctttgctg gtatctaatc    420

taggaattct aacaggataa agcttatatt tatcttttgc agttatgaat gccatatttt    480

ggtaagaaag tggccccagc ttgaacttta aaggcatctt gtcgccattt ttttcaatcg    540

gttgatcatt tacagtcata gggaccagga tagccccgct gactgggtcc cttttatata    600

gttgttcttc ttcatcggtc ttgttattac taagttgcgc cgttccgtcg tccaaaaaat    660

caaattgatc gacgtccata agtaatcgat ttgaatcatc gattgtcata tctgataatt    720

gcgttctggc tcacgcttat tgactcaact caagaccgta agttcaatgt tttctataca    780

actacaattt gtacaaggct tgacttccat ccaactaaaa aacctctccg tcgtgcgcga    840

tctgaaaaat ttcacttagc tcatctcaaa atgatcgcta agagggcact tggtcacaac    900

tacagaattg tttactagca taggaacatc tctgtctaag atttagcttg ccatcaatta    960

tctttggaaa aacagagagt atactgcact ttttgataat atgggtgatc ttacagaaga   1020

actatctatc ccagacaatg cccaagattt gtcgaaatta ctacgttcga cgagcacaaa   1080

accccatcaa attgccgaga tagtttcaaa atttgataaa ttagaaacct actttccaaa   1140

aaaagaaatt ttcgtcttag atttactcat tgataggctc aacaatggaa atttggatga   1200

ttttaagacc agtgaacata cttggataat tttcacgaga ttattagatg ctattaatga   1260

tccaatttcg ataaaaaaac tactcaaaaa attgaagact gtgcctgtaa tgataagaac   1320

atttttcctt tggcctaaag acaaattact tacacgtagc gtttcgttta taaaagcatt   1380

ttttgcgatt aatgactact tgattgtcaa tttttctgtt gaagagtctt ttcaactttt   1440

agaacatgcc ataaatggat taagttcgtg cccgacgact gactttgcgc tttcatactt   1500

gcaagatgcc tgcaatctaa ctcatgttga caatattact acaacggata acaaaattgc   1560

tacttgttac tgcaagcata tgctactacc aagtttaaga tatttcgcac agaccaaaaa   1620

ttctgcatct tcaaaccaat ccttcattcg tctatctcat tttatgggaa agttcctttt   1680
```

-continued

```
acaaccacgc atagattaca tgaaattaaa taaaaagttt gtccaagaga atgcgtccga   1740
aattaccgac gatatggctt attattattt tgccactttc gtcactttct tatcaaaaga   1800
caattttgct caactagaag tcatctttac aattttaggt gccaagaaac ctagtttaga   1860
atgcagattt ctgaatcttt tatcggaatc gaagaaaacc gtatctcaag agttccttga   1920
agcattattg cttgaaatgt tagcgtcgac tgatgaatct ggagtgttat cattaatacc   1980
aattatcctt aaattggata tcgaggttgc tattaaacat atttttcggt tacttgaatt   2040
gattcagctc gaaaatttga acgatcctct cttttcctct catatttggg atttaataat   2100
ccaatcacac gctaacgcaa gggaattatc agattttttt gccaaaaataa atgagtactg   2160
ttccagaaaa ggacccgatt cctatttttt gataaatcat cctgcatatg tcaagtctat   2220
aacgaagcaa ttgttcactt tatcttcttt acaatggaaa aatctattgc aagctttact   2280
tgaccaagtc aatcacgatt ccaccaacag ggttccttta tatttaatac gcatatgctt   2340
ggagggacta tcagagggcg catcgcgcgc aactctcgat gaggtaaagc ctattttatc   2400
tcaagtattt actttggaat catttaataa cagtcttcaa tgggacctaa agtatcatat   2460
aatggaagtc tacgatgata ttgtccctgc agaggaacta gaaaaaatcg attacgtgtt   2520
atcttctaat atttttgata ctacatcggc tgatgttgaa gaactgttct tttattgctt   2580
caaattgaga gaatatattt cgttcgatct ttctgatgca aaaaaaaaat tcatgaggca   2640
ctttgaaatc cttgacgaag aaagaaagtc aaacttatca tactctgttg tgtccaaatt   2700
tgcaacatta gtaaacaaca actttacaag agaacaaatt tcttctttaa ttgattcatt   2760
actattgaac tcgacaaatt tatcttcgtt attaaaaaat gatgacattt ttgaggagac   2820
aaatatcacg tacgctttaa taaacaagct tgcttcatca taccatcaaa ccttcgctct   2880
agaagctttg attcaaattc ctatccaatg catcaacaaa aacgttagag tggctctcat   2940
taacaatcta acatgcgaat cattttgcct tgattccgct actagagaat gcctccttca   3000
tttattgtca agcccgacct tcaagagcaa cattgaaaca aatttctacg aattatgtga   3060
gaaaacaata atgagccccg aaatggccat ttcagagaca ggtgatgaaa aaaaggaaat   3120
agaagacaaa atatctattt tcgaaaaagt ttggactaat catctgtcac aggcaaagga   3180
gcctgtgagt gagaagttct tagaatctgg ttacgatatc gttaaacagt caatgtcatt   3240
gtccaatggt gatagcaaac taattatcgc cgggtttact atcgcaaaat ttttgaaacc   3300
agataacaag catagagata tacaaggtat ggcaattagc tatgctgtta aaattttgga   3360
aaactactct gaaaatttg aatctgaaac aattcccctt ttcagaatat caatgtctac   3420
attgtacaag attataacga ccggacaagg cgatatttct aagcataaat cgagaattct   3480
ggatatattt tccaaaatta tgcttcgata tcattctaaa aaagtgtacc atgcgccaga   3540
agaacaggaa atgtttttgg ttcattcact ccttacagaa aacaagttgg agtatatttt   3600
tgcagagtac ttaaatattg agcatacaga taagtgcgat tctgccttgg ggttctgctt   3660
ggaagaaagt cttaaacaag gtcctgatgc gtttaaccgc ctgctctgga acagtgctaa   3720
atcgttttcc accattagcc aaccttgtgc tgaaaaattt gtgagagttt ttatcataat   3780
gtcaaaaagg attgcaagag acaataacct tggtcatcac ctatttgtga tagctttact   3840
tgaagcctac acctattgtg atatagaaaa atttggctac aagtcatact tgctactgtt   3900
caatgctatc aaggagttct tagtatcgaa accatggcta ttcagccaat actgtattga   3960
aatgctgctt cctttctgtt taaaaactct cgcttttata gtaaaccatg agtcaacgga   4020
tgaaatcaat gaaggcttta ttaacatcat cgaagtgata gatcatatgc tattagttca   4080
```

-continued

```
caggtttaaa ttttccaatc gtcaccattt gtttaactcc gttctttgcc agatactaga   4140

aataatagca attcatgatg gtacattgtg tgcaaattca gcagacgccg tagccagact   4200

aataacgaac tactgcgagc cttataatgt atcaaacgct caaaatgggc agaaaaataa   4260

cttaagctca aagataagtt tgataaagca gtccatcaga aaaaatgtac ttgtggttct   4320

aacgaaatat atacagttgt ctattacgac gcagttcagt ttaaacataa aaaagagtct   4380

gcagcccggt attcatgcga tttttgatat attatctcag aacgagttga atcaattgaa   4440

cgctttcctt gacacacctg ggaaacaata tttcaaagca ctttacctcc aatacaaaaa   4500

ggttggtaaa tggcgcgaag attaa                                          4525
```

```
<210> SEQ ID NO 40
<211> LENGTH: 1174
<212> TYPE: PRT
<213> ORGANISM: Saccharomyces cerevisiae

<400> SEQUENCE: 40

Met Gly Asp Leu Thr Glu Glu Leu Ser Ile Pro Asp Asn Ala Gln Asp
1               5                   10                  15

Leu Ser Lys Leu Leu Arg Ser Thr Ser Thr Lys Pro His Gln Ile Ala
            20                  25                  30

Glu Ile Val Ser Lys Phe Asp Lys Leu Glu Thr Tyr Phe Pro Lys Lys
        35                  40                  45

Glu Ile Phe Val Leu Asp Leu Leu Ile Asp Arg Leu Asn Asn Gly Asn
    50                  55                  60

Leu Asp Asp Phe Lys Thr Ser Glu His Thr Trp Ile Ile Phe Thr Arg
65                  70                  75                  80

Leu Leu Asp Ala Ile Asn Asp Pro Ile Ser Ile Lys Lys Leu Leu Lys
                85                  90                  95

Lys Leu Lys Thr Val Pro Val Met Ile Arg Thr Phe Phe Leu Trp Pro
            100                 105                 110

Lys Asp Lys Leu Leu Thr Arg Ser Val Ser Phe Ile Lys Ala Phe Phe
        115                 120                 125

Ala Ile Asn Asp Tyr Leu Ile Val Asn Phe Ser Val Glu Glu Ser Phe
    130                 135                 140

Gln Leu Leu Glu His Ala Ile Asn Gly Leu Ser Ser Cys Pro Thr Thr
145                 150                 155                 160

Asp Phe Ala Leu Ser Tyr Leu Gln Asp Ala Cys Asn Leu Thr His Val
                165                 170                 175

Asp Asn Ile Thr Thr Thr Asp Asn Lys Ile Ala Thr Cys Tyr Cys Lys
            180                 185                 190

His Met Leu Leu Pro Ser Leu Arg Tyr Phe Ala Gln Thr Lys Asn Ser
        195                 200                 205

Ala Ser Ser Asn Gln Ser Phe Ile Arg Leu Ser His Phe Met Gly Lys
    210                 215                 220

Phe Leu Leu Gln Pro Arg Ile Asp Tyr Met Lys Leu Asn Lys Lys Phe
225                 230                 235                 240

Val Gln Glu Asn Ala Ser Glu Ile Thr Asp Asp Met Ala Tyr Tyr Tyr
                245                 250                 255

Phe Ala Thr Phe Val Thr Phe Leu Ser Lys Asp Asn Phe Ala Gln Leu
            260                 265                 270

Glu Val Ile Phe Thr Ile Leu Gly Ala Lys Lys Pro Ser Leu Glu Cys
        275                 280                 285
```

-continued

```
Arg Phe Leu Asn Leu Leu Ser Glu Ser Lys Lys Thr Val Ser Gln Glu
    290                 295                 300

Phe Leu Glu Ala Leu Leu Leu Glu Met Leu Ala Ser Thr Asp Glu Ser
305                 310                 315                 320

Gly Val Leu Ser Leu Ile Pro Ile Ile Leu Lys Leu Asp Ile Glu Val
                325                 330                 335

Ala Ile Lys His Ile Phe Arg Leu Leu Glu Leu Ile Gln Leu Glu Asn
            340                 345                 350

Leu Asn Asp Pro Leu Phe Ser Ser His Ile Trp Asp Leu Ile Ile Gln
        355                 360                 365

Ser His Ala Asn Ala Arg Glu Leu Ser Asp Phe Phe Ala Lys Ile Asn
    370                 375                 380

Glu Tyr Cys Ser Arg Lys Gly Pro Asp Ser Tyr Phe Leu Ile Asn His
385                 390                 395                 400

Pro Ala Tyr Val Lys Ser Ile Thr Lys Gln Leu Phe Thr Leu Ser Ser
                405                 410                 415

Leu Gln Trp Lys Asn Leu Leu Gln Ala Leu Leu Asp Gln Val Asn His
            420                 425                 430

Asp Ser Thr Asn Arg Val Pro Leu Tyr Leu Ile Arg Ile Cys Leu Glu
        435                 440                 445

Gly Leu Ser Glu Gly Ala Ser Arg Ala Thr Leu Asp Glu Val Lys Pro
    450                 455                 460

Ile Leu Ser Gln Val Phe Thr Leu Glu Ser Phe Asn Asn Ser Leu Gln
465                 470                 475                 480

Trp Asp Leu Lys Tyr His Ile Met Glu Val Tyr Asp Asp Ile Val Pro
                485                 490                 495

Ala Glu Glu Leu Glu Lys Ile Asp Tyr Val Leu Ser Ser Asn Ile Phe
            500                 505                 510

Asp Thr Thr Ser Ala Asp Val Glu Glu Leu Phe Phe Tyr Cys Phe Lys
        515                 520                 525

Leu Arg Glu Tyr Ile Ser Phe Asp Leu Ser Asp Ala Lys Lys Lys Phe
    530                 535                 540

Met Arg His Phe Glu Ile Leu Asp Glu Glu Arg Lys Ser Asn Leu Ser
545                 550                 555                 560

Tyr Ser Val Val Ser Lys Phe Ala Thr Leu Val Asn Asn Asn Phe Thr
                565                 570                 575

Arg Glu Gln Ile Ser Ser Leu Ile Asp Ser Leu Leu Leu Asn Ser Thr
            580                 585                 590

Asn Leu Ser Ser Leu Leu Lys Asn Asp Asp Ile Phe Glu Glu Thr Asn
        595                 600                 605

Ile Thr Tyr Ala Leu Ile Asn Lys Leu Ala Ser Ser Tyr His Gln Thr
    610                 615                 620

Phe Ala Leu Glu Ala Leu Ile Gln Ile Pro Ile Gln Cys Ile Asn Lys
625                 630                 635                 640

Asn Val Arg Val Ala Leu Ile Asn Asn Leu Thr Cys Glu Ser Phe Cys
                645                 650                 655

Leu Asp Ser Ala Thr Arg Glu Cys Leu Leu His Leu Leu Ser Ser Pro
            660                 665                 670

Thr Phe Lys Ser Asn Ile Glu Thr Asn Phe Tyr Glu Leu Cys Glu Lys
        675                 680                 685

Thr Ile Met Ser Pro Glu Met Ala Ile Ser Glu Thr Gly Asp Glu Lys
    690                 695                 700
```

-continued

```
Lys Glu Ile Glu Asp Lys Ile Ser Ile Phe Glu Lys Val Trp Thr Asn
705                 710                 715                 720

His Leu Ser Gln Ala Lys Glu Pro Val Ser Glu Lys Phe Leu Glu Ser
                725                 730                 735

Gly Tyr Asp Ile Val Lys Gln Ser Met Ser Leu Ser Asn Gly Asp Ser
            740                 745                 750

Lys Leu Ile Ile Ala Gly Phe Thr Ile Ala Lys Phe Leu Lys Pro Asp
        755                 760                 765

Asn Lys His Arg Asp Ile Gln Gly Met Ala Ile Ser Tyr Ala Val Lys
    770                 775                 780

Ile Leu Glu Asn Tyr Ser Glu Asn Phe Glu Ser Glu Thr Ile Pro Leu
785                 790                 795                 800

Phe Arg Ile Ser Met Ser Thr Leu Tyr Lys Ile Ile Thr Thr Gly Gln
                805                 810                 815

Gly Asp Ile Ser Lys His Lys Ser Arg Ile Leu Asp Ile Phe Ser Lys
            820                 825                 830

Ile Met Leu Arg Tyr His Ser Lys Lys Val Tyr His Ala Pro Glu Glu
        835                 840                 845

Gln Glu Met Phe Leu Val His Ser Leu Leu Thr Glu Asn Lys Leu Glu
    850                 855                 860

Tyr Ile Phe Ala Glu Tyr Leu Asn Ile Glu His Thr Asp Lys Cys Asp
865                 870                 875                 880

Ser Ala Leu Gly Phe Cys Leu Glu Glu Ser Leu Lys Gln Gly Pro Asp
                885                 890                 895

Ala Phe Asn Arg Leu Leu Trp Asn Ser Ala Lys Ser Phe Ser Thr Ile
            900                 905                 910

Ser Gln Pro Cys Ala Glu Lys Phe Val Arg Val Phe Ile Ile Met Ser
        915                 920                 925

Lys Arg Ile Ala Arg Asp Asn Asn Leu Gly His His Leu Phe Val Ile
    930                 935                 940

Ala Leu Leu Glu Ala Tyr Thr Tyr Cys Asp Ile Glu Lys Phe Gly Tyr
945                 950                 955                 960

Lys Ser Tyr Leu Leu Leu Phe Asn Ala Ile Lys Glu Phe Leu Val Ser
                965                 970                 975

Lys Pro Trp Leu Phe Ser Gln Tyr Cys Ile Glu Met Leu Leu Pro Phe
            980                 985                 990

Cys Leu Lys Thr Leu Ala Phe Ile  Val Asn His Glu Ser  Thr Asp Glu
        995                 1000                1005

Ile Asn  Glu Gly Phe Ile Asn  Ile Ile Glu Val Ile  Asp His Met
    1010                 1015                 1020

Leu Leu  Val His Arg Phe Lys  Phe Ser Asn Arg His  His Leu Phe
    1025                 1030                 1035

Asn Ser  Val Leu Cys Gln Ile  Leu Glu Ile Ile Ala  Ile His Asp
    1040                 1045                 1050

Gly Thr  Leu Cys Ala Asn Ser  Ala Asp Ala Val Ala  Arg Leu Ile
    1055                 1060                 1065

Thr Asn  Tyr Cys Glu Pro Tyr  Asn Val Ser Asn Ala  Gln Asn Gly
    1070                 1075                 1080

Gln Lys  Asn Asn Leu Ser Ser  Lys Ile Ser Leu Ile  Lys Gln Ser
    1085                 1090                 1095

Ile Arg  Lys Asn Val Leu Val  Val Leu Thr Lys Tyr  Ile Gln Leu
    1100                 1105                 1110
```

-continued

```
Ser Ile  Thr Thr Gln Phe Ser  Leu Asn Ile Lys Lys  Ser Leu Gln
    1115                 1120                 1125

Pro Gly  Ile His Ala Ile Phe  Asp Ile Leu Ser Gln  Asn Glu Leu
    1130                 1135                 1140

Asn Gln  Leu Asn Ala Phe Leu  Asp Thr Pro Gly Lys  Gln Tyr Phe
    1145                 1150                 1155

Lys Ala  Leu Tyr Leu Gln Tyr  Lys Lys Val Gly Lys  Trp Arg Glu
    1160                 1165                 1170

Asp
```

```
<210> SEQ ID NO 41
<211> LENGTH: 2394
<212> TYPE: DNA
<213> ORGANISM: Saccharomyces cerevisiae

<400> SEQUENCE: 41

catggctgga ggaaagattc ctattgtagg aattgtggca tgtttacagc cggagatggg     60

gataggattt cgtggaggtc taccatggag gttgcccagt gaaatgaagt atttcagaca    120

ggtcacttca ttgacgaaag atccaaacaa aaaaaatgct ttgataatgg gaaggaagac    180

atgggaatcc ataccgccca agtttcgccc actgcccaat agaatgaatg tcattatatc    240

gagaagcttc aaggacgatt ttgtccacga taaagagaga tcaatagtcc aaagtaattc    300

attggcaaac gcaataatga acctagaaag caattttaag gagcatctgg aaagaatcta    360

cgtgattggg ggtggcgaag tttatagtca aatcttctcc attacagatc attggctcat    420

cacgaaaata aatccattag ataaaaacgc aactcctgca atggacactt tccttgatgc    480

gaagaaattg gaagaagtat ttagcgagca agatccggcc cagctgaaag aatttcttcc    540

ccctaaagta gagttgcccg aaacagactg tgatcaacgc tactcgctgg aagaaaaagg    600

ttattgcttc gaattcactc tatacaatcg taaatgaaac ctctccgccc gtatattttt    660

tttaatatgt taaatagtga tagaactgat aagcctcatt ttcttttatt gggctccaag    720

acgcgaactg ttcgtagggt aaccgtttga cacctaaacg acctttcagc ctcacctgca    780

gtatttcttc aacaacgcct gtcgctatgt taaataatag caatcgtttg tgatcaccat    840

tgtcgaattt gacgcgctta aacaaaaacc attgttttgg cctcgttccc tgcattcaac    900

aaaagagcaa ggtatgccgt caaacagtcg ttaaaagaga aggtttataa actatcttgt    960

tttgtacttt gctgtcccgg atccagttgg gtcttctttt caacctgtct gagtccgatc   1020

tttctttccc tacttgaagc tccatatatc taagtcatct aagtgtatcc tgctagatta   1080

caaacgaaaa tgtctcaaca cgcaagctca tcttcttgga cttctttttt gaaatcgata   1140

agttcgttca acggagatct atcgtctttg tctgcaccac cgtttattct ttctcccact   1200

tccttaacag agttttctca gtattgggct gaacatccag ctttatttct ggagccttcg   1260

ttgattgatg gtgaaaacta caaagatcac tgtccctttg acccaaatgt ggaatcaaag   1320

gaagtggcgc agatgttggc ggttgttagg tggtttattt ctactttgag atctcaatac   1380

tgctctagaa gcgaatcgat gggttctgaa aagaagcctt tgaacccatt cttgggtgag   1440

gtatttgttg gaaagtggaa aaatgatgag catccagagt ttggtgaaac ggttctttta   1500

agtgagcaag tttcacatca tccacctatg acagcatttt cgatttttaa tgaaaaaaat   1560

gatgtttctg ttcaaggata caatcaaatt aaaactggtt ttaccaaaac attgacgcta   1620

acggtcaaac catacgggca tgtcattttg aagattaaag atgagaccta cctgattaca   1680

accccgcctt tgcatatcga aggtatttta gtcgcttctc catttgttga attaggaggc   1740
```

-continued

```
aggtcattca tacagtcatc aaatggtatg ttatgtgtta tagaattttc aggaaggggg   1800

tatttcacag ggaagaagaa ctcctttaag gcaagaattt acagaagccc acaagagcat   1860

agtcataaag aaaatgcgct atacctaatc tctggccaat ggtcaggtgt ttcaacaatt   1920

ataaaaaaag actcgcaagt ttcacatcag ttttacgatt catcggaaac tcctactgaa   1980

catttattag ttaagccaat cgaagaacaa catcctctgg aaagtaggag ggcatggaag   2040

gatgtggcag aagcaatcag acaaggaaat attagtatga taaaaaagac taaggaagaa   2100

ctagaaaata agcaaagagc cttgagagaa caagaacgcg taaaaggtgt ggaatggcaa   2160

agaagatggt tcaaacaagt ggactacatg aatgaaaata catcaaatga tgtagagaaa   2220

gcaagtgaag atgatgcctt taggaaattg gcgtccaaac tgcagctttc tgtgaaaaat   2280

gtgccaagtg ggacattgat tggcggcaaa gatgataaga aagatgtttc aaccgcattg   2340

cattggaggt ttgataaaaa tttgtggatg agggagaacg aaattactat ataa         2394
```

<210> SEQ ID NO 42
<211> LENGTH: 434
<212> TYPE: PRT
<213> ORGANISM: Saccharomyces cerevisiae

<400> SEQUENCE: 42

```
Met Ser Gln His Ala Ser Ser Ser Ser Trp Thr Ser Phe Leu Lys Ser
1               5                   10                  15

Ile Ser Ser Phe Asn Gly Asp Leu Ser Ser Leu Ser Ala Pro Pro Phe
            20                  25                  30

Ile Leu Ser Pro Thr Ser Leu Thr Glu Phe Ser Gln Tyr Trp Ala Glu
        35                  40                  45

His Pro Ala Leu Phe Leu Glu Pro Ser Leu Ile Asp Gly Glu Asn Tyr
    50                  55                  60

Lys Asp His Cys Pro Phe Asp Pro Asn Val Glu Ser Lys Glu Val Ala
65                  70                  75                  80

Gln Met Leu Ala Val Val Arg Trp Phe Ile Ser Thr Leu Arg Ser Gln
                85                  90                  95

Tyr Cys Ser Arg Ser Glu Ser Met Gly Ser Glu Lys Lys Pro Leu Asn
            100                 105                 110

Pro Phe Leu Gly Glu Val Phe Val Gly Lys Trp Lys Asn Asp Glu His
        115                 120                 125

Pro Glu Phe Gly Glu Thr Val Leu Leu Ser Glu Gln Val Ser His His
    130                 135                 140

Pro Pro Met Thr Ala Phe Ser Ile Phe Asn Glu Lys Asn Asp Val Ser
145                 150                 155                 160

Val Gln Gly Tyr Asn Gln Ile Lys Thr Gly Phe Thr Lys Thr Leu Thr
                165                 170                 175

Leu Thr Val Lys Pro Tyr Gly His Val Ile Leu Lys Ile Lys Asp Glu
            180                 185                 190

Thr Tyr Leu Ile Thr Thr Pro Pro Leu His Ile Glu Gly Ile Leu Val
        195                 200                 205

Ala Ser Pro Phe Val Glu Leu Gly Gly Arg Ser Phe Ile Gln Ser Ser
    210                 215                 220

Asn Gly Met Leu Cys Val Ile Glu Phe Ser Gly Arg Gly Tyr Phe Thr
225                 230                 235                 240

Gly Lys Lys Asn Ser Phe Lys Ala Arg Ile Tyr Arg Ser Pro Gln Glu
                245                 250                 255
```

-continued

```
His Ser His Lys Glu Asn Ala Leu Tyr Leu Ile Ser Gly Gln Trp Ser
            260                 265                 270

Gly Val Ser Thr Ile Ile Lys Lys Asp Ser Gln Val Ser His Gln Phe
        275                 280                 285

Tyr Asp Ser Ser Glu Thr Pro Thr Glu His Leu Leu Val Lys Pro Ile
    290                 295                 300

Glu Glu Gln His Pro Leu Glu Ser Arg Arg Ala Trp Lys Asp Val Ala
305                 310                 315                 320

Glu Ala Ile Arg Gln Gly Asn Ile Ser Met Ile Lys Lys Thr Lys Glu
                325                 330                 335

Glu Leu Glu Asn Lys Gln Arg Ala Leu Arg Glu Gln Glu Arg Val Lys
            340                 345                 350

Gly Val Glu Trp Gln Arg Arg Trp Phe Lys Gln Val Asp Tyr Met Asn
        355                 360                 365

Glu Asn Thr Ser Asn Asp Val Glu Lys Ala Ser Glu Asp Asp Ala Phe
    370                 375                 380

Arg Lys Leu Ala Ser Lys Leu Gln Leu Ser Val Lys Asn Val Pro Ser
385                 390                 395                 400

Gly Thr Leu Ile Gly Gly Lys Asp Asp Lys Lys Asp Val Ser Thr Ala
                405                 410                 415

Leu His Trp Arg Phe Asp Lys Asn Leu Trp Met Arg Glu Asn Glu Ile
            420                 425                 430

Thr Ile


<210> SEQ ID NO 43
<211> LENGTH: 334
<212> TYPE: PRT
<213> ORGANISM: Rattus sp.

<400> SEQUENCE: 43

Met Arg Lys Val Val Leu Ile Thr Gly Ala Ser Ser Gly Ile Gly Leu
1               5                   10                  15

Ala Leu Cys Gly Arg Leu Leu Ala Glu Asp Asp Asp Leu His Leu Cys
            20                  25                  30

Leu Ala Cys Arg Asn Leu Ser Lys Ala Gly Ala Val Arg Asp Ala Leu
        35                  40                  45

Leu Ala Ser His Pro Ser Ala Glu Val Ser Ile Val Gln Met Asp Val
    50                  55                  60

Ser Asn Leu Gln Ser Val Val Arg Gly Ala Glu Glu Val Lys Arg Arg
65                  70                  75                  80

Phe Gln Arg Leu Asp Tyr Leu Tyr Leu Asn Ala Gly Ile Met Pro Asn
                85                  90                  95

Pro Gln Leu Asn Leu Lys Ala Phe Phe Cys Gly Ile Phe Ser Arg Asn
            100                 105                 110

Val Ile His Met Phe Ser Thr Ala Glu Gly Leu Leu Thr Gln Asn Asp
        115                 120                 125

Lys Ile Thr Ala Asp Gly Phe Gln Glu Val Phe Glu Thr Asn Leu Phe
    130                 135                 140

Gly His Phe Ile Leu Ile Arg Glu Leu Glu Pro Leu Leu Cys His Ser
145                 150                 155                 160

Asp Asn Pro Ser Gln Leu Ile Trp Thr Ser Ser Arg Asn Ala Lys Lys
                165                 170                 175

Ser Asn Phe Ser Leu Glu Asp Ile Gln His Ala Lys Gly Gln Glu Pro
            180                 185                 190
```

-continued

```
Tyr Ser Ser Ser Lys Tyr Ala Thr Asp Leu Leu Asn Val Ala Leu Asn
        195                 200                 205

Arg Asn Phe Asn Gln Lys Gly Leu Tyr Ser Ser Val Thr Cys Pro Gly
    210                 215                 220

Val Val Met Thr Asn Leu Thr Tyr Gly Ile Leu Pro Pro Phe Val Trp
225                 230                 235                 240

Thr Leu Leu Leu Pro Val Ile Trp Leu Leu Arg Phe Phe Ala His Ala
                245                 250                 255

Phe Thr Val Thr Pro Tyr Asn Gly Ala Glu Ala Leu Val Trp Leu Phe
            260                 265                 270

His Gln Lys Pro Glu Ser Leu Asn Pro Leu Thr Lys Tyr Leu Ser Gly
        275                 280                 285

Thr Thr Gly Leu Gly Thr Asn Tyr Val Lys Gly Gln Lys Met Asp Val
    290                 295                 300

Asp Glu Asp Thr Ala Glu Lys Phe Tyr Lys Thr Leu Leu Glu Leu Glu
305                 310                 315                 320

Lys Gln Val Arg Ile Thr Ile Gln Lys Ser Asp His His Ser
                325                 330
```

<210> SEQ ID NO 44
<211> LENGTH: 2955
<212> TYPE: DNA
<213> ORGANISM: Saccharomyces cerevisiae

<400> SEQUENCE: 44

```
taatataaat actagtcgtt agatgatagt tgcttcttat tccgaaaatg agtatggaag     60

tgttgcatat gatagggcgg ctacagtgat ggtaaacata agatacttta gcgggaaatt    120

agcaactgga agttaaatta tctagacata agtgtggcgg tcacgctgaa cgcaggagat    180

cggatagatt gataagctga tcaagaacat tgatcggttt gttgtttaaa gaatggtttt    240

tgaaaacgtt tgaccagttg cttctcccag acgcttaccg atatgatgat aaagataata    300

tcttcaattg aataccccgt ggatcagcac gaataacaga aaaaaagggt gaaattcacc    360

gtaagcatga tacgcactac gttcttctta cctttgccaa cgtgttgtct ttgacgtacg    420

taattatggg agatcgttga tgattagccc cagctcactt tcttcttaat gactgacccg    480

ctactatcaa aattaaggtg tcaaatatca tgatgaatga ggtctctagg cgactcaatt    540

atacatcttt tagagatttt tttactactt gcagataatt tctcaaggga ttagattcaa    600

atctggcttg tcaattacgc ccttttcaag ctcatcaaat tgcgtatgtc attcatgctt    660

ccattaggaa ccatagaagc atggctgaaa tggcaatata cggcttccca atttcaactc    720

taaagtaatg gcggtcgaat ttaatctata ttttacagtt ttatacgtac tttaaaagca    780

atcagtaaac acctctggtg ctattcaagg gttttttgcc tttatttgtt actgtcaatt    840

gtctggcgct gtgataaaaa acaaggcata aagctccccc gtcatgaaca ttaagactcg    900

ctagacgaga gagtgaaata taatgcattt cctgatttaa atgcgctaca aacatggtgt    960

aaatctggcc cggagtgagt gcttgccaat ttggcttcta agggagaaag atcaaaccac   1020

tcccaattgc gtcattttga aagagtggcc acctcgcgag cgtctgtcga actaactgat   1080

gaataaatat ataaggagaa aatcacttca acttcgctac aagtagtcac tatttgtagc   1140

aactgtaaac gaacacatca aagaataaga ttacattcta tatctaagac taaattttaa   1200

atgtccgcta aatcgtttga agtcacagat ccagtcaatt caagtctcaa agggtttgcc   1260

cttgctaacc cctccattac gctggtccct gaagaaaaaa ttctcttcag aaagaccgat   1320
```

-continued

```
tccgacaaga tcgcattaat ttctggtggt ggtagtggac atgaacctac acacgccggt   1380

ttcattggta agggtatgtt gagtggcgcc gtggttggcg aaatttttgc atccccttca   1440

acaaaacaga ttttaaatgc aatccgttta gtcaatgaaa atgcgtctgg cgttttattg   1500

attgtgaaga actacacagg tgatgttttg cattttggtc tgtccgctga gagagcaaga   1560

gccttgggta ttaactgccg cgttgctgtc ataggtgatg atgttgcagt tggcagagaa   1620

aagggtggta tggttggtag aagagcattg gcaggtaccg ttttggttca taagattgta   1680

ggtgccttcg cagaagaata ttctagtaag tatggcttag acggtacagc taaagtggct   1740

aaaattatca acgacaattt ggtgaccatt ggatcttctt tagaccattg taaagttcct   1800

ggcaggaaat tcgaaagtga attaaacgaa aaacaaatgg aattgggtat gggtattcat   1860

aacgaacctg gtgtgaaagt tttagaccct attccttcta ccgaagactt gatctccaag   1920

tatatgctac caaaactatt ggatccaaac gataaggata gagcttttgt aaagtttgat   1980

gaagatgatg aagttgtctt gttagttaac aatctcggcg gtgtttctaa ttttgttatt   2040

agttctatca cttccaaaac tacggatttc ttaaaggaaa attacaacat aaccccggtt   2100

caaacaattg ctggcacatt gatgacctcc ttcaatggta atgggttcag tatcacatta   2160

ctaaacgcca ctaaggctac aaaggctttg caatctgatt ttgaggagat caaatcagta   2220

ctagacttgt tgaacgcatt tacgaacgca ccgggctggc caattgcaga ttttgaaaag   2280

acttctgccc catctgttaa cgatgacttg ttacataatg aagtaacagc aaaggccgtc   2340

ggtacctatg actttgacaa gtttgctgag tggatgaaga gtggtgctga acaagttatc   2400

aagagcgaac cgcacattac ggaactagac aatcaagttg gtgatggtga ttgtggttac   2460

actttagtgg caggagttaa aggcatcacc gaaaaccttg acaagctgtc gaaggactca   2520

ttatctcagg cggttgccca aatttcagat ttcattgaag gctcaatggg aggtacttct   2580

ggtggtttat attctattct tttgtcgggt ttttcacacg gattaattca ggtttgtaaa   2640

tcaaaggatg aacccgtcac taaggaaatt gtggctaagt cactcggaat tgcattggat   2700

actttataca aatatacaaa ggcaaggaag ggatcatcca ccatgattga tgctttagaa   2760

ccattcgtta aagaatttac tgcatctaag gatttcaata aggcggtaaa agctgcagag   2820

gaaggtgcta aatccactgc tacattcgag gccaaatttg gcagagcttc gtatgtcggc   2880

gattcatctc aagtagaaga tcctggtgca gtaggcctat gtgagttttt gaaggggggtt   2940

caaagcgcct tgtaa                                                    2955
```

<210> SEQ ID NO 45
<211> LENGTH: 584
<212> TYPE: PRT
<213> ORGANISM: Saccharomyces cerevisiae

<400> SEQUENCE: 45

```
Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80
```

-continued

```
Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140

Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
            180                 185                 190

Ser Leu Asp His Cys Lys Val Pro Gly Arg Lys Phe Glu Ser Glu Leu
        195                 200                 205

Asn Glu Lys Gln Met Glu Leu Gly Met Gly Ile His Asn Glu Pro Gly
    210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Asp Glu Val Val Leu Leu Val Asn Asn Leu
            260                 265                 270

Gly Gly Val Ser Asn Phe Val Ile Ser Ser Ile Thr Ser Lys Thr Thr
        275                 280                 285

Asp Phe Leu Lys Glu Asn Tyr Asn Ile Thr Pro Val Gln Thr Ile Ala
    290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
            340                 345                 350

Trp Pro Ile Ala Asp Phe Glu Lys Thr Ser Ala Pro Ser Val Asn Asp
        355                 360                 365

Asp Leu Leu His Asn Glu Val Thr Ala Lys Ala Val Gly Thr Tyr Asp
    370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
            420                 425                 430

Leu Asp Lys Leu Ser Lys Asp Ser Leu Ser Gln Ala Val Ala Gln Ile
        435                 440                 445

Ser Asp Phe Ile Glu Gly Ser Met Gly Gly Thr Ser Gly Gly Leu Tyr
    450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495
```

-continued

```
Ile Ala Leu Asp Thr Leu Tyr Lys Tyr Thr Lys Ala Arg Lys Gly Ser
            500                 505                 510

Ser Thr Met Ile Asp Ala Leu Glu Pro Phe Val Lys Glu Phe Thr Ala
        515                 520                 525

Ser Lys Asp Phe Asn Lys Ala Val Lys Ala Ala Glu Glu Gly Ala Lys
    530                 535                 540

Ser Thr Ala Thr Phe Glu Ala Lys Phe Gly Arg Ala Ser Tyr Val Gly
545                 550                 555                 560

Asp Ser Ser Gln Val Glu Asp Pro Gly Ala Val Gly Leu Cys Glu Phe
                565                 570                 575

Leu Lys Gly Val Gln Ser Ala Leu
            580


<210> SEQ ID NO 46
<211> LENGTH: 2286
<212> TYPE: DNA
<213> ORGANISM: Saccharomyces cerevisiae

<400> SEQUENCE: 46

atgattctga cgaccctttg atagtggcaa tgatcaaaaa gaaaaaaaaa agataagacg     60

gtagtgtgaa gatgacatat agcgctactc tatactcgtc caacttcgaa aataatatgt    120

ggtcgttggt acgttcagat aagagaatac atctcgcgcg tacgcataat tgtggtctaa    180

aaaaccgctg aaattttctc aatactgaat agaatcacgc tactacgaca agactcggtt    240

actgtgccta aaataatcct gtgataaacg agttatgtta aacgcagtac aggggttaaa    300

gggcattgag tttttgtgag tggaaatgcc cccgttatag cttccagttt aattacaaat    360

tatcaattta agcaaatata actggaggat tggggaggcg actaaaaatg gctaccacgc    420

tattagacat acaacattga gtattttatg taattttgtt actgctagca cggccatgca    480

attggcaact gaaagctatc tgacaactta aatgattctt aaaacaatga cgactataat    540

cttctctaag aagtttcata tccatcttcc tcattattca gtttcttttt cctcttgaaa    600

gtatcgtaaa gaacaacgtc ttcacattag ctattagaag accattgaac taccggatat    660

gagtaagagt gatcttgccg gagagataat agctgcacaa aggccaagga ttagattaat    720

gggtgcattg tacgaaaaaa aatagtttac agtcatttat tcgcaataaa tcaatttttt    780

tttcaaaaaa tatgtaagtc tgataaaaaa ttcttcactg aagagagatg cttacattct    840

aattcttgaa taaaagactc tctaacgctg tgaattctct ttagctgtaa cggaaacaga    900

gagttattcc gtagtcactg aatttttttt ttttgacgct attatttaaa acctaggata    960

tccgtcccat acaaaacggc cacgagtttc aatcccagaa tgtacgagtt ataattctcc   1020

tagatgcatg atactcgtgc attcgtttaa caatcatacc aatttcccat tttcgggata   1080

ttaaacatga acatactttt ttactgtgag aatgtggttt cacaattatt ccatacaggt   1140

ataaaaacgc acagaacttc aaacgggaag actatctacc cacattgatg gacaaacgca   1200

atgatttctg ctaattcatt acttatttcc actttgtgcg cttttgcgat cgcaacacct   1260

ttgtcaaaaa gagattcctg taccctaaca ggatcttctt tgtcttcact ctcaaccgtg   1320

aaaaaatgta gcagcatcgt tattaaagac ttaactgtcc cagctggaca gactttagat   1380

ttaactgggt taagcagtgg tactactgtt acgtttgaag gcacaaccac atttcagtac   1440

aaggaatgga gcggcccttt aatttcaatc tcagggtcta aaatcagcgt tgttggtgct   1500

tcgggacata ccattgatgg tcaaggagca aaatggtggg atggcttagg tgatagcggt   1560

aaagtcaaac cgaagtttgt aaagttggcg ttgacgggaa catctaaggt caccggattg   1620
```

-continued

```
aatattaaaa atgctccaca ccaagtcttc agcatcaata aatgttcaga tttaaccatc   1680

agcgacataa caattgatat cagagacggt gattcggctg gtggtcataa tacggatggg   1740

tttgatgttg gtagttctag taacgtctta attcaaggat gtactgttta taatcaggat   1800

gactgtattg ctgtgaattc cggttcaact attaaattta tgaacaacta ctgctacaat   1860

ggccatggta tttctgtagg ttctgttggt ggccgttctg ataatacagt caatggtttc   1920

tgggctgaaa ataaccatgt tatcaactct gacaacgggt tgagaataaa aaccgtagaa   1980

ggtgcgacag gcacagtcac taatgtcaac tttatcagta ataaaattag cggcataaaa   2040

agttatggta ttgttatcga aggcgattat ttgaatagta agactactgg aactgctaca   2100

ggtggcgttc ccatttcgaa tttagtaatg aaggatatca ccgggagcgt gaactccaca   2160

gcgaagaggg ttaaaatttt ggtgaaaaac gctactaact ggcaatggtc tggggtgtca   2220

attaccggtg gttcttccta ttctggatgt tctggaatcc catctggatc tggtgcaagc   2280

tgttaa                                                              2286
```

<210> SEQ ID NO 47
<211> LENGTH: 933
<212> TYPE: DNA
<213> ORGANISM: Saccharomyces cerevisiae

<400> SEQUENCE: 47

```
ttcgtttctg tcttgtctcc cgctgttacc taataacttc atgtgatctg ctcccccttc     60

tcgttaaata ccaccttttc atcaaccccg tagggcgcga cacgtctaaa atattaacct    120

ctgaatactt attgggtcaa aatgaatgtt gataactttc ctttacaaaa aaaaaactaa    180

tagagtatat gcatttcggt agtgaaatat tcgttaatgc taatatgctc agtagtgatc    240

ctagattacc agttttactg cagccatcgt acaattttgg aacgagtata aagagagaaa    300

ttaaaaacga caagaaatat tcgtactagc ttctcttccg gcttgatgac agtcttaata    360

tcatctgcaa ctcttgaaat cttgctttat agtcaaaatt tacgtacgct tttcactata    420

taatatgatt tgtcaatgtg atgagtgaat gtctccctgt tacccggttt tcatgttgat    480

ttttgtttca ggctctaaat gtttgatgca atatttaaca aggagaacag aaatgttttg    540

tgacagcacc tgtcaatttt aggatagtag caatcgcaaa cgttctcaat aattctaaga    600

atgacatcag ttcaaaactc tccacgctta caacaacctc aggaacagca acagcaacag    660

caacagcttt ccttaaagat aaaacaattg aagttaaaaa gaatcaacga acttaacaat    720

aaactgagga aagaactcag ccgtgaaaga attactgctt caaatgcatg tcttacaata    780

ataaactata cctcgaatac aaaagattat acattaccag aactatgggg ctaccccgta    840

gcaggatcaa atcattttat agagggtttg aaaaatgctc aaaaaaatag ccaaatgtca    900

aactcaaata gtgtttgttg tacgcttatg taa                                 933
```

<210> SEQ ID NO 48
<211> LENGTH: 110
<212> TYPE: PRT
<213> ORGANISM: Saccharomyces cerevisiae

<400> SEQUENCE: 48

```
Met Thr Ser Val Gln Asn Ser Pro Arg Leu Gln Gln Pro Gln Glu Gln
1               5                   10                  15

Gln Gln Gln Gln Gln Gln Leu Ser Leu Lys Ile Lys Gln Leu Lys Leu
            20                  25                  30
```

-continued

```
Lys Arg Ile Asn Glu Leu Asn Asn Lys Leu Arg Lys Glu Leu Ser Arg
        35                  40                  45

Glu Arg Ile Thr Ala Ser Asn Ala Cys Leu Thr Ile Ile Asn Tyr Thr
    50                  55                  60

Ser Asn Thr Lys Asp Tyr Thr Leu Pro Glu Leu Trp Gly Tyr Pro Val
65                  70                  75                  80

Ala Gly Ser Asn His Phe Ile Glu Gly Leu Lys Asn Ala Gln Lys Asn
                85                  90                  95

Ser Gln Met Ser Asn Ser Asn Ser Val Cys Cys Thr Leu Met
            100                 105                 110


<210> SEQ ID NO 49
<211> LENGTH: 361
<212> TYPE: PRT
<213> ORGANISM: Saccharomyces cerevisiae

<400> SEQUENCE: 49

Met Ile Ser Ala Asn Ser Leu Leu Ile Ser Thr Leu Cys Ala Phe Ala
1               5                   10                  15

Ile Ala Thr Pro Leu Ser Lys Arg Asp Ser Cys Thr Leu Thr Gly Ser
            20                  25                  30

Ser Leu Ser Ser Leu Ser Thr Val Lys Lys Cys Ser Ser Ile Val Ile
        35                  40                  45

Lys Asp Leu Thr Val Pro Ala Gly Gln Thr Leu Asp Leu Thr Gly Leu
    50                  55                  60

Ser Ser Gly Thr Thr Val Thr Phe Glu Gly Thr Thr Thr Phe Gln Tyr
65                  70                  75                  80

Lys Glu Trp Ser Gly Pro Leu Ile Ser Ile Ser Gly Ser Lys Ile Ser
                85                  90                  95

Val Val Gly Ala Ser Gly His Thr Ile Asp Gly Gln Gly Ala Lys Trp
            100                 105                 110

Trp Asp Gly Leu Gly Asp Ser Gly Lys Val Lys Pro Lys Phe Val Lys
        115                 120                 125

Leu Ala Leu Thr Gly Thr Ser Lys Val Thr Gly Leu Asn Ile Lys Asn
    130                 135                 140

Ala Pro His Gln Val Phe Ser Ile Asn Lys Cys Ser Asp Leu Thr Ile
145                 150                 155                 160

Ser Asp Ile Thr Ile Asp Ile Arg Asp Gly Asp Ser Ala Gly Gly His
                165                 170                 175

Asn Thr Asp Gly Phe Asp Val Gly Ser Ser Ser Asn Val Leu Ile Gln
            180                 185                 190

Gly Cys Thr Val Tyr Asn Gln Asp Asp Cys Ile Ala Val Asn Ser Gly
        195                 200                 205

Ser Thr Ile Lys Phe Met Asn Asn Tyr Cys Tyr Asn Gly His Gly Ile
    210                 215                 220

Ser Val Gly Ser Val Gly Gly Arg Ser Asp Asn Thr Val Asn Gly Phe
225                 230                 235                 240

Trp Ala Glu Asn Asn His Val Ile Asn Ser Asp Asn Gly Leu Arg Ile
                245                 250                 255

Lys Thr Val Glu Gly Ala Thr Gly Thr Val Thr Asn Val Asn Phe Ile
            260                 265                 270

Ser Asn Lys Ile Ser Gly Ile Lys Ser Tyr Gly Ile Val Ile Glu Gly
        275                 280                 285

Asp Tyr Leu Asn Ser Lys Thr Thr Gly Thr Ala Thr Gly Gly Val Pro
    290                 295                 300
```

-continued

```
Ile Ser Asn Leu Val Met Lys Asp Ile Thr Gly Ser Val Asn Ser Thr
305                 310                 315                 320

Ala Lys Arg Val Lys Ile Leu Val Lys Asn Ala Thr Asn Trp Gln Trp
                325                 330                 335

Ser Gly Val Ser Ile Thr Gly Gly Ser Ser Tyr Ser Gly Cys Ser Gly
            340                 345                 350

Ile Pro Ser Gly Ser Gly Ala Ser Cys
        355                 360
```

<210> SEQ ID NO 50
<211> LENGTH: 1775
<212> TYPE: DNA
<213> ORGANISM: Saccharomyces cerevisiae

<400> SEQUENCE: 50

```
gagaattatt cgcgacttca ggttatccaa tcgtgtatgt aatcgtatgt aggcaaaagt     60
aaatagatat gaactacatt ttcctgcttt acttagacta gagatgtgac ctcaaagaat    120
cttctcaagt agtatatctg gaaaagagag tttgcaataa cgacgcccaa ttggaagatg    180
gaccaccatt taacacgatc gttggtcgac tctgcagtat ttctatgcgt cctttctcta    240
ataacaatat aactttgttc gtccttgact tccctggtta atttggacaa ctttctgaca    300
gcactatcca atgtattggt gtttgggtcg tccaaatcca catataccac cccatgaatg    360
ttgaaagtca cgtcttttgt ctcgataccg gtgttctcgt tcaagaaaca gtattggaaa    420
tgtcccttgt atggagcaga caatgtgatt tcaccgtgcg acgtgtccct aaccgttttc    480
aaaacttcat gtctttccgg cccgtagatg ataaagtcac cagtcagctg gctactggat    540
tgagggtttc tatcaccgaa ctggaacgaa atggagagct cgtcaccctt actcaagtct    600
tcgaagaagc atctacggcc ataagctgga agaaggacat tatgggcgga cgccgagaag    660
aacaggaagc aagcaatgac aaacttagta gcaaatgagg ccatccttat gcgtgtgtat    720
ttttgtgcgg agggatacta ttaagattgc agtttcacca agtatagctt tttatttcat    780
tataagtttc gtgtcaaaat gtttaagcga cccgatctct caggctgttt tgcacgactt    840
ttctgacttt cctcgcgtct tttttcatga aaattggatt acccggagtg atgattttct    900
cacagtgatt tttcgtcccc ttttacaata gcaaatgaag ctgttttagc aatatttgta    960
gaaagatatg tcacaagagg gcaggcaaaa tgtcatacgg aagagaagac actacgattg   1020
agcccgactt catagaacca gatgcacctt tggctgcttc cgggggtgtt gctgacaaca   1080
taggcggaac tatgcagaat tcaggcagca gagggacgct cgacgagact gtgctgcaaa   1140
cactaaagcg agatgtggtg gagattaatt ccagactgaa acaagtggta tacccgcatt   1200
tcccctcatt ctttagcccc tctgatgacg ggataggggc ggctgataac gacatttcag   1260
ccaattgcga cctgtgggcg ccccttgcgt ttatcatatt gtattctcta tttgtatcgc   1320
atgcgcggtc gctgttctcg agcctatttg tgtctagttg gttcattttg ctggtgatgg   1380
cattgcatct gagactcacc aagccacacc agagggtgtc gctgatttcg tacatctcca   1440
tttccgggta ttgcttattc ccacaagtgc tgaatgcctt agtctcgcag atactacttc   1500
cattggccta ccatattgga aagcaaaatc gctggattgt gagggtcctg tcgctcgtga   1560
aactggtggt catggcgctg tgcctgatgt ggtctgtggc cgccgtttcg tgggttacca   1620
agagcaagac cattatcgag atatacctct ggcactctgt cttttttggc atggctggtt   1680
gtcaactatt ttataacact agttacatat gtataaaacc caatattcat ggacatagaa   1740
ttgcctatct cgcgagccac ggcagaaagt tctga                              1775
```

-continued

<210> SEQ ID NO 51
<211> LENGTH: 261
<212> TYPE: PRT
<213> ORGANISM: Saccharomyces cerevisiae

<400> SEQUENCE: 51

```
Met Ser Tyr Gly Arg Glu Asp Thr Thr Ile Glu Pro Asp Phe Ile Glu
1               5                   10                  15

Pro Asp Ala Pro Leu Ala Ala Ser Gly Gly Val Ala Asp Asn Ile Gly
            20                  25                  30

Gly Thr Met Gln Asn Ser Gly Ser Arg Gly Thr Leu Asp Glu Thr Val
        35                  40                  45

Leu Gln Thr Leu Lys Arg Asp Val Val Glu Ile Asn Ser Arg Leu Lys
    50                  55                  60

Gln Val Val Tyr Pro His Phe Pro Ser Phe Phe Ser Pro Ser Asp Asp
65                  70                  75                  80

Gly Ile Gly Ala Ala Asp Asn Asp Ile Ser Ala Asn Cys Asp Leu Trp
                85                  90                  95

Ala Pro Leu Ala Phe Ile Ile Leu Tyr Ser Leu Phe Val Ser His Ala
            100                 105                 110

Arg Ser Leu Phe Ser Ser Leu Phe Val Ser Ser Trp Phe Ile Leu Leu
        115                 120                 125

Val Met Ala Leu His Leu Arg Leu Thr Lys Pro His Gln Arg Val Ser
    130                 135                 140

Leu Ile Ser Tyr Ile Ser Ile Ser Gly Tyr Cys Leu Phe Pro Gln Val
145                 150                 155                 160

Leu Asn Ala Leu Val Ser Gln Ile Leu Leu Pro Leu Ala Tyr His Ile
                165                 170                 175

Gly Lys Gln Asn Arg Trp Ile Val Arg Val Leu Ser Leu Val Lys Leu
            180                 185                 190

Val Val Met Ala Leu Cys Leu Met Trp Ser Val Ala Ala Val Ser Trp
        195                 200                 205

Val Thr Lys Ser Lys Thr Ile Ile Glu Ile Tyr Leu Trp His Ser Val
    210                 215                 220

Phe Phe Gly Met Ala Gly Cys Gln Leu Phe Tyr Asn Thr Ser Tyr Ile
225                 230                 235                 240

Cys Ile Lys Pro Asn Ile His Gly His Arg Ile Ala Tyr Leu Ala Ser
                245                 250                 255

His Gly Arg Lys Phe
            260
```

<210> SEQ ID NO 52
<211> LENGTH: 25
<212> TYPE: DNA
<213> ORGANISM: Artificial
<220> FEATURE:
<223> OTHER INFORMATION: PCR Primer

<400> SEQUENCE: 52
gattgaattc aattgaaatc gatag 25

<210> SEQ ID NO 53
<211> LENGTH: 25
<212> TYPE: DNA
<213> ORGANISM: Artificial
<220> FEATURE:
<223> OTHER INFORMATION: PCR Primer -continued

<400> SEQUENCE: 53
ccgaggcgcc gaattttcga gttat 25

<210> SEQ ID NO 54
<211> LENGTH: 25
<212> TYPE: DNA
<213> ORGANISM: Artificial
<220> FEATURE:
<223> OTHER INFORMATION: PCR Primer

<400> SEQUENCE: 54
catgtctaga ggagaagaac ttttc 25

<210> SEQ ID NO 55
<211> LENGTH: 25
<212> TYPE: DNA
<213> ORGANISM: Artificial
<220> FEATURE:
<223> OTHER INFORMATION: PCR Primer

<400> SEQUENCE: 55
cgcgaattcc tatttgtata gttca 25

<210> SEQ ID NO 56
<211> LENGTH: 30
<212> TYPE: DNA
<213> ORGANISM: Artificial
<220> FEATURE:
<223> OTHER INFORMATION: PCR Primer

<400> SEQUENCE: 56
cggcgcgccg cggccgcatg gccggccaat 30

<210> SEQ ID NO 57
<211> LENGTH: 38
<212> TYPE: DNA
<213> ORGANISM: Artificial
<220> FEATURE:
<223> OTHER INFORMATION: PCR Primer

<400> SEQUENCE: 57
ctagattggc cggccatgcg gccgcggcgc gccgcatg 38

<210> SEQ ID NO 58
<211> LENGTH: 13
<212> TYPE: DNA
<213> ORGANISM: Artificial
<220> FEATURE:
<223> OTHER INFORMATION: PCR Primer

<400> SEQUENCE: 58
ccccggagac gtc 13

<210> SEQ ID NO 59
<211> LENGTH: 10
<212> TYPE: DNA
<213> ORGANISM: Artificial
<220> FEATURE:
<223> OTHER INFORMATION: PCR Primer

<400> SEQUENCE: 59
tcccccacca 10